(12) United States Patent
Chaki et al.

(10) Patent No.: US 7,314,888 B1
(45) Date of Patent: Jan. 1, 2008

(54) COMPOUNDS AND MEDICINAL USE THEREOF

(75) Inventors: Hisaaki Chaki, Toyama (JP);
Tadakazu Takakura, Toyama (JP);
Keiichi Tsuchida, Toyama (JP);
Hironori Kotsubo, Toyama (JP);
Yukihiko Aikawa, Toyama (JP);
Shuichi Hirono, Tokyo (JP); Shunichi Shiozawa, Hyogo (JP)

(73) Assignee: Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/830,559

(22) PCT Filed: Nov. 5, 1999

(86) PCT No.: PCT/JP99/06166

§ 371 (c)(1),
(2), (4) Date: May 7, 2001

(87) PCT Pub. No.: WO00/27792

PCT Pub. Date: May 18, 2000

(30) Foreign Application Priority Data

Nov. 5, 1998 (JP) .............................. 10-328792
Mar. 25, 1999 (JP) .............................. 11-080693

(51) Int. Cl.
*A61K 31/18* (2006.01)
*A61K 31/19* (2006.01)
*A61K 31/195* (2006.01)
*A61K 31/235* (2006.01)

(52) U.S. Cl. ................. 514/532; 514/538; 514/539; 514/544; 514/545; 514/567; 514/568; 514/570; 514/571; 560/9; 560/19; 560/20; 560/21; 560/52; 560/101; 562/426; 562/435; 562/441; 562/560

(58) Field of Classification Search ............. 514/568, 514/570, 545; 560/52; 562/460
See application file for complete search history.

(56) References Cited

U.S. PATENT DOCUMENTS

| 3,478,087 A | | 11/1969 | McGrath et al. | |
| 4,389,416 A | * | 6/1983 | Plattner | 514/539 |
| 5,235,064 A | * | 8/1993 | Gapinski | 548/253 |
| 5,434,186 A | * | 7/1995 | Cohen et al. | 514/571 |
| 5,852,046 A | | 12/1998 | Lang et al. | 514/419 |

FOREIGN PATENT DOCUMENTS

| DE | 1 138 792 | 10/1962 |
| DE | 2 064 304 | 7/1972 |
| EP | 0 150 166 | 7/1985 |
| EP | 0 276 064 | 1/1988 |
| EP | 639 572 | 7/1991 |
| EP | 0 531 823 A1 | 8/1992 |
| EP | 639 573 | 2/1995 |
| EP | 0 856 582 | 8/1998 |
| JP | 7-145149 | 6/1995 |
| JP | 10-36272 | 2/1998 |
| JP | 10-130201 | 5/1998 |
| WO | WO 96/40189 | 12/1996 |

OTHER PUBLICATIONS

J. N. M. Glover, et al., Letters To Nature, vol. 373, No. 6511, pp. 257-261, "Crystal Structure of the Heterodimeric bZIP Transcription Factor c-Fos-c-JUN Bound to DNA," Jan. 19, 1995.
Y. Nishibata, et al., Tetrahedron, vol. 47, No. 43, pp. 8985-8990, "Automatic Creation of Drug Candidate Structures Based on Receptor Structure. Starting Point for Artificial Lead Generation," 1991.
Y. C. Martin, et al., Journal Of Medicinal Chemistry, vol. 35, No. 12, pp. 2145-2154, "3D Database Searching in Drug Design," Jun. 12, 1992.
S. Yao, et al., Biopolymers, vol. 47, No. 4, pp. 277-283, "Uncoiling c-JUN Coiled Coils: Inhibitory Effects of Truncated FOS Peptides on JUN Dimerization and DNA Binding In Vitro," 1998.
M. Cushman, et al., Journal of Medicinal Chemistry, vol. 41, No. 12, pp. 2076-2089, "New Alkenyldiarylmethanes With Enhanced Potencies as Anti-HIV Agents Which Act as Non-Nucleoside Reverse Transcriptase Inhibitors," 1998.
N. Neamati, et al., Journal of Medicinal Chemistry, vol. 40, No. 6, pp. 942-951, "Depsides and Depsidones as Ingibitors of HIV-1 Integrase: Discovery of Novel Inhibitors Through 3D Database Searching," 1997.
M. Cushman, et al., Biochemical and Biophysical Research Communications, vol. 185, No. 1, pp. 85-90, "Inhibition of HIV-1 Integration Protein by Aurintricarboxylic Acid Monomers, Monomer Analogs, and Polymer Fractions," May 29, 1992.
Andrea Fanjui, et al., "A New Class of Retinoids With Selective Inhibition of AP-1 Inhibits Proliferation," Letter to Nature, XP-000579772, vol. 372, No. 6501, Nov. 3, 1994, pp. 107-111.

(Continued)

Primary Examiner—Peter O'Sullivan
(74) Attorney, Agent, or Firm—Oblon, Spivak, McClelland, Maier & Neustadt, P.C.

(57) ABSTRACT

A compound or a salt thereof having the atom corresponding to $N_3$ and the two or more atoms selected from $N_1$, $N_2$, $N_4$ and $N_5$, said atoms constitute the pharmacophore represented by the following formula:

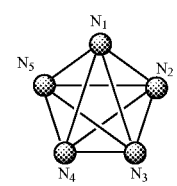

[1]

and inhibits the activity of transcription factor AP-1 and is useful as an agent for preventing and treating the diseases into which over expression of AP-1 participates and as an AP-1 inhibitor.

23 Claims, No Drawings

OTHER PUBLICATIONS

Robert W. Sullivan, et al., "2-Chloro-4-(Trifluoromethyl)Pyrimidine-5-N-(3',5'-Bis(Trifluoromethyl)Phenyl)-Carboxamide: A Potent Inhibitor of NF-Kb- and AP-1-Mediated Gene Expression Identified Using Solution-Phase Combinatorial Chemistry," Journal of Medicinal Chemistry, American Chemical Society, XP-002328712, vol. 41, No. 4, Jan. 24, 1998, pp. 413-419.

M. E. Goldman, et al., "SP100030 is a Novel T-Cell-Specific Transcription Factor Inhibitor That Possesses Immunosuppressive Activity In Vivo," Transplantation Proceedings, XP-001095817, vol. 28, No. 6, Dec. 1996, pp. 3106-3109.

Masaki Goto, et al., "K1115 A, A New Anthraquinone Derivative That Inhibits the Binding of Activator Protein-1 (AP-1) to Its Recognition Sites," The Journal of Antibiotics, XP-008066756, vol. 51, No. 6, Jun. 1998, pp. 539-544.

Keiichi Tsuchida, et al., "Design, Synthesis and Biological Evaluation of New Cyclic Disulfide Decapeptides That Inhibit the Binding of AP-1 to DNA," Journal of Medicinal Chemistry, XP-002390592, vol. 47, No. 17, Aug. 12, 2004, pp. 4239-4246.

Kossoy, A.D., et al. : "Novel Computational Method for the Determination of Partition Coefficients by Planar Chromatography" Anal. Chem, vol. 64, No. 13, 1992, pp. 1345-1349, XP-002421882.

Gapinski, D.M., et al., "Benzophenone Dicarboxylic Acid Antagonists of Leukotriene B₄. 1. Structure-Activity Relationships of the Benzophenone Nucleus" J. Med. Chem, vol. 33, No. 1990, pp. 2798-2807, XP00241883.

Bhavsar, M.D., et al.: "Synthesis Of Hydroxy-Aryl Ketones as UV Absorbers-IV", Man-Made Textiles in India, vol. 31, No. 12, 1988, pp. 529-535, 556, XP009079332.

Van Der Zanden, J.M., et al.: Polymerization of ortho-methoxyallybenzene. Dimerization combined with hydration Recueil des Travaux Chimiques des Pays-Bas et de la Belgique, vol. 74, 1955, pp. 876-888, XP009079324.

Reichel, I., et al. "Neue Erkenntnisse zur Synthese aromatischer Ketonsäuren und Beiträge zur Kenntnis der molekularen Additionsverbindung (A1C13×CH3N02)" Rev. Chim. Acad. Rep. Populaire Roumaine, vol. 5, No. 1, 1960, pp. 67-84, XP009079368.

Mitter, P.C. et al.: "Friedel and Crafts Reaction with Phenolic Acids", J. Indian Chem. Soc., vol. 9, 1932, pp. 247-250, XP009079322.

Heller, G., et al.: "Über die o-[p'-Brom-m'-toluyl]-benzoesäure" Berichte der Deutschen Chemischen Gesellschaft [Abteilung]B: Abhandlungen, vol. 50B, 1925, pp. 497-499, XP009079321.

Carpenter, A.T., et al.: "Phenol-formaldehyde and allied resins. III. Further synthesis of resole molecules", J. Appl. Chem., vol. 3, 1953, pp. 486-495, XP009079323.

Dutta, P.L., et al.: "Synthesis and biological activity of a series of aspartate transcarbarnoylase inhibitors: N-substituted diethyl aspartates and N-substituted-3-oxo-1, 4-piperazine-2-acetic c acid esters" J. Pharm., Sciences, vol. 79, No. 5, 1990, XP009078747.

Quellet, R., et al., No. 303. Chlorométhylation de l'acide salicylique et des éthers phénoliques correspondants. Préparation de phénols (et ethers phénoliques) amido aminés en position 1-2-4, Préparation de dérivés du diphényl méthane et de la benzophénone et bis-benzophénones Bulletin de la Societe Chimique de France, vol. 5, 1969. pp. 1698-1705, XP009078837.

Kuhlmann, R., et al.: "Transient photocurrents induced by laser flash phototysis of aromatic carbonyl compounds in solution" J. Photochem,. vol. 7, 1977, pp. 287-296, XP002421893.

Philip, J,. et al,: "The synthesis of disalicyl alcohols", J. Med. Chem., vol. 8, No. 3, 1965, p. 405, XP002421894.

Prajapati, S.P.. et al.; "Studies on 4, 4'-dihydroxydiphenyl methane" J. Indian Chem. Soc., vol. 49, 1972, pp. 391-396, XP009079553.

Sapunov, V. I. , et al., "Order of formulation of Intermediate acids during liquid-phase oxidation of tetramethylbenzophenone" J. Org. Chem. USSR (Engl. Transl.), vol. 9, 1973, pp. 2386-2388, XP009079542.

Calvet, F. et al,: "119. The condensation of chloral with salicylic acid" J. Chem. Soc., 1936, pp. 554-556, XP009079555.

Dong, Z., et al.: "Inhibition of tumor promoter-induced activator protein 1 activation and cell transformation by tea polyphenols, (-)-epigallocatechin gallate, and theaflavins", Cancer Research, vol. 57, 1997I, pp. 4414-4419, XP-002421895.

Chung, J.Y., et al.,: Inhibition of activator protein 1 activity and cell growth by purified green tea and black tea polyphenols in H-ras-transformed cells: Structure-activity relationship and mechanisms involved Cancer Research, vol. 59, Sep. 15, 1999, pp. 4610-4617, XP002421896.

Tsuchida, K., et al.::"Discovery of non-peptidic small-molecule AP-1 inhibitors: Lead hopping based on a three-dimensional pharmacophore model" J. Med Chem., vol. 49, No. 1, Jan. 12, 2005, pp. 80-91, XP002421897.

* cited by examiner

SEQUENCE LISTING

```
<160> NUMBER OF SEQ ID NOS: 14

<210> SEQ ID NO 1
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: X = any polar amino acid
<220> FEATURE:
<221> NAME/KEY: MISC_FEATURE
<222> LOCATION: (4)..(4)
<223> OTHER INFORMATION: X = any hydrophobic amino acid
<220> FEATURE:
<221> NAME/KEY: MISC_FEATURE
<222> LOCATION: (5)..(5)
<223> OTHER INFORMATION: X = any amino acid with a carboxyl group or
    hydroxyl group on its side chain
<220> FEATURE:
<221> NAME/KEY: MISC_FEATURE
<222> LOCATION: (6)..(7)
<223> OTHER INFORMATION: X = any hydrophobic amino acid
<220> FEATURE:
<221> NAME/KEY: MISC_FEATURE
<222> LOCATION: (8)..(8)
<223> OTHER INFORMATION: X = any amino acid
<220> FEATURE:
<221> NAME/KEY: DISULFID
<222> LOCATION: (1)..(10)
<223> OTHER INFORMATION:

<400> SEQUENCE: 1

Cys Gly Xaa Xaa Xaa Xaa Xaa Xaa Gly Cys
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: X = any amino acid or bonding unit
```

```
<220> FEATURE:
<221> NAME/KEY: MISC_FEATURE
<222> LOCATION: (4)..(4)
<223> OTHER INFORMATION: X = any polar amino acid
<220> FEATURE:
<221> NAME/KEY: MISC_FEATURE
<222> LOCATION: (5)..(6)
<223> OTHER INFORMATION: X = any hydrophobic amino acid
<220> FEATURE:
<221> NAME/KEY: MISC_FEATURE
<222> LOCATION: (7)..(7)
<223> OTHER INFORMATION: X = any amino acid
<220> FEATURE:
<221> NAME/KEY: MISC_FEATURE
<222> LOCATION: (8)..(8)
<223> OTHER INFORMATION: X = any hydrophobic amino acid
<220> FEATURE:
<221> NAME/KEY: MISC_FEATURE
<222> LOCATION: (10)..(10)
<223> OTHER INFORMATION: X = any amino acid with a carboxyl group or
      hydroxyl on its side chain
<220> FEATURE:
<221> NAME/KEY: DISULFID
<222> LOCATION: (2)..(11)
<223> OTHER INFORMATION:

<400> SEQUENCE: 2

Xaa Cys Gly Xaa Xaa Xaa Xaa Xaa Gly Xaa Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(10)
<223> OTHER INFORMATION:

<400> SEQUENCE: 3

Cys Gly Gln Leu Asp Leu Ala Asp Gly Cys
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 4

Gln Leu Asp Leu Ala
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: DISULFID
<222> LOCATION: (1)..(10)
<223> OTHER INFORMATION:

<400> SEQUENCE: 5

Cys Gly Gln Leu Asp Leu Ala Leu Gly Cys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(10)
<223> OTHER INFORMATION:

<400> SEQUENCE: 6

Cys Gly Gln Leu Ser Leu Ala Leu Gly Cys
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(10)
<223> OTHER INFORMATION:

<400> SEQUENCE: 7

Cys Gly Gln Leu Asp Leu Ala Gly Gly Cys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(10)
<223> OTHER INFORMATION:

<400> SEQUENCE: 8

Cys Gly Gln Leu Asp Leu Ala Asn Gly Cys
1               5                   10

<210> SEQ ID NO 9
<211> LENGTH: 10
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(10)
<223> OTHER INFORMATION:

<400> SEQUENCE: 9

Cys Gly Gln Leu Ser Leu Ala Asp Gly Cys
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(11)
<223> OTHER INFORMATION:

<400> SEQUENCE: 10

Asn Cys Gly Asn Leu Leu Ala Leu Gly Ser Cys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(10)
<223> OTHER INFORMATION:

<400> SEQUENCE: 11

Cys Gly Asn Leu Leu Ala Leu Gly Ser Cys
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(11)
<223> OTHER INFORMATION:

<400> SEQUENCE: 12

Asn Cys Gly Asn Ala Leu Ala Leu Gly Ser Cys
1               5                   10
```

```
<210> SEQ ID NO 13
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(10)
<223> OTHER INFORMATION:

<400> SEQUENCE: 13

Cys Gly Asn Leu Leu Ala Leu Gly Asp Cys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(10)
<223> OTHER INFORMATION:

<400> SEQUENCE: 14

Cys Gly Asn Leu Leu Ser Leu Gly Asp Cys
1               5                   10
```

COMPOUNDS AND MEDICINAL USE THEREOF

TECHNICAL FIELD

This invention relates to compounds that inhibit the activity of transcription factor AP-1, salts thereof, agents containing these compounds and/or useful for preventing and treating the diseases into which an overexpression of AP-1 participates, AP-1 inhibitor, and a method for inhibiting the AP-1 activity.

BACKGROUND ART

DNA constituting the essentiality of gene is regulated by various factors and thereby its genetic information is controlled. That is, the transcription from DNA to mRNA is controlled and regulated by a plurality of DNA binding proteins which recognize the sequence of several to dozens of bases on the gene and combine thereto. AP-1 known as one of such DNA binding proteins was identified as an important transcription factor dealing with proliferation of cells (Biochem. Biophys. Acta, Vol. 1072, Pages 129-157, 1991). Further, in some succeeding studies, it became apparent that AP-1 extensively participates in the induction of the expression of many genes and in the control and regulation of biological phenomena.

When AP-1 binds to AP-1 binding sequence (5'-TGAGTCA-3') on genes, it exhibits a function as a transcription factor. As substances having such a sequence on the gene, proteins such as collagenases, stromelysin, metallothionein, interleukin-2 and the like and viruses such as SV40, polyoma virus and the like are known (Cell, Vol. 49, Pages 729-739, 1987).

Hitherto, as therapeutic drugs for may diseases, therapeutic drugs for controlling the function of proteins participating in the pathology such as enzymes and receptors have been developed. It is considered that, however, in the diseases caused by a quantitative abnormality of functional molecules existing in cells or on cell membranes, a treatment in the true sense is to control the quantity of transcription of the genes of the functional molecule and normalize the quantity of its expression rather than to control the activity of the functional molecules.

The gene expression and production of these functional proteins are controlled by a plurality of transcription factors. Since a transcription binding AP-1 sequence is common to exist in the promoter region of many genes, it is expected that various diseases may be effectively treated by controlling the AP-1 activity.

Up to today, it has been disclosed that glucocorticoids (Cell, Vol. 82. Pages 1189-1204, 1990) and retinoid derivatives (Nature, Vol. 372, Pages 107-111, 1994) can suppress the activity of AP-1. The action mechanism is considered as follows at the present time. Thus, these substances can form a complex together with respective receptor, and association of the complex with AP-1 can suppress of the binding of AP-1 to gene.

Steroidal agents used as therapeutic drugs for various diseases are known to exhibit a controlling action at the stage of expression of gene through intermediation of a glucocorticoid receptor. In fact, it has been reported that steroidal agents inhibit the activity of AP-1 and suppresses the production of cytokines and other proteins (Cell, Vol. 62, Pages 1189-1204, 1990). On the other hand, the use of steroidal agents are restricted from the viewpoint of hormone actions and side effects, and their side effects have a problem when they are administered excessively and/or for a long period of time.

In the recent years, a novel chemical drug is usually developed by a rational drug design base on the three-dimensional structure of biopolymers such as proteins (e.g., receptors and enzymes) and nucleic acid, which play an important physiological role (Shin Seikagaku Jikken Koza, Vol. 13, Pages 291-337, Tokyo Kagaku Dojin, 1993).

For applying this method, it is indispensably necessary to know the three-dimensional structure of the target bipolymer. The three-dimensional structure of the complex of transcription factor AP-1 and the complexes of its binding sequence have been elucidated by X ray crystallographic analysis (Nature, Vol. 373, Pages 257-261, 1995).

Accordingly, it has been desired to develop an agent for prevention and/or treatment of diseases in which overexpression of AP-1 participates, which suppresses the excessive expression of a wide variety of genes on the basis of AP-1 inhibitory action with lessened side reactions.

DISCLOSURE OF THE INVENTION

In the above-mentioned state of things, the present inventors have conducted extensive studies to find that compounds comprising the atom corresponding to $N_3$ and the two or more atoms selected from $N_1$, $N_2$, $N_4$ and $N_5$ said atoms constitute the pharmacophore represented by the following formula:

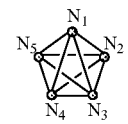

[1]

wherein $N_1$ represents an atom to which a donative hydrogen atom in a hydrogen-bond donating group is bonded or a hydrogen-bond accepting atom in a hydrogen-bond accepting group; $N_3$ represents a hydrogen-bond accepting atom in a hydrogen bond accepting group; and $N_2$, $N_4$ and $N_5$ independently represent an arbitrary carbon atom constituting a hydrophobic group and the distance between $N_1$ and $N_2$ is not less than 5 angstroms and not more than 12 angstroms, the distance between $N_1$ and $N_3$ is not less than 9 angstroms and not more than 15 angstroms, the distance between $N_1$ and $N_4$ is not less than 3 angstroms and not more than 13 angstroms, the distance between $N_1$ and $N_5$ is not less than 8 angstroms and not more than 16 angstroms, the distance between $N_2$ and $N_3$ is not less than 3 angstroms and not more than 10 angstroms, the distance between $N_2$ and $N_4$ is not less than 6 angstroms and not more than 14 angstroms, the distance between $N_2$ and $N_5$ is not less than 9 angstroms and not more than 14 angstroms, the distance between $N_3$ and $N_4$ is not less than 4 angstroms and not more than 11 angstroms, the distance between $N_3$ and $N_5$ is not less than 3 angstroms and not more than 10 angstroms, and the distance between $N_4$ and $N_5$ is not less than 4 angstroms and not more than 9 angstroms; and, in the optimized three-dimensional structure thereof, the distances between the atom corresponding to $N_3$ and the two or more atoms selected from $N_1$, $N_2$, $N_4$ and $N_5$ are the interatomic distances in the pharmacophore; or salts thereof; inhibit activity on transcription factor AP-1, and are useful for prevention and treatment of diseases into which an overexpression of AP-1 participates. Further, it has also been found that specific compounds conforming to the above-mentioned definition of pharmacophore, having an inhibitory activity upon transcription factor AP-1 and useful as an agent for prevention and treatment of the diseases into which an overexpression of AP-1 participates include the following:

a peptide having 10 residues represented by the following amino acid sequence:

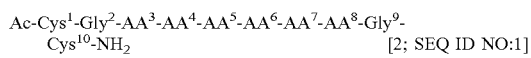
[2; SEQ ID NO:1]

wherein Ac represents an acetyl group, $AA^3$ represents a polar amino acid residue, $AA^4$, $AA^6$ and $AA^7$ independently represent a hydrophobic amino acid residue, $AA^5$ represents an amino acid residue having carboxyl group or hydroxyl group on side chain thereof, and $AA^8$ represents an arbitrary amino acid residue; and having a disulfide linkage between the first and tenth cysteine residues; or salts thereof;

a peptide having 10 or 11 residues represented by the following amino acid sequence:

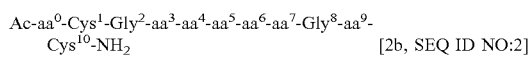
[2b, SEQ ID NO:2]

wherein Ac represents an acetyl group, $aa^o$ represents an arbitrary amino acid residue or a bonding unit, $aa^3$ represents a polar amino acid residue, $aa^4$, $aa^5$ and $aa^7$ independently represent a hydrophobic amino acid residue, $aa^6$ represents an arbitrary amino acid residue, and $aa^9$ represents an amino acid residue having carboxyl group or hydroxyl group on side chain thereof; provided that when $aa^o$ is a bonding unit, a disulfide linkage exists between the 2nd and 11th cysteine residues; or salts thereof;

benzene derivatives represented by the following general formula:

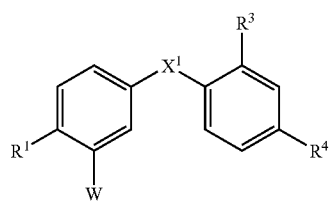
[3]

wherein $R^1$ represents halogen atom, cyano group, nitro group, unprotected or protected hydroxyl group, unprotected or protected amino group, mercapto group or unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; $R^3$ represents halogen atom, cyano group, nitro group, unprotected or protected carboxyl group, unprotected or protected hydroxyl group, unprotected or protected amino group, mercapto group, carbamoyl group or unsubstituted or substituted alkyl, alkenyl, cycloalkyl, aryl, aralkyl, alkoxy, aryloxy, acyl, alkoxycarbonyl, aryloxycarbonyl, alkylthio, alkylsulfinyl, alkylsulfonyl, alkylamino, acylamino, alkylsulfonylamino, arylsulfonylamino or heterocyclic group; $R^4$ represents hydrogen atom, cyano group, nitro group, unprotected or protected carboxyl group, unprotected or protected hydroxyl group, unprotected or protected amino group, mercapto group or unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group;

$X^1$ represents —C(O)—, —CH(OH)—, —$CH_2$— or a group of any one of the following formulas:

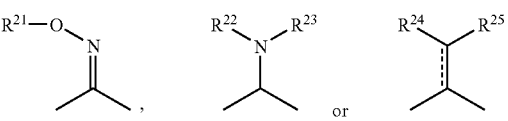

wherein $R^{21}$ represents unsubstituted or substituted alkyl, alkenyl, cycloalkyl, aryl, aralkyl, acyl or heterocycle-lower alkyl group; $R^{22}$ and $R^{23}$ may be the same or different and independently represent hydrogen atom, unsubstituted or substituted alkyl, alkenyl, cycloalkyl, aryl, aralkyl, acyl, carbamoyl, alkylsulfinyl, alkylsulfonyl, arylsulfonyl or heterocyclic group; $R^{24}$ and $R^{25}$ may be the same or different and independently represent hydrogen atom, halogen atom, cyano group, nitro group, unprotected or protected carboxyl group, unprotected or protected hydroxyl group, unprotected or protected amino group, mercapto group or unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; and the double line in which one line is a broken line represents a single bond or a double bond; and W represents —Z—$COR^{26}$, —Z—$COOR^2$, —O—$CH^2COOR^2$ or —O—$CH_2CH_2COOR^2$, wherein Z is —$(CH_2)_n$— (n is 0, 1, 2 or 3), —$CH_2CH(CH_3)$—, —CH═CH— or —$CH_2$CH═CH—; $R^2$ represents hydrogen atom or a protecting group for carboxyl group; and $R^{26}$ represents —$NHR^{27}$ or $NHSO_2R^{28}$ ($R^{27}$ and $R^{28}$ independently represent unsubstituted or substituted alkyl, alkenyl, cycloalkyl, aryl or aralkyl group); or salts thereof;

benzene derivatives represented by the following general formula:

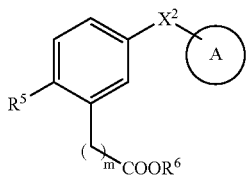
[4]

wherein $R^5$ represents hydrogen atom, halogen atom, cyano group, nitro group, unprotected or protected carboxyl group, unprotected or protected hydroxyl group, unprotected or protected amino group, mercapto group or unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; $R^6$ represents hydrogen atom or a protecting group for carboxyl group; $X^2$ represents —C(O)—; m represents 0, 1 or 2; ring A represents a group represented by the following formula:

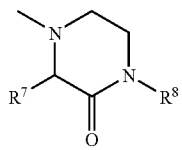

in which R⁷ represents hydrogen atom, halogen atom, cyano group, nitro group, unprotected or protected carboxyl group, unprotected or protected hydroxyl group, unprotected or protected amino group, mercapto group or unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; R⁸ represents hydrogen atom, unprotected or protected amino group or unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; or a group represented by the following formula:

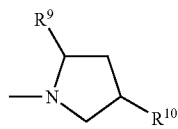

wherein R⁹ and R¹⁰ may be the same or different and independently represent halogen atom, cyano group, nitro group, unprotected or protected carboxyl group, unprotected or protected hydroxyl group, unprotected or protected amino group, mercapto group or unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, alkanoyloxy, arylsulfonylamino or heterocyclic group; or salts thereof;

benzene derivatives represented by the following formula:

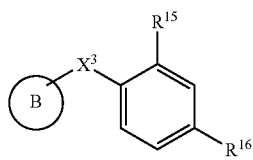

[5]

wherein R¹⁵ and R¹⁶ may be the same or different and independently represent hydrogen atom, halogen atom, cyano group, nitro group, unprotected or protected carboxyl group, unprotected or protected hydroxyl group, unprotected or protected amino group, mercapto group or unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; X³ represents —C(O)—; and ring B represents a group of the following formula:

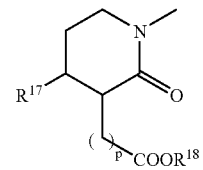

in which R¹⁷ represents hydrogen atom or unsubstituted or substituted alkyl, alkenyl, cycloalkyl, aryl, aralkyl, acyl, alkoxycarbonyl, aryloxycarbonyl, carbamoyl, alkylsulfonyl or heterocyclic group; R¹⁸ represents hydrogen atom or a protecting group for carboxyl group; and p represents 0, 1 or 2; or salts thereof;

benzene derivatives represented by the following formula:

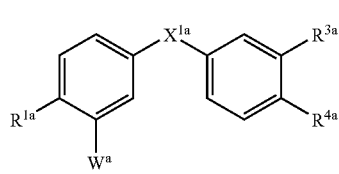

[a]

wherein R¹ᵃ represents halogen atom, cyano group, nitro group, unprotected or protected hydroxyl group, mercapto group or unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; R³ᵃ and R⁴ᵃ may be the same or different and independently represent halogen atom, cyano group, nitro group, unprotected or protected carboxyl group, unprotected or protected hydroxyl group, unprotected or protected amino group, mercapto group or unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; X¹ᵃ represents —C(O)—, —CH(OH)—, —CH₂— or a group of the following formula:

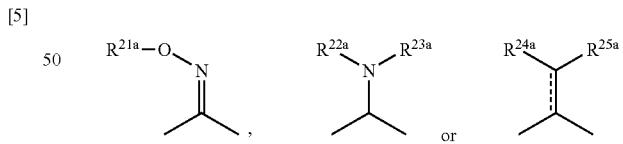

in which R²¹ᵃ represents unsubstituted or substituted alkyl, alkenyl, cycloalkyl, aryl, aralkyl, acyl or heterocycle-lower alkyl group; R²²ᵃ and R²³ᵃ may be the same or different and independently represent hydrogen atom, or unsubstituted or substituted alkyl, alkenyl, cycloalkyl, aryl, aralkyl, acyl, carbamoyl, alkylsulfinyl, alkylsulfonyl, arylsulfonyl or heterocyclic group; and R²⁴ᵃ and R²⁵ᵃ may be the same or different and independently represent hydrogen atom, halogen atom, cyano group, nitro group, unprotected or protected carboxyl group, unprotected or protected hydroxyl group, unprotected or protected amino group, mercapto group or unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; and the double line in which one line is a broken line represents a single bond or a double bond; and $W^a$ represents —$Z^a$—$COR^{26a}$, —$Z^a$—$COOR^{2a}$, —O—$CH_2COOR^{2a}$ or —O—$CH_2CH_2COOR^{2a}$; in which $Z^a$ represents —$(CH_2)_n{}^a$— ($n^a$ represents 0, 1, 2 or 3), $CH_2CH(CH_3)$—, —CH=CH— or —$CH_2$CH=CH—; $R^{2a}$ represents hydrogen atom or a protecting group for carboxyl group; and $R^{26a}$ represents —$NHR^{27a}$ or —$NHSO_2R^{28a}$ ($R^{27a}$ and $R^{28a}$ independently represent unsubstituted or substituted alkyl, alkenyl, cycloalkyl, aryl or aralkyl group); or salts thereof;

benzene derivatives represented by the following general formula:

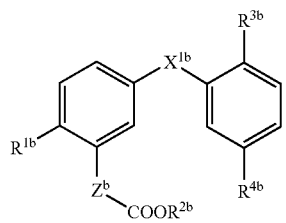

[b]

wherein $R^{1b}$ represents halogen atom, cyano group, nitro group, unprotected or protected hydroxyl group, unprotected or protected amino group, mercapto group or unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; $R^{2b}$ represents hydrogen atom or a protecting group for carboxyl group; $R^{3b}$ and $R^{4b}$ may be the same or different and independently represent cyano group, nitro group, unprotected or protected carboxyl group, unprotected or protected hydroxyl group, unprotected or protected amino group, mercapto group or unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; and $X^{1b}$ represents —C(O)—, —CH(OH)— or —$CH_2$—; and $Z^b$ represents —$(CH_2)_n{}^b$— ($n^b$ represents 0, 1 or 2) or —CH=CH—; or salts thereof;

benzene derivatives represented by the following general formula:

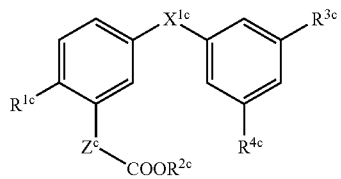

[c]

wherein $R^{1c}$ represents halogen atom, cyano group, nitro group, unprotected or protected hydroxyl group, unprotected or protected amino group, mercapto group or unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; $R^{2c}$ represents hydrogen atom or a protecting group for carboxyl group; $R^{3c}$ and $R^{4c}$ may be the same or different and independently represent halogen atom, cyano group, nitro group, unprotected or protected carboxyl group, unprotected or protected hydroxyl group, unprotected or protected amino group, mercapto group or unsubstituted or substituted alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; $X^{1c}$ represents —C(O)—, —CH(OH)— or —$CH_2$—; and $Z^c$ represents —$(CH_2)_n{}^c$— ($n^c$ represents 0, 1 or 2) or —CH=CH— or salts thereof;

benzene derivatives represented by the following general formula:

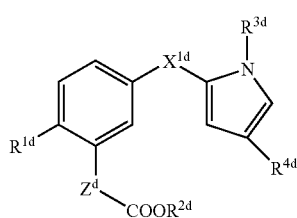

[d]

wherein $R^{1d}$ represents halogen atom, cyano group, nitro group, unprotected or protected hydroxyl group, unprotected or protected amino group, mercapto group or unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; $R^{2d}$ represents hydrogen atom or a protecting group for carboxyl group; $R^{3d}$ represents hydrogen atom or unsubstituted or substituted alkyl, alkenyl, cycloalkyl, aryl or aralkyl group; $R^{4d}$ represents alkyl, alkenyl, cycloalkyl, aryl, aralkyl, acyl, alkoxycarbonyl, aryloxycarbonyl, alkylsulfonyl, alkylsulfonylamino or arylsulfonylamino group; $X^{1d}$ represents —C(O)—, —CH(OH)— or —$CH_2$—; and $Z^d$ represents —$(CH_2)_n{}^d$— ($n^d$ represents 0, 1 or 2) or —CH=CH—; or salts thereof;

benzene derivatives represented by the following general formula:

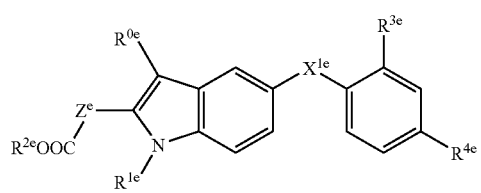

[e]

wherein $R^{0e}$ represents hydrogen atom, halogen atom, nitro group or unsubstituted or substituted alkyl, alkenyl, cycloalkyl, aryl, aralkyl, acyl, alkoxycarbonyl, aryloxycarbonyl, alkylsulfonylamino or arylsulfonylamino group; $R^{1e}$ represents unsubstituted or substituted alkyl, alkenyl, cycloalkyl, aryl, aralkyl, acyl, alkoxycarbonyl, aryloxycarbonyl or alkylsulfonyl group; $R^{2e}$ represents hydrogen atom or a protecting group for carboxyl group; $R^{3e}$ and $R^{4e}$ may be the same or different and independently represent hydrogen atom, halogen atom, unprotected or protected hydroxyl group, unprotected or protected amino group, mercapto group or unsubstituted or substituted alkyl, alkenyl, cycloalkyl, aryl, aralkyl, alkoxy, aryloxy, alkylthio, alkylamino, acylamino, alkylsulfonylamino, arylsulfonylamino or heterocyclic group; $X^{1e}$ represents —C(O)—, —CH(OH)— or —CH$_2$—; and $Z^e$ represents —(CH$_2$)$_{n^e}$— ($n^e$ represents 0, 1 or 2) or —CH=CH—; or salts thereof;

benzene derivatives represented by the following general formula:

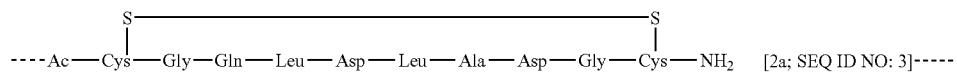

[f]

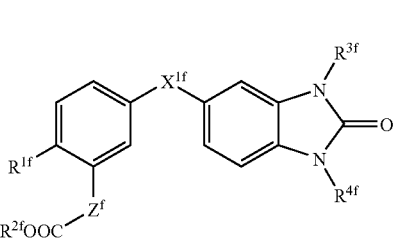

wherein $R^{1f}$ represents halogen atom, unprotected or protected hydroxyl group, unprotected or protected amino group, mercapto group or unsubstituted or substituted alkyl, alkenyl, cycloalkyl, aryl, aralkyl, alkoxy, aryloxy, alkylthio, alkylamino, acylamino, alkylsulfonylamino, arylsulfonylamino or heterocyclic group; $R^{2f}$ represents hydrogen atom or a protecting group for carboxyl group; $R^{3f}$ and $R^{4f}$ may be the same or different and independently represent hydrogen atom or unsubstituted or substituted alkyl, alkenyl, cycloalkyl, aryl or aralkyl group; $X^{1f}$ represents —C(O)—, —CH(OH)— or —CH$_2$—; and $Z^f$ represents —(CH$_2$)$_{n^f}$— ($n^f$ represents 1 or 2) or —CH=CH—; or salts thereof; and benzene derivatives represented by the following general formula:

[g]

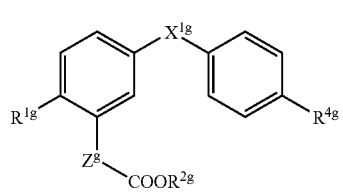

wherein $R^{1g}$ and $R^{4g}$ may be the same or different and independently represent unprotected or protected hydroxyl group or unsubstituted or substituted alkoxy group; $X^{1g}$ represents —C(O)—, —CH(OH)— or —CH$_2$—; $Z^g$ represents —(CH$_2$)$_{n^g}$— ($n^g$ represents 1 or 2); and $R^{2g}$ represents hydrogen atom or a protecting group for carboxyl group; or salts thereof;

and agents comprising the above-mentioned compounds.

Based on these findings, this invention has been accomplished.

First, the present inventors took out only the three-dimensional structure of transcription factor AP-1 from the three-dimensional structure of a partial structure containing the DNA binding site of AP-1 and its binding sequence (oligonucleotide containing 5'-TGAGTCA-3') (Nature, Vol. 373, Pages 257-261, 1995) by using the molecular modeling software "SYBYL" (TRIPOS Co., USA), and searched for a compound binding to AP-1 and antagonistic to the AP-1 binding sequence. As its result, it was found that a peptide of the following formula:

----Ac—Cys—Gly—Gln—Leu—Asp—Leu—Ala—Asp—Gly—Cys—NH$_2$   [2a; SEQ ID NO: 3]-----

(with a disulfide bond S—S between the two Cys residues)

can bind to with AP-1 and have an antagonistic activity to the AP-1 binding sequence.

Subsequently, a three-dimensional structure of a complex compound of peptide [2a; SEQ ID NO:3] and a partial structure containing the DNA binding site of AP-1 were prepared by the use of SYBYL, and a molecular dynamics simulation was carried out according to the molecular dynamics calculation program AMBER (Oxford Molecular Co., GB) (Fundamentals of Protein Engineering Physics and Chemistry, published by Kyoritsu Shuppan, Page 192, 1991) by using the three-dimensional structure obtained above as an initial structure to obtain a plurality of three-dimensional structures of AP-1-cyclic peptide [2a; SEQ ID NO:3] complex in water.

On the other hand, nuclear magnetic resonance (NMR) spectrum of peptide [2a; SEQ ID NO:3] was measured, and the result was treated according to a structural analysis software X-PLOR (MSI Co., USA) to obtain a plurality of three-dimensional structures of peptide [2a; SEQ ID NO:3] in water experimentally (Shinsei Kagaku Jikken Koza I, Proteins III, Pages 139-147, 1990, published by Tokyo Kagaku Dojin).

The experimentally obtained three-dimensional structures were compared with the three-dimensional structures of cyclic peptide [2a; SEQ ID NO:3] in the complex obtained from the molecular dynamics simulation. As a result, a high level of similarity was found out between eleven of the experimentally confirmed three-dimensional structures and fourteen of the three-dimensional structures obtained from molecular dynamics simulation in the partial three-dimensional structure of Gln-Leu-Asp-Leu-Ala [SEQ ID NO:4]. Based on this finding, it could be confirmed that the five atoms $N_1$, $N_2$, $N_3$, $N_4$ and $N_5$ expressed by the following formula:

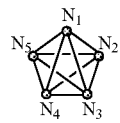

wherein $N_1$ represents an atom to which a donative hydrogen atom in a hydrogen-bond donating group is bonded or a hydrogen-bond accepting atom in a hydrogen-bond accepting group; $N_3$ represents a hydrogen-bond accepting atom in a hydrogen-bond accepting group; and $N_2$, $N_4$ and $N_5$ independently represent an arbitrary carbon atom constituting a hydrophobic group, constitute a pharmacophore necessary for the binding to AP-1 and the expression of an antagonistic activity to AP-1 binding sequence (Souyaku Kagaku, Kagaku Dojin, Pages 11-13, 1995).

Further, distances between five atoms $N_1$, $N_2$, $N_3$, $N_4$ and $N_5$, which are selected therefrom in these 25 three-dimensional structures, and which constitute the pharmacophore necessary for the binding to AP-1 and the expression of the antagonistic activity to AP-1 binding sequence were measured. As $N_1$, the nitrogen atom or oxygen atom of amide group was taken into consideration. As $N_2$, the four carbon atoms of isobutyl group were taken into consideration. As $N_3$, the two oxygen atoms of carboxyl group were taken into consideration. As $N_4$, the four carbon atoms of isobutyl group were taken into consideration. As $N_5$, the carbon atom of methyl group was taken into consideration. On all the possible combinations of the five atoms, distances were measured. As a result, it was found that the condition represented by the following formula:

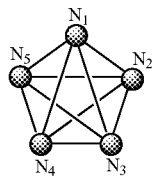

wherein $N_1$ represents an atom to which to a donative hydrogen atom in the hydrogen-bond donating group is bonded or a hydrogen-bond accepting atom in the hydrogen-bond accepting group, $N_3$ represents a hydrogen-bond accepting atom in the hydrogen-bond accepting group, and $N_2$, $N_4$ and $N_5$ independently represent an arbitrary carbon atom constituting a hydrophobic group, and the distance between $N_1$ and $N_2$ is not less than 5 angstroms and not more than 12 angstroms, the distance between $N_1$ and $N_3$ is not less than 9 angstroms and not more than 15 angstroms, the distance between $N_1$ and $N_4$ is not less than 3 angstroms and not more than 13 angstroms, the distance between $N_1$ and $N_5$ is not less than 8 angstroms and not more than 16 angstroms, the distance between $N_2$ and $N_3$ is not less than 3 angstroms and not more than 10 angstroms, the distance between $N_2$ and $N_4$ is not less than 6 angstroms and not more than 14 angstroms, the distance between $N_2$ and $N_5$ is not less than 9 angstroms and not more than 14 angstroms, the distance between $N_3$ and $N_4$ is not less than 4 angstroms and not more than 11 angstroms, the distance between $N_3$ and $N_5$ is not less than 3 angstroms and not more than 10 angstroms, and the distance between $N_4$ and $N_5$ is not less than 4 angstroms and not more than 9 angstroms are necessary for binding to AP-1 and expressing the antagonistic activity to AP-1 binding sequence. Based on these findings, the pharmacophore model was completed.

Further, compounds conforming to the above-mentioned pharmacophore model were extensively searched to find out non-peptide compounds which can bind to AP-1 and have the antagonistic activity to AP-1 binding sequence. It was found that compounds comprising the atom corresponding to $N_3$ and the two or more atoms selected from $N_1$, $N_2$, $N_4$ and $N_5$, said atoms constitute the pharmacophore represented by the following formula:

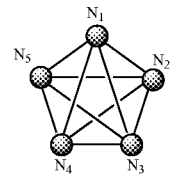

wherein $N_1$ represents an atom bonded to a donative hydrogen atom in the hydrogen-bond donating group or a hydrogen-bond accepting atom in the hydrogen-bond accepting group, $N_3$ represents a hydrogen-bond accepting atom in the hydrogen bond-accepting group, and $N_2$, $N_4$ and $N_5$ independently represent an arbitrary carbon atom constituting a hydrophobic group, and the distance between $N_1$ and $N_2$ is not less than 5 angstroms and not more than 12 angstroms, the distance between $N_1$ and $N_3$ is not less than 9 angstroms and not more than 15 angstroms, the distance between $N_1$ and $N_4$ is not less than 3 angstroms and not more than 13 angstroms, the distance between $N_1$ and $N_5$ is not less than 8 angstroms and not more than 16 angstroms, the distance between $N_2$ and $N_3$ is not less than 3 angstroms and not more than 10 angstroms, the distance between $N_2$ and $N_4$ is not less than 6 angstroms and not more than 14 angstroms, the distance between $N_2$ and $N_5$ is not less than 9 angstroms and not more than 14 angstroms, the distance between $N_3$ and $N_4$ is not less than 4 angstroms and not more than 11 angstroms, the distance between $N_3$ and $N_5$ is not less than 3 angstroms and not more than 10 angstroms, and the distance between $N_4$ and $N_5$ is not less than 4 angstroms and not more than 9 angstroms, and in the optimized three-dimensional structure thereof, the distances between the atom corresponding to $N_3$ and the two or more atoms selected from $N_1$, $N_2$, $N_4$ and $N_5$ are the interatomic distances in the pharmacophore; or salts thereof inhibit the activity of transcription factor AP-1 and are useful as an agent for preventing and treating the diseases into which overexpression of AP-1 participates.

The compounds of this invention inhibit the binding activity of transcription factor AP-1. That is, the compounds of this invention antagonistically inhibit the bind of AP-1 to the AP-1-recognizing sequence on DNA, and thereby suppress the transcription of AP-1-related DNA, and thereby can reduce the expression of protein corresponding to said genes having AP-1 binding sequence. Accordingly, the compounds of this invention can suppress the expression of gene in tissue-destroying enzymes such as collagenase, stromelysin, gelatinases and the like; cytokines such as interleukin-1, interleukin-2, interleukin-3, interleukin-6, interleukin-8, TNFα, granulocyte-macrophage colony stimulating factor (GM-CSF), monocyte chemotactic factor (MCP-1) and the like; cell surface molecule groups such as interleukin-2 receptor, immunoglobulins, major histocompatibility complex (MHC) class II, vascular cell adhesion molecule-1 (VCAM-1), fibroblast growth factor (FGF) receptors and the like; growth factors such as monocyte growth factor, insulin-like growth factor (IGF), nervous growth factor (NGF) and the like; proteins such as metallothionein, collagens, osteocalcin, amyloid precursor proteins, apolipoprotein-1 and the like; and viruses such as SV40, polyoma virus and the like, and thereby can prevent and treat the diseases related with these genes. As the diseases to which these genes relate, for instance, various autoimmune diseases such as rheumatoid arthritis, systemic erythematosus, scleroderma, Behchet's disease, rheumatic fever, polymyositis, polyarteritis nodosa, Sjoegren's syndrome, active chronic hepatitis, glomerulonephritis and the like; various intractable diseases basically with inflammations such as osteoarthritis, gout, atherosclerosis, psoriasis, atopic dermatitis, lung diseases with granuloma, various encephalitis, and the like; lung diseases with granuloma such as pneumonitis; endotoxin shock; sepsis; inflammatory colitis; diabetes mellitus; acute myeloblastic leukemia; encephalomyelitis; acute hepatitis; chronic hepatitis; drug-induced hepatitis; alcoholic hepatitis; viral hepatitis; jaundice; cirrhosis; liver failure; atrial myxoma; Castleman's syndrome; multiple myeloma; cancer; metastases of cancer; AIDS; epilepsy; ischemic heart disease; hemangioendothelial hyperplasia (arteriosclerosis); Alzheimer's disease; ischemia-nerve cell death; etc. The compounds of this invention are expected to be effective for prevention and treatment of these diseases.

The compounds of this invention will be detailed below.

Unless otherwise defined, the term "halogen atom" used in this specification means fluorine atom, chlorine atom, bromine atom and iodine atom; "alkyl group" means straight or branched chain $C_{1-12}$ alkyl groups such as methyl, ethyl, n-propyl, isopropyl, n-butyl, sec-butyl, isobutyl, tert-butyl, pentyl, isopentyl, hexyl, heptyl, octyl and the like; "lower alkyl group" means straight or branched chain $C_{1-6}$ alkyl groups such as methyl, ethyl, n-propyl, isopropyl, n-butyl, sec-butyl, isobutyl, tert-butyl, pentyl, isopentyl and the like; "halogeno lower alkyl group" means straight or branched chain halogeno-$C_{1-6}$ alkyl groups such as fluoromethyl, chloromethyl, bromomethyl, dichloromethyl, trifluoromethyl, trichloromethyl, chloroethyl, dichloroethyl, trichloroethyl, chloropropyl and the like; "lower alkoxy lower alkyl group" means straight or branched chain $C_{1-6}$ alkoxy-$C_{1-6}$ alkyl groups such as methoxymethyl, ethoxymethyl, n-propoxymethyl, methoxyethyl, ethoxyethyl and the like; "hydroxy lower alkyl group" means straight or branched chain hydroxy-$C_{1-6}$ alkyl groups such as hydroxymethyl, hydroxyethyl, hydroxypropyl and the like; "amino lower alkyl group" means amino-$C_{1-6}$ alkyl groups such as aminomethyl, aminoethyl, aminopropyl and the like;

"alkenyl group" means straight or branched chain $C_{2-12}$ alkenyl groups such as vinyl, allyl, propenyl, isopropenyl, butenyl, isobutenyl, pentenyl, hexenyl, heptenyl, octenyl and the like; "lower alkenyl group" means straight or branched chain $C_{2-6}$ alkenyl groups such as vinyl, allyl, propenyl, isopropenyl, butenyl, isobutenyl, pentenyl and the like; "cycloalkyl group" means $C_{3-6}$ cycloalkyl groups such as cyclopropyl, cyclobutyl, cyclopentyl, cyclohexyl and the like; "ar-lower alkyl group" means ar-$C_{1-6}$ alkyl groups such as benzyl, diphenylmethyl, trityl, phenethyl and the like;

"aryl group" means phenyl, tolyl, naphthyl and the like; "aralkyl group" means benzyl, diphenylmethyl, trityl, phenethyl, 4-methylbenzyl, naphthylmethyl and the like; "aryloxy group" means phenoxy, naphthoxy and the like; "aryloxycarbonyl group" means phenoxycarbonyl, naphthoxycarbonyl and the like;

"alkoxy group" means straight or branched chain $C_{1-12}$ alkoxy groups such as methoxy, ethoxy, n-propoxy, isopropoxy, n-butoxy, isobutoxy, sec-butoxy, tert-butoxy, pentyloxy, isopentyloxy, hexyloxy, heptyloxy, octyloxy and the like; "lower alkoxy group" means straight or branched chain $C_{1-6}$ alkoxy groups such as methoxy, ethoxy, n-propoxy, isopropoxy, n-butoxy, isobutoxy, sec-butoxy, tert-butyoxy, pentyloxy, isopentyloxy and the like; "alkoxycarbonyl group" means straight or branched chain $C_{1-12}$ alkoxycarbonyl groups such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, pentyloxycarbonyl and the like; "lower alkoxycarbonyl group" means straight or branched chain $C_{1-6}$ alkyloxycarbonyl groups such as methoxycarbonyl, ethoxycarbonyl, propoxycarbonyl and the like;

"lower alkoxycarbonyl lower alkyl group" means straight or branched chain $C_{1-6}$ alkoxycarbonyl-$C_{1-6}$ alkyl groups such as methoxycarbonylmethyl, ethoxycarbonylmethyl, n-propoxycarbonylmethyl, methoxycarbonylethyl, ethoxycarbonylethyl and the like; "lower alkoxyimino group" means straight or branched chain $C_{1-6}$ alkoxyimino groups such as methoxyimino, ethoxyimino and the like; "alkylamino group" means straight or branched chain $C_{1-12}$ alkylamino groups such as methylamino, ethylamino, propylamino, butylamino, pentylamino, hexylamino, heptylamino, octylamino and the like; "lower alkylamino group" means straight or branched chain mono- or di-$C_{1-6}$ alkylamino groups such as methylamino, ethylamino, propylamino, dimethylamino, diethylamino, methylethylamino and the like; "lower alkylamino lower alkyl group" means mono- or di-$C_{1-6}$ alkylamino-$C_{1-6}$ alkyl groups such as methylaminomethyl, methylaminoethyl, ethylaminomethyl, methylaminopropyl, propylaminoethyl, dimethylaminomethyl, diethylamino-methyl, diethylaminoethyl, dimethylaminopropyl and the like; "lower alkylidene group" means $C_{1-6}$ alkylidene groups such as methylene, ethylidene, propylidene, isopropylidene and the like;

"acyl group" inclusively means straight or branched chain $C_{2-12}$ alkanoyl groups such as formyl, acetyl, isovaleryl, propionyl and the like, aralkylcarbonyl groups such as benzylcarbonyl and the like, aroyl groups such as benzoyl, naphthoyl and the like, and heterocycle-carbonyl groups such as nicotinoyl, thenoyl, pyrrolidinocarbonyl, furoylcarbonyl and the like; "acylamino group" means $C_{1-6}$ acylamino groups such as formylamino, acetylamino, propionylamino, butyrylamino and the like; "alkanoyloxy group" means $C_{2-12}$ alkanoyloxy groups such as acetyloxy, propionyloxy and the like;

"cyclic amino group" may be any of saturated cyclic amino groups and unsaturated cyclic amino groups, and may contain one or more hetero atoms such as nitrogen atoms, oxygen atoms, sulfur atoms and the like and carbonyl carbon atoms additionally in the ring thereof, and may be any of monocyclic, bicyclic and tricyclic groups, which more specifically include saturated or unsaturated, monocyclic, 3- to 7-membered cyclic amino groups having one nitrogen atom such as aziridin-1-yl, azetidin-1-yl, pyrrolidin-1-yl, pyrrolin-1-yl, pyrrol-1-yl, dihydropyridin-1-yl, piperidino, dihydroazepin-1-yl, perhydroazepin-1-yl and the like; saturated or unsaturated, monocyclic, 3- to 7-membered cyclic amino groups having 2 nitrogen atoms such as imidazol-1-yl, imidazolidin-1-yl, imidazolin-1-yl, pyrazolidin-1-yl, piperazin-1-yl, 1,4-dihydropyrazin-1-yl, 1,2-dihydropyrimidin-1-yl, perhydropyrazin-1-yl, homopiperazin-1-yl and the like; saturated or unsaturated, monocyclic, 3- to 7-membered cyclic amino groups having 3 or more nitrogen atoms such as 1,2,4-triazol-1-yl, 1,2,3-triazol-1-yl, 1,2-dihydro-1,2,4-triazin-1-yl, perhydro-s-triazin-1-yl and the like; saturated or unsaturated, monocyclic, 3- to 7-membered cyclic amino groups having 1 to 4 hetero atoms selected from the group consisting of oxygen atom and sulfur atom in addition to nitrogen atoms such as oxazolidin-3-yl, isoxazolidin-2-yl, morpholino, thiazolidin-3-yl, isothiazolidin-2-yl, thiomorpholino, homothiomorpholin-4-yl, 1,2,4-thiadiazolin-2-yl and the like; saturated or unsaturated, 2- or 3-membered cyclic amino groups such as isoindolin-2-yl, indolin-1-yl, 1H-indazol-1-yl, purin-7-yl, tetrahydroquinolin-1-yl and the like; and spiro type or crosslinked type of saturated or unsaturated, 5- to 12-membered cyclic amino groups such as 5-azaspiro[2.4]heptan-5-yl, 2,8-diazabicyclo[4.3.0]nonan-8-yl, 3-azabicyclo[3.1.0]-hexan-3-yl, 2-oxa-5,8-diazabicyclo[4.3.0]nonan-8-yl, 2,8-diazaspiro[4.4]nonan-2-yl, 7-azabicyclo[2.2.1]heptan-7-yl and the like;

"alkylthio group" means straight or branched chain $C_{1-12}$ alkylthio groups such as methylthio, ethylthio, n-propylthio, isopropylthio, n-butylthio, isobutylthio, sec-butylthio, tert-butylthio, pentylthio, isopentylthio, hexylthio, heptylthio, octylthio and the like; "lower alkylthio group" means straight or branched chain $C_{1-6}$ alkylthio groups such as methylthio, ethylthio, n-propylthio, isopropylthio, n-butylthio, isobutylthio, sec-butylthio, tert-butylthio, pentylthio, isopentylthio and the like; "alkylsulfinyl group" means straight or branched chain $C_{1-12}$ alkylsulfinyl groups such as methylsulfinyl, ethylsulfinyl, n-propylsulfinyl, isopropylsulfinyl, n-butylsulfinyl, isobutylsulfinyl, sec-butylsulfinyl, tert-butylsulfinyl, pentylsulfinyl, isopentylsulfinyl, hexylsulfinyl, heptylsulfinyl, octylsulfinyl and the like; "alkylsulfonyl group" means straight or branched chain $C_{1-12}$ alkylsulfonyl groups such as methylsulfonyl, ethylsulfonyl, n-propylsulfonyl, isopropylsulfonyl, n-butylsulfonyl, isobutylsulfonyl, sec-butylsulfonyl, tert-butylsulfonyl, pentylsulfonyl, isopentylsulfonyl, hexylsulfonyl, heptylsulfonyl, octylsulfonyl and the like; "alkylsulfonylamino group" means straight or branched chain $C_{1-12}$ alkylsulfonylamino groups such as methylsulfonylamino, ethylsulfonylamino, n-propylsulfonylamino, isopropylsulfonylamino, n-butylsulfonylamino, isobutylsulfonylamino, sec-butylsulfonylamino, tert-butylsulfonylamino, pentylsulfonylamino, isopentylsulfonylamino, hexylsulfonylamino, heptylsulfonylamino, octylsulfonylamino and the like; "arylsulfonylamino group" means aryl-$SO_2NH$— groups such as phenylsulfonylamino, naphthylsulfonylamino and the like; and "heterocycle-lower alkyl group" means heterocycle-$CH_2$— group and the like such as pyrrolidinylmethyl, piperidylmethyl, piperazinylmethyl, pyrazolylmethyl, tetrahydropyridylmethyl, morpholinylmethyl, thiomorpholinylmethyl, tetrahydro-quinolinylmethyl, tetrahydroisoquinolinylmethyl, quinacridinylmethyl, tetrazolylmethyl, thiadiazolylmethyl, pyrazolidinylmethyl, purinylmethyl, indazolylmethyl, 2-thienylmethyl, 2-furfurylmethyl, 2-pyranylmethyl, 1-isobenzofurylmethyl, 2-pyrrolylmethyl, 2-imidazolylmethyl, 1-pyrazolylmethyl, 3-isothiazolylmethyl, 3-isoxazolylmethyl, 2-pyridylmethyl, 2-pyrazinylmethyl, 2-pyrimidinylmethyl, 2-pyridazinylmethyl, 1-isoindolylmethyl, 2-indolylmethyl, 1-isoquinolylmethyl, 2-quinolylmethyl, 1-phthalazinylmethyl, 2-naphthyridinylmethyl, 2-quinoxalinylmethyl, 2-quinazolinylmethyl, 3-cinnolinylmethyl, 2-oxazolylmethyl, 2-thiazolylmethyl, 2-benzo[b]furylmethyl, 2-benzo[b]thienylmethyl, 2-benz[d]imidazolylmethyl, 2-benz[d]oxazolylmethyl and the like.

"Nitrogen-containing heterocyclic group" means 5- or 6-membered ring, fused ring or crosslinked ring type heterocyclic groups which contain at least one nitrogen atoms as hetero atoms constituting the ring and may contain at least one oxygen atom or sulfur atom in addition to said nitrogen atoms, such as pyrrolyl, pyrrolidinyl, piperidyl, piperazinyl, imidazolyl, pyrazolyl, pyridyl, tetrahydropyridyl, pyrimidinyl, morpholinyl, thiomorpholinyl, quinolyl, quinolizinyl, tetrahydroquinolinyl, tetrahydro-isoquinolinyl, quinacridinyl, thiazolyl, tetrazolyl, thiadiazolyl, pyrrolinyl, imidazolinyl, imidazolidinyl, pyrazolinyl, pyrazolidinyl, purinyl, indazolyl and the like; and "heterocyclic group" inclusively means the above-mentioned nitrogen-containing heterocyclic groups and 5- or 6-membered ring, fused ring or crosslinked ring type heterocyclic groups which may contain at least one oxygen atoms or sulfur atoms as hetero atoms constituting the ring and contain at least one hetero atom selected from the group consisting of nitrogen, oxygen and sulfur atoms, such as furyl, thienyl, benzothienyl, pyranyl, isobenzofuranyl, oxazolyl, benzofuranyl, indolyl, benzimidazolyl, benzoxazolyl, benzothiazolyl, quinoxalyl, dihydroquinoxalinyl, 2,3-dihydrobenzothienyl, 2,3-dihydrobenzopyrrolyl, 2,3-dihydro-4H-1-thianaphthyl, 2,3-dihydrobenzofuranyl, benzo[b]dioxanyl, imidazo[2.3-a]pyridyl, benzo[b]piperazinyl, chromenyl, isothiazolyl, isoxazolyl, thiadiazolyl, oxadiazolyl, pyridazinyl, isoindolyl, isoquinolyl and the like.

As the protecting group for carboxyl group, all the groups which can conventionally be used as a protecting group for carboxyl group can be referred to. Examples thereof include alkyl groups such as methyl, ethyl, n-propyl, iso-propyl, 1,1-dimethylpropyl, n-butyl, tert-butyl and the like; aryl groups such as phenyl, naphthyl and the like; aralkyl groups such as benzyl, diphenylmethyl, trityl, p-nitrobenzyl, p-methoxybenzyl, bis(p-methoxyphenyl)methyl and the like; acyl-alkyl groups such as acetylmethyl, benzoylmethyl, p-nitrobenzoylmethyl, p-bromobenzoylmethyl, p-methanesulfonylbenzoylmethyl and the like; oxygen-containing heterocyclic groups such as 2-tetrahydropyranyl, 2-tetrahydrofuranyl and the like; halogeno-alkyl groups such as 2,2,2-trichloroethyl and the like; alkylsilylalkyl groups such as 2-(trimethylsilyl)ethyl and the like; acyloxyalkyl groups such as acetoxymethyl, propionyloxymethyl, pivaloyloxymethyl and the like; nitrogen-containing heterocycle-alkyl groups such as phthalimidomethyl, succinimidomethyl and the like; cycloalkyl groups such as cyclohexyl and the like; alkoxy-alkyl groups such as methoxymethyl, methoxyethoxymethyl, 2-(trimethylsilyl)-ethoxymethyl and the like; ar-alkoxy-alkyl groups such as benzyloxymethyl and the like; alkylthio-alkyl groups such as methylthiomethyl, 2-methylthioethyl and the like; arylthioalkyl groups such as phenylthiomethyl and the like; alkenyl groups such as 1,1-dimethyl-2-propenyl, 3-methyl-3-butenyl, allyl and the like; and substituted silyl groups such as trimethylsilyl, triethylsilyl, triisopropylsilyl, diethyliso-propylsilyl, tert-butyldimethylsilyl, tert-butyldiphenylsilyl, diphenylmethylsilyl, tert-butylmethoxyphenylsilyl and the like.

As the protecting group for amino group, all the groups which can conventionally be used as a protecting group for amino group can be referred to. Examples thereof include acyl groups such as trichloroethoxycarbonyl, tribromoethoxycarbonyl, benzyloxycarbonyl, p-nitrobenzyloxycarbonyl, o-bromobenzyloxycarbonyl, (mono-, di- and tri-)chloroacetyl, trifluoroacetyl, phenylacetyl, formyl, acetyl, benzoyl, tert-amyloxycarbonyl, tert-butoxycarbonyl, p-methoxybenzyloxycarbonyl, 3,4-dimethoxybenzyloxycarbonyl, 4-(phenylazo)-benzyloxycarbonyl, 2-furfuryloxycarbonyl, diphenylmethoxycarbonyl, 1,1-dimethylpropoxycarbonyl, isopropoxycarbonyl, phthaloyl, succinyl, alanyl, leucyl, 1-adamantyloxycarbonyl, 8-quinolyloxycarbonyl and the like; aralkyl groups such as benzyl, diphenylmethyl, trityl and the like; arylthio groups such as 2-nitrophenylthio, 2,4-dinitrophenylthio and the like; alkyl- or aryl-sulfonyl groups such as methanesulfonyl, p-toluenesulfonyl and the like; dialkylamino-alkylidene groups such as N,N-dimethylaminomethylene and the like; aralkylidene groups such as benzylidene, 2-hydroxybenzylidene, 2-hydroxy-5-chlorobenzylidene, 2-hydroxy-1-naphthylmethylene and the like; nitrogen-containing heterocyclic alkylidene groups such as 3-hydroxy-4-pyridylmethylene and the like; cycloalkylidene groups such as cyclohexylidene, 2-ethoxycarbonylcyclo-hexylidene, 2-ethoxycarbonylcyclopentylidene, 2-acetylcyclohexylidene, 3,3-dimethyl-5-oxycyclohexylidene and the like; diaryl- or dialkyl-phosphoryl groups such as diphenylphosphoryl, dibenzylphosphoryl and the like; oxygen-containing heterocyclic alkyl groups such as 5-methyl-2-oxo-2H-1,3-dioxol-4-yl-methyl and the like; and substituted silyl groups such as trimethylsilyl and the like.

As protecting group for hydroxyl group, all the groups which can conventionally be used as a protecting group for hydroxyl group can be referred to. Examples thereof include acyl groups such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)-ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl and the like; alkyl groups such as methyl, tert-butyl, 2,2,2-trichloroethyl, 2-trimethylsilylethyl and the like; alkenyl groups such as allyl and the like; aralkyl groups such as benzyl, p-methoxybenzyl, 3,4-dimethoxybenzyl, diphenylmethyl, trityl and the like; oxygen-containing and sulfur-containing heterocyclic groups such as tetrahydrofuryl, tetrahydropyranyl, tetrahydrothiopyranyl and the like; alkoxyalkyl groups such as methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl and the like; alkyl- and aryl-sulfonyl groups such as methanesulfonyl, p-toluenesulfonyl and the like; and substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like.

The term "amino acid residue" means a structure —NH-CHRCO— which appears when an amino acid is incorporated into a protein or peptide while forming a peptide bond with loss of a water molecule, wherein R represents an amino acid side chain. As used herein, the term "amino acid" means an L-amino acid and a D-amino acid, namely compounds having carboxyl group and amino group in one molecule, unless otherwise defined. Examples of said amino acid include glycine, alanine, valine, leucine, isoleucine, serine, threonine, asparagine, aspartic acid, glutamine, glutamic acid, lysine, arginine, histidine, methionine, tyrosine, phenylalanine, tryptophan, proline, cysteine, homocysteine, β-alanine, γ-aminobutyric acid, ornithine, 3,4-dihydroxyphenylalanine and the like. For expression of amino acids and amino acid residues, the three letters expression prescribed by IUPAC and IUB is used.

The term "polar amino acid", means amino acids such as asparagine, glutamine, aspartic acid, glutamic acid, serine, threonine, tyrosine, lysine, arginine, histidine, citrulline, homocitrulline, homoserine, hydroxyproline, β-hydroxyvaline, ornithine and the like, for example.

The term "hydrophobic amino acid" means amino acids such as leucine, isoleucine, valine, alanine, glycine, methionine, proline, phenylalanine, tryptophan, norleucine, norvaline, γ-aminobutyric acid, β-cyclohexylalanine and the like, for example.

As the salt of compound in the compound conforming to the pharmacophore of formula 1, the compounds of general formulas [2], [2b], [3], [4], [5], [a], [b], [c], [d], [e], [f] and [g] or salts thereof, conventionally known salts at the site of basic group such as amino group and the like and conventionally known salts at the site of acidic group such as hydroxyl group, carboxyl group and the like can be referred to. As the salts at the site of basic group, for example, salts of mineral acids such as hydrochloric acid, hydrobromic acid, sulfuric acid and the like, salts of organic carboxylic acids such as tartaric acid, formic acid, citric acid, trichloroacetic acid, trifluoroacetic acid and the like, and salts of sulfonic acids such as methanesulfonic acid, benzenesulfonic acid, p-toluenesulfonic acid, mesitylenesulfonic acid, naphthalenesulfonic acid and the like can be referred to. As the salts at the site of acidic group, for example, salts of alkali metals such as sodium, potassium and the like, salts of alkaline earth metals such as calcium, magnesium and the like, ammonium salts, and salts of nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, N,N'-dibenzylethylenediamine and the like can be referred to. Further, among the salts mentioned above, preferable salts of the compound conforming to the pharmacophore of formula 1 and the compounds of formulas [2], [2b], [3], [4], [5], [a], [b], [c], [d], [e], [f] and [g], pharmacologically acceptable ones can be referred to.

As the "atom to which a donative hydrogen atom in the hydrogen-bond donating group is bonded", the nitrogen atom of unsubstituted or substituted amino, ammonium, amido, thioamido, ureido, isoureido, amidino, guanidino, thioureido, hydrazino or hydrazono group to which one or more hydrogen atoms are bonded, the carbon atom of ethenyl group to which a hydrogen atom is bonded, the nitrogen atom of imino group to which a hydrogen atom is bonded, the oxygen atom of hydroxyl group, the nitrogen atom to which the hydrogen atom of an unsubstituted or substituted nitrogen-containing heterocyclic group is bonded, and the like can be referred to.

The "hydrogen-bond accepting atom in hydrogen-bond accepting group" may be any atom, so far as it has an unshared electron pair. Examples thereof include the oxygen atom of carbonyl group, the sulfur atom of thiocarbonyl group, the nitrogen atom of unsubstituted or substituted imino group, the oxygen atom of sulfonic group, the oxygen atom of sulfonyl group, the oxygen atom of sulfinyl group, the oxygen atom of sulfonyloxy group, the oxygen atom of carboxyl group, the oxygen atom of ether, the sulfur atom of thioether, the oxygen atom of hydroxyl group, the oxygen atom of ester, the nitrogen atom to which no hydrogen atom is bonded in an unsubstituted or substituted nitrogen-containing heterocyclic group, the nitrogen atom of sulfonamido group, the nitrogen atom of acylsulfonamido group, etc.

As the "arbitrary carbon atom constituting a hydrophobic group", the carbon atom of alkyl group, the carbon atom of alkenyl group, the carbon atom of aryl group, the carbon atom of alkoxy group and the like can be referred to, and preferably the carbon atom of branched chain-like alkyl group, the carbon atom of alkenyl group and the carbon atom of alkoxy group can be referred to.

The term "optimized structure" means the energy-minimized structure obtained by a usual geometry optimization calculation (Keisan kagaku Njumon, Kodansha, Page 55, 1994) according to a calculation program such as SYBYL (TRIPOS, USA) or the like.

The alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonyl-amino, arylsulfonylamino or heterocyclic group in $R^1$, $R^{1a}$, $R^{1b}$, $R^{1c}$, rd, $R^{3a}$, $R^{3b}$, $R^4$, $R^{4a}$, $R^{4b}$, $R^5$, $R^7$, $R^8$, $R^9$, $R^{10}$, $R^{15}$, $R^{16}$, $R^{24}$, $R^{24a}$, $R^{25}$ and $R^{25a}$; the alkyl, alkenyl, cycloalkyl, aryl, aralkyl, alkoxy, aryloxy, alkylthio, alkylamino, acylamino, alkylsulfonylamino, arylsulfonylamino or heterocyclic group in $R^{1f}$, $R^{3e}$ and $R^{4e}$; the alkyl, alkenyl, cycloalkyl, aryl, aralkyl, acyl, alkoxycarbonyl, aryloxycarbonyl, alkylsulfonyl-amino or arylsulfonylamino group in $R^{0e}$; the alkyl, alkenyl, cycloalkyl, aryl, aralkyl, acyl, alkoxycarbonyl, aryloxycarbonyl or alkylsulfonyl group in $R^{1e}$ the alkoxy group in $R^{1g}$ and $R^{4g}$; the alkyl, alkenyl, cycloalkyl, aryl, aralkyl, alkoxy, aryloxy, acyl, alkoxycarbonyl, aryloxycarbonyl, alkylthio, alkylsulfinyl, alkylsulfonyl, alkylamino, acylamino, alkylsulfonylamino, arylsulfonylamino or heterocyclic group in $R^3$; the alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group in $R^{3c}$ and $R^{4c}$; the alkyl, alkenyl, cycloalkyl, aryl or aralkyl group in $R^{3d}$, $R^{3f}$ and $R^{4f}$; the alkyl, alkenyl, cycloalkyl, aryl, aralkyl, acyl, alkoxycarbonyl, aryloxycarbonyl, alkylsulfonyl, alkylsulfonylamino or arylsulfonylamino group in $R^{4d}$; the alkyl, alkenyl, cycloalkyl, aryl, aralkyl, acyl, alkoxycarbonyl, aryloxycarbonyl, carbamoyl, alkylsulfonyl or heterocyclic group in $R^{17}$; the alkyl, alkenyl, cycloalkyl, aryl, aralkyl, acyl or heterocycle-lower alkyl group in $R^{21}$ and $R^{21a}$; the alkyl, aralkyl or heterocycle-lower alkyl group in $R^{21a'}$; the alkyl, alkenyl, cycloalkyl, aryl, aralkyl, acyl, carbamoyl, alkylsulfinyl, alkylsulfonyl, arylsulfonyl or heterocyclic group in $R^{22}$, $R^{22a}$, $R^{23}$ and $R^{23a}$; the alkyl, alkoxycarbonyl, aryloxycarbonyl or carbamoyl group in $R^{24a'}$ and $R^{25a'}$; the alkyl, alkenyl, cycloalkyl, aryl or aralkyl group in $R^{27}$, $R^{27a}$, $R^{28}$ and $R^{28a}$; and the alkyl group in $R^{28'}$ and $R^{28a'}$ may additionally be substituted with at least one groups selected from the following substituents:

substituents: cyano group, nitro group, unprotected or protected carboxyl group, unprotected or protected hydroxyl group, unprotected or protected amino group, lower alkyl group, lower alkoxy group, lower alkoxycarbonyl group, acyl group, aryl group, cycloalkyl group, lower alkenyl group, aralkyl group, lower alkylidene group, mercapto group, lower alkylthio group, halogeno-lower alkyl group, lower alkoxy-lower alkyl group, unprotected or protected hydroxy-lower alkyl group, unprotected or protected amino-lower alkyl group, lower alkoxycarbonyl-lower alkyl group, unprotected or protected cyclic amino group, unprotected or protected lower alkylamino group, lower alkoxyimino group, and unprotected or protected lower alkylamino-lower alkyl group.

Among the compounds conforming to the pharmacophore of formula 1 of this invention, preferred are compounds conforming to a pharmacophore in which the distances between the atoms constituting the pharmacophore are as follows, namely the distance between $N_1$ and $N_2$ is not less than 5.09 angstroms and not more than 11.67 angstroms, the distance between $N_1$ and $N_3$ is not less than 9.47 angstroms and not more than 14.30 angstroms, the distance between $N_1$ and $N_4$ is not less than 3.48 angstroms and not more than 12.60 angstroms, the distance between $N_1$ and $N_5$ is not less than 8.77 angstroms and not more than 15.67 angstroms, the distance between $N_2$ and $N_3$ is not less than 3.78 angstroms and not more than 9.78 angstroms, the distance between $N_2$ and $N_4$ is not less than 6.97 angstroms and not more than 13.26 angstroms, the distance between $N_2$ and $N_5$ is not less than 9.37 angstroms and not more than 13.32 angstroms, the distance between $N_3$ and $N_4$ is not less than 4.83 angstroms and not more than 10.51 angstroms, the distance between $N_3$ and $N_5$ is not less than 3.31 angstroms and not more than 9,97 angstroms, and the distance between $N_4$ and $N_5$ is not less than 4.32 angstroms and not more than 8.25 angstroms, and more preferred are compounds conforming to a pharmacophore in which $N_1$ constituting the pharmacophore is a nitrogen atom of unsubstituted or substituted amino, ammonium, amido, thioamido, ureido, isoureido, amidino, guanidino, thioureido, hydrazino or hydrazono group to which one or more hydrogen atoms are bonded, a carbon atom of ethenyl group to which a hydrogen atom is bonded, an oxygen atom of carbonyl group, a sulfur atom of thiocarbonyl group, a nitrogen atom of unsubstituted or substituted imino group, an oxygen atom of sulfonyl group, an oxygen atom of sulfonyloxy group, an oxygen atom of sulfonic group, an oxygen atom of sulfinyl group, an oxygen atom of carboxyl group, an oxygen atom of ether, a sulfur atom of thioether, a sulfur atom of mercapto group, an oxygen atom of hydroxyl group, an oxygen atom of ester, or a nitrogen atom of unsubstituted or substituted nitrogen-containing heterocyclic group; $N_3$ is an oxygen atom of carbonyl group, a sulfur atom of thiocarbonyl group, a nitrogen atom of imino group, an oxygen atom of sulfo group, an oxygen atom of sulfonyl group, an oxygen atom of sulfinyl group, an oxygen atom of sulfonyloxy group, an oxygen atom of carboxyl group, an oxygen atom of ether, a sulfur atom of thioether, an oxygen atom of hydroxyl group, an oxygen atom of ester, a nitrogen atom of unsubstituted or substituted nitrogen-containing heterocyclic group to which no hydrogen atom is bonded, a nitrogen atom of sulfonamido group or a nitrogen atom of acylsulfonamido group; and each of $N_2$, $N_4$ and $N_5$ is arbitrary carbon atom constituting a carbon atom of alkyl group, a carbon atom of alkenyl group, a carbon atom of aryl group and a carbon atom of alkoxy group; and further preferred are compounds having an activity on the binding reaction between AP-1 and its recognition sequence.

Among the compounds of general formula [2] of this invention, preferred are those in which $AA^3$ is L-asparagine residue or L-glutamine residue; $AA^4$, $AA^6$ and $AA^7$ are L-leucine residue, L-isoleucine residue, L-alanine residue or L-valine residue; and $AA^5$ is L-aspartic acid residue, L-glutamic acid residue, L-serine residue or L-threonine residue.

Among the compounds of general formula [2b] of this invention, preferred are those in which $aa^3$ is L-asparagine residue or L-glutamine residue; $aa^4$, $aa^5$ and $aa^7$ are L-leucine residue, L-isoleucine residue, L-alanine residue or L-valine residue; and $aa^9$ is L-aspartic acid residue, L-glutamic acid residue, L-serine residue or L-threonine residue.

Among the compounds of general formula [3] of this invention, preferred are those in which W is —Z'—COOR²—, —Z'—CONH—SO₂R²⁸'—, —CONH—CH₂COOR²'— or —CONH—CH₂CH₂COOR²' (in these formulas, Z' represents —(CH₂)ₙ'— in which n' is 0, 1 or 2 or —CH=CH—, $R^{28'}$ represents unsubstituted or substituted alkyl group, $R^{2'}$ represents hydrogen atom or a protecting group for carboxyl group, and $X^1$ represents —C(O)—, —CH(OH)— or —CH₂—; more preferred are those in which $R^1$ is unprotected or protected hydroxyl group or unsubstituted or substituted alkoxy group, $R^3$ is unprotected or protected hydroxyl group or unsubstituted or substituted alkoxy group, and $R^4$ is unprotected or protected hydroxyl group or unsubstituted or substituted alkoxy group; further preferred are those in which $R^3$ is alkoxy group, hydroxyl group or alkylcarbonyloxy group, and $X^1$ is —C(O)—; and yet further preferred are those in which $R^1$ is alkoxy group and $R^4$ is alkoxy group.

Among the compounds of general formula [4] of this invention, preferred are those in which $R^5$ is alkoxy group or acylamino group, and ring A is a group represented by the following formula:

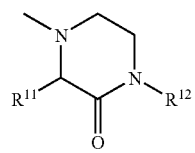

wherein $R^{11}$ is alkyl or alkoxycarbonyl group and $R^{12}$ is alkyl group, or a group represented by the following formula:

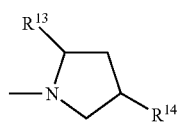

wherein $R^{13}$ is alkyl or alkoxycarbonyl group and $R^{14}$ is alkoxy or alkanoyloxy group.

Among the compounds of general formula [5] of this invention, preferred are those in which $R^{15}$ and $R^{16}$ are the same or different and represent alkoxy group, and ring B represents the following formula:

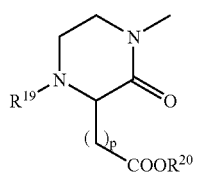

wherein $R^{19}$ represents acyl group, and $R^{20}$ represents a protecting group for carboxyl group and p represents 0, 1 or 2.

Among the compounds of general formula [a] of this invention, preferred are those in which $R^{1a}$ is unprotected or protected hydroxyl group or unsubstituted or substituted alkoxy group, $R^{3a}$ and $R^{4a}$ are the same or different and represent unprotected or protected hydroxyl group or unsubstituted or substituted alkoxy group, $X^{1a}$ represents —C(O)—, —CH(OH)—, —CH$_2$— or the following formulas:

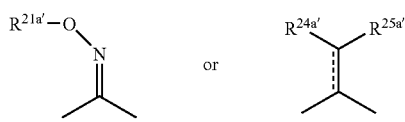

wherein $R^{21a'}$ represents unsubstituted or substituted alkyl, aralkyl or heterocycle-lower alkyl group, $R^{24a'}$ and $R^{25a'}$ are the same or different and represent hydrogen atom, unprotected or protected carboxyl group or unsubstituted or substituted alkyl, alkoxycarbonyl, aryloxycarbonyl or carbamoyl group, $W^a$ represents —$Z^{a'}$—COR$^{26a'}$, —$Z^{a'}$—COOR$^{2a'}$, —O—CH$_2$COOR$^{2a'}$, —O—CH$_2$CH$_2$—COOR$^{2a'}$, —CONH—CH$_2$COOR$^{2a'}$ or —CONH—CH$^2$CH$_2$COOR$^{2a'}$ (in these formulas, $Z^{a'}$ represents —(CH$_2$)$_{n^{a'}}$— wherein $n^{a'}$ is 0, 1, 2 or 3, —CH$_2$CH(CH$_3$)—, —CH=CH— or —CH$_2$CH=CH—, $R^{2a'}$ represents hydrogen atom or a protecting group for carboxyl group, and $R^{26a'}$ represents —NHSO$_2$R$^{28a'}$ wherein $R^{28a'}$ is unsubstituted or substituted alkyl group.

Among the compounds of general formula [b] of this invention, preferred are those in which $R^{1b}$ represents unsubstituted or substituted alkoxy group, $R^{3b}$ and $R^{4b}$ are the same or different and represent unprotected or protected hydroxyl group or unsubstituted or substituted alkoxy group, $X^{1b}$ is —C(O)—, and $Z^b$ is —(CH$_2$)$_2$—.

Among the compounds of general formula [c] of this invention, preferred are those in which $R^{1c}$ represents unsubstituted or substituted alkoxy group; $R^{2c}$ represents hydrogen atom or a protecting group for carboxyl group; $R^{3c}$ and $R^{4c}$ may be the same or different and represent unsubstituted or substituted alkoxy group; $X^{1c}$ is —C(O)—; and $Z^c$ is —(CH$_2$)$_2$—.

Among the compounds of general formula [d] of this invention, preferred are those in which $R^1$ 1d is unsubstituted or substituted alkoxy group; $R^{3d}$ is unsubstituted or substituted alkyl group; $R^{4d}$ is unsubstituted or substituted acyl group; $X^{1d}$ is —C(O)—; and $Z^d$ is —(CH$_2$)$_2$—.

Among the compounds of general formula [e] of this invention, preferred are those in which $R^{0e}$ is hydrogen atom or halogen atom; $R^{1e}$ is unsubstituted or substituted alkyl group; $R^{3e}$ and $R^{4e}$ independently represent unsubstituted or substituted alkoxy group; $X^{1e}$ is —C(O)—; and $Z^e$ is a bonding unit.

Among the compounds of general formula [f] of this invention, preferred are those in which $R^{1f}$ is unsubstituted or substituted alkoxy group; $R^{3f}$ and $R^{4f}$ independently represent unsubstituted or substituted alkyl group; $X^{1f}$ is —C(O)—; and $Z^f$ is —CH$_2$—.

As typical compounds of this invention, the following compounds can be referred to, for example, provided that Ac represents an acetyl group.

Ac-Cys-Gly-Gln-Leu-Asp-Leu-Ala-Leu-Gly-Cys-NH$_2$ [SEQ ID NO:5] (having a disulfide linkage between the first and tenth L-cysteine residues)

Ac-Cys-Gly-Gln-Leu-Ser-Leu-Ala-Leu-Gly-Cys-NH$_2$ [SEQ ID NO:6] (having a disulfide linkage between the first and tenth L-cysteine residues)

Ac-Cys-Gly-Gln-Leu-Asp-Leu-Ala-Gly-Gly-Cys-NH$_2$ [SEQ ID NO:7] (having a disulfide linkage between the first and tenth L-cysteine residues)

Ac-Cys-Gly-Gln-Leu-Asp-Leu-Ala-Asn-Gly-Cys-NH$_2$ [SEQ ID NO:8] (having a disulfide linkage between the first and tenth L-cysteine residues)

Ac-Cys-Gly-Gln-Leu-Ser-Leu-Ala-Asp-Gly-Cys-NH$_2$ [SEQ ID NO:9] (having a disulfide linkage between the first and tenth cysteine residues)

Ac-Cys-Gly-Asn-Leu-Asp-Leu-Ala-Asp-Gly-Cys-NH$_2$ [SEQ ID NO:3] (having a disulfide linkage between the first and tenth L-cysteine residues)

Ac-Asn-Cys-Gly-Asn-Leu-Leu-Ala-Leu-Gly-Ser-Cys-NH$_2$ [SEQ ID NO:10] (having a disulfide linkage between the second and eleventh L-cysteine residues)

Ac-Cys-Gly-Asn-Leu-Leu-Ala-Leu-Gly-Ser-Cys-NH$_2$ [SEQ ID NO:11] (having a disulfide linkage between the first and tenth L-cysteine residues)

Ac-Asn-Cys-Gly-Asn-Ala-Leu-Ala-Leu-Gly-Ser-Cys-NH$_2$ [SEQ ID NO:12] (having a disulfide linkage between the second and eleventh L-cysteine residues)

Ac-Cys-Gly-Asn-Leu-Leu-Ala-Leu-Gly-Asp-Cys-NH$_2$ [SEQ ID NO:13] (having a disulfide linkage between the first and tenth L-cysteine residues)

Ac-Cys-Gly-Asn-Leu-Leu-Ser-Leu-Gly-Asp-Cys-NH$_2$ [SEQ ID NO:14] (having a disulfide linkage between the first and tenth L-cysteine residues)

Ac-Cys-Gly-Asn-Leu-Leu-Ala-Leu-Gly-Ser-Cys-NH$_2$ (having a disulfide linkage between the first and tenth L-cysteine residues)

Ac-Asn-Cys-Gly-Asn-Ala-Leu-Ala-Leu-Gly-Ser-Cys-NH$_2$ (having a disulfide linkage between the second and eleventh L-cysteine residues)

Ac-Cys-Gly-Asn-Leu-Leu-Ala-Leu-Gly-Asp-Cys-NH$_2$ (having a disulfide linkage between the first and tenth L-cysteine residues)

Ac-Cys-Gly-Asn-Leu-Leu-Ser-Leu-Gly-Asp-Cys-NH$_2$ (having a disulfide linkage between the first and tenth L-cysteine residues)

(3S)-8-(3-methylbutylidene)-4-(4-methylpentanoyl)-1-thia-4-azaspiro[4.5]-deecane-3-carboxylic acid 2-[(2S)-4-(2,4-diisobutoxybenzoyl)-1-(3-methylbutanoyl)-3-oxohexahydro-2-pyrazinyl]-acetic acid 2-(2-isobutoxy-5-{[(2S,4R)-4-(isobutyryloxy)-2-(isopropoxycarbonyl)tetrahydro-1H-1-pyrrolyl]carbonyl}-phenyl)-acetic acid 2-(2-isobutoxy-5-{[(2S)-4-isopentyl-2-(isopropoxycarbonyl)-3-oxohexahydro-1-pyrazinyl]carbonyl}-phenyl)-acetic acid 2-(5-{[(2R)-2,4-diisopentyl-3-oxohexahydro-1-pyrazinyl]-carbonyl}-2-isobutoxyphenyl)-acetic acid Further, the compounds of the following Tables 1 to 37 can also be referred to.

In the tables, meanings of the abbreviations are as follows:

Me: CH$_3$; Et: C$_2$H$_5$; nPr: CH$_2$CH$_2$CH$_3$; iPr: CHCH$_3$)$_2$; iBu: CH$_2$CH(CH$_3$)$_2$; iAm: CH$_2$CH$_2$CH(CH$_3$)$_2$; Ph: phenyl; Py: pyridyl

TABLE 1

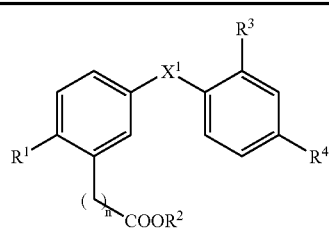

| n | X$^1$ | R$^1$ | R$^2$ | R$^3$ | R$^4$ |
|---|---|---|---|---|---|
| 0 | C(O) | O-iBu | H | CN | CN |
| 0 | C(O) | O-iBu | H | NO$_2$ | NO$_2$ |
| 0 | C(O) | O-iBu | H | COOCH$_3$ | COOCH$_3$ |
| 0 | C(O) | OCH$_2$C$_6$H$_5$ | H | OCH$_2$C$_6$H$_5$ | OCH$_2$C$_6$H$_5$ |
| 0 | C(O) | O-iBu | H | O-iBu | O-iBu |
| 1 | C(O) | O-iBu | H | O-iBu | O-iBu |
| 2 | C(O) | O-iBu | H | O-iBu | O-iBu |
| 0 | C(O) | O-iBu | CH$_2$CH$_3$ | O-iBu | O-iBu |
| 1 | C(O) | O-iBu | CH$_2$CH$_3$ | O-iBu | O-iBu |
| 2 | C(O) | O-iBu | CH$_2$CH$_3$ | O-iBu | O-iBu |
| 0 | C(O) | O-iBu | CH$_3$ | O-iBu | O-iBu |
| 1 | C(O) | O-iBu | CH$_3$ | O-iBu | O-iBu |
| 2 | C(O) | O-iBu | CH$_3$ | O-iBu | O-iBu |
| 2 | C(O) | S-iBu | H | S-iBu | S-iBu |
| 2 | C(O) | NH-iBu | H | NH-iBu | NH-iBu |

TABLE 1-continued

| n | X$^1$ | R$^1$ | R$^2$ | R$^3$ | R$^4$ |
|---|---|---|---|---|---|
| 0 | C(O) | SCH$_3$ | H | SCH$_3$ | SCH$_3$ |
| 0 | C(O) | CH$_2$COOH | H | CH$_2$COOH | CH$_2$COOH |
| 0 | C(O) | CH$_3$ | H | CH$_3$ | CH$_3$ |
| 1 | C(O) | CH$_3$ | H | CH$_3$ | CH$_3$ |
| 0 | C(O) | CHCHC$_6$H$_5$ | H | CHCHC$_6$H$_5$ | CHCHC$_6$H$_5$ |
| 0 | C(O) | C$_6$H$_{11}$ | H | C$_6$H$_{11}$ | C$_6$H$_{11}$ |
| 0 | C(O) | C$_6$H$_5$ | H | C$_6$H$_5$ | C$_6$H$_5$ |
| 0 | C(O) | CH$_2$C$_6$H$_5$ | H | CH$_2$C$_6$H$_5$ | CH$_2$C$_6$H$_5$ |
| 0 | C(O) | OCH$_3$ | H | OCH$_3$ | OCH$_3$ |
| 0 | C(O) | OC$_6$H$_5$ | H | OC$_6$H$_5$ | OC$_6$H$_5$ |
| 0 | C(O) | O-iBu | H | COCH$_3$ | COCH$_3$ |
| 0 | C(O) | O-iBu | H | COOC$_2$H$_5$ | COOC$_2$H$_5$ |
| 0 | C(O) | O-iBu | H | COOC$_6$H$_5$ | COOC$_6$H$_5$ |
| 0 | C(O) | O-iBu | H | CONH$_2$ | CONH$_2$ |
| 0 | C(O) | O-iBu | H | S(O)CH$_3$ | S(O)CH$_3$ |
| 0 | C(O) | O-iBu | H | S(O)$_2$CH$_3$ | S(O)$_2$CH$_3$ |
| 0 | C(O) | NH$_2$ | H | NH$_2$ | NH$_2$ |
| 0 | C(O) | 2-Py | H | 2-Py | 2-Py |
| 0 | CH(OH) | O-iBu | H | CN | CN |
| 0 | CH(OH) | O-iBu | H | NO$_2$ | NO$_2$ |
| 0 | CH(OH) | O-iBu | H | COOCH$_3$ | COOCH$_3$ |
| 0 | CH(OH) | OCH$_2$C$_6$H$_5$ | H | OCH$_2$C$_6$H$_5$ | OCH$_2$C$_6$H$_5$ |
| 0 | CH(OH) | O-iBu | H | O-iBu | O-iBu |
| 1 | CH(OH) | O-iBu | H | O-iBu | O-iBu |
| 2 | CH(OH) | O-iBu | H | O-iBu | O-iBu |
| 0 | CH(OH) | O-iBu | CH$_3$ | O-iBu | O-iBu |
| 1 | CH(OH) | O-iBu | CH$_3$ | O-iBu | O-iBu |
| 2 | CH(OH) | O-iBu | CH$_3$ | O-iBu | O-iBu |
| 0 | CH(OH) | SCH$_3$ | H | SCH$_3$ | SCH$_3$ |
| 0 | CH(OH) | CH$_2$COOH | H | CH$_2$COOH | CH$_2$COOH |
| 0 | CH(OH) | CH$_3$ | H | CH$_3$ | CH$_3$ |
| 1 | CH(OH) | CH$_3$ | H | CH$_3$ | CH$_3$ |
| 0 | CH(OH) | CHCHC$_6$H$_5$ | H | CHCHC$_6$H$_5$ | CHCHC$_6$H$_5$ |
| 0 | CH(OH) | C$_6$H$_{11}$ | H | C$_6$H$_{11}$ | C$_6$H$_{11}$ |
| 0 | CH(OH) | C$_6$H$_5$ | H | C$_6$H$_5$ | C$_6$H$_5$ |
| 0 | CH(OH) | CH$_2$C$_6$H$_5$ | H | CH$_2$C$_6$H$_5$ | CH$_2$C$_6$H$_5$ |
| 0 | CH(OH) | OCH$_3$ | H | OCH$_3$ | OCH$_3$ |
| 0 | CH(OH) | OC$_6$H$_5$ | H | OC$_6$H$_5$ | OC$_6$H$_5$ |
| 0 | CH(OH) | O-iBu | H | COCH$_3$ | COCH$_3$ |
| 0 | CH(OH) | O-iBu | H | COOC$_2$H$_5$ | COOC$_2$H$_5$ |
| 0 | CH(OH) | O-iBu | H | COOC$_6$H$_5$ | COOC$_6$H$_5$ |
| 0 | CH(OH) | O-iBu | H | CONH$_2$ | CONH$_2$ |
| 0 | CH(OH) | O-iBu | H | S(O)CH$_3$ | S(O)CH$_3$ |
| 0 | CH(OH) | O-iBu | H | S(O)$_2$CH$_3$ | S(O)$_2$CH$_3$ |
| 0 | CH(OH) | NH$_2$ | H | NH$_2$ | NH$_2$ |
| 0 | CH(OH) | 2-Py | H | 2-Py | 2-Py |
| 0 | CH$_2$ | O-iBu | H | CN | CN |
| 0 | CH$_2$ | O-iBu | H | NO$_2$ | NO$_2$ |
| 0 | CH$_2$ | O-iBu | H | COOCH$_3$ | COOCH$_3$ |
| 0 | CH$_2$ | OCH$_2$C$_6$H$_5$ | H | OCH$_2$C$_6$H$_5$ | OCH$_2$C$_6$H$_5$ |
| 0 | CH$_2$ | O-iBu | H | O-iBu | O-iBu |
| 1 | CH$_2$ | O-iBu | H | O-iBu | O-iBu |
| 2 | CH$_2$ | O-iBu | H | O-iBu | O-iBu |
| 0 | CH$_2$ | O-iBu | CH$_3$ | O-iBu | O-iBu |
| 1 | CH$_2$ | O-iBu | CH$_3$ | O-iBu | O-iBu |
| 2 | CH$_2$ | O-iBu | CH$_3$ | O-iBu | O-iBu |
| 0 | CH$_2$ | CH$_2$COOH | H | CH$_2$COOH | CH$_2$COOH |
| 0 | CH$_2$ | CH$_3$ | H | CH$_3$ | CH$_3$ |
| 1 | CH$_2$ | CH$_3$ | H | CH$_3$ | CH$_3$ |
| 0 | CH$_2$ | CHCHC$_6$H$_5$ | H | CHCHC$_6$H$_5$ | CHCHC$_6$H$_5$ |
| 0 | CH$_2$ | C$_6$H$_{11}$ | H | C$_6$H$_{11}$ | C$_6$H$_{11}$ |
| 0 | CH$_2$ | C$_6$H$_5$ | H | C$_6$H$_5$ | C$_6$H$_5$ |
| 0 | CH$_2$ | CH$_2$C$_6$H$_5$ | H | CH$_2$C$_6$H$_5$ | CH$_2$C$_6$H$_5$ |
| 0 | CH$_2$ | OCH$_3$ | H | OCH$_3$ | OCH$_3$ |
| 0 | CH$_2$ | OC$_6$H$_5$ | H | OC$_6$H$_5$ | OC$_6$H$_5$ |

TABLE 1-continued

| n | X¹ | R¹ | R² | R³ | R⁴ |
|---|----|----|----|----|----|
| 0 | CH₂ | O-iBu | H | COCH₃ | COCH₃ |
| 0 | CH₂ | O-iBu | H | COOC₂H₅ | COOC₂H₅ |
| 0 | CH₂ | O-iBu | H | COOC₆H₅ | COOC₆H₅ |
| 0 | CH₂ | O-iBu | H | CONH₂ | CONH₂ |
| 0 | CH₂ | SCH₃ | H | SCH₃ | SCH₃ |
| 0 | CH₂ | O-iBu | H | S(O)CH₃ | S(O)CH₃ |
| 0 | CH₂ | O-iBu | H | S(O)₂CH₃ | S(O)₂CH₃ |
| 0 | CH₂ | NH₂ | H | NH₂ | NH₂ |
| 0 | CH₂ | 2-Py | H | 2-Py | 2-Py |
| 0 | CH₂ | NHC(O)-iBu | H | NHC(O)-iBu | NHC(O)-iBu |
| 1 | CH₂ | NHC(O)-iBu | H | NHC(O)-iBu | NHC(O)-iBu |
| 2 | CH₂ | NHC(O)-iBu | H | NHC(O)-iBu | NHC(O)-iBu |
| 0 | C(O) | NHC(O)-iBu | H | NHC(O)-iBu | NHC(O)-iBu |
| 1 | C(O) | NHC(O)-iBu | H | NHC(O)-iBu | NHC(O)-iBu |
| 2 | C(O) | NHC(O)-iBu | H | NHC(O)-iBu | NHC(O)-iBu |
| 0 | CH(OH) | NHC(O)-iBu | H | NHC(O)-iBu | NHC(O)-iBu |
| 1 | CH(OH) | NHC(O)-iBu | H | NHC(O)-iBu | NHC(O)-iBu |
| 2 | CH(OH) | NHC(O)-iBu | H | NHC(O)-iBu | NHC(O)-iBu |
| 0 | CH₂ | NHC(O)-iPr | H | NHC(O)-iPr | NHC(O)-iPr |
| 1 | CH₂ | NHC(O)-iPr | H | NHC(O)-iPr | NHC(O)-iPr |
| 2 | CH₂ | NHC(O)-iPr | H | NHC(O)-iPr | NHC(O)-iPr |
| 0 | C(O) | NHC(O)-iPr | H | NHC(O)-iPr | NHC(O)-iPr |
| 1 | C(O) | NHC(O)-iPr | H | NHC(O)-iPr | NHC(O)-iPr |
| 2 | C(O) | NHC(O)-iPr | H | NHC(O)-iPr | NHC(O)-iPr |
| 0 | CH(OH) | NHC(O)-iPr | H | NHC(O)-iPr | NHC(O)-iPr |
| 1 | CH(OH) | NHC(O)-iPr | H | NHC(O)-iPr | NHC(O)-iPr |
| 2 | CH(OH) | NHC(O)-iPr | H | NHC(O)-iPr | NHC(O)-iPr |

TABLE 2

| m | X² | R⁵ | R⁶ | R⁷ | R⁸ |
|---|----|----|----|----|----|
| 1 | C(O) | O-iBu | H | n-Bu | iAm |
| 0 | C(O) | H | CH₃ | H | H |
| 0 | C(O) | Cl | H | Cl | C(O)CH₃ |
| 1 | C(O) | CN | H | CN | C(O)CH(CH₃)₂ |
| 1 | C(O) | NO₂ | H | NO₂ | C(O)-iBu |
| 1 | C(O) | COOCH₃ | H | COOCH₃ | COOCH₃ |
| 1 | C(O) | OCH₂C₆H₅ | H | OCH₂C₆H₅ | OCH₂C₆H₅ |
| 1 | C(O) | O-iBu | H | iAm | iAm |
| 1 | C(O) | O-iBu | H | C(O)OCH(CH₃)₂ | iAm |
| 2 | C(O) | O-iBu | H | iAm | iAm |
| 1 | C(O) | NHC(O)-iBu | H | iAm | iAm |
| 1 | C(O) | NHC(O)-iBu | H | C(O)OCH(CH₃)₂ | iAm |
| 2 | C(O) | NHC(O)-iBu | H | iAm | iAm |
| 1 | C(O) | NHC(O)-iPr | H | iAm | iAm |
| 1 | C(O) | NHC(O)-iPr | H | C(O)OCH(CH₃)₂ | iAm |
| 2 | C(O) | NHC(O)-iPr | H | iAm | iAm |
| 1 | C(O) | O-iAm | CH₃ | iAm | O-iAm |
| 1 | C(O) | CH₂COOH | H | CH₂COOH | CH₂COOH |
| 0 | C(O) | CH₃ | H | CH₃ | CH₃ |
| 1 | C(O) | CH₃ | H | CH₃ | CH₃ |

TABLE 2-continued

| m | X² | R⁵ | R⁶ | R⁷ | R⁸ |
|---|----|----|----|----|----|
| 1 | C(O) | CHCHC₆H₅ | H | CHCHC₆H₅ | CHCHC₆H₅ |
| 1 | C(O) | C₆H₁₁ | H | C₆H₁₁ | C₆H₁₁ |
| 1 | C(O) | C₆H₅ | H | C₆H₅ | C₆H₅ |
| 1 | C(O) | CH₂C₆H₅ | H | CH₂C₆H₅ | CH₂C₆H₅ |
| 1 | C(O) | OCH₃ | H | OCH₃ | OCH₃ |
| 1 | C(O) | OC₆H₅ | H | OC₆H₅ | OC₆H₅ |
| 1 | C(O) | COCH₃ | H | COCH₃ | COCH₃ |
| 1 | C(O) | COOC₂H₅ | H | COOC₂H₅ | COOC₂H₅ |
| 1 | C(O) | COOC₆H₅ | H | COOC₆H₅ | COOC₆H₅ |
| 1 | C(O) | CONH₂ | H | CONH₂ | CONH₂ |
| 1 | C(O) | SCH₃ | H | SCH₃ | SCH₃ |
| 1 | C(O) | S(O)CH₃ | H | S(O)CH₃ | S(O)CH₃ |
| 1 | C(O) | S(O)₂CH₃ | H | S(O)₂CH₃ | S(O)₂CH₃ |
| 1 | C(O) | NH₂ | H | NH₂ | NH₂ |
| 2 | C(O) | 2-Py | H | 2-Py | 2-Py |

TABLE 3

| m | X² | R⁵ | R⁶ | R⁹ | R¹⁰ |
|---|----|----|----|----|----|
| 1 | C(O) | O-iBu | H | CH₂CH₂-iBu | O-iBu |
| 0 | C(O) | Cl | CH₃ | Cl | Cl |
| 0 | C(O) | CN | CH₃ | CN | CN |
| 0 | C(O) | NO₂ | H | NO₂ | NO₂ |
| 0 | C(O) | COOCH₃ | H | COOCH₃ | COOCH₃ |
| 0 | C(O) | OCH₂C₆H₅ | H | OCH₂C₆H₅ | OCH₂C₆H₅ |
| 0 | C(O) | O-iBu | H | COO-iBu | O-iBu |
| 1 | C(O) | O-iBu | H | COO-iBu | O-iBu |
| 2 | C(O) | O-iBu | H | COO-iBu | O-iBu |
| 0 | C(O) | NHC(O)-iBu | H | NHC(O)-iBu | NHC(O)-iBu |
| 1 | C(O) | NHC(O)-iBu | H | NHC(O)-iBu | NHC(O)-iBu |
| 2 | C(O) | NHC(O)-iBu | H | NHC(O)-iBu | NHC(O)-iBu |
| 0 | C(O) | NHC(O)-iPr | H | NHC(O)-iPr | NHC(O)-iPr |
| 1 | C(O) | NHC(O)-ipr | H | NHC(O)-iPr | NHC(O)-iPr |
| 2 | C(O) | NHC(O)-iPr | H | NHC(O)-iPr | NHC(O)-iPr |
| 0 | C(O) | O-iAm | H | O-iAm | O-iAm |
| 1 | C(O) | CH₂COOH | H | CH₂COOH | CH₂COOH |
| 0 | C(O) | CH₃ | H | CH₃ | CH₃ |
| 1 | C(O) | CH₃ | H | CH₃ | CH₃ |
| 1 | C(O) | CHCHC₆H₅ | H | CHCHC₆H₅ | CHCHC₆H₅ |
| 1 | C(O) | C₆H₁₁ | H | C₆H₁₁ | C₆H₁₁ |
| 1 | C(O) | C₆H₅ | H | C₆H₅ | C₆H₅ |
| 1 | C(O) | CH₂C₆H₅ | H | CH₂C₆H₅ | CH₂C₆H₅ |
| 1 | C(O) | OCH₃ | H | OCH₃ | OCH₃ |
| 1 | C(O) | OC₆H₅ | H | OC₆H₅ | OC₆H₅ |
| 1 | C(O) | COCH₃ | H | COCH₃ | COCH₃ |
| 1 | C(O) | COOC₂H₅ | H | COOC₂H₅ | COOC₂H₅ |
| 1 | C(O) | COOC₆H₅ | H | COOC₆H₅ | COOC₆H₅ |
| 1 | C(O) | CONH₂ | H | CONH₂ | CONH₂ |
| 1 | C(O) | SCH₃ | H | SCH₃ | SCH₃ |
| 1 | C(O) | S(O)CH₃ | H | S(O)CH₃ | S(O)CH₃ |
| 1 | C(O) | S(O)₂CH₃ | H | S(O)₂CH₃ | S(O)₂CH₃ |

TABLE 3-continued

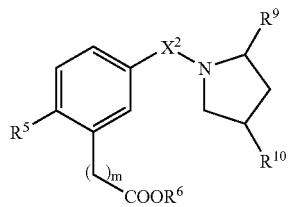

| m | $X^2$ | $R^5$ | $R^6$ | $R^9$ | $R^{10}$ |
|---|---|---|---|---|---|
| 1 | C(O) | $NH_2$ | H | $NH_2$ | $NH_2$ |
| 1 | C(O) | 2-Py | H | 2-Py | 2-Py |

TABLE 4

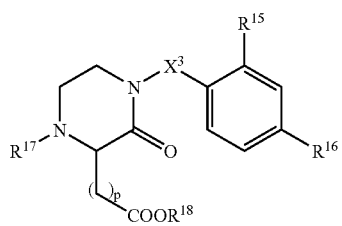

| n | $X^3$ | $R^{15}$ | $R^{16}$ | $R^{17}$ | $R^{18}$ |
|---|---|---|---|---|---|
| 1 | C(O) | Cl | Cl | $C(O)CH_3$ | $CH_3$ |
| 1 | C(O) | CN | CN | $C(O)CH(CH_3)_2$ | $CH_3$ |
| 1 | C(O) | $NO_2$ | $NO_2$ | C(O)-iBu | H |
| 1 | C(O) | $COOCH_3$ | $COOCH_3$ | $COOCH_3$ | H |
| 0 | C(O) | O-iBu | O-iBu | $C(O)CH(CH_3)_2$ | H |
| 1 | C(O) | O-iBu | O-iBu | $C(O)CH(CH_3)_2$ | H |
| 2 | C(O) | O-iBu | O-iBu | $C(O)CH(CH_3)_2$ | H |
| 1 | C(O) | O-iBu | O-iBu | C(O)-iBu | H |
| 1 | C(O) | O-iBu | O-iBu | $C(O)CH_2$-iBu | H |
| 1 | C(O) | O-iBu | O-iBu | iBu | H |
| 1 | C(O) | O-iBu | O-iBu | iAm | H |

TABLE 4-continued

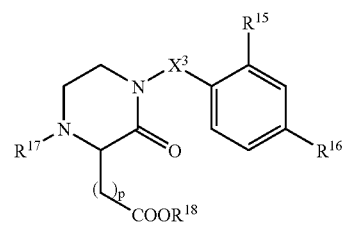

| n | $X^3$ | $R^{15}$ | $R^{16}$ | $R^{17}$ | $R^{18}$ |
|---|---|---|---|---|---|
| 1 | C(O) | O-iBu | O-iBu | $CH_2CH_2$-iBu | H |
| 1 | C(O) | NHC(O)-iBu | NHC(O)-iBu | iBu | H |
| 1 | C(O) | NHC(O)-iBu | NHC(O)-iBu | iAm | H |
| 1 | C(O) | NHC(O)-iBu | NHC(O)-iBu | $CH_2CH_2$-iBu | H |
| 1 | C(O) | NHC(O)-iPr | NHC(O)-iPr | iBu | H |
| 1 | C(O) | NHC(O)-iPr | NHC(O)-iPr | iAm | H |
| 1 | C(O) | NHC(O)-iPr | NHC(O)-iPr | $CH_2CH_2$-iBu | H |
| 1 | C(O) | $CH_2COOH$ | $CH_2COOH$ | $CH_2COOH$ | H |
| 1 | C(O) | $CH_3$ | $CH_3$ | $CH_3$ | H |
| 1 | C(O) | $CHCHC_6H_5$ | $CHCHC_6H_5$ | $CHCHC_6H_5$ | H |
| 1 | C(O) | $C_6H_{11}$ | $C_6H_{11}$ | $C_6H_{11}$ | H |
| 1 | C(O) | $C_6H_5$ | $C_6H_5$ | $C_6H_5$ | H |
| 1 | C(O) | $CH_2C_6H_5$ | $CH_2C_6H_5$ | $CH_2C_6H_5$ | H |
| 1 | C(O) | $COCH_3$ | $COCH_3$ | $COCH_3$ | H |
| 1 | C(O) | $COOC_2H_5$ | $COOC_2H_5$ | $COOC_2H_5$ | H |
| 1 | C(O) | $COOC_6H_5$ | $COOC_6H_5$ | $COOC_6H_5$ | H |
| 1 | C(O) | $CONH_2$ | $CONH_2$ | $CONH_2$ | H |
| 1 | C(O) | $S(O)_2CH_3$ | $S(O)_2CH_3$ | $S(O)_2CH_3$ | H |
| 1 | C(O) | 2-Py | 2-Py | 2-Py | H |

TABLE 5

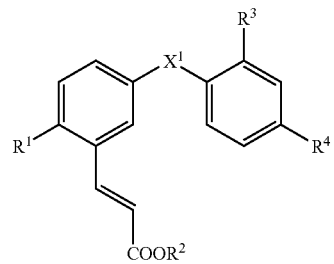

| $X^1$ | $R^1$ | $R^2$ | $R^3$ | $R^4$ |
|---|---|---|---|---|
| C(O) | O-iBu | H | CN | CN |
| C(O) | O-iBu | H | $NO_2$ | $NO_2$ |
| C(O) | O-iBu | H | $COOCH_3$ | $COOCH_3$ |
| C(O) | O-iBu | H | $OCH_2C_6H_5$ | $OCH_2C_6H_5$ |
| C(O) | O-iBu | H | O-iBu | O-iBu |
| C(O) | O-iBu | $CH_3$ | O-iBu | O-iBu |
| C(O) | $SCH_3$ | H | $SCH_3$ | $SCH_3$ |
| C(O) | $CH_2COOH$ | H | $CH_2COOH$ | $CH_2COOH$ |
| C(O) | $CH_3$ | H | $CH_3$ | $CH_3$ |
| C(O) | $CHCHC_6H_5$ | H | $CHCHC_6H_5$ | $CHCHC_6H_5$ |
| C(O) | $C_6H_{11}$ | H | $C_6H_{11}$ | $C_6H_{11}$ |
| C(O) | $C_6H_5$ | H | $C_6H_5$ | $C_6H_5$ |
| C(O) | $CH_2C_6H_5$ | H | $CH_2C_6H_5$ | $CH_2C_6H_5$ |

TABLE 5-continued

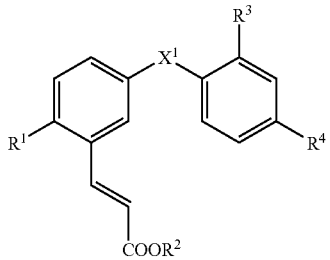

| X¹ | R¹ | R² | R³ | R⁴ |
|---|---|---|---|---|
| C(O) | NHC(O)-iPr | H | NHC(O)-iPr | NHC(O)-iPr |
| C(O) | NHC(O)-iPr | H | O-iBu | O-iBu |
| C(O) | O-iBu | H | NHC(O)-iPr | O-iBu |
| C(O) | O-iBu | H | O-iBu | NHC(O)-iPr |
| C(O) | O-iBu | H | NHC(O)-iPr | NHC(O)-iPr |
| C(O) | C(O)CH$_2$CH(CH$_3$)$_2$ | H | C(O)CH$_2$CH(CH$_3$)$_2$ | C(O)CH$_2$CH(CH$_3$)$_2$ |
| C(O) | C(O)CH$_2$CH(CH$_3$)$_2$ | H | O-iBu | O-iBu |
| C(O) | O-iBu | H | C(O)CH$_2$CH(CH$_3$)$_2$ | C(O)CH$_2$CH(CH$_3$)$_2$ |
| C(O) | CH$_2$CH$_2$CH(CH$_3$)$_2$ | H | CH$_2$CH$_2$CH(CH$_3$)$_2$ | CH$_2$CH$_2$CH(CH$_3$)$_2$ |
| C(O) | CH$_2$CH$_2$CH(CH$_3$)$_2$ | H | O-iBu | O-iBu |
| C(O) | O-iBu | H | CH$_2$CH$_2$CH(CH$_3$)$_2$ | CH$_2$CH$_2$CH(CH$_3$)$_2$ |
| C(O) | C(O)NH-iPr | H | O-iBu | O-iBu |
| C(O) | O-iBu | H | C(O)NH-iPr | C(O)NH-iPr |
| CH(OH) | O-iBu | H | O-iBu | O-iBu |
| CH$_2$ | O-iBu | H | O-iBu | O-iBu |

TABLE 6

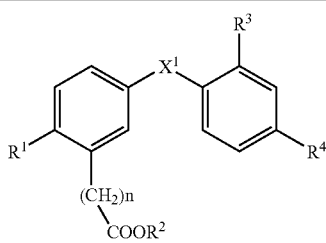

| n | X¹ | R¹ | R² | R³ | R⁴ |
|---|---|---|---|---|---|
| 3 | C(O) | O-iBu | H | O-iBu | O-iBu |
| 0 | C(O) | O-iAm | H | O-iAm | O-iAm |
| 1 | C(O) | O-iAm | CH$_3$ | O-iAm | O-iAm |
| 1 | C(O) | O-iAm | H | O-iAm | O-iAm |
| 2 | C(O) | O-iAm | H | O-iAm | O-iAm |
| 3 | C(O) | O-iAm | H | O-iAm | O-iAm |
| 2 | C(O) | O-iAm | H | O-iBu | O-iBu |
| 2 | C(O) | O-iAm | H | O-iBu | O-iAm |
| 2 | C(O) | O-iBu | H | OH | O-iBu |
| 2 | C(O) | O-iBu | H | OH | O-iAm |
| 2 | C(O) | S-iBu | H | OH | S-iBu |
| 2 | C(O) | NH-iBu | H | OH | NH-iBu |
| 2 | C(O) | OH | H | O-iBu | O-iBu |
| 2 | C(O) | O-iBu | H | H | O-iBu |
| 2 | C(O) | O-iBu | H | OCH$_3$ | O-iBu |

TABLE 7

| n | X¹ | R¹ | R² | R³ | R⁴ |
|---|---|---|---|---|---|
| 2 | C(O) | O-iBu | H | F | O-iBu |
| 2 | C(O) | O-iBu | H | OCO-iPr | O-iBu |
| 2 | C(O) | O-iBu | H | O(CH$_2$)$_3$COOH | O-iBu |
| 2 | C(O) | O-iBu | H | O(CH$_2$)$_5$CONH$_2$ | O-iBu |
| 2 | C=N—OH | O-iBu | H | O-iBu | O-iBu |
| 2 | C=N—OCH$_2$CH$_3$ | O-iBu | H | O-iBu | O-iBu |

TABLE 7-continued

| n | X¹ | R¹ | R² | R³ | R⁴ |
|---|---|---|---|---|---|
| 2 | C=N—OCH$_2$COOH | O-iBu | H | O-iBu | O-iBu |
| 2 | C=N—OCH$_2$CONH$_2$ | O-iBu | H | O-iBu | O-iBu |
| 2 | C=N—OCH$_2$C$_6$H$_5$ | O-iBu | H | O-iBu | O-iBu |
| 2 | C=N—OCH$_2$-3-Py | O-iBu | H | O-iBu | O-iBu |
| 2 | C=N—OH | O-iBu | H | OH | O-iBu |
| 2 | C=N—OCH$_2$CONH$_2$ | O-iBu | H | OH | O-iBu |
| 2 | C=N—OCH$_2$C$_6$H$_5$ | O-iBu | H | OH | O-iBu |
| 2 | CHNHSO$_2$CH$_3$ | O-iBu | H | O-iBu | O-iBu |
| 2 | CHNHCOCH$_3$ | O-iBu | H | O-iBu | O-iBu |
| 2 | CHNHCONH$_2$ | O-iBu | H | O-iBu | O-iBu |
| 2 | C=CH—COOH | O-iBu | H | O-iBu | O-iBu |
| 2 | C=CH—COOC$_2$H$_5$ | O-iBu | H | O-iBu | O-iBu |
| 2 | CHCH$_2$COOH | O-iBu | H | O-iBu | O-iBu |
| 2 | CHCH$_2$CONH$_2$ | O-iBu | H | O-iBu | O-iBu |

TABLE 8

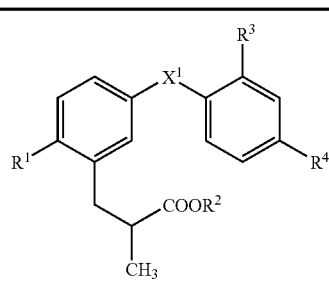

| X¹ | R¹ | R² | R³ | R⁴ |
|---|---|---|---|---|
| C(O) | O-iBu | H | O-iBu | O-iBu |
| C(O) | O-iBu | CH$_3$ | O-iBu | O-iBu |
| C(O) | O-iAm | H | O-iAm | O-iAm |
| C(O) | O-iBu | H | O-iAm | O-iBu |
| C(O) | O-iBu | H | O-iAm | O-iAm |

TABLE 8-continued

Structure: biphenyl with X¹ linker, R¹ on left ring, R³/R⁴ on right ring, and -CH₂-CH(CH₃)-COOR² chain.

| X¹ | R¹ | R² | R³ | R⁴ |
|---|---|---|---|---|
| C(O) | O-iBu | H | OH | O-iBu |
| C(O) | O-iBu | H | OH | O-iAm |
| C(O) | OH | H | O-iBu | O-iBu |
| C(O) | O-iBu | H | OCH₃ | O-iBu |
| C(O) | O-iBu | H | F | O-iBu |
| C(O) | O-iBu | H | OCO-iPr | O-iBu |
| C(O) | O-iBu | H | O(CH₂)₃COOH | O-iBu |
| C(O) | O-iBu | H | O(CH₂)₅CONH₂ | O-iBu |

TABLE 9

| X¹ | R¹ | R² | R³ | R⁴ |
|---|---|---|---|---|
| C=N—OH | O-iBu | H | O-iBu | O-iBu |
| C=N—OCH₂CH₂CH₃ | O-iBu | H | O-iBu | O-iBu |
| C=N—OCH₂COOH | O-iBu | H | O-iBu | O-iBu |
| C=N—OCH₂CONH₂ | O-iBu | H | O-iBu | O-iBu |
| C=N—OCH₂C₆H₅ | O-iBu | H | O-iBu | O-iBu |
| C=N—OCH₂-3-Py | O-iBu | H | O-iBu | O-iBu |
| CHNHSO₂CH₃ | O-iBu | H | O-iBu | O-iBu |
| CHNHCOCH₃ | O-iBu | H | O-iBu | O-iBu |
| CHNHCONH₂ | O-iBu | H | O-iBu | O-iBu |
| C=CH—COOH | O-iBu | H | O-iBu | O-iBu |
| C=CH—COOC₂H₅ | O-iBu | H | O-iBu | O-iBu |
| CHCH₂COOH | O-iBu | H | O-iBu | O-iBu |
| CHCH₂CONH₂ | O-iBu | H | O-iBu | O-iBu |

TABLE 10

Structure: biphenyl with X¹ linker and -CH=CH-COOR² (trans acrylate) chain.

| X¹ | R¹ | R² | R³ | R⁴ |
|---|---|---|---|---|
| C(O) | O-iBu | H | OH | O-iBu |
| C(O) | OH | H | O-iBu | O-iBu |
| C(O) | O-iBu | H | OCH₃ | O-iBu |
| C(O) | O-iBu | H | F | O-iBu |
| C(O) | O-iBu | H | OCO-iPr | O-iBu |
| C(O) | O-iBu | H | O(CH₂)₃COOH | O-iBu |
| C(O) | O-iBu | H | O(CH₂)₅CONH₂ | O-iBu |
| C=N—OH | O-iBu | H | O-iBu | O-iBu |
| C=N—OCH₂CH₂CH₃ | O-iBu | H | O-iBu | O-iBu |
| C=N—OCH₂COOH | O-iBu | H | O-iBu | O-iBu |
| C=N—OCH₂CONH₂ | O-iBu | H | O-iBu | O-iBu |
| C=N—OCH₂C₆H₅ | O-iBu | H | O-iBu | O-iBu |

TABLE 10-continued

| X¹ | R¹ | R² | R³ | R⁴ |
|---|---|---|---|---|
| C=N—OCH₂-3-Py | O-iBu | H | O-iBu | O-iBu |
| CHNHSO₂CH₃ | O-iBu | H | O-iBu | O-iBu |
| CHNHCOCH₃ | O-iBu | H | O-iBu | O-iBu |
| CHNHCONH₂ | O-iBu | H | O-iBu | O-iBu |
| C=CH—COOH | O-iBu | H | O-iBu | O-iBu |
| C=CH—COOC₂H₅ | O-iBu | H | O-iBu | O-iBu |
| CHCH₂COOH | O-iBu | H | O-iBu | O-iBu |
| CHCH₂CONH₂ | O-iBu | H | O-iBu | O-iBu |

TABLE 11

Structure: biphenyl with X¹ linker and -CH₂-CH=CH-COOR² chain.

| X¹ | R¹ | R² | R³ | R⁴ |
|---|---|---|---|---|
| C(O) | O-iBu | H | O-iBu | O-iBu |
| C(O) | O-iBu | CH₃ | O-iBu | O-iBu |
| C(O) | O-iBu | H | OH | O-iBu |
| C(O) | OH | H | O-iBu | O-iBU |
| C(O) | O-iBu | H | OCH₃ | O-iBu |
| C(O) | O-iBu | H | F | O-iBu |
| C(O) | O-iBu | H | OCO-iPr | O-iBu |
| C(O) | O-iBu | H | O(CH₂)₃COOH | O-iBu |
| C(O) | O-iBu | H | O(CH₂)₅CONH₂ | O-iBu |
| C=N—OH | O-iBu | H | O-iBu | O-iBu |
| C=N—OCH₂CH₂CH₃ | O-iBu | H | O-iBu | O-iBu |
| C=N—OCH₂CONH₂ | O-iBu | H | O-iBu | O-iBu |
| C=N—OCH₂C₆H₅ | O-iBu | H | O-iBu | O-iBu |
| C=N—OCH₂-3-Py | O-iBu | H | O-iBu | O-iBu |
| CHNHSO₂CH₃ | O-iBu | H | O-iBu | O-iBu |
| CHNHCOCH₃ | O-iBu | H | O-iBu | O-iBu |
| CHNHCONH₂ | O-iBu | H | O-iBu | O-iBu |
| C=CH—COOH | O-iBu | H | O-iBu | O-iBu |
| C=CH—COOC₂H₅ | O-iBu | H | O-iBu | O-iBu |
| CHCH₂COOH | O-iBu | H | O-iBu | O-iBu |
| CHCH₂CONH₂ | O-iBu | H | O-iBu | O-iBu |

TABLE 12

| n | $X^1$ | $R^1$ | $R^{26}$ | $R^3$ | $R^4$ |
|---|---|---|---|---|---|
| 2 | C(O) | O-iBu | $NHSO_2CH_3$ | O-iBu | O-iBu |
| 2 | C(O) | O-iBu | $NHSO_2CH_3$ | OH | O-iBu |
| 2 | C(O) | OH | $NHSO_2CH_3$ | O-iBu | O-iBu |
| 2 | C(O) | O-iBu | $NHSO_2CH_3$ | $OCH_3$ | O-iBu |
| 2 | C(O) | O-iBu | $NHSO_2CH_3$ | F | O-iBu |
| 2 | C(O) | O-iBu | $NHSO_2CH_3$ | OCO-iPr | O-iBu |
| 2 | C=N—OH | O-iBu | $NHSO_2CH_3$ | O-iBu | O-iBu |
| 2 | C=N—$OCH_2CH_2CH_3$ | O-iBu | $NHSO_2CH_3$ | O-iBu | O-iBu |
| 2 | C=N—$OCH_2CONH_2$ | O-iBu | $NHSO_2CH_3$ | O-iBu | O-iBu |
| 2 | C=N—$OCH_2C_6H_5$ | O-iBu | $NHSO_2CH_3$ | O-iBu | O-iBu |
| 2 | C=N—$OCH_2$-3-Py | O-iBu | $NHSO_2CH_3$ | O-iBu | O-iBu |
| 2 | $CHNHSO_2CH_3$ | O-iBu | $NHSO_2CH_3$ | O-iBu | O-iBu |
| 2 | $CHNHCOCH_3$ | O-iBu | $NHSO_2CH_3$ | O-iBu | O-iBu |
| 2 | $CHNHCONH_2$ | O-iBu | $NHSO_2CH_3$ | O-iBu | O-iBu |
| 2 | C=CH—COOH | O-iBu | $NHSO_2CH_3$ | O-iBu | O-iBu |
| 2 | C=CH—$COOC_2H_5$ | O-iBu | $NHSO_2CH_3$ | O-iBu | O-iBu |
| 2 | $CHCH_2COOH$ | O-iBu | $NHSO_2CH_3$ | O-iBu | O-iBu |
| 2 | $CHCH_2CONH_2$ | O-iBu | $NHSO_2CH_3$ | O-iBu | O-iBu |

TABLE 13

| $X^1$ | $R^1$ | $R^{26}$ | $R^3$ | $R^4$ |
|---|---|---|---|---|
| C(O) | O-iBu | $NHSO_2CH_3$ | OH | O-iBu |
| C(O) | O-iBu | $NHSO_2CH_3$ | $OCH_3$ | O-iBu |
| C(O) | O-iBu | $NHSO_2CH_3$ | OCO-iPr | O-iBu |
| C(O) | O-iBu | $NHSO_2CH_3$ | O-iBu | O-iBu |
| C=N—OH | O-iBu | $NHSO_2CH_3$ | O-iBu | O-iBu |
| C=N—$OCH_2CH_2CH_3$ | O-iBu | $NHSO_2CH_3$ | O-iBu | O-iBu |
| C=N—$OCH_2CONH_2$ | O-iBu | $NHSO_2CH_3$ | O-iBu | O-iBu |
| C=N—$OCH_2C_6H_5$ | O-iBu | $NHSO_2CH_3$ | O-iBu | O-iBu |
| C=N—$OCH_2$-3-Py | O-iBu | $NHSO_2CH_3$ | O-iBu | O-iBu |
| $CHNHSO_2CH_3$ | O-iBu | $NHSO_2CH_3$ | O-iBu | O-iBu |
| $CHNHCOCH_3$ | O-iBu | $NHSO_2CH_3$ | O-iBu | O-iBu |
| $CHNHCONH_2$ | O-iBu | $NHSO_2CH_3$ | O-iBu | O-iBu |
| C=CH—COOH | O-iBu | $NHSO_2CH_3$ | O-iBu | O-iBu |
| C=CH—$COOC_2H_5$ | O-iBu | $NHSO_2CH_3$ | O-iBu | O-iBu |
| $CHCH_2COOH$ | O-iBu | $NHSO_2CH_3$ | O-iBu | O-iBu |
| $CHCH_2CONH_2$ | O-iBu | $NHSO_2CH_3$ | O-iBu | O-iBu |

TABLE 14

| $X^1$ | $R^1$ | $R^{26}$ | $R^3$ | $R^4$ |
|---|---|---|---|---|
| C(O) | O-iBu | $NHSO_2CH_3$ | O-iBu | O-iBu |
| C(O) | O-iBu | $NHSO_2CH_3$ | OH | O-iBu |
| C(O) | O-iBu | $NHSO_2CH_3$ | $OCH_3$ | O-iBu |
| C(O) | O-iBu | $NHSO_2CH_3$ | F | O-iBu |
| C(O) | O-iBu | $NHSO_2CH_3$ | OCO-iPr | O-iBu |
| C=N—OH | O-iBu | $NHSO_2CH_3$ | O-iBu | O-iBu |
| C=N—$OCH_2CH_2CH_3$ | O-iBu | $NHSO_2CH_3$ | O-iBu | O-iBu |
| C=N—$OCH_2CONH_2$ | O-iBu | $NHSO_2CH_3$ | O-iBu | O-iBu |
| C=N—$OCH_2C_6H_5$ | O-iBu | $NHSO_2CH_3$ | O-iBu | O-iBu |
| C=N—$OCH_2$-3-Py | O-iBu | $NHSO_2CH_3$ | O-iBu | O-iBu |
| $CHNHSO_2CH_3$ | O-iBu | $NHSO_2CH_3$ | O-iBu | O-iBu |
| $CHNHCOCH_3$ | O-iBu | $NHSO_2CH_3$ | O-iBu | O-iBu |
| $CHNHCONH_2$ | O-iBu | $NHSO_2CH_3$ | O-iBu | O-iBu |
| C=CH—COOH | O-iBu | $NHSO_2CH_3$ | O-iBu | O-iBu |
| C=CH—$COOC_2H_5$ | O-iBu | $NHSO_2CH_3$ | O-iBu | O-iBu |
| $CHCH_2COOH$ | O-iBu | $NHSO_2CH_3$ | O-iBu | O-iBu |
| $CHCH_2CONH_2$ | O-iBu | $NHSO_2CH_3$ | O-iBu | O-iBu |

TABLE 15

| $X^1$ | $R^1$ | $R^{26}$ | $R^3$ | $R^4$ |
|---|---|---|---|---|
| $CH_2$ | O-iBu | $NHSO_2CH_3$ | O-iBu | O-iBu |
| C(O) | O-iBu | $NHSO_2CH_3$ | OH | O-iBu |
| C(O) | O-iBu | $NHSO_2CH_3$ | $OCH_3$ | O-iBu |
| C(O) | O-iBu | $NHSO_2CH_3$ | F | O-iBu |
| C(O) | O-iBu | $NHSO_2CH_3$ | OCO-iPr | O-iBu |
| C=N—OH | O-iBu | $NHSO_2CH_3$ | O-iBu | O-iBu |
| C=N—$OCH_2CH_2CH_3$ | O-iBu | $NHSO_2CH_3$ | O-iBu | O-iBu |
| C=N—$OCH_2CONH_2$ | O-iBu | $NHSO_2CH_3$ | O-iBu | O-iBu |
| C=N—$OCH_2C_6H_5$ | O-iBu | $NHSO_2CH_3$ | O-iBu | O-iBu |
| C=N—$OCH_2$-3-Py | O-iBu | $NHSO_2CH_3$ | O-iBu | O-iBu |
| $CHNHSO_2CH_3$ | O-iBu | $NHSO_2CH_3$ | O-iBu | O-iBu |
| $CHNHCOCH_3$ | O-iBu | $NHSO_2CH_3$ | O-iBu | O-iBu |
| $CHNHCONH_2$ | O-iBu | $NHSO_2CH_3$ | O-iBu | O-iBu |
| C=CH—COOH | O-iBu | $NHSO_2CH_3$ | O-iBu | O-iBu |
| C=CH—$COOC_2H_5$ | O-iBu | $NHSO_2CH_3$ | O-iBu | O-iBu |
| $CHCH_2COOH$ | O-iBu | $NHSO_2CH_3$ | O-iBu | O-iBu |
| $CHCH_2CONH_2$ | O-iBu | $NHSO_2CH_3$ | O-iBu | O-iBu |

TABLE 16

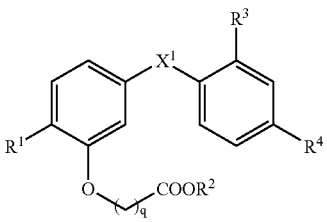

| q | X¹ | R¹ | R² | R³ | R⁴ |
|---|---|---|---|---|---|
| 1 | C(O) | O-iBu | H | O-iBu | O-iBu |
| 1 | C(O) | O-iBu | CH₃ | O-iBu | O-iBu |
| 1 | C(O) | O-iBu | H | OH | O-iBu |
| 1 | C(O) | OH | H | O-iBu | O-iBu |
| 1 | C(O) | O-iBu | H | OCH₃ | O-iBu |
| 1 | C(O) | O-iBu | H | F | O-iBu |
| 1 | C(O) | O-iBu | H | OCO-iPr | O-iBu |
| 1 | C=N—OH | O-iBu | H | O-iBu | O-iBu |
| 1 | C=N—OCH₂CH₃ | O-iBu | H | O-iBu | O-iBu |
| 1 | C=N—OCH₂CONH₂ | O-iBu | H | O-iBu | O-iBu |
| 1 | C=N—OCH₂C₆H₅ | O-iBu | H | O-iBu | O-iBu |
| 1 | C=N—OCH₂-3-Py | O-iBu | H | O-iBu | O-iBu |
| 1 | CHNHSO₂CH₃ | O-iBu | H | O-iBu | O-iBu |
| 1 | CHNHCOCH₃ | O-iBu | H | O-iBu | O-iBu |
| 1 | CHNHCONH₂ | O-iBu | H | O-iBu | O-iBu |
| 1 | C=CH—COOH | O-iBu | H | O-iBu | O-iBu |
| 1 | C=CH—COOC₂H₅ | O-iBu | H | O-iBu | O-iBu |
| 1 | CHCH₂COOH | O-iBu | H | O-iBu | O-iBu |
| 1 | CHCH₂CONH₂ | O-iBu | H | O-iBu | O-iBu |

TABLE 17

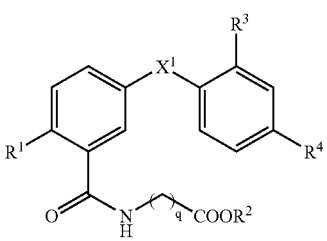

| q | X¹ | R¹ | R² | R³ | R⁴ |
|---|---|---|---|---|---|
| 1 | C(O) | O-iBu | H | O-iBu | O-iBu |
| 1 | C(O) | O-iBu | CH₃ | O-iBu | O-iBu |
| 1 | C(O) | O-iBu | H | OH | O-iBu |
| 1 | C(O) | OH | H | O-iBu | O-iBu |
| 1 | C(O) | O-iBu | H | OCH₃ | O-iBu |
| 1 | C(O) | O-iBu | H | F | O-iBu |
| 1 | C(O) | O-iBu | H | OCO-iPr | O-iBu |
| 1 | C=N—OH | O-iBu | H | O-iBu | O-iBu |
| 1 | C=N—OCH₂CH₃ | O-iBu | H | O-iBu | O-iBu |
| 1 | C=N—OCH₂CONH₂ | O-iBu | H | O-iBu | O-iBu |
| 1 | C=N—OCH₂C₆H₅ | O-iBu | H | O-iBu | O-iBu |
| 1 | C=N—OCH₂-3-Py | O-iBu | H | O-iBu | O-iBu |
| 1 | CHNHSO₂CH₃ | O-iBu | H | O-iBu | O-iBu |
| 1 | CHNHCOCH₃ | O-iBu | H | O-iBu | O-iBu |
| 1 | CHNHCONH₂ | O-iBu | H | O-iBu | O-iBu |
| 1 | C=CH—COOH | O-iBu | H | O-iBu | O-iBu |
| 1 | C=CH—COOC₂H₅ | O-iBu | H | O-iBu | O-iBu |
| 1 | CHCH₂COOH | O-iBu | H | O-iBu | O-iBu |
| 1 | CHCH₂CONH₂ | O-iBu | H | O-iBu | O-iBu |

TABLE 18

| q | X¹ᵃ | R¹ᵃ | R²ᵃ | R³ᵃ | R⁴ᵃ |
|---|---|---|---|---|---|
| 1 | C(O) | O-iBu | H | O-iBu | O-iBu |
| 2 | C(O) | O-iBu | CH₃ | O-iBu | O-iBu |
| 2 | C(O) | O-iBu | H | O-iBu | O-iBu |
| 2 | CH(OH) | O-iBu | H | O-iBu | O-iBu |
| 2 | CH₂ | O-iBu | H | O-iBu | O-iBu |
| 2 | C(O) | O-iBu | H | OCO-iPr | O-iBu |
| 2 | C=N—OH | O-iBu | H | O-iBu | O-iBu |
| 2 | C=N—OCH₂CH₃ | O-iBu | H | O-iBu | O-iBu |
| 2 | C=N—OCH₂CONH₂ | O-iBu | H | O-iBu | O-iBu |
| 2 | C=N—OCH₂C₆H₅ | O-iBu | H | O-iBu | O-iBu |
| 2 | C=N—OCH₂-3-Py | O-iBu | H | O-iBu | O-iBu |
| 2 | CHNHSO₂CH₃ | O-iBu | H | O-iBu | O-iBu |
| 2 | CHNHCOCH₃ | O-iBu | H | O-iBu | O-iBu |
| 2 | CHNHCONH₂ | O-iBu | H | O-iBu | O-iBu |
| 2 | C=CH—COOH | O-iBu | H | O-iBu | O-iBu |
| 2 | C=CH—COOC₂H₅ | O-iBu | H | O-iBu | O-iBu |
| 2 | CHCH₂COOH | O-iBu | H | O-iBu | O-iBu |
| 2 | CHCH₂CONH₂ | O-iBu | H | O-iBu | O-iBu |

TABLE 19

| X¹ᵃ | R¹ᵃ | R²ᵃ | R³ᵃ | R⁴ᵃ |
|---|---|---|---|---|
| C(O) | O-iBu | H | O-iBu | O-iBu |
| C(O) | O-iBu | CH₃ | O-iBu | O-iBu |
| CH(OH) | O-iBu | H | O-iBu | O-iBu |
| CH₂ | O-iBu | H | O-iBu | O-iBu |
| C=N—OH | O-iBu | H | O-iBu | O-iBu |
| C=N—OCH₂CH₃ | O-iBu | H | O-iBu | O-iBu |
| C=N—OCH₂CONH₂ | O-iBu | H | O-iBu | O-iBu |
| C=N—OCH₂C₆H₅ | O-iBu | H | O-iBu | O-iBu |
| C=N—OCH₂-3-Py | O-iBu | H | O-iBu | O-iBu |
| CHNHSO₂CH₃ | O-iBu | H | O-iBu | O-iBu |
| CHNHCOCH₃ | O-iBu | H | O-iBu | O-iBu |
| CHNHCONH₂ | O-iBu | H | O-iBu | O-iBu |
| C=CH—COOH | O-iBu | H | O-iBu | O-iBu |
| C=CH—COOC₂H₅ | O-iBu | H | O-iBu | O-iBu |
| CHCH₂COOH | O-iBu | H | O-iBu | O-iBu |
| CHCH₂CONH₂ | O-iBu | H | O-iBu | O-iBu |

TABLE 20

| $X^{1a}$ | $R^{1a}$ | $R^{2a}$ | $R^{3a}$ | $R^{4a}$ |
|---|---|---|---|---|
| C(O) | O-iBu | H | O-iBu | O-iBu |
| C(O) | O-iBu | $CH_3$ | O-iBu | O-iBu |
| CH(OH) | O-iBu | H | O-iBu | O-iBu |
| $CH_2$ | O-iBu | H | O-iBu | O-iBu |
| C(O) | O-iBu | H | OCO-iPr | O-iBu |
| C=N—OH | O-iBu | H | O-iBu | O-iBu |
| C=N—$OCH_2CH_3$ | O-iBu | H | O-iBu | O-iBu |
| C=N—$OCH_2CONH_2$ | O-iBu | H | O-iBu | O-iBu |
| C=N—$OCH_2C_6H_5$ | O-iBu | H | O-iBu | O-iBu |
| C=N—$OCH_2$-3-Py | O-iBu | H | O-iBu | O-iBu |
| $CHNHSO_2CH_3$ | O-iBu | H | O-iBu | O-iBu |
| $CHNHCOCH_3$ | O-iBu | H | O-iBu | O-iBu |
| $CHNHCONH_2$ | O-iBu | H | O-iBu | O-iBu |
| C=CH—COOH | O-iBu | H | O-iBu | O-iBu |
| C=CH—$COOC_2H_5$ | O-iBu | H | O-iBu | O-iBu |
| $CHCH_2COOH$ | O-iBu | H | O-iBu | O-iBu |
| $CHCH_2CONH_2$ | O-iBu | H | O-iBu | O-iBu |

TABLE 21

| $X^{1a}$ | $R^{1a}$ | $R^{2a}$ | $R^{3a}$ | $R^{4a}$ |
|---|---|---|---|---|
| C(O) | O-iBu | H | O-iBu | O-iBu |
| C(O) | O-iBu | $CH_3$ | O-iBu | O-iBu |
| CH(OH) | O-iBu | H | O-iBu | O-iBu |
| $CH_2$ | O-iBu | H | O-iBu | O-iBu |
| C(O) | O-iBu | H | OCO-iPr | O-iBu |
| C=N—OH | O-iBu | H | O-iBu | O-iBu |
| C=N—$OCH_2CH_3$ | O-iBu | H | O-iBu | O-iBu |
| C=N—$OCH_2CONH_2$ | O-iBu | H | O-iBu | O-iBu |
| C=N—$OCH_2C_6H_5$ | O-iBu | H | O-iBu | O-iBu |
| C=N—$OCH_2$-3-Py | O-iBu | H | O-iBu | O-iBu |
| $CHNHSO_2CH_3$ | O-iBu | H | O-iBu | O-iBu |
| $CHNHCOCH_3$ | O-iBu | H | O-iBu | O-iBu |
| $CHNHCONH_2$ | O-iBu | H | O-iBu | O-iBu |
| C=CH—COOH | O-iBu | H | O-iBu | O-iBu |
| C=CH—$COOC_2H_5$ | O-iBu | H | O-iBu | O-iBu |
| $CHCH_2COOH$ | O-iBu | H | O-iBu | O-iBu |
| $CHCH_2CONH_2$ | O-iBu | H | O-iBu | O-iBu |

TABLE 22

| $n^a$ | $X^{1a}$ | $R^{1a}$ | $R^{2a}$ | $R^{3a}$ | $R^{4a}$ |
|---|---|---|---|---|---|
| 2 | C(O) | O-iBu | $NHSO_2CH_3$ | O-iBu | O-iBu |
| 2 | C(O) | O-iBu | $NHSO_2CH_3$ | OCO-iPr | O-iBu |
| 2 | C=N—OH | O-iBu | $NHSO_2CH_3$ | O-iBu | O-iBu |
| 2 | C=N—$OCH_2CH_3$ | O-iBu | $NHSO_2CH_3$ | O-iBu | O-iBu |
| 2 | C=N—$OCH_2CONH_2$ | O-iBu | $NHSO_2CH_3$ | O-iBu | O-iBu |
| 2 | C=N—$OCH_2C_6H_5$ | O-iBu | $NHSO_2CH_3$ | O-iBu | O-iBu |
| 2 | C=N—$OCH_2$-3-Py | O-iBu | $NHSO_2CH_3$ | O-iBu | O-iBu |
| 2 | $CHNHSO_2CH_3$ | O-iBu | $NHSO_2CH_3$ | O-iBu | O-iBu |
| 2 | $CHNHCOCH_3$ | O-iBu | $NHSO_2CH_3$ | O-iBu | O-iBu |
| 2 | $CHNHCONH_2$ | O-iBu | $NHSO_2CH_3$ | O-iBu | O-iBu |
| 2 | C=CH—COOH | O-iBu | $NHSO_2CH_3$ | O-iBu | O-iBu |
| 2 | C=CH—$COOC_2H_5$ | O-iBu | $NHSO_2CH_3$ | O-iBu | O-iBu |
| 2 | $CHCH_2COOH$ | O-iBu | $NHSO_2CH_3$ | O-iBu | O-iBu |
| 2 | $CHCH_2CONH_2$ | O-iBu | $NHSO_2CH_3$ | O-iBu | O-iBu |

TABLE 23

| $X^{1a}$ | $R^{1a}$ | $R^{26a}$ | $R^{3a}$ | $R^{4a}$ |
|---|---|---|---|---|
| C(O) | O-iBu | $NHSO_2CH_3$ | O-iBu | O-iBu |
| CH(OH) | O-iBu | $NHSO_2CH_3$ | O-iBu | O-iBu |
| $CH_2$ | O-iBu | $NHSO_2CH_3$ | O-iBu | O-iBu |
| C(O) | O-iBu | $NHSO_2CH_3$ | OCO-iPr | O-iBu |
| C=N—OH | O-iBu | $NHSO_2CH_3$ | O-iBu | O-iBu |
| C=N—$OCH_2CH_3$ | O-iBu | $NHSO_2CH_3$ | O-iBu | O-iBu |
| C=N—$OCH_2CONH_2$ | O-iBu | $NHSO_2CH_3$ | O-iBu | O-iBu |
| C=N—$OCH_2C_6H_5$ | O-iBu | $NHSO_2CH_3$ | O-iBu | O-iBu |
| C=N—$OCH_2$-3-Py | O-iBu | $NHSO_2CH_3$ | O-iBu | O-iBu |
| $CHNHSO_2CH_3$ | O-iBu | $NHSO_2CH_3$ | O-iBu | O-iBu |
| $CHNHCOCH_3$ | O-iBu | $NHSO_2CH_3$ | O-iBu | O-iBu |
| $CHNHCONH_2$ | O-iBu | $NHSO_2CH_3$ | O-iBu | O-iBu |
| C=CH—COOH | O-iBu | $NHSO_2CH_3$ | O-iBu | O-iBu |
| C=CH—$COOC_2H_5$ | O-iBu | $NHSO_2CH_3$ | O-iBu | O-iBu |
| $CHCH_2COOH$ | O-iBu | $NHSO_2CH_3$ | O-iBu | O-iBu |
| $CHCH_2CONH_2$ | O-iBu | $NHSO_2CH_3$ | O-iBu | O-iBu |

TABLE 24

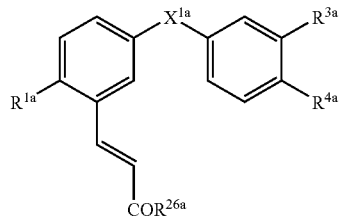

| $X^{1a}$ | $R^{1a}$ | $R^{26a}$ | $R^{3a}$ | $R^{4a}$ |
|---|---|---|---|---|
| C(O) | O-iBu | NHSO$_2$CH$_3$ | O-iBu | O-iBu |
| CH(OH) | O-iBu | NHSO$_2$CH$_3$ | O-iBu | O-iBu |
| CH$_2$ | O-iBu | NHSO$_2$CH$_3$ | O-iBu | O-iBu |
| C(O) | O-iBu | NHSO$_2$CH$_3$ | OCO-iPr | O-iBu |
| C=N—OH | O-iBu | NHSO$_2$CH$_3$ | O-iBu | O-iBu |
| C=N—OCH$_2$CH$_2$CH$_3$ | O-iBu | NHSO$_2$CH$_3$ | O-iBu | O-iBu |
| C=N—OCH$_2$CONH$_2$ | O-iBu | NHSO$_2$CH$_3$ | O-iBu | O-iBu |
| C=N—OCH$_2$C$_6$H$_5$ | O-iBu | NHSO$_2$CH$_3$ | O-iBu | O-iBu |
| C=N—OCH$_2$-3-Py | O-iBu | NHSO$_2$CH$_3$ | O-iBu | O-iBu |
| CHNHSO$_2$CH$_3$ | O-iBu | NHSO$_2$CH$_3$ | O-iBu | O-iBu |
| CHNHCOCH$_3$ | O-iBu | NHSO$_2$CH$_3$ | O-iBu | O-iBu |
| CHNHCONH$_2$ | O-iBu | NHSO$_2$CH$_3$ | O-iBu | O-iBu |
| C=CH—COOH | O-iBu | NHSO$_2$CH$_3$ | O-iBu | O-iBu |
| C=CH—COOC$_2$H$_5$ | O-iBu | NHSO$_2$CH$_3$ | O-iBu | O-iBu |
| CHCH$_2$COOH | O-iBu | NHSO$_2$CH$_3$ | O-iBu | O-iBu |
| CHCH$_2$CONH$_2$ | O-iBu | NHSO$_2$CH$_3$ | O-iBu | O-iBu |

TABLE 25

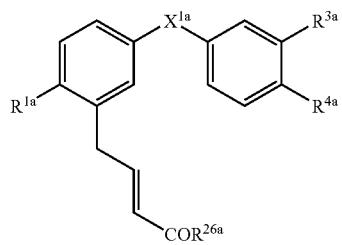

| $X^{1a}$ | $R^{1a}$ | $R^{26a}$ | $R^{3a}$ | $R^{4a}$ |
|---|---|---|---|---|
| C(O) | O-iBu | NHSO$_2$CH$_3$ | O-iBu | O-iBu |
| CH(OH) | O-iBu | NHSO$_2$CH$_3$ | O-iBu | O-iBu |
| CH$_2$ | O-iBu | NHSO$_2$CH$_3$ | O-iBu | O-iBu |
| C(O) | O-iBu | NHSO$_2$CH$_3$ | OCO-iPr | O-iBu |
| C=N—OH | O-iBu | NHSO$_2$CH$_3$ | O-iBu | O-iBu |
| C=N—OCH$_2$CH$_2$CH$_3$ | O-iBu | NHSO$_2$CH$_3$ | O-iBu | O-iBu |
| C=N—OCH$_2$CONH$_2$ | O-iBu | NHSO$_2$CH$_3$ | O-iBu | O-iBu |
| C=N—OCH$_2$C$_6$H$_5$ | O-iBu | NHSO$_2$CH$_3$ | O-iBu | O-iBu |
| C=N—OCH$_2$-3-Py | O-iBu | NHSO$_2$CH$_3$ | O-iBu | O-iBu |
| CHNHSO$_2$CH$_3$ | O-iBu | NHSO$_2$CH$_3$ | O-iBu | O-iBu |
| CHNHCOCH$_3$ | O-iBu | NHSO$_2$CH$_3$ | O-iBu | O-iBu |
| CHNHCONH$_2$ | O-iBu | NHSO$_2$CH$_3$ | O-iBu | O-iBu |
| C=CH—COOH | O-iBu | NHSO$_2$CH$_3$ | O-iBu | O-iBu |
| C=CH—COOC$_2$H$_5$ | O-iBu | NHSO$_2$CH$_3$ | O-iBu | O-iBu |
| CHCH$_2$COOH | O-iBu | NHSO$_2$CH$_3$ | O-iBu | O-iBu |
| CHCH$_2$CONH$_2$ | O-iBu | NHSO$_2$CH$_3$ | O-iBu | O-iBu |

TABLE 26

| q | $X^{1a}$ | $R^{1a}$ | $R^{2a}$ | $R^{3a}$ | $R^{4a}$ |
|---|---|---|---|---|---|
| 1 | C(O) | O-iBu | H | O-iBu | O-iBu |
| 1 | C(O) | O-iBu | CH$_3$ | O-iBu | O-iBu |
| 1 | CH(OH) | O-iBu | H | O-iBu | O-iBu |
| 1 | CH$_2$ | O-iBu | H | O-iBu | O-iBu |
| 1 | C(O) | O-iBu | H | OCO-iPr | O-iBu |
| 1 | C=N—OH | O-iBu | H | O-iBu | O-iBu |
| 1 | C=N—OCH$_2$CH$_2$CH$_3$ | O-iBu | H | O-iBu | O-iBu |
| 1 | C=N—OCH$_2$CONH$_2$ | O-iBu | H | O-iBu | O-iBu |
| 1 | C=N—OCH$_2$C$_6$H$_5$ | O-iBu | H | O-iBu | O-iBu |
| 1 | C=N—OCH$_2$-3-Py | O-iBu | H | O-iBu | O-iBu |
| 1 | CHNHSO$_2$CH$_3$ | O-iBu | H | O-iBu | O-iBu |
| 1 | CHNHCOCH$_3$ | O-iBu | H | O-iBu | O-iBu |
| 1 | CHNHCONH$_2$ | O-iBu | H | O-iBu | O-iBu |
| 1 | C=CH—COOH | O-iBu | H | O-iBu | O-iBu |
| 1 | C=CH—COOC$_2$H$_5$ | O-iBu | H | O-iBu | O-iBu |
| 1 | CHCH$_2$COOH | O-iBu | H | O-iBu | O-iBu |
| 1 | CHCH$_2$CONH$_2$ | O-iBu | H | O-iBu | O-iBu |

TABLE 27

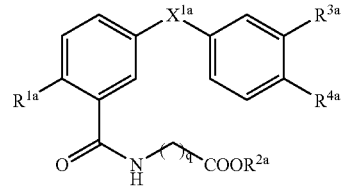

| q | $X^{1a}$ | $R^{1a}$ | $R^{2a}$ | $R^{3a}$ | $R^{4a}$ |
|---|---|---|---|---|---|
| 1 | C(O) | O-iBu | H | O-iBu | O-iBu |
| 1 | C(O) | O-iBu | CH$_3$ | O-iBu | O-iBu |
| 2 | C(O) | O-iBu | H | O-iBu | O-iBu |
| 1 | CH(OH) | O-iBu | H | O-iBu | O-iBu |
| 1 | CH$_2$ | O-iBu | H | O-iBu | O-iBu |
| 1 | C(O) | O-iBu | H | OCO-iPr | O-iBu |
| 1 | C=N—OH | O-iBu | H | O-iBu | O-iBu |
| 1 | C=N—OCH$_2$CH$_2$CH$_3$ | O-iBu | H | O-iBu | O-iBu |
| 1 | C=N—OCH$_2$CONH$_2$ | O-iBu | H | O-iBu | O-iBu |
| 1 | C=N—OCH$_2$C$_6$H$_5$ | O-iBu | H | O-iBu | O-iBu |
| 1 | C=N—OCH$_2$-3-Py | O-iBu | H | O-iBu | O-iBu |
| 1 | CHNHSO$_2$CH$_3$ | O-iBu | H | O-iBu | O-iBu |
| 1 | CHNHCOCH$_3$ | O-iBu | H | O-iBu | O-iBu |
| 1 | CHNHCONH$_2$ | O-iBu | H | O-iBu | O-iBu |
| 1 | C=CH—COOH | O-iBu | H | O-iBu | O-iBu |
| 1 | C=CH—COOC$_2$H$_5$ | O-iBu | H | O-iBu | O-iBu |
| 1 | CHCH$_2$COOH | O-iBu | H | O-iBu | O-iBu |
| 1 | CHCH$_2$CONH$_2$ | O-iBu | H | O-iBu | O-iBu |

TABLE 28

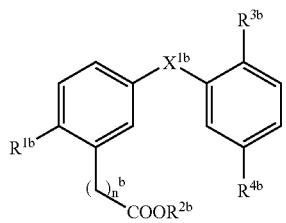

| $n^b$ | $X^{1b}$ | $R^{1b}$ | $R^{2b}$ | $R^{3b}$ | $R^{4b}$ |
|---|---|---|---|---|---|
| 0 | C(O) | OCH$_2$C$_6$H$_5$ | H | OCH$_2$C$_6$H$_5$ | OCH$_2$C$_6$H$_5$ |
| 1 | C(O) | O-iBu | H | O-iBu | O-iBu |
| 2 | C(O) | O-iBu | H | O-iBu | O-iBu |
| 2 | C(O) | O-iBu | CH$_2$CH$_3$ | O-iBu | O-iBu |
| 1 | C(O) | CHCHC$_6$H$_5$ | H | CHCHC$_6$H$_5$ | CHCHC$_6$H$_5$ |
| 1 | C(O) | C$_6$H$_{11}$ | H | C$_6$H$_{11}$ | C$_6$H$_{11}$ |
| 1 | C(O) | CH$_2$C$_6$H$_5$ | H | CH$_2$C$_6$H$_5$ | CH$_2$C$_6$H$_5$ |
| 1 | C(O) | O-iBu | H | COOC$_2$H$_5$ | COOC$_2$H$_5$ |
| 2 | CH(OH) | O-iBu | H | O-iBu | O-iBu |
| 2 | CH$_2$ | O-iBu | H | O-iBu | O-iBu |
| 2 | CH$_2$ | NHC(O)-iPr | H | NHC(O)-iPr | NHC(O)-iPr |
| 2 | C(O) | NHC(O)-iPr | H | NHC(O)-iPr | NHC(O)-iPr |
| 2 | CH(OH) | NHC(O)-iPr | H | NHC(O)-iPr | NHC(O)-iPr |
| 2 | C(O) | O-iBu | H | OCO-iPr | O-iBu |

TABLE 29

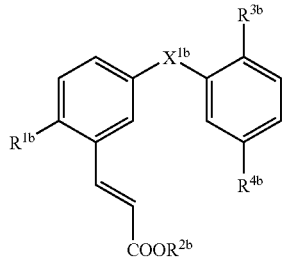

| $X^{1b}$ | $R^{1b}$ | $R^{2b}$ | $R^{3b}$ | $R^{4b}$ |
|---|---|---|---|---|
| C(O) | O-iBu | CH$_3$ | O-iBu | O-iBu |
| CH(OH) | O-iBu | H | O-iBu | O-iBu |
| CH$_2$ | O-iBu | CH$_3$ | O-iBu | O-iBu |
| C(O) | NHC(O)-iPr | H | NHC(O)-iPr | NHC(O)-iPr |
| C(O) | O-iBu | H | OCO-iPr | O-iBu |

TABLE 30

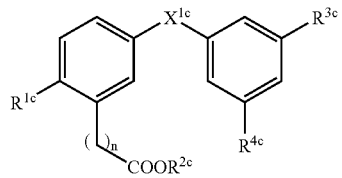

| n | $X^{1c}$ | $R^{1c}$ | $R^{2c}$ | $R^{3c}$ | $R^{4c}$ |
|---|---|---|---|---|---|
| 1 | C(O) | O-iBu | H | O-iBu | O-iBu |
| 2 | C(O) | O-iBu | H | O-iBu | O-iBu |
| 2 | C(O) | O-iBu | CH$_2$CH$_3$ | O-iBu | O-iBu |
| 2 | CH$_2$ | O-iBu | H | O-iBu | O-iBu |
| 2 | C(O) | NHC(O)-iBu | H | NHC(O)-iBu | NHC(O)-iBu |
| 2 | C(O) | O-iBu | H | OCO-iPr | O-iBu |

TABLE 31

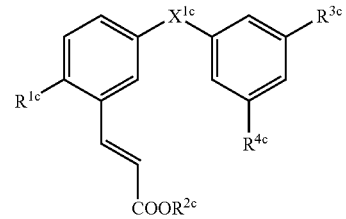

| $X^{1c}$ | $R^{1c}$ | $R^{2c}$ | $R^{3c}$ | $R^{4c}$ |
|---|---|---|---|---|
| C(O) | O-iBu | H | O-iBu | O-iBu |
| C(O) | O-iBu | CH$_3$ | O-iBu | O-iBu |
| CH$_2$ | O-iBu | H | O-iBu | O-iBu |
| C(O) | NHC(O)-iBu | H | NHC(O)-iBu | NHC(O)-iBu |
| C(O) | O-iBu | H | OCO-iPr | O-iBu |

TABLE 32

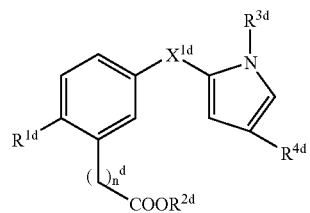

| $n^d$ | $X^{1d}$ | $R^{1d}$ | $R^{2d}$ | $R^{3d}$ | $R^{4d}$ |
|---|---|---|---|---|---|
| 1 | C(O) | C$_6$H$_{11}$ | H | iAm | CO-iBu |
| 1 | C(O) | C$_6$H$_5$ | H | iAm | CO-iBu |
| 1 | C(O) | CH$_2$C$_6$H$_5$ | H | iAm | CO-iBu |
| 1 | C(O) | OC$_6$H$_5$ | H | iAm | CO-iBu |
| 1 | C(O) | S-iBu | H | iAm | CO-iBu |
| 1 | C(O) | 2-Py | H | iAm | CO-iBu |
| 1 | C(O) | CO-iBu | H | C$_6$H$_{11}$ | CO-iBu |
| 1 | C(O) | CO-iBu | H | C$_6$H$_5$ | CO-iBu |
| 1 | C(O) | CO-iBu | H | CH$_2$C$_6$H$_5$ | CO-iBu |
| 1 | C(O) | CO-iBu | H | iAm | CH$_2$C$_6$H$_5$ |
| 1 | C(O) | CO-iBu | H | iAm | C$_6$H$_{11}$ |
| 1 | C(O) | CO-iBu | H | iAm | NHSO$_2$C$_6$H$_5$ |
| 2 | C(O) | O-iAm | H | iAm | CO-iBu |
| 2 | CH(OH) | CO-iBu | H | iAm | CO-iBu |
| 2 | CH$_2$ | CO-iBu | H | iAm | CO-iBu |
| 2 | C(O) | O-iAm | CH$_3$ | iAm | CO-iBu |

TABLE 33

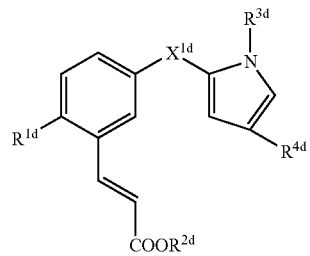

| $X^{1d}$ | $R^{1d}$ | $R^{2d}$ | $R^{3d}$ | $R^{4d}$ |
|---|---|---|---|---|
| C(O) | CH$_2$C$_6$H$_5$ | H | iAm | CO-iBu |
| C(O) | C$_6$H$_{11}$ | H | iAm | CO-iBu |
| C(O) | C$_6$H$_5$ | H | iAm | CO-iBu |
| C(O) | OC$_6$H$_5$ | H | iAm | CO-iBu |
| C(O) | S-iBu | H | iAm | CO-iBu |
| C(O) | NHSO$_2$C$_6$H$_5$ | H | iAm | CO-iBu |

TABLE 33-continued

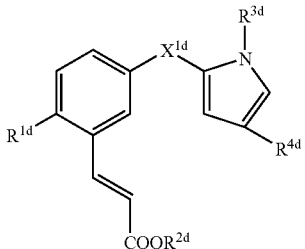

| X$^{1d}$ | R$^{1d}$ | R$^{2d}$ | R$^{3d}$ | R$^{4d}$ |
|---|---|---|---|---|
| C(O) | 2-Py | H | iAm | CO-iBu |
| C(O) | CO-iBu | H | C$_6$H$_{11}$ | CO-iBu |
| C(O) | CO-iBu | H | C$_6$H$_5$ | CO-iBu |
| C(O) | CO-iBu | H | CH$_2$C$_6$H$_5$ | CO-iBu |
| C(O) | CO-iBu | H | iAm | CH$_2$C$_6$H$_5$ |
| C(O) | CO-iBu | H | iAm | C$_6$H$_{11}$ |
| C(O) | CO-iBu | H | iAm | C$_6$H$_5$ |
| C(O) | CO-iBu | H | iAm | NHSO$_2$C$_6$H$_5$ |
| CH(OH) | CO-iBu | H | iAm | CO-iBu |
| CH$_2$ | CO-iBu | H | iAm | CO-iBu |
| C(O) | CO-iBu | CH$_3$ | iAm | CO-iBu |

TABLE 34

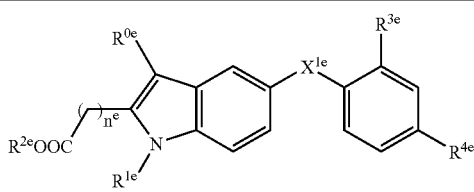

| n$^e$ | X$^{1e}$ | R$^{0e}$ | R$^{1e}$ | R$^{2e}$ | R$^{3e}$ | R$^{4e}$ |
|---|---|---|---|---|---|---|
| 0 | C(O) | H | iBu | H | O-iBu | O-iBu |
| 0 | C(O) | H | iBu | CH$_3$ | O-iBu | O-iBu |
| 0 | C(O) | Br | iBu | H | O-iBu | O-iBu |
| 1 | C(O) | NO$_2$ | iBu | H | O-iBu | O-iBu |
| 1 | C(O) | COCH$_3$ | iBu | H | O-iBu | O-iBu |
| 1 | C(O) | COOCH$_3$ | iBu | H | O-iBu | O-iBu |
| 1 | C(O) | NHSO$_2$CH$_3$ | iBu | H | O-iBu | O-iBu |
| 0 | CH(OH) | H | iBu | H | O-iBu | O-iBu |
| 0 | CH$_2$ | H | iBu | H | O-iBu | O-iBu |
| 1 | C(O) | H | CH$_2$C$_6$H$_5$ | H | O-iBu | CO-iBu |
| 1 | C(O) | H | C$_6$H$_{11}$ | H | O-iBu | CO-iBu |
| 1 | C(O) | H | C$_6$H$_5$ | H | O-iBu | CO-iBu |
| 1 | C(O) | H | iBu | H | O-iBu | C$_6$H$_5$ |
| 1 | C(O) | H | iBu | H | OCH$_3$ | CH$_2$C$_6$H$_5$ |
| 1 | C(O) | H | iBu | H | O-iBu | OC$_6$H$_5$ |
| 1 | C(O) | H | iBu | H | O-iBu | S-iBu |
| 1 | C(O) | H | iBu | H | O-iBu | NHSO$_2$CH$_3$ |
| 1 | C(O) | H | iBu | H | O-iBu | 2-Py |

TABLE 35

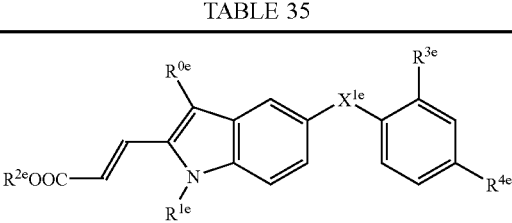

| X$^{1e}$ | R$^{0e}$ | R$^{1e}$ | R$^{2e}$ | R$^{3e}$ | R$^{4e}$ |
|---|---|---|---|---|---|
| C(O) | H | iBu | H | O-iBu | O-iBu |
| C(O) | H | iBu | CH$_3$ | O-iBu | O-iBu |

TABLE 35-continued

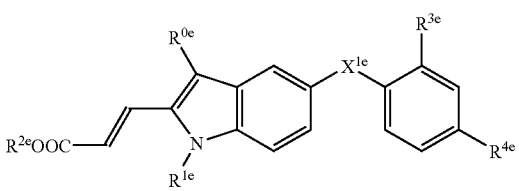

| X$^{1e}$ | R$^{0e}$ | R$^{1e}$ | R$^{2e}$ | R$^{3e}$ | R$^{4e}$ |
|---|---|---|---|---|---|
| CH(OH) | H | iBu | H | O-iBu | O-iBu |
| CH$_2$ | H | iBu | H | O-iBu | O-iBu |
| C(O) | Cl | iBu | H | O-iBu | O-iBu |
| C(O) | H | CH$_2$C$_6$H$_5$ | H | O-iBu | CO-iBu |
| C(O) | H | C$_6$H$_{11}$ | H | O-iBu | CO-iBu |
| C(O) | H | C$_6$H$_5$ | H | O-iBu | CO-iBu |
| C(O) | H | iBu | H | O-iBu | C$_6$H$_{11}$ |
| C(O) | H | iBu | H | O-iBu | CH$_2$C$_6$H$_5$ |
| C(O) | H | iBu | H | O-iBu | S-iBu |
| C(O) | H | iBu | H | O-iBu | NHSO$_2$CH$_3$ |
| C(O) | H | iBu | H | O-iBu | 2-Py |

TABLE 36

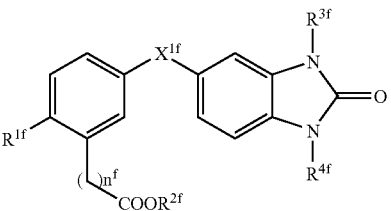

| n$^f$ | X$^{1f}$ | R$^{1f}$ | R$^{2f}$ | R$^{3f}$ | R$^{4f}$ |
|---|---|---|---|---|---|
| 1 | C(O) | CH$_2$C$_6$H$_5$ | H | iAm | iAm |
| 1 | C(O) | C$_6$H11 | H | iAm | iAm |
| 1 | C(O) | C$_6$H$_5$ | H | iAm | iAm |
| 1 | C(O) | O-iAm | H | iAm | iAm |
| 1 | C(O) | OC$_6$H$_5$ | H | iAm | iAm |
| 1 | C(O) | S-iBu | H | iAm | iAm |
| 1 | C(O) | NHSO$_2$C$_6$H$_5$ | H | iAm | iAm |
| 1 | CH(OH) | O-iBu | H | iAm | iAm |
| 1 | CH$_2$ | O-iBu | H | iAm | iAm |
| 1 | C(O) | O-iBu | H | CH$_2$C$_6$H$_5$ | CH$_2$C$_6$H$_5$ |
| 1 | C(O) | O-iBu | H | C$_6$H$_{11}$ | iAm |
| 1 | C(O) | O-iBu | H | CH$_2$C$_6$H$_5$ | iAm |

TABLE 37

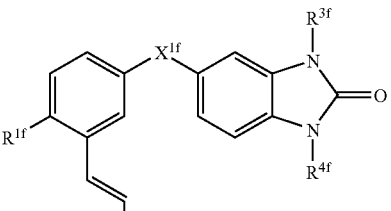

| X$^{1f}$ | R$^{1f}$ | R$^{2f}$ | R$^{3f}$ | R$^{4f}$ |
|---|---|---|---|---|
| C(O) | CH$_2$C$_6$H$_5$ | H | iAm | iAm |
| C(O) | C$_6$H$_{11}$ | H | iAm | iAm |

TABLE 37-continued

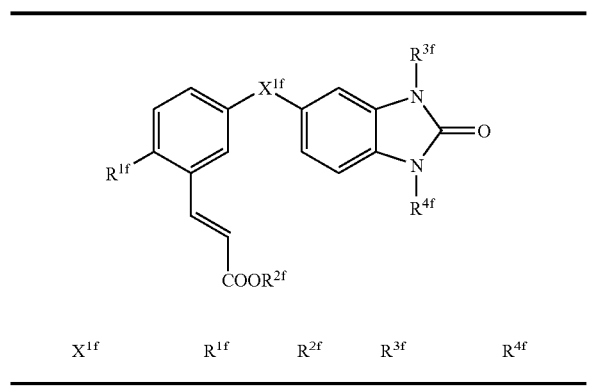

| $X^{1f}$ | $R^{1f}$ | $R^{2f}$ | $R^{3f}$ | $R^{4f}$ |
|---|---|---|---|---|
| C(O) | $C_6H_5$ | H | iAm | iAm |
| C(O) | $OC_6H_5$ | H | iAm | iAm |
| C(O) | S-iBu | H | iAm | iAm |
| C(O) | $NHSO_2C_6H_5$ | H | iAm | iAm |
| C(O) | O-iBu | H | iAm | iAm |
| C(O) | O-iBu | H | $CH_2C_6H_5$ | $CH_2C_6H_5$ |
| C(O) | O-iBu | H | $C_6H_{11}$ | iAm |
| C(O) | O-iBu | H | $C_6H_5$ | iAm |
| C(O) | O-iBu | H | $CH_2C_6H_5$ | iAm |

TABLE 37-continued

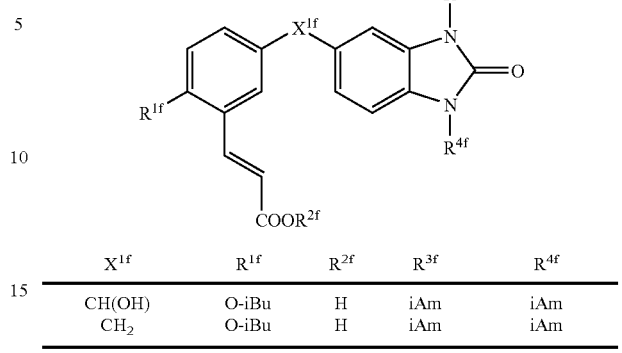

| $X^{1f}$ | $R^{1f}$ | $R^{2f}$ | $R^{3f}$ | $R^{4f}$ |
|---|---|---|---|---|
| CH(OH) | O-iBu | H | iAm | iAm |
| $CH_2$ | O-iBu | H | iAm | iAm |

In cases where the compounds conforming to the pharmacophore of formula 1, the compounds of general formulas [2], [2b], [3], [4], [5], [a], [b], [c], [d], [e], [f] and [g] or salts of these compounds have isomers such as optical isomers, geometrical isomers and tautomers, this invention involves these isomers, too, and involves solvated products, hydrated products and crystal of various forms, too.

Next, processes for producing the compounds of this invention will be explained.

The compound of this invention are produced by combining the processes which are well known in themselves, and, for example, according to the Production Processes 1 to 20.

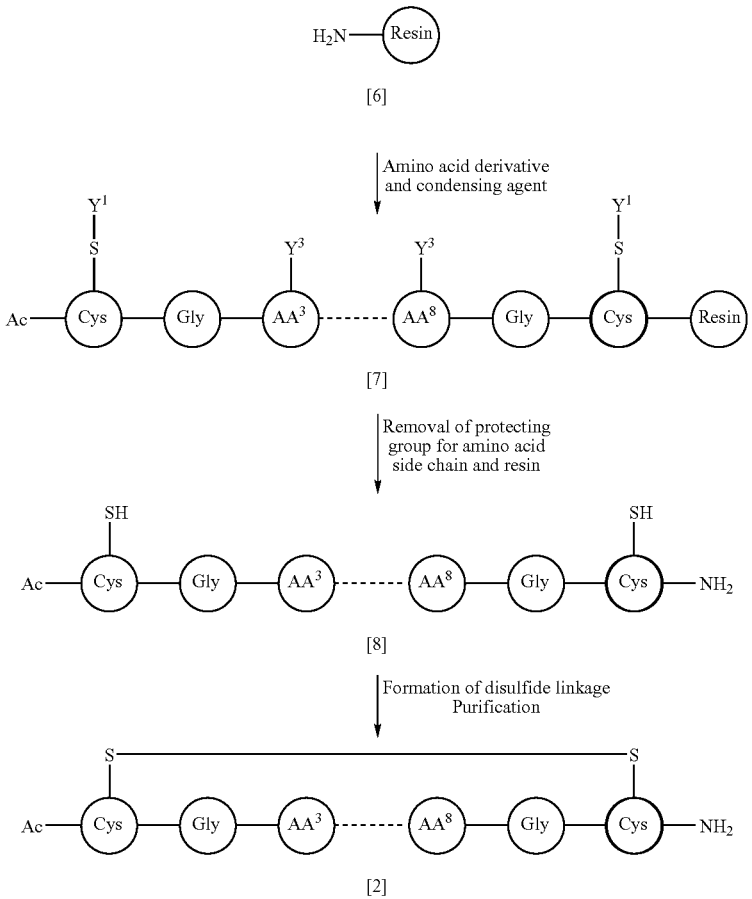

wherein AA³ and AA⁸ are as defined above, Ac is acetyl group, $Y^1$ is an optionally used protecting group for cysteine, and $Y^3$ and $Y^8$ independently represent a protecting group for functional group in the side chain of amino acid, provided that amino acid residues are expressed according to the three letters expression prescribed in IUPAC and IUB.

The peptide of this invention is produced by a liquid phase method or a solid phase method according to a combination of methods which are well known in themselves (Izumiya et al., Fundamentals and Experiments of Peptide Syntheses, Pages 194-283, published by Maruzen Shuppan).

The peptide-bonded resin of general formula [7; SEQ ID NO:1] can be obtained by subjecting the resin of general formula [6] to a solid phase method. The construction of peptide chain by solid phase method is carried out by repeating a condensation of amino acid having an amino-acid functional group protected with appropriate protecting group and de-protection of the protecting group of α-amino acid. Condensation of amino acid is carried out successively one by one from the terminal amino acid according to the order of amino acids in the sequence to be synthesized. The procedure of the solid phase method will be mentioned below. A series of reactions used therein are preferably carried out in an atmosphere of nitrogen. Any of the manual method and the method of using an automatic synthesizing apparatus may be adopted.

(1) A peptide-bonded resin having a protected N terminal can be obtained by condensing a resin with an amino acid derivative. Concretely speaking, a resin is introduced into a reactor, and a solvent is added to swell the resin. After filtering off the solvent, an amino acid derivative and a condensing agent are added, a solvent is again added, and a reaction is carried out.

As the resin of general formula [6] used in this reaction, those resins which are conventionally used in the solid phase method can be referred to. Examples thereof include benzhydrylamine resin, 4-methylbenzhydrylamine resin, Rink amide resin and the like. The solvents used in this reaction include N,N-dimethylformamide, dichloromethane, chloroform, N-methylpyrrolidone and the like. Although the amount of the solvent is not critical, it is 5-100 ml and preferably 5-20 ml per gram of resin when the solvent is used for swelling a resin, and the amount of solvent is 5-100 ml and preferably 5-50 ml per gram of resin when the solvent is used for reaction. The amino acid derivatives used in this reaction are those in which α-amino acid is protected with t-butyloxycarbonyl group (Boc), 9-fluorenylmethoxy-carbonyl (Fmoc) or the like. The protecting groups for functional group in side chain are as follows. Thus, for protecting the side chain carboxyl group of aspartic acid and glutamic acid, t-butyl ester group, benzyl ester group, cyclohexyl ester group and the like are used. For protecting the side chain hydroxyl group of serine, threonine and tyrosine, t-butyl group, benzyl group, 2,6-dibromobenzyl group and the like are used. For protecting the side chain thiol group of cysteine, trityl group, acetamidomethyl group, t-butyl group and the like are used. Preferable amino acid derivative is Fmoc-amino acid. As the condensing agents which can be used in this reaction, dicyclohexylcarbodiimide, diisopropylcarbodiimide, benzotriazole-1-yl-oxy-tris-pyrrolidino-phosphonium hexafluorophosphate (PyBOP), bromo-tris-pyrrolidino-phosphonium hexafluorophosphate (PyBROP) and the like can be referred to. The condensing agent may be used in an amount of 1-10 equivalents per equivalent of amino group in the resin. When PyBOP or PyBROP is used, an amine such as diisopropylethylamine, triethylamine or the like may be added in an amount of 1-5 equivalents per equivalent of the condensing agent. Further, an active ester-forming agent such as N-hydroxybenzotriazole, N-hydroxy-7-azabenzotriazole or the like may be added in an amount of 0.5-2 equivalents per equivalent of the condensing agent. The reaction is carried out usually at 10-40° C. and preferably 20-30° C., for a period of 5-120 minutes.

(2) The peptide of which N terminal is de-protected can be obtained by reacting the α-amino protecting group of peptide-bonded resin having a protected N terminal in the presence of de-protecting agent to eliminate the protecting group. Concretely speaking, a peptide-bonded resin of which N terminal is protected is reacted with an acid or a base in the presence or absence of a solvent.

The de-protecting agent used in this reaction is appropriately selected in accordance with the kind of α-amino protecting group. When the protecting group of α-amino group is Boc group, an acid such as trifluoroacetic acid, methanesulfonic acid or the like is used. When the protecting group is Fmoc group, a base such as piperidine, 1,8-diazabicyclo[5.4.0]undec-7-ene or the like is used. The solvents used in this reaction are not limited so far as they exercise no adverse influence upon the reaction. When an acid is used, dichloromethane, dichloroethane and the like are used. When a base is used, N,N-dimethylformamide, N-methylpyrrolidone and the like are used. In a case where a solvent is used, the solvent is used in an amount of 5-20 ml per gram of the resin. The reaction is carried out usually at 10-40° C. and preferably 20-30° C., for a period of 5-120 minutes.

(3) Peptide-bonded resins having ten residues can be obtained by repeating the procedure of (1) or (2) ten times on the peptide-bonded resin obtained above.

(4) The peptide of general formula (7; SEQ ID NO:1) can be obtained by acetylating a peptide-bonded resin having 10 residues. Concretely, it can be obtained by reacting a peptide-bonded resin of 10 residues with acetic anhydride in the presence or absence of an amine.

In this reaction, acetic anhydride is used in an amount of 1-20 equivalents and preferably 5-10 equivalents per equivalent of amino group in the resin. As the amine used in this reaction according to the need, diisopropylamine, triethylamine and the like can be referred to, and the amount thereof is 0.2-2 equivalents per equivalent of acetic anhydride. Although the solvent used in this reaction is not particularly limited so far as it exercises no adverse influence upon the reaction, N,N-dimethylformamide, dichloromethane, chloroform, N-methylpyrrolidone and the like are used. These solvents may be used either alone or in the form of mixture of two or more. Although the amount of the solvent is not particularly limited, the solvent may be used in an amount of 5-20 ml per gram of resin. The reaction is carried out at 10-40° C. and preferably 20-30° C., for a period of 10-120 minutes.

The peptide of general formula [8; SEQ ID NO:1] can be obtained by removing the protecting group of amino side chain and the resin from the protected peptide resin of general formula [7; SEQ ID NO:1] in the presence of an acid.

The acid used in this reaction can appropriately be selected in accordance with combination of the resin used and the protecting group for amino group. For example, trifluoromethanesulfonic acid, anhydrous hydrogen fluoride, trifluoroacetic acid and the like can be used as said acid. When the resin is benzhydrylamine resin, 4-methylbenzhydrylamine resin or the like and the protecting group for amino acid side chain is a group selected from benzyl ester group, cyclohexyl ester group, benzyl group and 2,6-dibromobenzyl group, trifluoromethanesulfonic acid, anhydrous hydrogen fluoride or the like may be used as said acid. When the resin is Rink amide resin or the like and the protecting group for amino acid side chain is a group selected from t-butyl ester group, t-butyl group and trityl group, trifluoroacetic acid and the like may be used as said acid. Although the solvent used in this reaction is not particularly limited so far as it exercises no adverse influence on the reaction, dichloromethane may be used, for example, as said acid. Although amount of the solvent is not critical, it may be 5-100 ml per gram of resin. In this reaction, anisole, thioanisole, m-cresol, p-cresol, ethanedithiol, water, etc. may be added, and the amount thereof is preferably 0.1-20% by volume based on the solvent used. A combined use of these compounds is also allowable, if desired. This reaction is carried out at −10° C. to 40° C. and preferably 0-20° C., for a period of 30-300 minutes.

The cyclic peptide of general formula [2; SEQ ID NO:1] can be obtained by forming a disulfide linkage between the cysteine side chains of the peptide of general formula [8; SEQ ID NO:1]. The formation of intramolecular disulfide linkage between two cysteine residues can be effected according to a known method.

Concretely speaking, when the side chain thiol group of cysteine is not protected, air oxidation in a dilute aqueous ammonia solution, or the method of using 5-20% dimethyl sulfoxide/trifluoroacetic acid solution may be used. When the side chain thiol group of cysteine is protected with triacetamidomethyl group or the like, the iodine oxidation method or the method of de-protection using silver tetrafluoroborate followed by air oxidation may be used. When the side chain thiol group of cysteine is protected with t-butyl, the silyl chloride-diphenyl sulfoxide method may be used (Development of Pharmaceuticals, Peptide syntheses, Hirokawa Shoten, Pages 233-258).

The cyclic peptides of general formula [2; SEQ ID NO:1] or salts thereof thus obtained can be isolated and purified according to conventional methods such as extraction, crystallization, gel filtration, liquid chromatography and/or column chromatography. For example, the isolation and purification can be effected by the gel filtration method using a gel filter such as Sephadex G-10, G-25 or the like, the column chromatography using a reverse phase type synthetic polymer resin or a chemically modified silica gel carrier and/or a high performance liquid chromatography, or the like.

[Production Process 1a]

The cyclic peptide of general formula [2b; SEQ ID NO:2] can be obtained by the same method as Production Process 1.

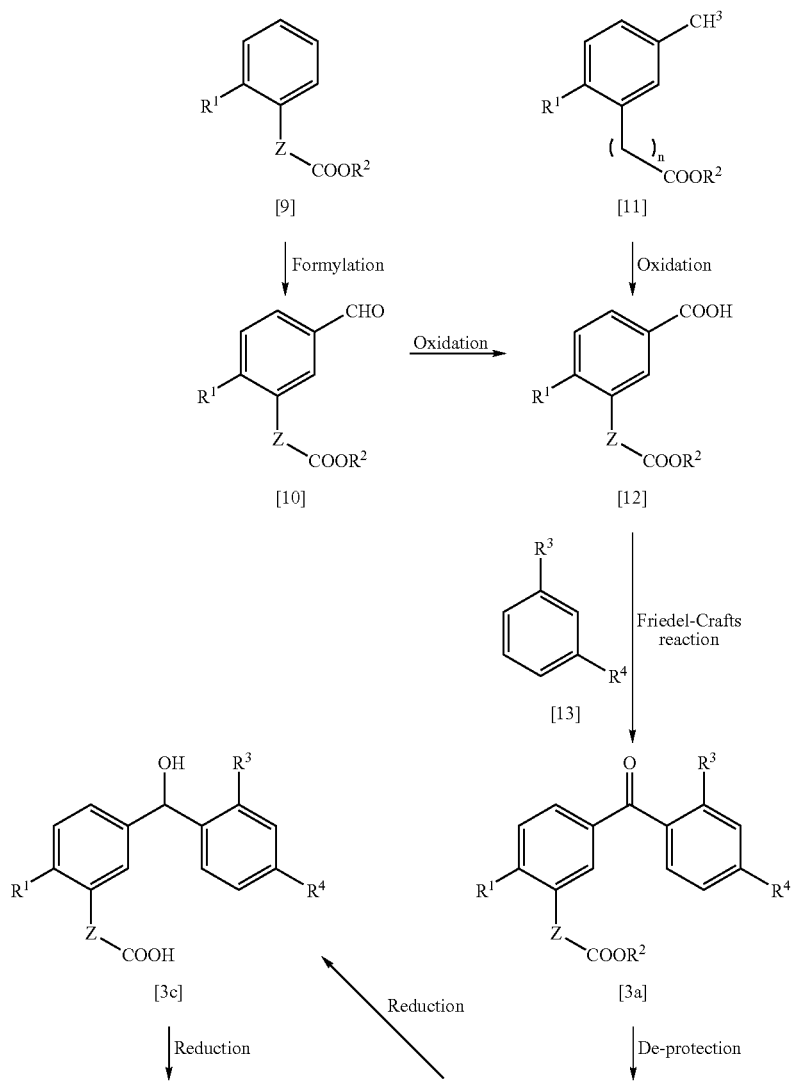

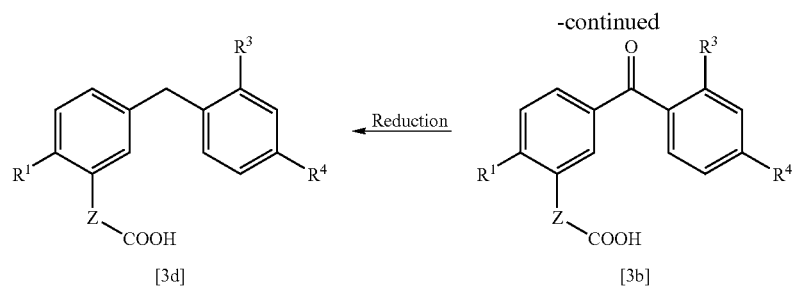
[Production Process 3]
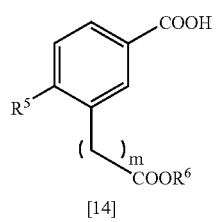
[14]
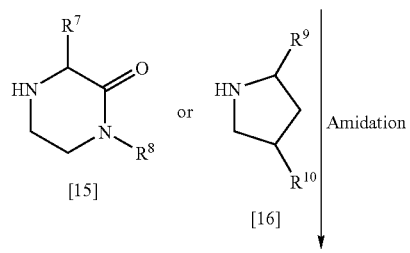
[15] or [16]
| Amidation
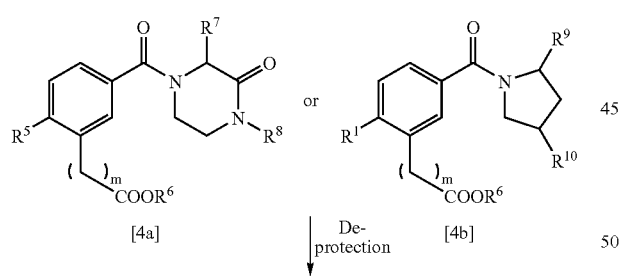
[4a] or [4b]
| De-protection
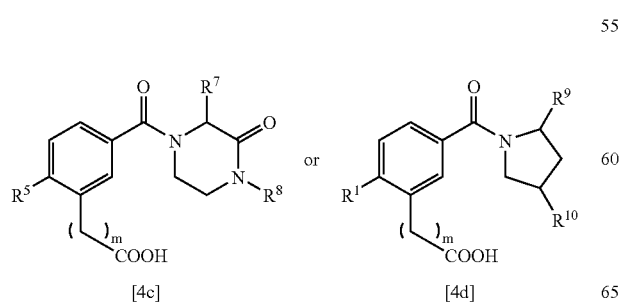
[4c] or [4d]
[Production Process 4]
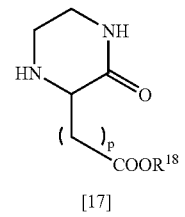
[17]
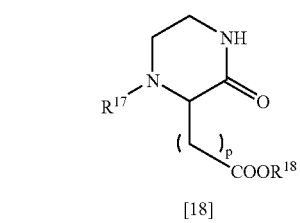
[18]
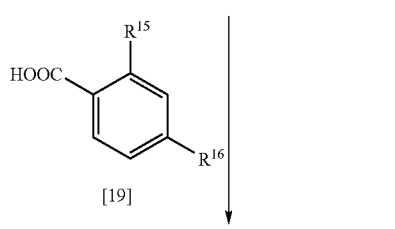
[19]
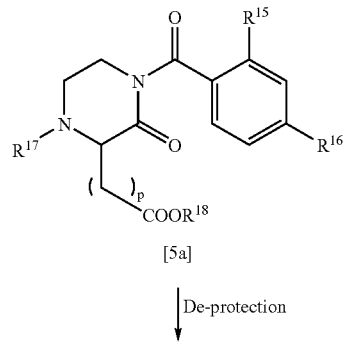
[5a]
| De-protection -continued

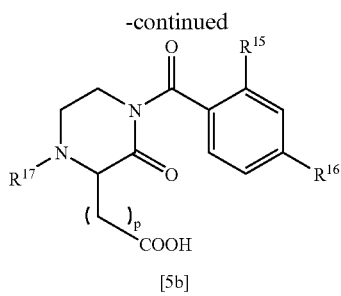

[5b]

wherein $R^1$, $R^2$ (hydrogen atom is excepted), $R^3$, $R^4$, $R^5$, $R^6$ (hydrogen atom is excepted), $R^7$, $R^8$, $R^9$, $R^{10}$, $R^{15}$, $R^{16}$, $R^{17}$, $R^{18}$ (hydrogen atom is excepted), Z, n, m and p are as defined above.

[Production Process 2]

The compound of general formula [10] can be obtained by reacting a compound of general formula [9] and a formylating agent in the presence of an acid. As the acid used in this reaction, titanium tetrachloride, stannic chloride, aluminum chloride, phosphorus oxychloride and the like can be referred to, and amount thereof is 1-10 mol and preferably 1-2 mol per mol of the compound of formula [9]. As the formylating agent, α,α-dichloromethyl methyl ether, N,N-dimethylformamide, ethyl orthoformate and the like can be referred to, and amount thereof is 1-10 mol and preferably 1-2 mol per mol of the compound of general formula [9]. As the solvent used in this reaction, halogenated hydrocarbons such as methylene chloride, chloroform, carbon tetrachloride and the like and aliphatic hydrocarbons such as n-hexane, cyclohexane and the like can be referred to, and these solvents may be used either alone or in the form of mixture of two or more. The reaction is carried out usually at a temperature ranging from −78° C. to reflux temperature of the solvent and preferably at 0-30° C., for a period of 30 minutes to 24 hours.

The compound of general formula [12] can be obtained by reacting a compound of general formula [10] with an oxidant in the presence or absence of an acid or a base.

As the acid which can be used in this reaction according to need, hydrochloric acid, sulfuric acid, acetic acid, sulfamic acid and the like can be referred to, and amount thereof is 1-1,000 mol and preferably 1-100 mol per mol of the compound of general formula [10]. As the base which can be used according to need, alkali metal hydroxides such as sodium hydroxide, potassium hydroxide and the like and pyridine and the like can be referred to, and amount thereof is 1-1,000 mol and preferably 1-100 mol per mol of the compound of general formula [10]. As the oxidant used in this reaction, sodium chlorite, sodium hypochlorite, chromic acid, potassium permanganate, hydrogen peroxide, ruthenium oxide, nickel oxide, silver oxide, silver nitrate and the like can be referred to, and amount thereof is 1-10 mol and preferably 1-3 mol per mol of the compound of general formula [10]. Although the solvent used in this reaction is not particularly limited so far as it exercises no adverse influence on the reaction, ethers such as tetrahydrofuran, ethyl ether, dioxane and the like, halogenated hydrocarbons such as methylene chloride, chloroform, carbon tetrachloride and the like, nitriles such as acetonitrile and the like, aliphatic hydrocarbons such as n-hexane, cyclohexane and the like, aromatic hydrocarbons such as toluene, benzene and the like, dimethyl sulfoxide, pyridine, water, etc. can be referred to. These solvents may be used either alone or in the form of mixture of two or more. This reaction is carried out usually at a temperature ranging from 0° C. to reflux temperature of the solvent for a period of 30 minutes to 24 hours.

The compound of general formula [12] can be obtained by reacting a compound of general formula [11] with an oxidant in the presence or absence of an acid or a base.

As the acid which can be used in this reaction according to the need, sulfuric acid, acetic acid and the like can be referred to, and amount thereof is 1-1,000 mol and preferably 1-100 mol per mol of the compound of general formula [11]. As the base which can be used in this reaction according to the need, alkali metal hydroxides such as sodium hydroxide, potassium hydroxide and the like and pyridine and the like can be referred to, and amount thereof is 1-1,000 mol and preferably 1-100 mol per mol of the compound of general formula [11]. As the oxidant used in this reaction, chromic acid, potassium permanganate and the like can be referred to, and amount thereof is 1-10 mol and preferably 1-2 mol per mol of the compound of general formula [11]. Although the solvent used in this reaction is not particularly limited so far as it exercises no adverse influence on the reaction, halogenated hydrocarbons such as methylene chloride, chloroform, carbon tetrachloride and the like, aliphatic hydrocarbons such as n-hexane, cyclohexane and the like, pyridine, water and the like can be referred to, for example, and these solvents may be used either alone or in the form of mixture of two or more. The reaction is carried out usually at a temperature ranging from 0° C. to reflux temperature of the solvent, for a period of 30 minutes to 24 hours.

The compound of general formula [3a] can be obtained by subjecting an acid chloride or an acid anhydride of a compound of general formula [12] and a compound of general formula [13] to Friedel-Crafts reaction in the presence of an acid.

The acid chloride or acid anhydride of the compound of general formula [12] used in this reaction can be obtained by reacting a compound of general formula [12] with an activating agent such as thionyl chloride, oxalyl chloride, phosphorus pentachloride, acetic anhydride, ethyl chloroformate or the like, and amount thereof is 1-10 mol and preferably 1-2 mol per mol of the compound of general formula [12]. As the acid used in this reaction, stannic chloride, aluminum chloride, boron trifluoride, zinc chloride and the like can be referred to, and amount thereof is 1-10 mol and preferably 1-5 mol per mol of the compound of general formula [12]. The compound of general formula [13] is used in an amount of 1-10 mol and preferably 1-2 mol per mol of the compound of general formula [12]. As the solvent used in this reaction, halogenated hydrocarbons such as methylene chloride, chloroform, carbon tetrachloride and the like, aliphatic hydrocarbons such as n-hexane, cyclohexane and the like, nitrobenzene, carbon disulfide and the like can be referred to, and these solvents may be used either alone or in the form of mixture of two or more. This reaction is carried out usually at a temperature ranging from −78° C. to reflux temperature of the solvent and preferably at 0-30° C., for a period of 30 minutes to 24 hours.

The compound of general formula [3b] can be obtained by subjecting a compound of general formula [3a] to a deprotecting reaction such as a hydrolysis using an acid or a base, a de-esterification reaction using a salt, a reductive de-esterification reaction including hydrogenation in the presence of metallic catalyst, etc. As the acid which can be used in this reaction, formic acid, hydrochloric acid, sulfuric acid, hydrobromic acid, trifluoroacetic acid, aluminum chloride, trimethyliodosilane and the like can be referred to, and amount thereof is 1-1,000 mol and preferably 1-100 mol per mol of the compound of general formula [3a]. As the base, alkali metal hydroxides such as sodium hydroxide, potassium hydroxide, barium hydroxide and the like, tetrabutylammonium fluoride and the like can be referred to, and amount thereof is 1-1,000 mol and preferably 1-50 mol per mol of the compound of general formula [3a]. As the salt used in this reaction, lithium iodide, sodium chloride and the like can be referred to, and amount thereof is 1-100 mol and preferably 1-10 mol per mol of the compound of general formula [3a]. As the catalyst used in the reductive de-esterification reaction, palladium-carbon, palladium-black, palladium hydroxide and the like can be referred to, and amount thereof is 0.001 to 1 mol and preferably 0.01 to 0.5 mol per one mol of the compound of general formula [3a]. As the reductant, hydrogen, formic acid, cyclohexene, zinc and the like can be referred to, and amount thereof is 1-100 mol and preferably 1-10 mol per mol of the compound of general formula [3a]. Although the solvent which can be used in this reaction is not particularly limited so far as it exercises no adverse influence on the reaction, alcohols such as methanol, ethanol, isopropyl alcohol and the like, ethers such as tetrahydrofuran, ethyl ether, dioxane, anisole and the like, halogenated hydrocarbons such as methylene chloride, chloroform, carbon tetrachloride and the like, nitrites such as acetonitrile and the like, aliphatic hydrocarbons such as n-hexane, cyclohexane and the like, esters such as ethyl acetate and the like, aromatic hydrocarbons such as toluene, benzene, xylene and the like, dimethyl sulfoxide, N,N-dimethylformamide, nitromethane, pyridine, water, etc. can be used. These solvents may be used either alone or in the form of mixture of two or more. The reaction is carried out usually at −78° C. to 100° C. and preferably 5-80° C., for a period of 10 minutes to 24 hours.

The compound of general formula [3c] can be obtained by reacting a compound of general formula [3b] with a reductant in the presence or absence of an acid, a base or a salt. As the acid which can be used in this reaction according to need, hydrochloric acid, sulfuric acid, trifluoroacetic acid, aluminum chloride, boron trifluoride and the like can be referred, and amount thereof is 1-10 mol and preferably 1-2 mol per mol of the compound of general formula [3b]. As the base which can be used according to the need, alkali metal hydroxides such as sodium hydroxide, potassium hydroxide and the like and pyridine and the like can be referred to, and amount thereof is 1-1,000 mol and preferably 1-100 mol per mol of the compound of general formula [3b]. As the salt which can be used according to the need, lithium chloride, magnesium chloride, calcium chloride and the like can be referred to, and amount thereof is 1-10 mol and preferably 1-5 mol per mol of the compound of general formula [3b]. As the reductant, sodium borohydride, lithium borohydride, diisobutylaluminum hydride, lithium aluminum hydride and the like can be used, and amount thereof is 0.25-10 mol and preferably 1-8 mol per mol of the compound of general formula [3b]. Although the solvent used in this reaction is not particularly limited so far as it exercises no adverse influence on the reaction, halogenated hydrocarbons such as methylene chloride, chloroform, carbon tetrachloride and the like, ethers such as tetrahydrofuran, ethyl ether and the like, alcohols such as methanol, ethanol, isopropyl alcohol and the like, aromatic hydrocarbons such as toluene, benzene, xylene and the like, aliphatic hydrocarbons such as n-hexane, cyclohexane and the like, dimethyl sulfoxide, N,N-dimethylformamide, pyridine, water, etc. can be used. These solvents may be used either alone or in the form of mixture of two or more. The reaction is carried out usually at a temperature ranging from −78° C. to reflux temperature of the solvent and preferably at −78° C. to 70° C., for a period of 30 minutes to 24 hours.

The compound of general formula [3d] can be obtained by subjecting a compound of general formula [3b] or [3c] to reduction including hydrogenation using a metallic catalyst, in the presence or absence of an acid, a base or a salt. As the acid which can be used in this reaction according to need, hydrochloric acid, sulfuric acid, trifluoroacetic acid, aluminum chloride, boron trifluoride and the like can be referred, and amount thereof is 1-10 mol and preferably 1-2 mol per mol of the compound of general formula [3b] or [3c]. As the base which can be used according to the need, alkali metal hydroxides such as sodium hydroxide, potassium hydroxide and the like and pyridine and the like can be referred to, and amount thereof is 1-1,000 mol and preferably 1-100 mol per mol of the compound of general formula [3b] or [3c]. As the salt which can be used according to the need, lithium chloride, magnesium chloride, calcium chloride and the like can be referred to, and amount thereof is 1-50 mol and preferably 1-10 mol per mol of the compound of general formula [3b] or [3c]. As the reductant, sodium borohydride, lithium borohydride, diisobutylaluminum hydride, lithium aluminum hydride, triethylsilane, hydrogen, cyclohexene and the like can be used, and amount thereof is 1-10 mol and preferably 1-2 mol per mol of the compound of general formula [3b] or [3c]. As the catalyst, palladium-carbon, palladium-black, palladium hydroxide and the like can be used, and amount thereof is 0.001-1 mol and preferably 0.01-0.5 mol per mol of the compound of general formula [3b] or [3c]. Although the solvent used in this reaction is not particularly limited so far as it exercises no adverse influence on the reaction, halogenated hydrocarbons such as methylene chloride, chloroform, carbon tetrachloride and the like, ethers such as tetrahydrofuran, ethyl ether and the like, alcohols such as methanol, ethanol, isopropyl alcohol and the like, aromatic hydrocarbons such as toluene, benzene, xylene and the like, aliphatic hydrocarbons such as n-hexane, cyclohexane and the like, esters such as ethyl acetate and the like, N,N-dimethylformamide, acetic acid, pyridine, water, etc. can be used. These solvents may be used either alone or in the form of mixture of two or more. The reaction is carried out usually at a temperature ranging from −78° C. to reflux temperature of the solvent and preferably at 0-30° C., for a period of 30 minutes to 24 hours.

[Production Process 3]

The compound of general formula [4a] or [4b] can be obtained by reacting a compound of general formula [14] with a compound of general formula [15] or [16] by the use of a condensing agent in the presence or absence of an acid or a base. Otherwise, it can be obtained by reacting an acid chloride or acid anhydride of a compound of general formula [14] with a compound of general formula [15] or [16].

The acid chloride or acid anhydride of the compound of general formula [14] used in this reaction can be obtained by reacting a compound of general formula [14] with an activating agent such as thionyl chloride, oxalyl chloride, phosphorus pentachloride, acetic anhydride, ethyl chloroformate and the like. The activating agent is used in an amount of 1-10 mol and preferably 1-2 mol per mol of the compound of general formula [14]. As the acid used in this reaction according to the need, toluenesulfonic acid, N-hydroxysuccinimide and the like can be referred to, and amount thereof is 1-10 mol and preferably 1-5 mol per mol of the compound of general formula [14]. As the base which can be used according to the need, N,N-dimethylaminopyridine, pyridine, triethylamine and the like can be referred to, and amount thereof is 1-100 mol and preferably 1-10 mol per mol of the compound of general formula [14]. As the condensing agent used in this reaction, dicyclohexylcarbodiimide, diphenylphosphoryl acid azide, N,N'-carbonyldiimidazole and the like can be referred to, and amount thereof is 1-10 mol and preferably 1-2 mol per mol of the compound of general formula [14]. The compound of general formula [15] or [16] is used in an amount of 1-10 mol and preferably 1-2 mol per mol of the compound of general formula [14]. Although the solvent used in this reaction is not particularly limited so far as it exercises no adverse influence on the reaction, ethers such as tetrahydrofuran, ethyl ether and the like, aromatic hydrocarbons such as toluene, benzene, xylene and the like, halogenated hydrocarbons such as methylene chloride, chloroform, carbon tetrachloride and the like, nitriles such as acetonitrile and the like, aliphatic hydrocarbons such as n-hexane, cyclohexane and the like, esters such as ethyl acetate and the like, ketones such as acetone and the like, pyridine, N,N-dimethylformamide, etc. can be used. These solvents may be used either alone or in the form of mixture of two or more. The reaction is carried out usually at a temperature ranging from −78° C. to reflux temperature of the solvent and preferably at 0-30° C., for a period of 30 minutes to 24 hours.

The compound of general formula [4c] or [4d] can be obtained by subjecting a compound of general formula [4a] or [4b] to a de-protection reaction such as hydrolysis using an acid or a base, a de-esterification reaction using a salt, a reductive de-esterification reaction including hydrogenation using a metallic catalyst, or the like.

As the acid used in this reaction, formic acid, hydrochloric acid, sulfuric acid, hydrobromic acid, trifluoroacetic acid, aluminum chloride, trimethyliodosilane and the like can be referred to, and amount thereof is 1-1,000 mol and preferably 1-100 mol per mol of the compound of general formula [4a] or [4b]. As the base, alkali metal hydroxides such as sodium hydroxide, potassium hydroxide, barium hydroxide and the like, tetrabutylammonium fluoride and the like can be referred to, and amount thereof is 1-1,000 mol and preferably 1-30 mol per mol of the compound of general formula [4a] or [4b]. As the salt used in this reaction, lithium iodide, sodium chloride and the like can be referred to, and amount thereof is 1-100 mol and preferably 1-10 mol per mol of the compound of general formula [4a] or [4b]. As the catalyst used in the de-esterification reaction, palladium-carbon, palladium-black, palladium hydroxide and the like can be referred to, and amount thereof is 0.001-1 mol and preferably 0.01-0.5 mol per mol of the compound of general formula [4a] or [4b]. As the reductant used in this reaction, hydrogen, formic acid, cyclohexene, zinc and the like can be referred to, and amount thereof is 1-100 mol and preferably 1-10 mol per mol of the compound of general formula [4a] or [4b]. Although the solvent used in this reaction is not particularly limited so far as it exercises no adverse influence on the reaction, alcohols such as methanol, ethanol, isopropyl alcohol and the like, ethers such as tetrahydrofuran, ethyl ether, dioxane, anisole and the like, halogenated hydrocarbons such as methylene chloride, chloroform, carbon tetrachloride and the like, nitrites such as acetonitrile and the like, aliphatic hydrocarbons such as n-hexane, cyclohexane and the like, esters such as ethyl acetate and the like, aromatic hydrocarbons such as toluene, benzene, and the like, dimethyl sulfoxide, N,N-dimethylformamide, nitromethane, pyridine, water, etc. can be used, and these solvents may be used either alone or in the form of mixture of two or more. This reaction is carried out usually at a temperature ranging from 0° C. to reflux temperature of the solvent and preferably at 5-60° C., for a period of 10 minutes to 24 hours.

[Production Process 4]

The compound of general formula [18] can be obtained by reacting a compound of general formula [17] with an acid chloride in the presence or absence of an acid or a base. Otherwise, it can be obtained by reacting a compound of general formula [17] with a carboxylic acid by the use of a condensing agent.

As the acid used in this reaction according to the need, toluenesulfonic acid, N-hydroxysuccinic acid and the like can be referred to, and amount thereof is 1-10 mol per mol of the compound of general formula [17]. As the base used in this reaction according to the need, N,N-dimethylaminopyridine, pyridine, triethylamine and the like can be referred to, and amount thereof is 1-10 mol per mol of the compound of general formula [17]. The acid chloride or carboxylic acid is used in an amount of 1-10 mol and preferably 1-2 mol per mol of the compound of general formula [17]. As the condensing agent, dicyclohexylcarbodiimide, diphenylphosphoryl acid azide, N,N'-carbonyldiimidazole and the like can be referred to, and amount thereof is 1-10 mol and preferably 1-2 mol per mol of the compound of general formula [17]. Although the solvent used in this reaction is not particularly limited so far as it exercises no adverse influence on the reaction, ethers such as tetrahydrofuran, ethyl ether and the like, aromatic hydrocarbons such as toluene, benzene, xylene and the like, halogenated hydrocarbons such as methylene chloride, chloroform, carbon tetrachloride and the like, nitrites such as acetonitrile and the like, aliphatic hydrocarbons such as n-hexane, cyclohexane and the like, esters such as ethyl acetate and the like, ketones such as acetone and the like, pyridine, N,N-dimethylformamide, etc. can be referred to. These solvents may be used either alone or in the form of mixture of two or more. This reaction is carried out usually at a temperature ranging from −78° C. to reflux temperature of the solvent and preferably at 0-30° C., for a period of 30 minutes to 24 hours.

Further, it is also possible to obtain the compound of general formula [18] by subjecting a compound of general formula [17] to alkylation, amidation or sulfonamidation in the presence or absence of a base.

As the alkylating agent used in this reaction, methyl iodide, benzyl bromide and the like can be referred to. As the amidating agent, acid anhydrides such as acetic anhydride and the like and acyl halogenides such as acetyl chloride, benzoyl chloride and the like can be referred to. As the sulfonamidating agent, sulfonyl halides such as methanesulfonyl chloride, benzenesulfonyl chloride and the like can be referred to. These reagents are used in an amount of 1-20 mol and preferably 1-4 mol per mol of the compound of general formula [17]. As the base used in this reaction according to the need, for example, organic amines such as dimethylaminopyridine, triethylamine, pyridine and the like, and alkali metal carbonates such as potassium carbonate, sodium carbonate and the like can be referred to, and amount thereof is 1-20 mol and preferably 1-4 mol per mol of the compound of general formula [17]. Although the solvent used in this reaction is not particularly limited so far as it exercises no adverse influence on the reaction, aromatic hydrocarbons such as toluene, benzene, xylene and the like, ethers such as dioxane, tetrahydrofuran, anisole, diethylene glycol diethyl ether, dimethyl cellosolve and the like, esters such as methyl acetate, ethyl acetate and the like, nitriles such as acetonitrile and the like, amides such as N,N-dimethylformamide and the like, and halogenated hydrocarbons such as chloroform, methylene chloride and the like can be used as the solvent. These solvents may be used either alone or in the form of mixture of two or more. This reaction is carried out usually at 0-200° C. and preferably 10-150° C., for a period of 10 minutes to 24 hours. It is also possible to effect carbamoylation by reacting a compound of general formula [17] with triphosgene in the presence of a base and then treating the resulting active intermediate with aqueous ammonia. The triphosgen is used in an amount of 0.3-20 mol and preferably 1-4 mol per mol of the compound of general formula [17]. As the base used in this reaction, organic amines such as dimethylaminopyridine, triethylamine, pyridine and the like can be referred to, and amount thereof is 1-20 mol and preferably 1-4 mol per mol of the compound of general formula [17]. Although the solvent used in this reaction is not particularly limited so far as it exercises no adverse influence on the reaction, halogenated hydrocarbons such as chloroform, methylene chloride and the like can be used, for example. This reaction is carried out usually at 0-70° C. and preferably at 0-30° C., for a period of 30 minutes to 24 hours.

After the reaction, the reaction mixture is treated with 1-50 v/w, preferably 5-15 v/w, of 25% aqueous ammonia to obtain a carbamoylated product. This reaction is carried out usually at 0-100° C. and preferably 0-30° C., for a period of 10 minutes to 24 hours.

The compound of general formula [5a] can be obtained by reacting a compound of general formula [18] and a compound of general formula [19] by the use of a condensing agent, in the presence or absence of an acid or a base. Otherwise, it is also possible to obtain the compound of general formula [5a] by reacting an acid chloride or acid anhydride of the compound of general formula [19] with a compound of general formula [18].

The acid chloride or acid anhydride of the compound of general formula [19] used in this reaction can be obtained by reacting a compound of general formula [19] with an activating agent such as thionyl chloride, oxalyl chloride, phosphorus pentachloride, acetic anhydride, ethyl chloroformate or the like, and amount thereof is 1-10 mol and preferably 1-2 mol per mol of the compound of general formula [19]. As the acid used in this reaction according to the need, toluenesulfonic acid, N-hydroxysuccinimide and the like can be referred to, and amount thereof is 1-10 mol and preferably 1-5 mol per mol of the compound of general formula [19]. As the base which can be used in this reaction according to need, N,N-dimethylaminopyridine, pyridine, triethylamine and the like can be referred to, and amount thereof is 1-100 mol and preferably 1-10 mol per mol of the compound of general formula [19]. As the condensing agent used in this reaction, dicyclohexylcarbodiimide, diphenylphosphoryl acid azide, N,N'-carbonyldiimidazole and the like can be referred to, and amount thereof is 1-10 mol and preferably 1-2 mol per mol of the compound of general formula [19]. Although the solvent used in this reaction is not particularly limited so far as it exercises no adverse influence on the reaction, ethers such as tetrahydrofuran, ethyl ether and the like, aromatic hydrocarbons such as toluene, benzene, xylene and the like, halogenated hydrocarbons such as methylene chloride, chloroform, carbon tetrachloride and the like, nitriles such as acetonitrile and the like, aliphatic hydrocarbons such as n-hexane, cyclohexane and the like, esters such as ethyl acetate and the like, ketones such as acetone and the like, pyridine, N,N-dimethylformamide, etc. can be used. These solvents may be used either alone or in the form of mixture of two or more. The reaction is carried out at a temperature ranging from −78° C. to the reflux temperature of the solvent and preferably at 0-30° C., for a period of 30 minutes to 24 hours.

The compound of general formula [5b] can be obtained by subjecting a compound of general formula [5a] to a de-protecting reaction such as hydrolysis using an acid or a base, de-esterification using a base or reductive de-esterification including hydrogenation using a metallic catalyst. As the acid which can be used in this reaction, formic acid, hydrochloric acid, sulfuric acid, hydrobromic acid, trifluoroacetic acid, aluminum chloride, trimethyliodosilane and the like can be referred to, and amount thereof is 1-1,000 mol and preferably 1-100 mol per mol of the compound of general formula [5a]. As the base, alkali metal hydroxides such as sodium hydroxide, potassium hydroxide, barium hydroxide and the like, tetrabutylammonium fluoride and the like can be referred to, and amount thereof is 1-1,000 mol and preferably 1-30 mol per mol of the compound of general formula [5a]. As the salt used in this reaction, lithium chloride, sodium chloride and the like can be referred to, and amount thereof is 1-100 mol and preferably 1-10 mol per mol of the compound of general formula [5a]. As the catalyst used in the reductive de-esterification reaction, palladium-carbon, palladium-black, palladium hydroxide and the like can be referred to, and amount thereof is 0.001 to 1 mol and preferably 0.01 to 0.5 mol per one mol of the compound of general formula [5a]. As the reductant, hydrogen, formic acid, cyclohexene, zinc and the like can be referred to, and amount thereof is 1-100 mol per mol of the compound of general formula [5a]. Although the solvent which can be used in this reaction is not particularly limited so far as it exercises no adverse influence on the reaction, alcohols such as methanol, ethanol, isopropyl alcohol and the like, ethers such as tetrahydrofuran, ethyl ether, dioxane, anisole and the like, halogenated hydrocarbons such as methylene chloride, chloroform, carbon tetrachloride and the like, nitriles such as acetonitrile and the like, aliphatic hydrocarbons such as n-hexane, cyclohexane and the like, esters such as ethyl acetate and the like, aromatic hydrocarbons such as toluene, benzene, xylene and the like, dimethyl sulfoxide, N,N-dimethylformamide, nitromethane, pyridine, water, etc. can be used. These solvents may be used either alone or in the form of mixture of two or more. This reaction is carried out usually at 0° C. to reflux temperature of the solvent and preferably 5-60° C., for a period of 10 minutes to 24 hours.

[Production Process 2a]

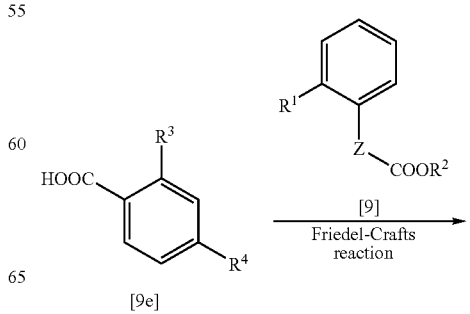

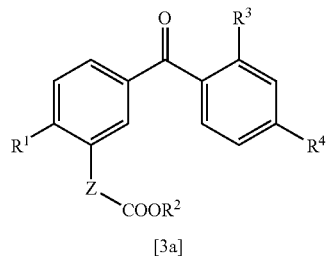

wherein $R^1$, $R^2$ (hydrogen atom is excepted), $R^3$, $R^4$ and Z are as defined above.

The reaction for obtaining a compound of general formula [3a] from a compound of general formula [9e] may be carried out by the same procedure as that of the reaction for obtaining a compound of general formula [3a] from a compound of general formula [12] described in Production Process 2.

wherein $R^{29}$, $R^{30}$ and $R^{31}$ may be the same or different and independently represent unsubstituted or substituted alkyl, cycloalkyl or aralkyl group; X represents halogen atom, alkylsulfonyloxy group or arylsulfonyloxy group; and $R^1$, $R^2$ (hydrogen atom is excepted) and Z are as defined above.

The compound of general formula [20a] can be obtained by subjecting an acid chloride or acid anhydride of a compound of general formula [12] and a compound of general formula [13'] to Friedel-Crafts reaction in the presence of an acid.

The acid chloride or acid anhydride of the compound of general formula [12] used in this reaction can be obtained by reacting a compound of general formula [12] with an activating agent such as thionyl chloride, oxalyl chloride, phosphorus pentachloride, acetic anhydride, ethyl chloroformate or the like, and amount thereof is 1-10 mol and preferably 1-2 mol per mol of the compound of general formula [12]. As the acid used in this reaction, stannic chloride, aluminum chloride, boron trifluoride, zinc chloride and the like can be referred to, and amount thereof is 0.5-10 mol and preferably 0.9-6 mol per mol of the compound of general formula [12]. The compound of general formula

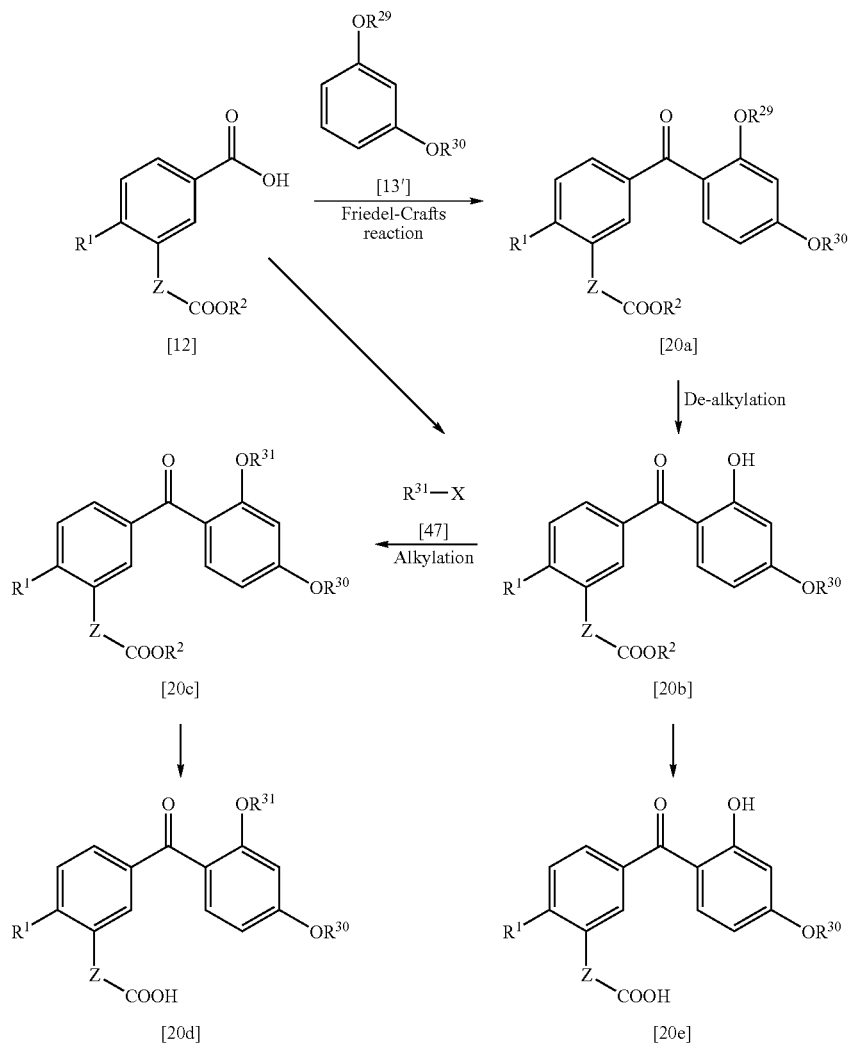

[13'] is used in an amount of 0.1-10 mol and preferably 0.3-3 mol per mol of the compound of general formula [12]. As the solvent used in this reaction, halogenated hydrocarbons such as methylene chloride, chloroform, carbon tetrachloride and the like, aliphatic hydrocarbons such as n-hexane, cyclohexane and the like, nitrobenzene, carbon disulfide and the like can be referred to, and these solvents may be used either alone or in the form of mixture of two or more. This reaction is carried out usually at a temperature ranging from −78° C. to reflux temperature of the solvent and preferably at −30° C. to 30° C., for a period of 10 minutes to 24 hours.

It is also possible to obtain a compound of general formula [20b] directly by this reaction while controlling the reaction conditions such as amount of acid, reaction temperature and/or amount of reaction solvent, etc.

The compound of general formula [20b] can be obtained by subjecting a compound of general formula [20a] to a de-alkylation reaction in the presence of an acid, a base or a salt.

As the acids which can be used in this reaction, mineral acids such as hydrochloric acid, sulfuric acid, hydrobromic acid and the like, organic acids such as trifluoroacetic acid, thiophenol and the like, and trimethyliodosilane, aluminum chloride, boron trifluoride, zinc chloride and the like can be referred to. As the bases which can be used in this reaction, sodium salt of ethylmercaptan, lithium diisopropylamide and the like can be referred to. As the salts which can be used in this reaction, sodium cyamide, lithium iodide, pyridine hydrochloride and the like can be referred to. Each of the acids, bases and salts is used in an amount of 1-50 mol and preferably 2-20 mol per mol of the compound of general formula [20a]. Although the solvent used in this reaction is not particularly limited so far as it exercises no adverse influence on the reaction, aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitrites such as acetonitrile and the like; alcohols such as methanol, ethanol, isopropyl alcohol and the like; amides such as N,N-dimethylformamide, N,N-dimethylacetamide and the like; halogenated hydrocarbons such as chloroform, methylene chloride and the like; and sulfoxides such as dimethyl sulfoxide and the like can be used. When a mineral acid is used, water may also be used, if desired. These solvents may be used either alone or in the form of mixture of two or more.

This reaction is carried out usually at a temperature ranging from −78° C. to reflux temperature of the solvent and preferably at 0-110° C., for a period of 30 minutes to 24 hours.

The compound of general formula [20c] can be obtained by subjecting a compound of general formula [20b] to an alkylation reaction with a compound of general formula [47] in the presence of a base.

In this reaction, the compound of general formula [47] is used in an amount of 1-20 mol and preferably 1-5 mol per mol of the compound of general formula [20b]. As the base used in this reaction, organic amines such as dimethylaminopyridine, triethylamine, pyridine and the like; alkali metal hydrides such as sodium hydride and the like; and alkali metal carbonates such as potassium carbonate, sodium carbonate and the like can be referred to, and amount thereof is 1-20 mol and preferably 1-5 mol per mol of the compound of general formula [20b]. Although the solvent used in this reaction is not particularly limited so far as it exercises no adverse influence on the reaction, aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; amides such as N,N-dimethylformamide and the like; halogenated hydrocarbons such as chloroform, methylene chloride and the like; and sulfoxides such as dimethyl sulfoxide and the like can be used. These solvents may be used either alone or in the form of mixture of two or more. The reaction is carried out usually at 0-200° C. and preferably at 25-150° C., for a period of 10 minutes to 24 hours.

The compound of general formula [20d] can be obtained by subjecting a compound of general formula [20c] to a de-protecting reaction such as hydrolysis using an acid or a base, de-esterification reaction using a salt, reductive de-esterification reaction including hydrogenation in the presence of metallic catalyst, etc.

As the acid which can be used in this reaction, formic acid, hydrochloric acid, sulfuric acid, hydrobromic acid, trifluoroacetic acid, aluminum chloride, trimethyliodosilane and the like can be referred to, and amount thereof is 1-1,000 mol and preferably 1-100 mol per mol of the compound of general formula [20c]. As the base used in this reaction, alkali metal hydroxides such as sodium hydroxide, potassium hydroxide, barium hydroxide and the like, tetrabutylammonium fluoride and the like can be referred to, and amount thereof is 1-1,000 mol and preferably 1-10 mol per mol of the compound of general formula [20c]. As the salt used in this reaction, lithium iodide, sodium chloride and the like can be referred to, and amount thereof is 1-10 mol and preferably 1-5 mol per mol of the compound of general formula [20c]. As the catalyst used in the reductive de-esterification reaction, palladium-carbon, palladium-black, palladium hydroxide and the like can be referred to, and amount thereof is 0.001 to 1 mol and preferably 0.01 to 0.5 mol per mol of the compound of general formula [20c]. As the reductant, hydrogen, formic acid, cyclohexene, zinc and the like can be referred to, and amount thereof is 1-100 mol and preferably 1-10 mol per mol of the compound of general formula [20c]. Although the solvent which can be used in this reaction is not particularly limited so far as it exercises no adverse influence on the reaction, alcohols such as methanol, ethanol, isopropyl alcohol and the like, ethers such as tetrahydrofuran, ethyl ether, dioxane, anisole and the like, halogenated hydrocarbons such as methylene chloride, chloroform, carbon tetrachloride and the like, nitriles such as acetonitrile and the like, aliphatic hydrocarbons such as n-hexane, cyclohexane and the like, esters such as ethyl acetate and the like, aromatic hydrocarbons such as toluene, benzene, xylene and the like, dimethyl sulfoxide, N,N-dimethylformamide, nitromethane, pyridine, water, etc. can be used. These solvents may be used either alone or in the form of mixture of two or more.

The reaction is carried out usually at −78° C. to 100° C. and preferably 5-60° C., for a period of 10 minutes to 24 hours.

The reaction for obtaining a compound of general formula [20e] from the compound of general formula [20b] may be effected in the same manner as the procedure for obtaining compound [20d] from compound [20c] in Production Process 5. If desired, the compound of general formula [20e] can be subjected to the same treatment for producing compound [28c] from compound [28b] in the Production Process 9 to acylate or alkylate the hydroxyl group thereof.

[Production Process 6]

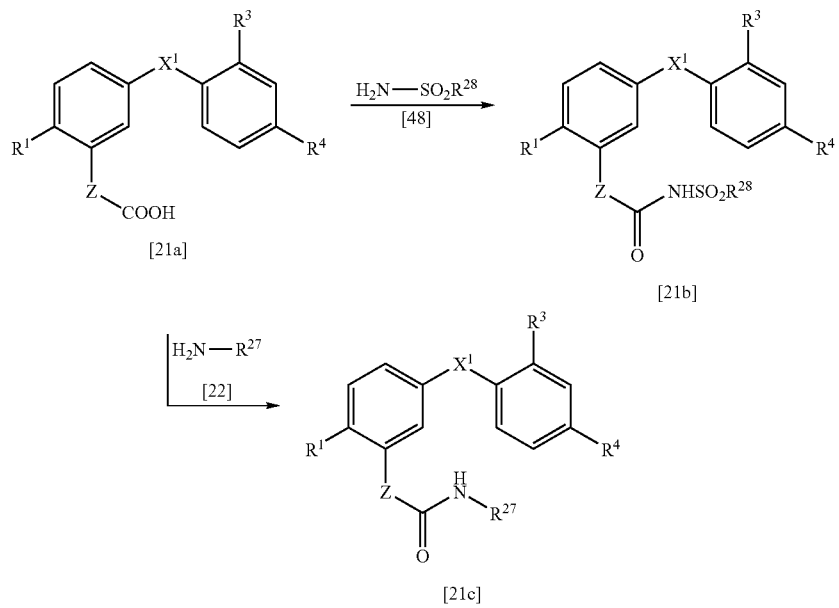

wherein $R^1$, $R^3$, $R^4$, Z, $X^1$, $R^{27}$ and $R^{28}$ are as defined above.

The compound of general formula [21b] can be obtained by subjecting a compound of general formula [21a] to a reaction with a compound of general formula [48].

This reaction can be carried out by a method via an acid chloride, a method via an acid anhydride, a method using a base, a condensing agent and an additive, etc. For example, in the method using a base, a condensing agent and an additive, the compound of general formula [48] used in this reaction is selected from methanesulfonamide, benzenesulfonamide and the like, and amount thereof is 1-10 mol and preferably 1-3 mol per mol of the compound of general formula [21a]. As the base used in this reaction, organic amines such as dimethylaminopyridine, 1,8-diazabicyclo [5.4.0]undec-7-ene, triethylamine, pyridine, N-methylmorpholine and the like, and alkali metal carbonates such as potassium carbonate, sodium carbonate and the like can be referred to, and amount thereof is 0.5-10 mol and preferably 1-3 mol per mol of the compound of general formula [21a]. As the condensing agent, dicyclohexylcarbodiimide, diisopropylcarbodiimide, N-ethyl-N'-3-dimethylaminopropylcarbodiimide, 1,1'-carbonyldiimidazole, diphenylphosphoryl azide and the like can be used. As the additive, 1-hydroxybenzotriazole, N-hydroxysuccinimide and the like can be used, and amount thereof is 0.5-10 mol and preferably 1-3 mol per mol of the compound of general formula [21a]. Although the solvent used in this reaction is not particularly limited so far as it exercises no adverse influence on the reaction, aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like can be used. These solvents may be used either alone or in the form of mixture of two or more. This reaction is carried out usually at a temperature of −20° C. to 150° C. and preferably at 0-120° C., for a period of 30 minutes to 24 hours.

The compound of general formula [21c] can be obtained by subjecting a compound of general formula [21a] and a compound of general formula [22] to an amidation reaction.

This reaction can be effected according to the conventional procedure of amidation. For example, it can be carried out by a method via an acid chloride, a method via an acid anhydride, a method using a base, a condensing agent and an additive, etc. In the method using a base, a condensing agent and an additive, the compound of general formula [22] is used in an amount of 1-10 mol and preferably 1-5 mol per mol of the compound of general formula [21a]. As the base used in this reaction, organic amines such as dimethylaminopyridine, triethylamine, pyridine, N-methylmorpholine and the like and alkali metal carbonates such as potassium carbonate, sodium carbonate and the like can be referred to, and amount thereof is 0.5-10 mol and preferably 1-3 mol per mol of the compound of general formula [21a]. As the condensing agent, dicyclohexylcarbodiimide, diisopropylcarbodiimide, N-ethyl-N'-3-dimethylaminopropylcarbodiimide, diphenylphosphoryl azide and the like can be used, and amount thereof is 1-10 mol and preferably 1-2 mol per mol of the compound of general formula [21a]. As the additive, 1-hydroxybenzotriazole, N-hydroxysuccinimide and the like can be used, and amount thereof is 0.5-10 mol and preferably 1-3 mol per mol of the compound of general formula [21a]. Although the solvent used in this reaction is not particularly limited so far as it exercises no adverse influence on the reaction, aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitriles such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like can be used. These solvents may be used either alone or in the form of mixture of two or more. This reaction is carried out usually at a temperature of −20° C. to 150° C. and preferably at 0-120° C., for a period of 30 minutes to 24 hours.

In cases where $X^1$ and $R^{27}$ in the Production Process 6 mentioned above has a group which has to be protected, such as carboxyl group or the like, the objective compound can be obtained by appropriately protecting the group to be protected before the reaction and carrying out de-protection after completion of the reaction.

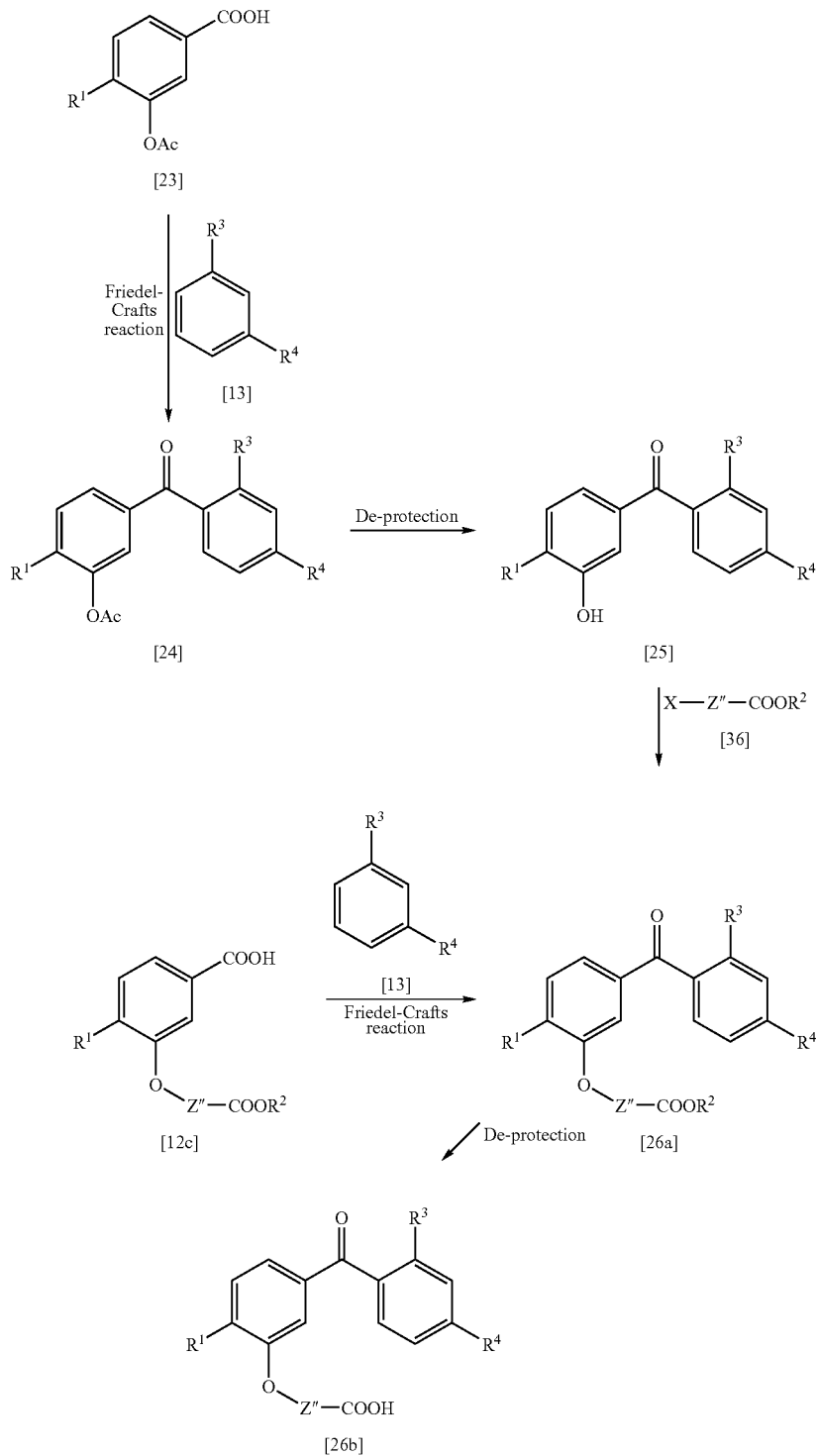

[Production Process 7]

wherein Ac is acetyl group; Z" is —CH$_2$— or —CH$_2$CH$_2$—; and R$^1$, R$^2$ (hydrogen atom is excepted), R$^3$, R$^4$ and X are as defined above.

The reaction for obtaining a compound of general formula [24] from a compound of general formula [23] is carried out by the same procedure as that for obtaining a compound of formula [20a] from a compound of formula [12] in Production Process 5.

The compound of general formula [25] can be obtained by subjecting a compound of general formula [24] to a deprotection reaction in the presence or absence of an acid or a base.

As the acid used in this reaction according to the need, hydrochloric acid, sulfuric acid, acetic acid, trifluoroacetic acid, p-toluenesulfonic acid and the like can be referred to, and amount thereof is 1-50 mol and preferably 10-30 mol per mol of the compound of general formula [24]. As the base which can be used in this reaction according to the need, alkali metal alkoxides such as sodium methoxide, sodium ethoxide, potassium tert-butoxide and the like; alkali metal hydrides such as sodium hydride, potassium hydride and the like; alkali metal carbonates such as potassium carbonate, sodium carbonate and the like; and alkali metal hydroxides such as sodium hydroxide, potassium hydroxides and the like can be referred to, and the amount thereof is 1-50 mol and preferably 1-30 mol per mol of the compound of general formula [24]. Although the solvent used in this reaction is not particularly limited so far as it exercises no adverse influence on the reaction, alcohols such as methanol, ethanol and the like; aromatic hydrocarbons such as benzene, toluene, xylene and the like; ethers such as dioxane, tetrahydrofuran, anisole, diethylene glycol diethyl ether, dimethyl cellosolve and the like; nitrites such as acetonitrile and the like; amides such as N,N-dimethylformamide, N,N-dimethylacetamide and the like; halogenated hydrocarbons such as chloroform, methylene chloride and the like; acetic acid; water; and sulfoxides such as dimethyl sulfoxide and the like can be used. These solvents may be used either alone or in the form of mixture of two or more. This reaction is carried out usually at a temperature of 0° C. to 150° C. and preferably at 25-120° C., for a period of 30 minutes to 24 hours.

The reaction for obtaining a compound of general formula [26a] from a compound of general formula [25] is carried out by the same procedure as that for obtaining a compound of formula [20c] from a compound of formula [20b] in Production Process 5.

The reaction for obtaining a compound of general formula [26b] from a compound of general formula [26a] is carried out by the same procedure as that for obtaining a compound of formula [20d] from a compound of formula [20c] in Production Process 5.

The reaction for obtaining a compound of general formula [26a] from a compound of general formula [12c] is carried out by the same procedure as that for obtaining a compound of formula [24] from a compound of formula [23] in Production Process 7.

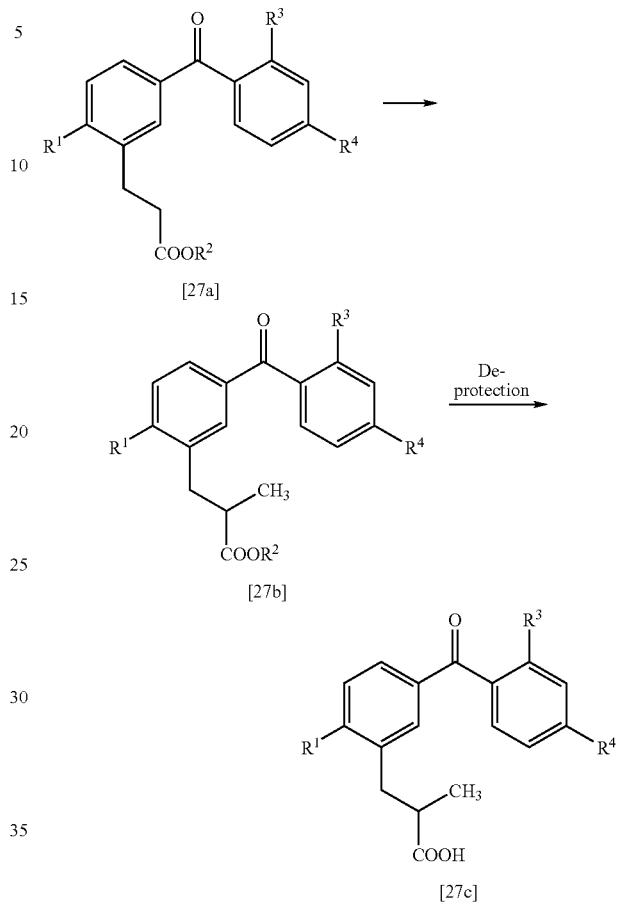

[Production Process 8a]

wherein R$^1$, R$^2$ (hydrogen atom is excepted), R$^3$ and R$^4$ are as defined above.

The compound of general formula [27b] can be obtained by reacting a compound of general formula [27a] with methyl iodide, methyl bromide or the like in the presence of a base.

As the base used for this reaction, organolithium compounds such as lithium diisopropyl-amide and the like; alkali metal alkoxides such as sodium methoxide, sodium ethoxide, potassium tert-butoxide and the like; alkali metal hydrides such as sodium hydride, potassium hydride and the like; alkali metal carbonates such as potassium carbonate, sodium carbonate and the like; and alkali metal hydroxides such as sodium hydroxide, potassium hydroxide and the like can be referred to. The base is used in an amount of 1-20 mol and preferably 1-10 mol per mol of the compound of general formula [27a]. Methyl iodide, methyl bromide and the like are used in an amount of 1-50 mol and preferably 1-20 mol per mol of the compound of general formula [27a]. Although the solvent used in this reaction is not particularly limited so far as it exercises no adverse influence on the reaction, aromatic hydrocarbons such as benzene, toluene, xylene and the like; ethers such as dioxane, tetrahydrofuran, anisole, diethylene glycol diethyl ether, dimethyl cellosolve and the like; nitriles such as acetonitrile and the like; amides such as N,N-dimethylformamide, N,N-dimethylacetamide and the like; halogenated hydrocarbons such as chloroform, methylene chloride and the like; and sulfoxides such as dimethyl sulfoxide and the like can be used. These solvents may be used either alone or in the form of mixture of two or more. This reaction is carried out usually at a temperature of −78° C. to 150° C. and preferably at −60° C. to 120° C., for a period of 30 minutes to 24 hours.

The reaction for forming the compound of general formula [27c] from the compound of [27b] is carried out by the same procedure as that for obtaining compound [20d] from compound [20c] in Production Process 5.

formula [50a]. As the alkyl halide used in this invention, methyl iodide, ethyl iodide, benzyl bromide and the like can be referred to, and amount thereof is 0.5-10 mol and preferably 1-3 mol per mol of the compound of general formula [50a]. Although the solvent used in this reaction is not particularly limited so far as it exercises no adverse influence on the reaction, aromatic hydrocarbons such as benzene, toluene, xylene and the like; ethers such as dioxane, tetrahydrofuran, anisole, diethylene glycol diethyl

[Production Process 8b]

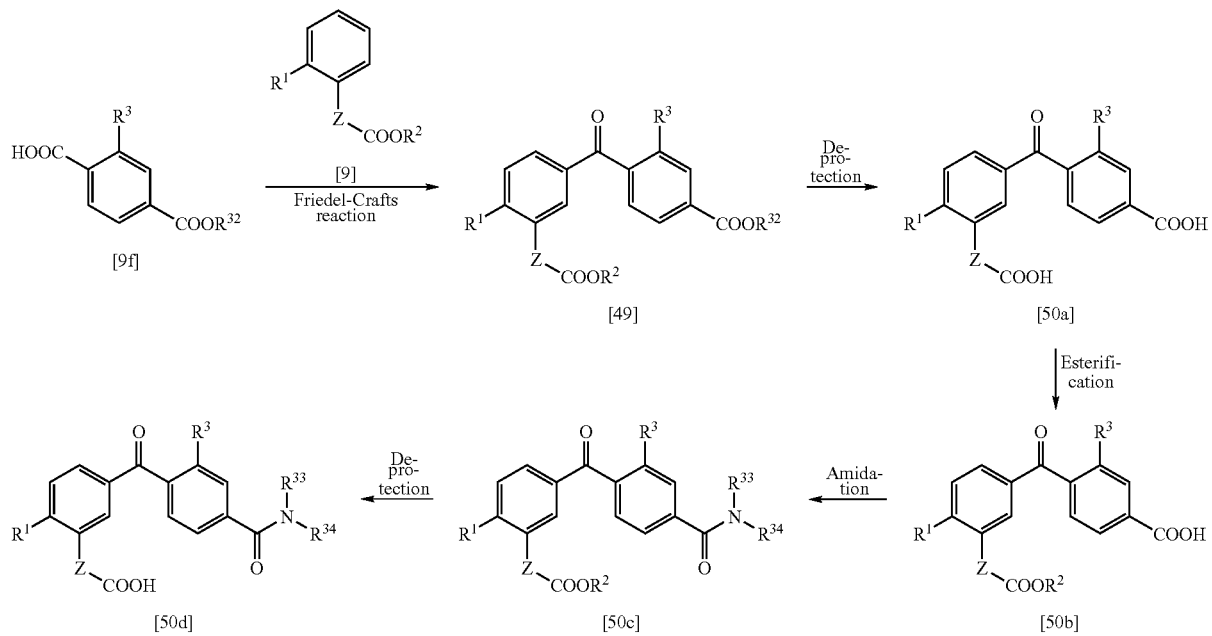

wherein $R^{32}$ is a protecting group for carboxyl group; $R^{33}$ and $R^{34}$ may be the same or different and independently represent hydrogen atom or alkyl, cycloalkyl, aralkyl, aryl or heterocyclic group; and $R^1$, $R^2$ (hydrogen atom is excepted), $R^3$ and Z are as defined above.

The reaction for forming the compound of general formula [49] from the compound of [9f] is carried out by the same procedure as that for obtaining compound [20a] from compound [12] in Production Process 5.

The reaction for forming the compound of general formula [50a] from the compound of [49] is carried out by the same procedure as that for obtaining compound [20d] from compound [20c] in Production Process 5.

The compound of general formula [50b] can be obtained by subjecting a compound of general formula [50a] to an esterification reaction.

This reaction can be effected according to the conventional procedure of esterification, and the methods for performing it include a method via an acid chloride, a method via an acid anhydride, a method using a base and alkyl halide, a method using a condensing agent and an additive, etc. When a base and an alkyl halide are used, the bases which can be used in this reaction include, for example, organic amines such as dimethylaminopyridine, triethylamine, N-methylmorpholine and the like; and alkali metal carbonates such as potassium carbonate, sodium carbonate and the like. The amount of said base is 0.5-10 mol and preferably 1-3 mol per mol of the compound of general ether, dimethyl cellosolve and the like; esters such as methyl acetate, ethyl acetate and the like; nitrites such as acetonitrile and the like; amides such as N,N-dimethylformamide and the like; halogenated hydrocarbons such as chloroform, methylene chloride and the like; and sulfoxides such as dimethyl sulfoxide and the like can be used. This reaction is carried out usually at a temperature of 0-200° C. and preferably at 5-100° C., for a period of 10 minutes to 24 hours. When a condensing agent and an additive are used, the intended product can be obtained by subjecting an alcohol such as methanol, ethanol, benzyl alcohol or the like to a condensation reaction with a condensing agent and an additive. As the condensing agent used in this reaction, for example, 1,1'-carbonyldiimidazole, dicyclohexylcarbodiimide, diisopropylcarbodiimide, N-ethyl-N'-3-dimethylaminopropylcarbodiimide, diphenyl-phosphoryl azide and the like can be referred to. As the additive used in this reaction, for example, 1-hydroxybenzotriazole, N-hydroxysuccinimide and the like can be referred to. In this reaction, each of the alcohol, condensing agent and additive is used in an amount of 0.5-10 mol and preferably 1-3 mol per mol of the compound of general formula [50a]. Although the solvent used in this reaction is not particularly limited so far as it exercises no adverse influence on the reaction, aromatic hydrocarbons such as benzene, toluene, xylene and the like; ethers such as dioxane, tetrahydrofuran, anisole, diethylene glycol diethyl ether, dimethyl cellosolve and the like; esters such as methyl-acetate, ethyl acetate and the like; nitriles such as acetonitrile and the like; amides such as N,N-dimethylformamide and the like; halogenated hydrocarbons such as chloroform, methylene chloride and the like; and sulfoxides such as dimethyl sulfoxide and the like can be used. The reaction is carried out usually at 0-200° C. and preferably at 5-100° C., for a period of 10 minutes to 24 hours.

The compound of general formula [50c] can be obtained by subjecting a compound of general formula [50b] to amidation reaction.

This reaction is a conventional amidation reaction, and includes a method via an acid chloride, a method via an acid anhydride, a method using a base, a condensing agent and an additive, etc. In the method of using a base, a condensing agent and an additive, the amines used in this reaction include primary amines such as ammonia, methylamine, benzylamine, aniline, phenethylamine, isopropylamine, aminothiazole and the like; and secondary amines such as dimethylamine, diethylamine, di-n-propylamine and the like, and amount thereof is 0.5-10 mol and preferably 1-3 mol per mol of the compound of general formula [50b]. As the base used in this reaction, for example, organic amines such as dimethylaminopyridine, triethylamine, pyridine, N-methylmorpholine and the like; and alkali metal carbonates such as potassium carbonate, sodium carbonate and the like can be referred to, and amount thereof is 0.5-10 mol and preferably 1-3 mol per mol of the compound of general formula [50b]. As the condensing agent, dicyclohexylcarbodiimide, diisopropylcarbodiimide, N-ethyl-N'-3-dimethylaminopropylcarbodiimide, diphenylphosphoryl azide and the like can be referred to, and amount thereof is 0.5-10 mol and preferably 1-3 mol per mol of the compound of general formula [50b]. As the additive used in this reaction, for example, 1-hydroxybenzotriazole, N-hydroxysuccinimide and the like can be referred to. In this reaction, each of the condensing agent and additive is used in an amount of 0.5-10 mol and preferably 1-3 mol per mol of the compound of general formula [50b]. Although the solvent used in this reaction is not particularly limited so far as it exercises no adverse influence on the reaction, aromatic hydrocarbons such as benzene, toluene, xylene and the like; ethers such as dioxane, tetrahydrofuran, anisole, diethylene glycol diethyl ether, dimethyl cellosolve and the like; esters such as methyl acetate, ethyl acetate and the like; nitrites such as acetonitrile and the like; amides such as N,N-dimethylformamide and the like; halogenated hydrocarbons such as chloroform, methylene chloride and the like; and sulfoxides such as dimethyl sulfoxide and the like can be used. The reaction is carried out usually at −20° C. to 150° C. and preferably at 0-120° C., for a period of 30 minutes to 24 hours.

The reaction for forming the compound of general formula [50d] from the compound of [50c] is carried out by the same procedure as that for obtaining compound [20d] from compound [20c] in Production Process 5.

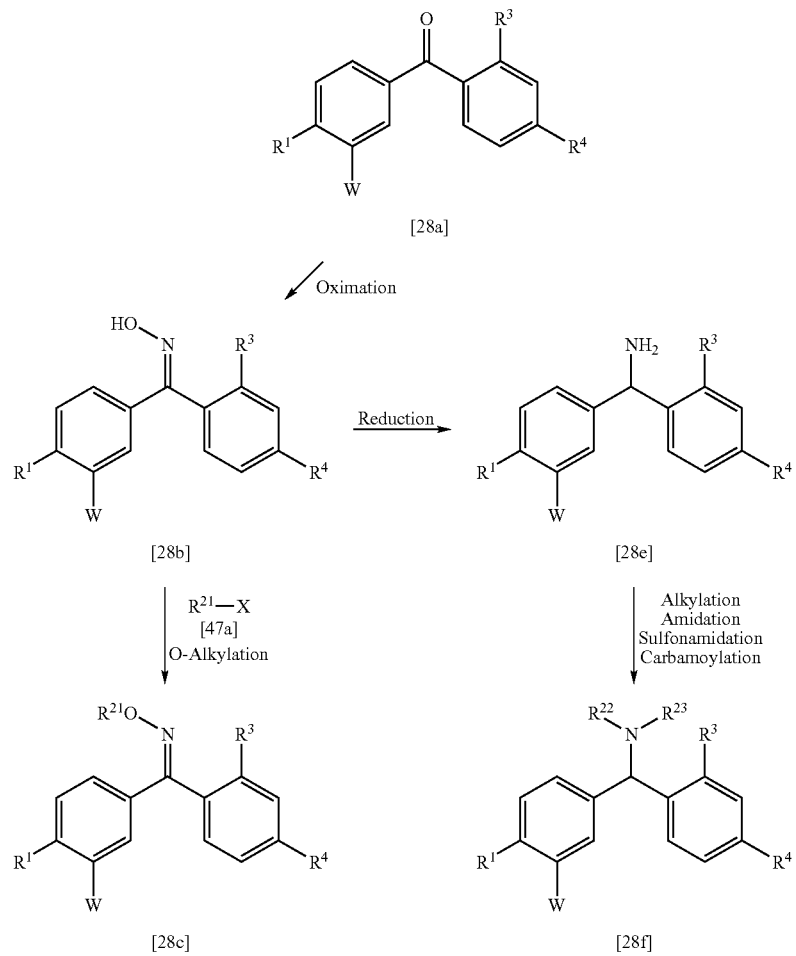

wherein $R^1$, W, $R^3$, $R^4$, $R^{21}$, $R^{22}$, $R^{23}$ and X are as defined above.

The compound of general formula [28b] can be obtained by reacting a compound of general formula [28a] with hydroxylamine hydrochloride in the presence or absence of a base.

In this reaction, hydroxylamine hydrochloride is used in an amount of 1-10 mol and preferably 1-5 mol per mol of the compound [28a]. As the base used in this reaction, alkali metal hydroxides such as sodium hydroxide and the like, organic amines such as dimethylaminopyridine, triethylamine, pyridine, N-methylmorpholine and the like, and alkali metal carbonates such as potassium carbonate, sodium carbonate and the like can be referred to, and the amount thereof is 0.5-20 mol and preferably 1-10 mol per mol of the compound of general formula [28a]. Although the solvent which can be used in this reaction is not particularly limited so far as it exercises no adverse influence on the reaction, alcohols such as methanol, ethanol, isopropyl alcohol and the like, ethers such as tetrahydrofuran, ethyl ether, dioxane, anisole and the like, halogenated hydrocarbons such as methylene chloride, chloroform, carbon tetrachloride and the like, nitriles such as acetonitrile and the like, aliphatic hydrocarbons such as n-hexane, cyclohexane and the like, esters such as ethyl acetate and the like, aromatic hydrocarbons such as toluene, benzene, xylene and the like, dimethyl sulfoxide, N,N-dimethylformamide, nitromethane, pyridine, water, etc. can be used. These solvents may be used either alone or in the form of mixture of two or more. The reaction is carried out usually at −20° C. to 150° C. and preferably 0-120° C., for a period of 30 minutes to 24 hours.

The compound of general formula [28c] can be obtained by subjecting a compound of general formula [28b] to an O-alkylating reaction or acylation reaction with a compound of general formula [47a] in the presence of base.

In this reaction, the compound of general formula [47a] is used in an amount of 1-20 mol and preferably 1-4 mol per mol of the compound of general formula [28b]. As the base used in this reaction, for example, organic amines such as dimethylaminopyridine, triethylamine, pyridine and the like; alkali metal hydrides such as sodium hydride and the like; and alkali metal carbonates such as potassium carbonate, sodium carbonate and the like can be referred to, and amount thereof is 2-20 mol and preferably 1-4 mol per mol of the compound of general formula [28b]. Although the solvent used in this reaction is not particularly limited so far as it exercises no adverse influence on the reaction, aromatic hydrocarbons such as benzene, toluene, xylene and the like, ethers such as dioxane, tetrahydrofuran, anisole, diethylene glycol diethyl ether, dimethyl cellosolve and the like, esters such as methyl acetate, ethyl acetate and the like, nitriles such as acetonitrile and the like, alcohols such as methanol, ethanol, isopropyl alcohol and the like, amides such as N,N-dimethylformamide and the like, halogenated hydrocarbons such as chloroform, methylene chloride and the like, and sulfoxides such as dimethyl sulfoxide and the like can be used as the solvent. These solvents may be used either alone or in the form of mixture of two or more. This reaction is carried out usually at 0-200° C. and preferably 10-150° C., for a period of 10 minutes to 24 hours.

The compound of general formula [28e] can be obtained by subjecting a compound of general formula [28b] to reduction including hydrogenation using a metallic catalyst in the presence or absence of an acid, a base or a salt.

As the acid used in this reaction according to the need, hydrochloric acid, sulfuric acid, acetic acid, trifluoroacetic acid, nickel chloride, aluminum chloride and the like can be referred to, and amount thereof is 1-10 mol and preferably 1-5 mol per mol of the compound of general formula [28b]. As the base used in this reaction according to the need, alkali metal hydroxides such as sodium hydroxide, potassium hydroxide and the like, ammonia, pyridine and the like can be referred to, and amount thereof is 1-1,000 mol and preferably 1-10 mol per mol of the compound of general formula [28b]. As the salt used in this reaction according to the need, lithium chloride, magnesium chloride, ammonium acetate and the like can be referred to, and amount thereof is 1-10 mol and preferably 1-5 mol per mol of the compound of general formula [28b]. As the reductant, sodium borohydride, lithium borohydride, diisobutylaluminum hydride, lithium aluminum hydride, triethylsilane, hydrogen, cyclohexene, diborane, sodium amalgam, Raney nickel and the like can be referred to, and amount thereof is 1-20 mol and preferably 1-10 mol per mol of the compound of general formula [28b]. As the catalyst, palladium-carbon, palladium-black, palladium hydroxide and the like can be referred to, and amount thereof is 0.001-1 mol per mol of the compound [28b]. Although the solvent used in this reaction is not particularly limited so far as it exercises no adverse influence on the reaction, halogenated hydrocarbons such as methylene chloride, chloroform, carbon tetrachloride and the like, ethers such as tetrahydrofuran, ethyl ether and the like, alcohols such as methanol, ethanol, isopropyl alcohol and the like, aromatic hydrocarbons such as toluene, benzene, xylene and the like, aliphatic hydrocarbons such as n-hexane, cyclohexane and the like, esters such as ethyl acetate and the like, N,N-dimethylformamide, acetic acid, pyridine water, etc. can be referred to, for example, and these solvents may be used either alone or in the form of mixture of two or more. The reaction is carried out usually at a temperature ranging from −78° C. to reflux temperature of the solvent and preferably at 0-30° C., for a period of 30 minutes to 24 hours.

The compound of general formula [28f] can be obtained by subjecting a compound of general formula [28e] to alkylation, amidation or sulfonamidation reaction in the presence of a base.

As the alkylating agent used in this reaction, for example, methyl iodide and benzyl bromide can be referred to. As the amidating agent, for example, acid anhydrides such as acetic anhydride and the like and acyl halides such as acetyl chloride, benzoyl chloride and the like can be referred to. As the sulfonamidating agent, sulfonyl halides such as methanesulfonyl chloride, benzenesulfonyl chloride and the like can be referred to. These reagents are used in an amount of 1-20 mol and preferably 1-4 mol per mol of the compound of general formula [28e]. As the base used in this reaction, for example, organic amines such as dimethylaminopyridine, triethylamine, pyridine and the like; and alkali metal carbonates such as potassium carbonate, sodium carbonate and the like can be referred to, and amount thereof is 1-20 mol and preferably 1-4 mol per mol of the compound [28e]. Although the solvent used in this reaction is not particularly limited so far as it exercises no adverse influence on the reaction, aromatic hydrocarbons such as benzene, toluene, xylene and the like, ethers such as dioxane, tetrahydrofuran, anisole, diethylene glycol diethyl ether, dimethyl cellosolve and the like, esters such as methyl acetate, ethyl acetate and the like, nitriles such as acetonitrile and the like, alcohols such as methanol, ethanol, isopropyl alcohol and the like, amides such as N,N-dimethylformamide and the like, and halogenated hydrocarbons such as chloroform, methylene chloride and the like can be used as the solvent. These solvents may be used either alone or in the form of mixture of two or more. This reaction is carried out usually at 0-200° C. and preferably 10-150° C., for a period of 10 minutes to 24 hours. It is also possible to carry out carbamoylation by reacting a compound of general formula [28e] with triphosgene and then treating the active intermediate thus obtained with aqueous ammonia. The amount of triphosgene used in this reaction is 0.3-20 mol and preferably 1-4 mol per mol of the compound of general formula [28e]. As the base used in this reaction, organic amines such as dimethylaminopyridine, triethylamine, pyridine and the like can be referred to, and amount thereof is 1-20 mol and preferably 1-4 mol per mol of the compound of general formula [28e]. Although the solvent used in this reaction is not particularly limited so far as it exercises no adverse influence on the reaction, halogenated hydrocarbons such as chloroform, methylene chloride and the like are used, for example. This reaction is carried out usually at 0-70° C. and preferably at 0-30° C., for a period of 30 minutes to 24 hours.

Thereafter, the compound of general formula [28e] is treated with 1-50 v/w, preferably 5-15 v/w, of 25% aqueous ammonia to obtain a carbamoyl compound. This reaction is carried out usually at 0-100° C. and preferably at 0-30° C., for a period of 10 minutes to 24 hours.

In cases where the compounds mentioned in Production Process 9 have a group which has to be protected, such as a carboxyl group or the like, the objective compound can be obtained by first appropriately protecting the group before the reaction and removing the protecting group after completion of the reaction.

Although the solvent used in this reaction is not particularly limited so far as it exercises no adverse influence on the reaction, aromatic hydrocarbons such as benzene, toluene and the like, ethers such as dioxane, tetrahydrofuran, diethyl ether and the like, esters such as ethyl acetate, butyl acetate and the like, nitrites such as acetonitrile and the like, amides such as N,N-dimethylformamide N,N-dimethylacetamide and the like, halogenated hydrocarbons such as chloroform, methylene chloride and the like, sulfones such as sulfolane and the like, and sulfoxides such as dimethyl sulfoxide and the like can be used as the solvent. These solvents may be used either alone or in the form of mixture of two or more. This reaction is carried out usually at a temperature of −78° C. to reflux temperature of the solvent and preferably 0-150° C., for a period of 30 minutes to 24 hours. If desired, this reaction may be carried out in the atmosphere of an inert gas such as argon or nitrogen.

The compound of general formula [3f] can be obtained by subjecting a compound of general formula [3b] to Grignard reaction.

Concretely speaking, the compound [3f] can be obtained by reacting a compound of general formula [3b] with a

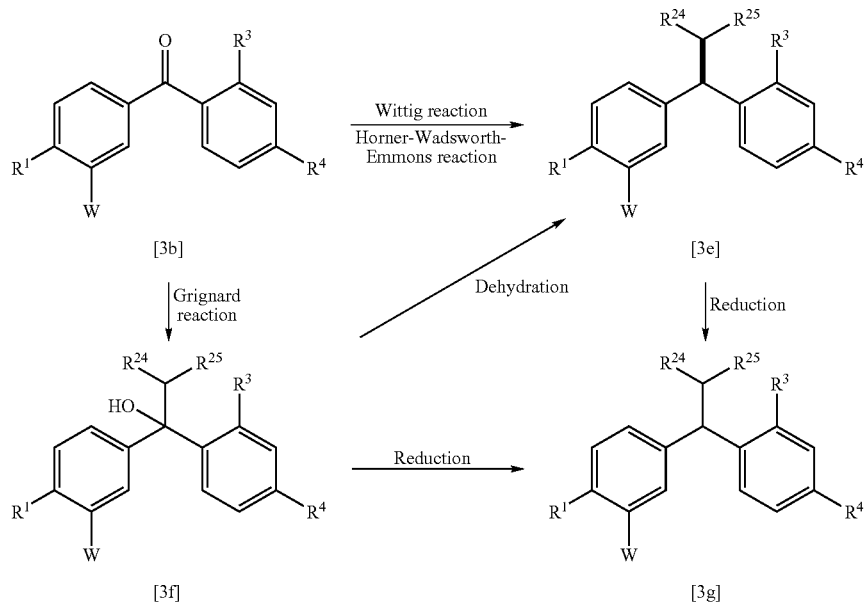

wherein $R^1$, W, $R^3$, $R^4$, $R^{24}$ and $R^{25}$ are as defined above.

The compound of general formula [3e] can be a obtained by reacting a compound of general formula [3b] with Wittig reagent or Horner-Wadsworth-Emmons reagent.

Concretely speaking, the compound of general formula [3e] can be obtained by reacting a compound of general formula [3b] with Wittig reagent synthesized according to the method described in Organic Syntheses Collective Volume, Vol. 5, Pages 751-754 (1973) or Horner-Wadsworth-Emmons reagent synthesized according to the method described in Organic Syntheses Collective Volume, Vol. 5, Pages 509-513 (1973).

The Wittig reagent and Horner-Wadsworth-Emmons reagent used in this reaction are used in an amount of 1-100 mol and preferably 1-10 mol per mol of the compound of general formula [3b].

Grignard reagent synthesized according to the method described in Organic Syntheses Collective Volume, Vol. 1, Pages 188-190 (1956).

In this reaction, the Grignard reagent is used in an amount of 1-100 mol and preferably 1-10 mol per mol of the compound of general formula [3b].

Although the solvent used in this reaction is not particularly limited so far as it exercises no adverse influence on the reaction, aromatic hydrocarbons such as benzene, toluene and the like, ethers such as dioxane, tetrahydrofuran, diethyl ether and the like, and sulfones such as sulfolane and the like can be used as the solvent. These solvents may be used either alone or in the form of mixture of two or more. This reaction is carried out usually at a temperature of −78° C. to reflux temperature of the solvent and preferably 0-150° C., for a period of 30 minutes to 24 hours. If desired, this reaction may be carried out in the atmosphere of an inert gas such as argon or nitrogen.

The compound of general formula [3e] can be obtained by dehydrating a compound of general formula [3f] in the presence or absence of an acid, a base or a dehydrating agent.

As the acid used in this reaction, mineral acids such as hydrochloric acid, sulfuric acid, phosphoric acid, hydrobromic acid and the like; and organic acids such as p-toluenesulfonic acid, trifluoroacetic acid and the like can be referred to, and amount thereof is 1-1,000 mol and preferably 1-100 mol per mol of the compound of general formula [3f]. As the base used in this reaction, alkali metal hydroxides such as sodium hydroxide and the like; and organic amines such as triethylamine, 1,8-diazabicyclo-[5.4.0]undec-7-ene and the like can be referred to, and amount thereof is 1-1,000 mol and preferably 1-100 mol per mol of the compound of general formula [3f]. As the dehydrating agent used in this reaction, diphosphorus pentoxide, polyphosphoric acid and the like can be referred to, and amount thereof 1-1,000 mol and preferably 1-100 mol per mol of the compound of general formula [3f].

Although the solvent used in this reaction is not particularly limited so far as it exercises no adverse influence on the reaction, aromatic hydrocarbons such as benzene, toluene and the like, ethers such as dioxane, tetrahydrofuran, diethyl ether and the like, esters such as ethyl acetate, butyl acetate and the like, nitriles such as acetonitrile and the like, amides such as N,N-dimethylformamide, N,N-dimethylacetamide and the like, halogenated hydrocarbons such as chloroform, methylene chloride and the like, sulfones such as sulfolane and the like, and sulfoxides such as dimethyl sulfoxide and the like can be used as the solvent. These solvents may be used either alone or in the form of mixture of two or more. This reaction is carried out usually at a temperature of $-78°$ C. to reflux temperature of the solvent and preferably 0-150° C., for a period of 30 minutes to 24 hours. If desired, this reaction may be carried out in the atmosphere of an inert gas such as argon or nitrogen.

The compound of general formula [3g] can be obtained by subjecting a compound of general formula [3e] or general formula [3f] to a reduction including hydrogenation using a metallic catalyst, in the presence or absence of an acid, a base or a salt.

As the acid used in this reaction, hydrochloric acid, sulfuric acid, hydrobromic acid, aluminum chloride, boron trifluoride, trifluoroacetic acid and the like can be referred to, and amount thereof is 1-1,000 mol and preferably 1-100 mol per mol of the compound of general formula [3e] or [3f]. As the base used in this reaction, alkali metal hydroxides such as sodium hydroxide and the like and organic amines such as triethylamine, pyridine and the like can be referred to, and amount thereof is 1-1,000 mol and preferably 1-100 mol per mol of the compound of general formula [3e] or [3f]. As the salt used in this reaction, lithium chloride, calcium chloride and the like can be referred to, and amount thereof is 1-100 mol and preferably 1-10 mol per mol of general formula [3e] or [3f]. As the reductant used in this reaction, sodium borohydride, lithium borohydride, lithium aluminum hydride, diisobutylaluminum hydride, triethylsilane, hydrogen, cyclohexene and the like can be used, and amount thereof is 1-10 mol and preferably 1-5 mol per mol of the compound of general formula [3e] or [3f]. As the catalyst used in this reaction, palladium-carbon, palladium-black, palladium hydroxide and the like can be referred to, and amount thereof is 0.001 to 1 mol and preferably 0.01 to 0.5 mol per mol of the compound of general formula [3e] or [3f]. Although the solvent used in this reaction is not particularly limited so far as it exercises no adverse influence on the reaction, aromatic hydrocarbons such as benzene, toluene and the like, ethers such as dioxane, tetrahydrofuran, diethyl ether and the like, esters such as ethyl acetate, butyl acetate and the like, alcohols such as methanol, ethanol and the like, amides such as N,N-dimethylformamide, N,N-dimethylacetamide and the like, halogenated hydrocarbons such as chloroform, methylene chloride and the like, sulfones such as sulfolane and the like, aliphatic hydrocarbons such as hexane, cyclohexane and the like, acetic acid, pyridine, water, etc. can be used as the solvent. These solvents may be used either alone or in the form of mixture of two or more. The reaction is carried out usually at a temperature from $-78°$ C. to reflux temperature of the solvent and preferably at 0-30° C., for a period of 30 minutes to 24 hours.

When $R^{24}$ and $R^{25}$ referred to in the reaction for obtaining compound [3e], [3f] or [3g] have an unprotected or protected carboxyl group, an unprotected or protected hydroxyl group or an unprotected or protected amino group, the objective compound can be obtained by appropriately carrying out a protecting reaction and a de-protecting reaction.

[Production Process 10]

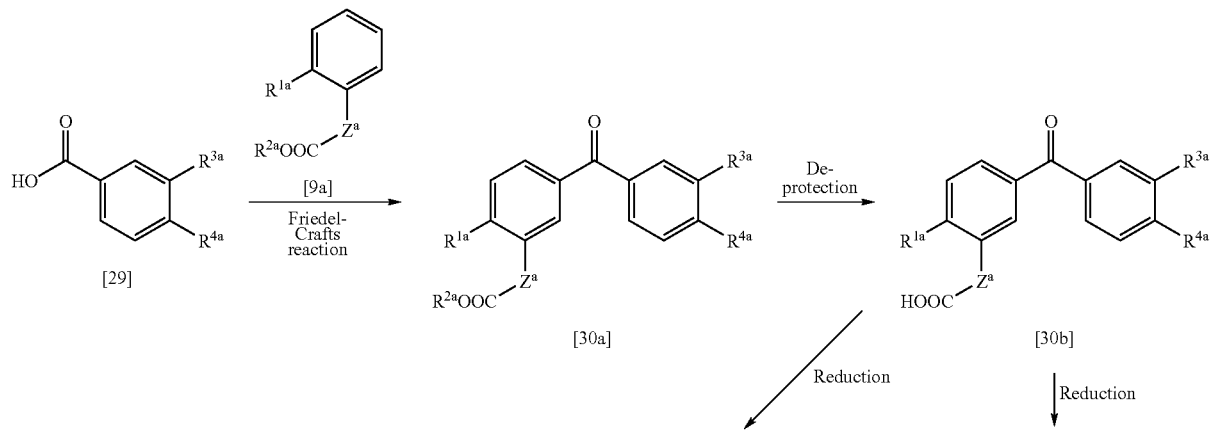

-continued

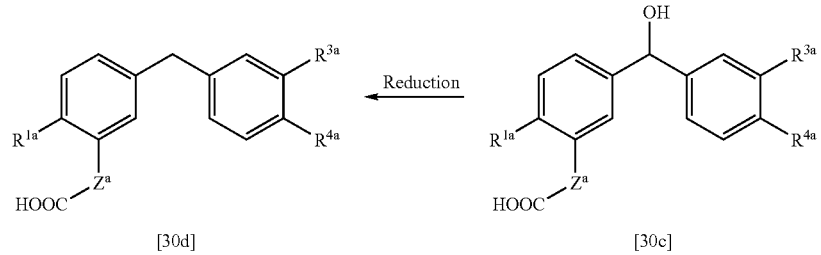

wherein $R^{1a}$, $R^{2a}$ (hydrogen atom is excepted), $R^{3a}$, $R^{4a}$ and $Z^a$ are as defined above.

The reaction for obtaining a compound of general formula [30a] from a compound of general formula [29] can be carried out by the same procedure as that for obtaining a compound of general formula [20a] from compound [12] in Production Process 5.

The reaction for obtaining a compound of general formula [30b] from a compound of general formula [30a] can be carried out by the same procedure as that for obtaining a compound of general formula [20d] from compound [20c] in Production Process 5.

The reaction for obtaining a compound of general formula [30c] from a compound of general formula [30b] can be carried out by the same procedure as that for obtaining a compound of general formula [3c] from compound [3b] in Production Process 2.

The reaction for obtaining a compound of general formula [30d] from a compound of general formula [30b] and [30c] can be carried out by the same procedure as that for obtaining a compound of general formula [3d] from compound [3b] and [3c] in Production Process 2.

wherein $R^{1a}$, $R^{3a}$, $R^{4a}$, $R^{27a}$, $R^{28a}$, $X^{1a}$ and $Z^a$ are as defined above.

The reaction for obtaining a compound of general formula [31b] from a compound of general formula [31a] can be carried out by the same procedure as that for obtaining a compound of general formula [21b] from compound [21a] in Production Process 6.

The reaction for obtaining a compound of general formula [31c] from a compound of general formula [31a] can be carried out by the same procedure as that for obtaining a compound of general formula [21c] from compound [21a] in Production Process 6.

When $X^{1a}$ or $R^{27a}$ described in Production Process 11 has a group which has to be protected such as a carboxyl group, the objective compound can be obtained by appropriately carrying out protection before the reaction and de-protection after completion of the reaction.

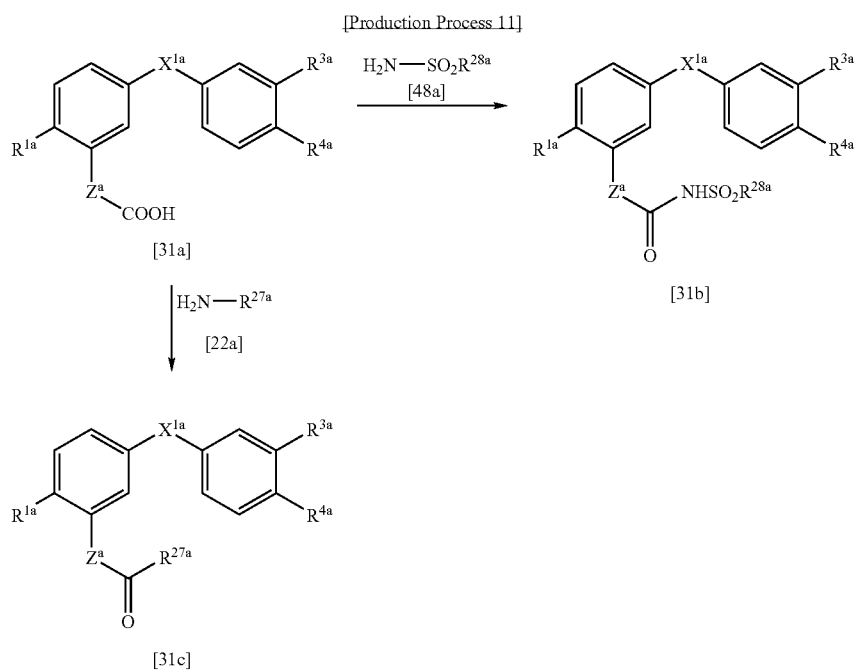

[Production Process 12]
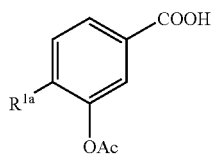
[32]
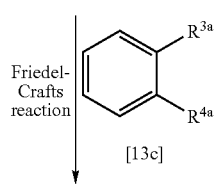
[13c]
Friedel-Crafts reaction
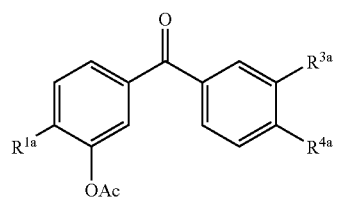
[33]
De-protection →
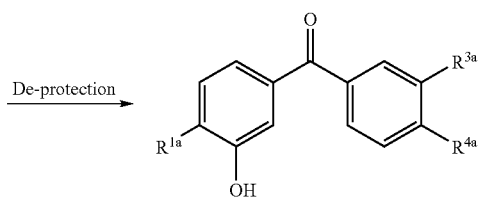
[34]
$X\!-\!Z^{a''}\!-\!COOR^{2a'}$
[36a]
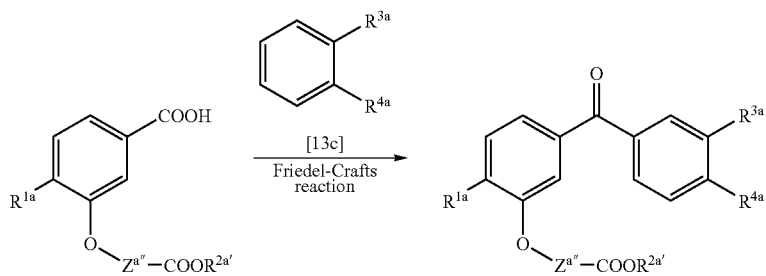
[12b]     [35a]
[13c]
Friedel-Crafts reaction
De-protection
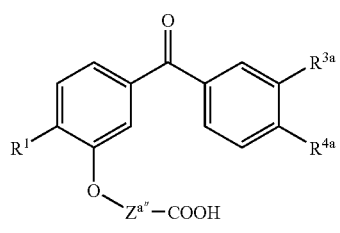
[35b]

wherein Ac represents acetyl group; $Z^{a''}$ represents —CH$_2$— or —CH$_2$—CH$_2$—; and $R^{1a}$, $R^{2a'}$ (hydrogen atom is excepted), $R^{3a}$, $R^{4a}$ and X are as defined above.

The reaction for obtaining a compound of general formula [33] from a compound of general formula [32] can be carried out by the same procedure as that for obtaining a compound of general formula [20a] from compound [12] in Production Process 5.

The reaction for obtaining a compound of general formula [34] from a compound of general formula [33] can be carried out by the same procedure as that for obtaining a compound of general formula [25] from compound [24] in Production Process 7.

The reaction for obtaining a compound of general formula [35a] from a compound of general formula [34] can be carried out by the same procedure as that for obtaining a compound of general formula [26a] from compound [25] in Production Process 7.

The reaction for obtaining a compound of general formula [35b] from a compound of general formula [35a] can be carried out by the same procedure as that for obtaining a compound of general formula [26b] from compound [26a] in Production Process 7.

The reaction for obtaining a compound of general formula [35a] from a compound of general formula [12b] can be carried out by the same procedure as that for obtaining a compound of general formula [33] from compound [32] in Production Process 12.

[Production Process 13]

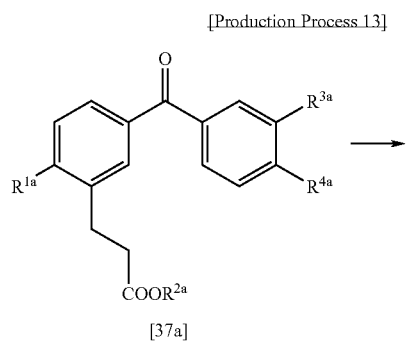

[37a]

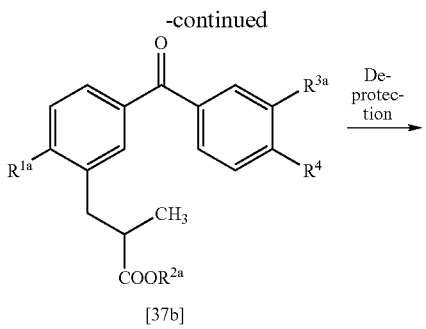

[37b]

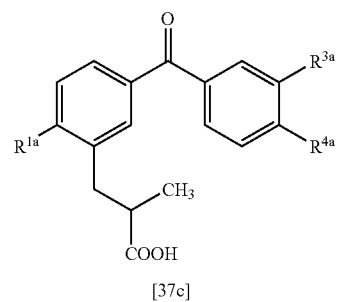

[37c]

wherein $R^{1a}$, $R^{2a}$ (hydrogen atom is excepted), $R^{3a}$ and $R^{4a}$ are as defined above.

The reaction for obtaining a compound of general formula [37b] from a compound of general formula [37a] can be carried out by the same procedure as that for obtaining a compound of general formula [27b] from compound [27a] in Production Process 8a.

The reaction for obtaining a compound of general formula [37c] from a compound of general formula [37b] can be carried out by the same procedure as that for obtaining a compound of general formula [27c] from compound [27b] in Production Process 8a.

[Production Process 14]

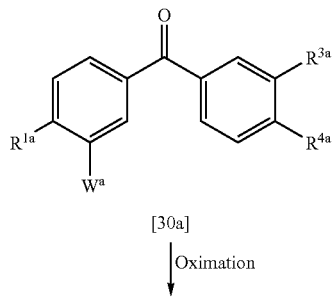

[30a]

↓ Oximation

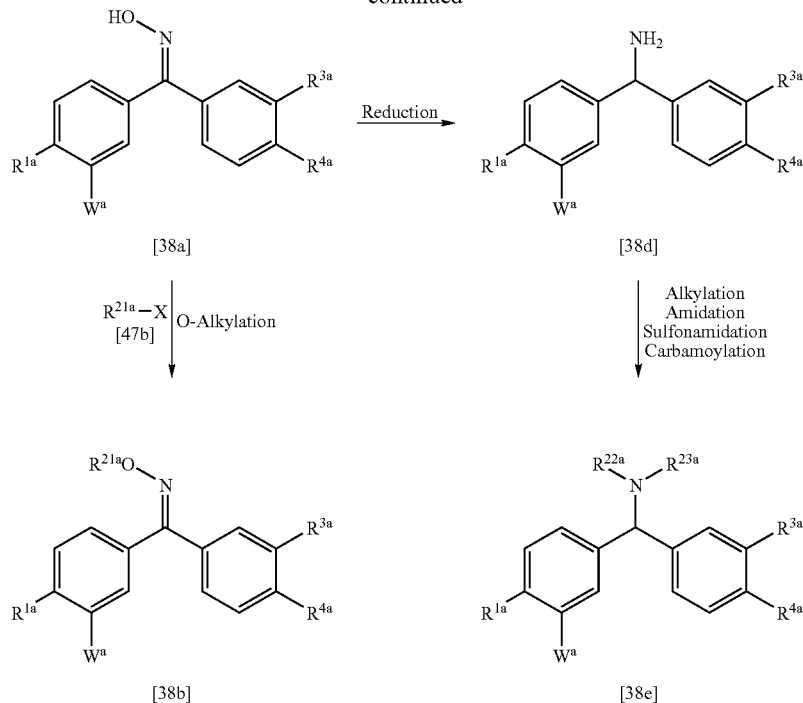

wherein $R^{1a}$, $W^a$, $R^{3a}$, $R^{4a}$, $R^{21a}$, $R^{22a}$, $R^{23a}$ and X are as defined above.

The reaction for obtaining a compound of general formula [38a] from a compound of general formula [30a] can be carried out by the same procedure as that for obtaining a compound of general formula [28b] from compound [28a] in Production Process 9.

The reaction for obtaining a compound of general formula [38b] from a compound of general formula [38a] can be carried out by the same procedure as that for obtaining a compound of general formula [28c] from compound [28b] in Production Process 9.

The reaction for obtaining a compound of general formula [38d] from a compound of general formula [38a] can be carried out by the same procedure as that for obtaining a compound of general formula [28e] from compound [28b] in Production Process 9.

The reaction for obtaining a compound of general formula [38e] from a compound of general formula [38d] can be carried out by the same procedure as that for obtaining a compound of general formula [28f] from compound [28e] in Production Process 9.

Some of the compounds mentioned in Production Process 14 may have a group which has to be protected, such as carboxyl group. In such a case, the objective compound can be obtained by carrying out protection before the reaction, then carrying out the reaction, and carrying out de-protection after the reaction.

[Production Process 14a]

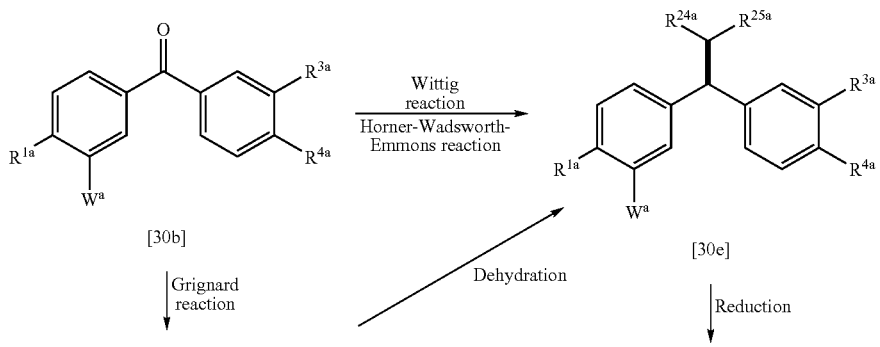

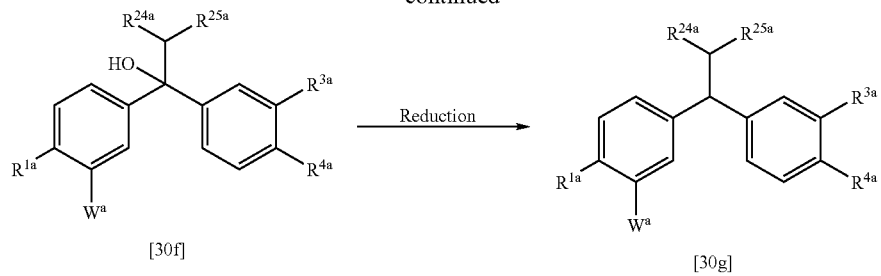

wherein $R^{1a}$, $W^a$, $R^{3a}$, $R^{4a}$, $R^{24a}$ and $R^{25a}$ are as defined above.

The reaction for obtaining a compound of general formula [30e] from a compound of general formula [30b] can be carried out by the same procedure as that for obtaining a compound of general formula [3e] from compound [3b] in Production Process 9a.

The reaction for obtaining a compound of general formula [30f] from a compound of general formula [30b] can be carried out by the same procedure as that for obtaining a compound of general formula [3f] from compound [3b] in Production Process 9a.

The reaction for obtaining a compound of general formula [30g] from a compound of general formula [30e] and a compound of [30f] can be carried out by the same procedure as that for obtaining a compound of general formula [3g] from compounds [3e] and [3f] in Production Process 9a.

In some of the reactions for obtaining the compounds of general formulas [30e], [30f] and [30g], $R^{24a}$ and $R^{25a}$ may involve an unprotected or protected carboxyl group, an unprotected or protected hydroxyl group or an unprotected or protected amino group. In such a case, the objective compound can be obtained by carrying out protecting and de-protecting reactions appropriately.

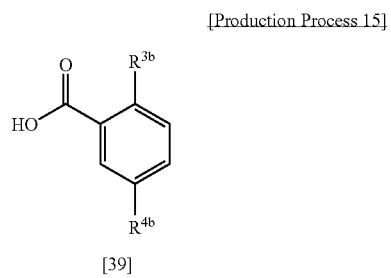

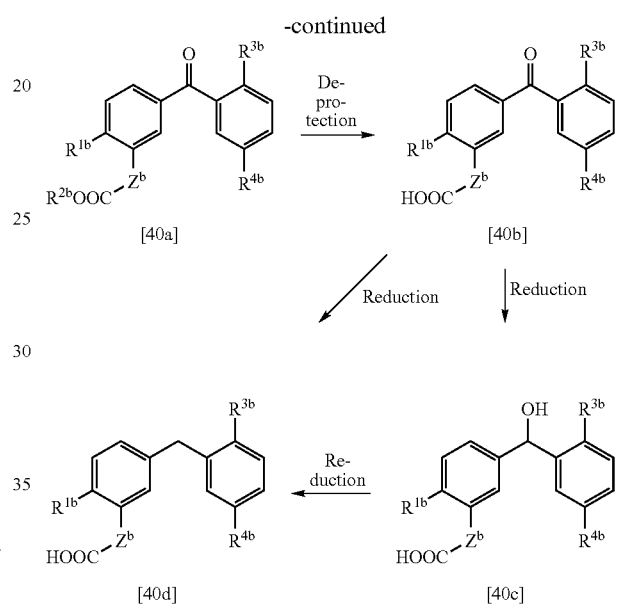

wherein $R^{1b}$, $R^{2b}$ (hydrogen atom is excepted), $R^{3b}$, $R^{4b}$ and $Z^b$ are as defined above.

The reaction for obtaining a compound of general formula [40a] from a compound of general formula [39] can be carried out by the same procedure as that for obtaining a compound of general formula [30a] from compound [29] in Production Process 10.

The reaction for obtaining a compound of general formula [40b] from a compound of general formula [40a] can be carried out by the same procedure as that for obtaining a compound of general formula [30b] from compound [30a] in Production Process 10.

The reaction for obtaining a compound of general formula [40c] from a compound of general formula [40b] can be carried out by the same procedure as that for obtaining a compound of general formula [30c] from compound [30b] in Production Process 10.

The reaction for obtaining a compound of general formula [40d] from compounds of general formulas [40b] and [40c] can be carried out by the same procedure as that for obtaining a compound of general formula [30d] from compounds [30b] and [30c] in Production Process 10.

[Production Process 16]

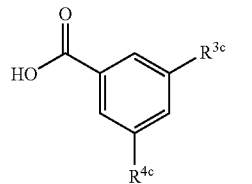

[41]

Friedel-Crafts reaction

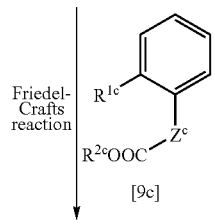

[9c]

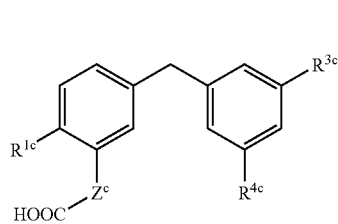

[42a]

De-protection →

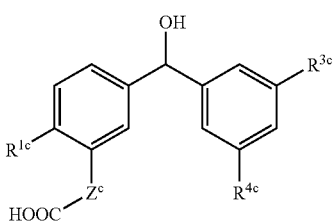

[42b]

Reduction

Reduction

OH

Reduction ←

[42d]    [42c]

wherein $R^{1c}$, $R^{2c}$ (hydrogen atom is excepted), $R^{3c}$, $R^{4c}$ and $Z^c$ are as defined above.

The reaction for obtaining a compound of general formula [42a] from a compound of general formula [41] can be carried out by the same procedure as that for obtaining a compound of general formula [30a] from compound [29] in Production Process 10

The reaction for obtaining a compound of general formula [42b] from a compound of general formula [42a] can be carried out by the same procedure as that for obtaining a compound of general formula [30b] from compound [30a] in Production Process 10.

The reaction for obtaining a compound of general formula [42c] from a compound of general formula [42b] can be carried out by the same procedure as that for obtaining a compound of general formula [30c] from compound [30b] in Production Process 10.

The reaction for obtaining a compound of general formula [42d] from compound of general formulas [42b] and [42c] can be carried out by the same procedure as that for obtaining a compound of general formula [30d] from compounds [30b] and [30c] in Production Process 10.

[Production Process 17]
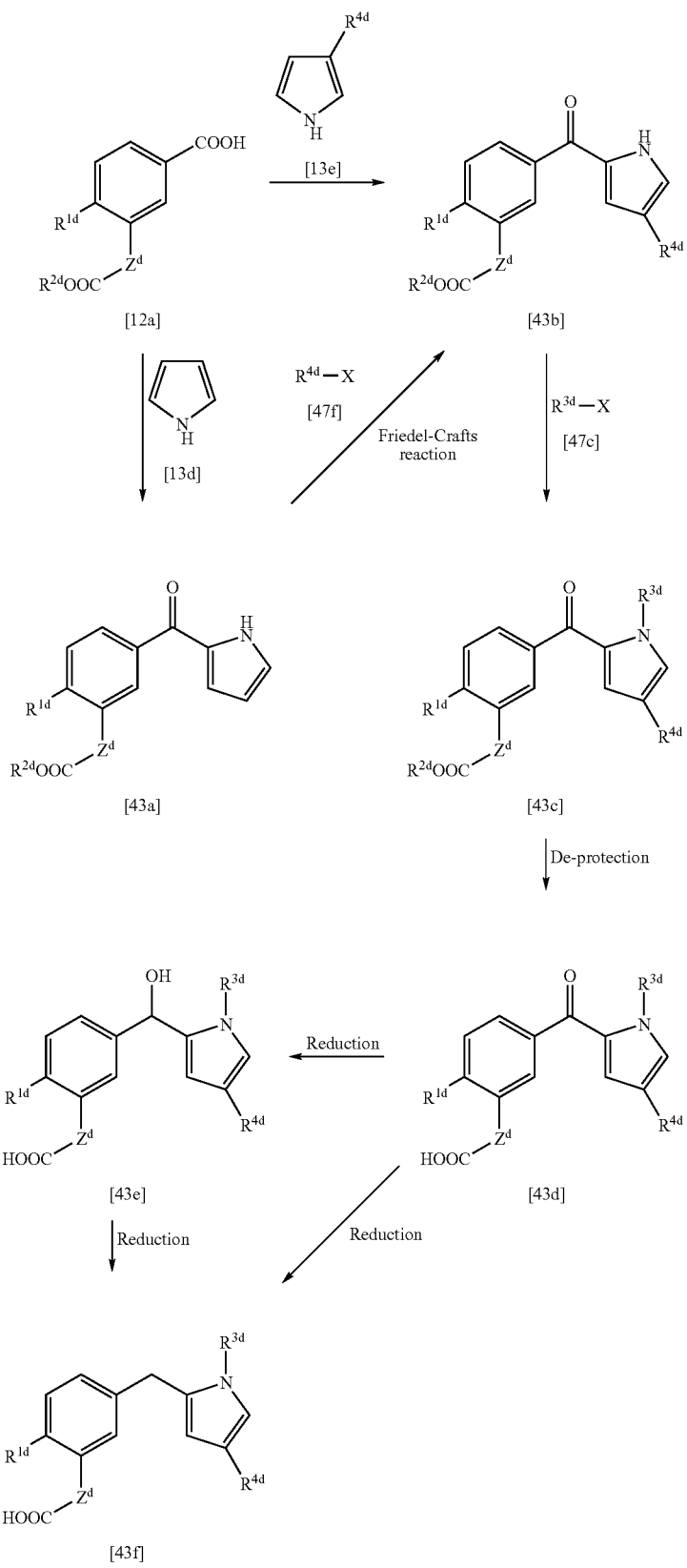

wherein $R^{1d}$, $R^{2d}$ (hydrogen atom is excepted), $R^{3d}$, $R^{4d}$, $Z^d$ and X are as defined above.

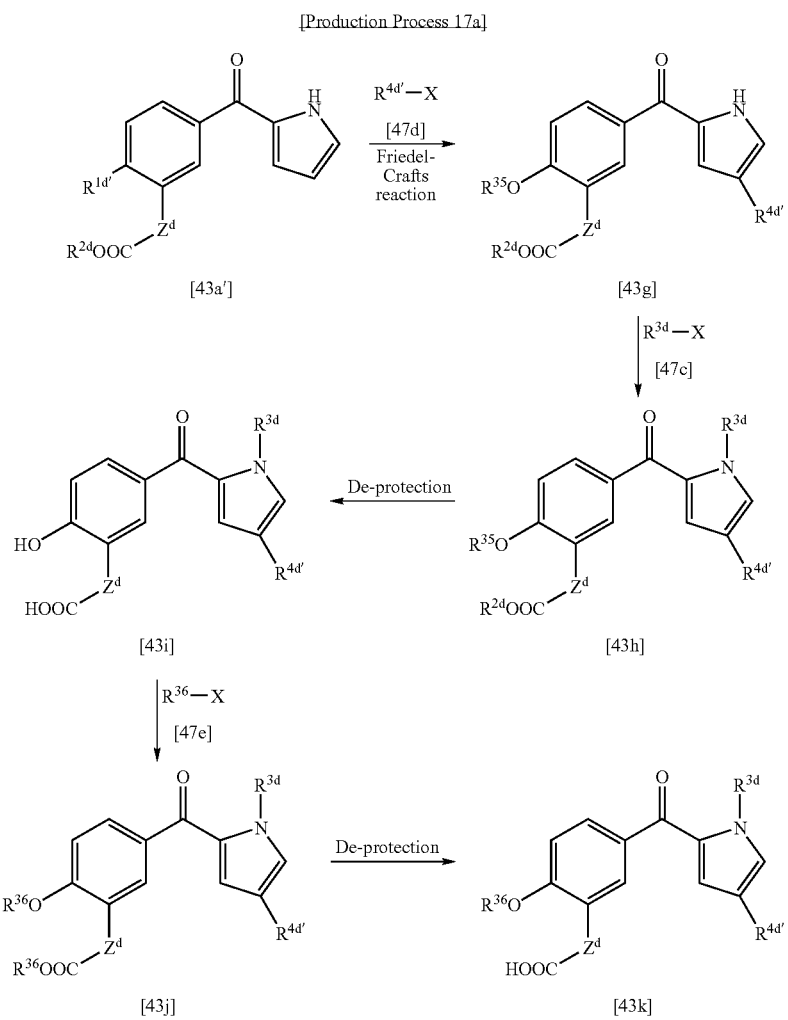

wherein $R^{1d'}$ represents alkoxyl group; $R^{35}$ represents hydrogen atom or acyl group; $R^{36}$ represents unsubstituted or substituted alkyl, cycloalkyl or aralkyl group; $R^{4d'}$ represents acyl group; and $R^{2d}$ (hydrogen atom is excepted), $R^{3d}$, X and $Z^d$ are as defined above.

The compound of general formula [43a] can be obtained by reacting an acid chloride or acid anhydride of a compound of general formula [12a] and a compound of general formula [13d] in the presence of a base.

The acid chloride or acid anhydride of compound [12a] used in this reaction can be obtained by reacting a compound of general formula [12a] with an activating agent such as thionyl chloride, oxalyl chloride, phosphorus pentoxide, acetic anhydride, ethyl chloroformate or the like, and amount thereof is 1-10 mol and preferably 1-2 mol per mol of the compound of general formula [12a]. As used herein, the amount of the compound of general formula [13d] is 1-20 mol and preferably 1-5 mol per mol of the compound of general formula [12a]. As the base used in this reaction, for example, organolithium compounds such as n-butyl-lithium, methyllithium, lithium diisopropylamide and the like; and organomagnesium compounds such as methyl magnesium bromide and the like can be referred to, and the base is used in an amount of 1-20 mol and preferably 1-3 mol per mol of the compound of general formula [12a]. Although the solvent used in this reaction is not particularly limited so far as it exercises no adverse influence on the reaction, for example, aromatic hydrocarbons such as benzene, toluene, xylene and the like; ethers such as dioxane, tetrahydrofuran, anisole, diethylene glycol diethyl ether, dimethyl cellosolve and the like; and aliphatic hydrocarbons such as hexane, cyclohexane and the like can be used as the solvent. These solvents may be used either alone or in the form of mixture of two or more.

This reaction is carried out usually at a temperature of −78° C. to 150° C. and preferably at −78° C. to 30° C., for a period of 30 minutes to 24 hours.

The reaction for obtaining a compound of general formula [43b] from a compound of [43a] can be carried out by the same procedure as that for obtaining a compound of general formula [20a] from a compound of general formula [12] in Production Process 5.

The reaction for obtaining a compound of general formula [43b] from a compound of [12a] can be carried out by the same procedure as that for obtaining a compound of general formula [43a] from a compound of general formula [12a] in Production Process 17.

The compound of general formula [43c] can be obtained by subjecting a compound of general formula [43b] to an alkylation reaction with and a compound of general formula [47c] in the presence of a base.

In this reaction, the compound of general formula [47c] is used in an amount of 1-20 mol and preferably 1-4 mol per mol of the compound of compound [43b]. As the base used in this reaction, organolithium compounds such as n-butyllithium, phenyllithium, lithium diisopropylamide and the like; alkali metal alkoxides such as sodium methoxide, sodium ethoxide, potassium tert-butoxide and the like; alkali metal hydrides such as sodium hydride, potassium hydride and the like; alkali metal carbonates such as potassium carbonate, sodium carbonate and the like; and alkali metal hydroxides such as sodium hydroxide, potassium hydroxide and the like can be referred to, and amount thereof is 2-20 mol and preferably 1-4 mol per mol of the compound of general formula [43b]. Although the solvent used in this reaction is not particularly limited so far as it exercises no adverse influence on the reaction, aromatic hydrocarbons such as benzene, toluene, xylene and the like; ethers such as dioxane, tetrahydrofuran, anisole, diethylene glycol diethyl ether, dimethyl cellosolve and the like; nitrites such as acetonitrile and the like; alcohols such as methanol, ethanol, isopropyl alcohol and the like; amides such as N,N-dimethylformamide and the like; halogenated hydrocarbons such as chloroform, methylene chloride and the like; and sulfoxides such as dimethyl sulfoxide and the like can be used as the solvent. These solvents may be used either alone or in the form of mixture of two or more. The reaction is carried out usually at a temperature ranging from −78° C. to 200° C. and preferably at −50° C. to 120° C., for a period of 10 minutes to 24 hours.

The reaction for obtaining a compound of general formula [43d] from a compound of general formula [43c] is carried out by the same procedure as that for obtaining compound of general formula [20d] from compound of general formula [20c] in Production Process 5.

The reaction for obtaining a compound of general formula [43e] from a compound of general formula [43d] is carried out by the same procedure as that for obtaining compound of general formula [3c] from compound of general formula [3b] in Production Process 2.

The reaction for obtaining a compound of general formula [43f] from compounds of general formulas [43d] and [43e] is carried out by the same procedure as that for obtaining compound of general formula [3d] from compounds of general formulas of [3b] and [3c] in Production Process 2.

The reaction for obtaining a compound of general formula [43g] from a compound of general formula [43a'] is carried out by the same procedure as that for obtaining compound of general formula [43b] from compound of general formula [43a] in Production Process 17.

The reaction for obtaining a compound of general formula [43h] from a compound of general formula [43g] is carried out by the same procedure as that for obtaining compound of general formula [43c] from compound of general formula [43b] in Production Process 17.

The reaction for obtaining a compound of general formula [43i] from a compound of general formula [43h] is carried out by the same procedure as that for obtaining compound of general formula [43d] from compound of general formula [43c] in Production Process 17.

The compound of general formula [43j] can be obtained by subjecting a compound of general formula [43i] to an O-alkylation reaction.

The reaction for obtaining a compound of general formula [43j] from a compound of general formula [43i] is carried out by the same procedure as that for obtaining compound of general formula [28c] from compound of general formula [28b] in Production Process 9.

The reaction for obtaining a compound of general formula [43k] from a compound of general formula [43j] is carried out by the same procedure as that for obtaining compound of general formula [20d] from compound of general formula [20c] in Production Process 5.

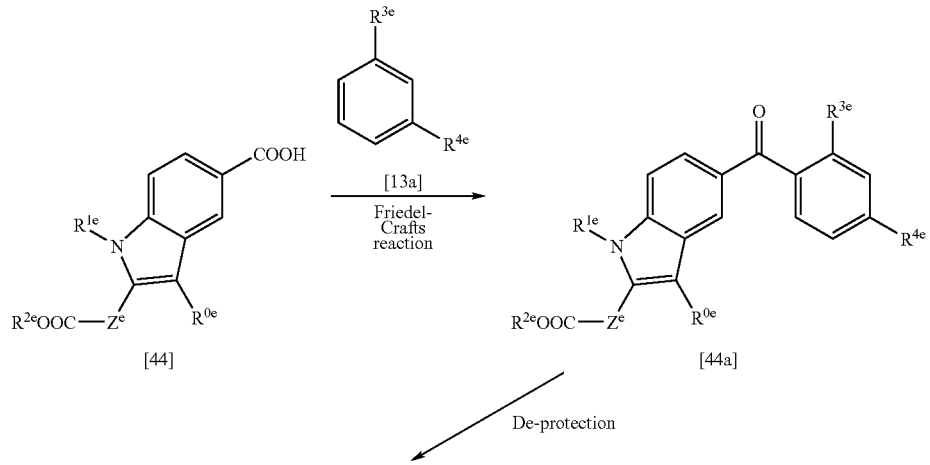

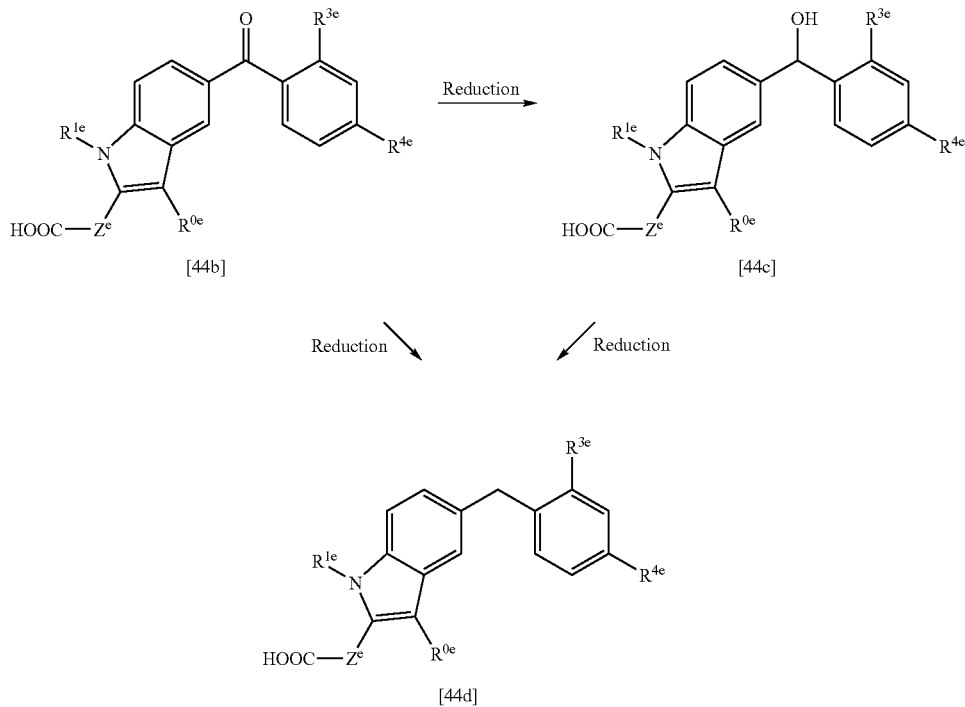

wherein $R^{0e}$, $R^{1e}$, $R^{2e}$ (hydrogen atom is excepted), $R^{3e}$, $R^{4e}$ and $Z^e$ are as defined above.

The reaction for obtaining a compound of general formula [44a] from a compound of general formula [44] is carried out by the same procedure as that for obtaining compound of general formula [30a] from compound of general formula [29] in Production Process 10.

The reaction for obtaining a compound of general formula [44b] from a compound of general formula [44a] is carried out by the same procedure as that for obtaining compound of general formula [30b] from compound of general formula [30a] in Production Process 10.

The reaction for obtaining a compound of general formula [44c] from a compound of general formula [44b] is carried out by the same procedure as that for obtaining compound of general formula [30c] from compound of general formula [30b] in Production Process 10.

The reaction for obtaining a compound of general formula [44d] from compounds of general formulas [44b] and [44c] is carried out by the same procedure as that for obtaining compound of general formula [30d] from compounds of general formulas [30b] and [30c] in Production Process 10.

[Production Process 19]

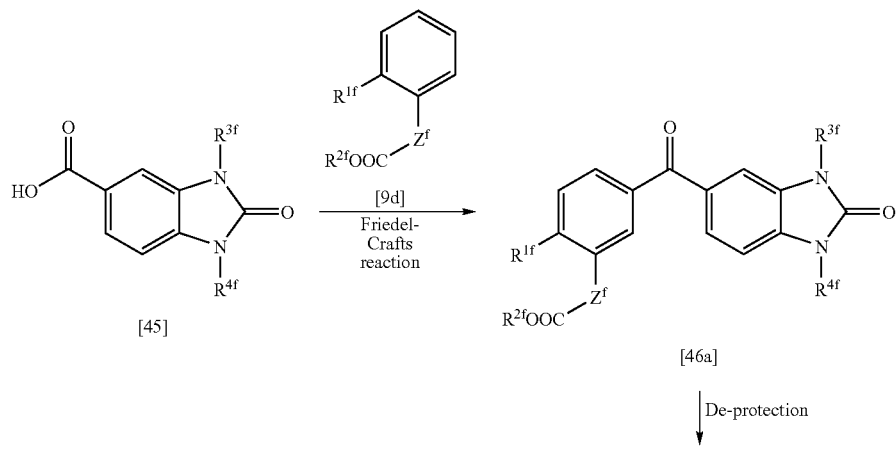

-continued

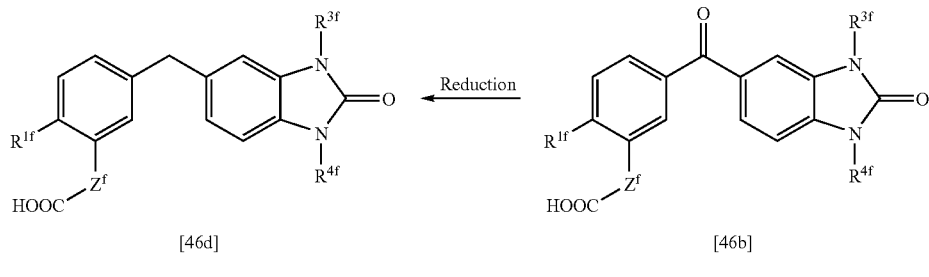

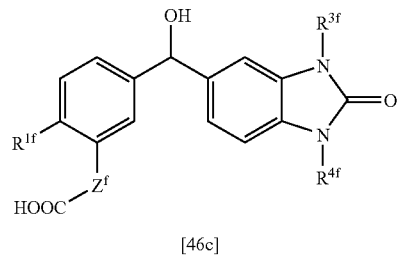

wherein $R^{1f}$, $R^{2f}$ (hydrogen atom is excepted), $R^{3f}$, $R^{4f}$ and $Z^f$ are as defined above.

The reaction for obtaining a compound of general formula [46a] from a compound of general formula [45] is carried out by the same procedure as that for obtaining a compound of general formula [30a] from a compound of general formula [29] in Production Process 10.

The reaction for obtaining a compound of general formula [46b] from a compound of general formula [46a] is carried out by the same procedure as that for obtaining a compound of general formula [30b] from a compound of general formula [30a] in Production Process 10.

The reaction for obtaining a compound of general formula [46c] from a compound of general formula [46b] is carried out by the same procedure as that for obtaining a compound of general formula [30c] from a compound of general formula [30b] in Production Process 10.

The reaction for obtaining a compound of general formula [46d] from compounds of general formulas [46b] and [46c] is carried out by the same procedure as that for obtaining a compound of general formula [30d] from compounds of general formulas [30b] and [30c] in Production Process 10.

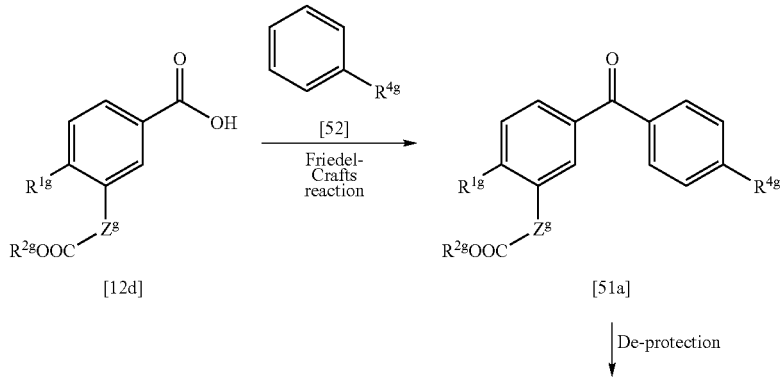

-continued

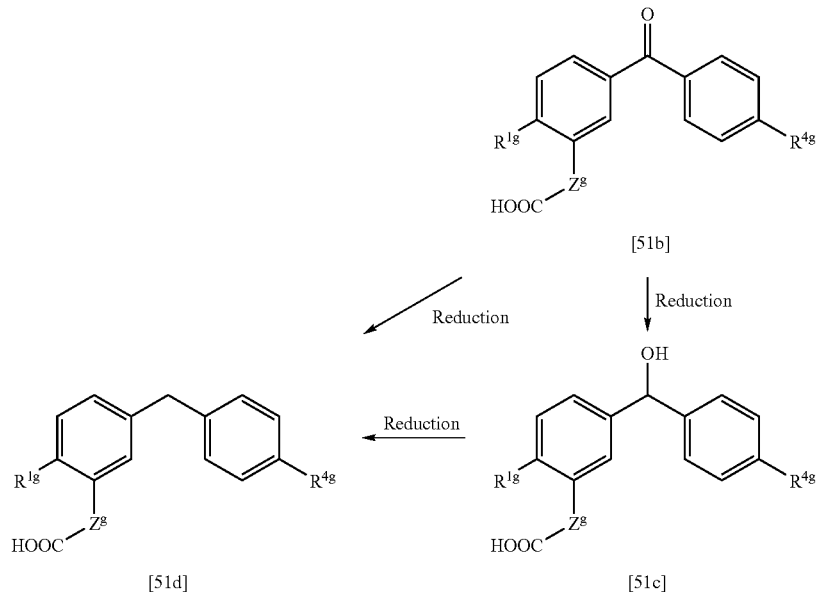

[51b]

[51d]

[51c]

wherein $R^{1g}$, $R^{2g}$ (hydrogen atom is excepted), $R^{4g}$ and $Z^g$ are as defined above.

The reaction for obtaining a compound of general formula [51a] from a compound of general formula [12d] is carried out by the same procedure as that for obtaining a compound of general formula [3a] from a compound of general formula [12] in Production Process 2.

The reaction for obtaining a compound of general formula [51b] from a compound of general formula [51a] is carried out by the same procedure as that for obtaining a compound of general formula [3b] from a compound of general formula [3a] in Production Process 2.

The reaction for obtaining a compound of general formula [51c] from a compound of general formula [51b] is carried out by the same procedure as that for obtaining a compound of general formula [3c] from a compound of general formula [3b] in Production Process 2.

The reaction for obtaining a compound of general formula [51d] from compounds of general formulas [51b] and [51c] is carried out by the same procedure as that for obtaining a compound of general formula [3d] from compounds of general formulas [3b] and [3c] in Production Process 2.

Among the compounds used in the above-mentioned production processes, those which can take a form of salt can be used as a salt. Examples of such salt include the same salts as mentioned in the paragraphs describing the compounds conforming to the pharmacophore of formula 1 and compounds of general formulas [2], [2b], [3], [4], [5], [a], [b], [c], [d], [e], [f] and [g].

Some of the compounds used in the above-mentioned production processes may have isomers such as optical isomers, geometric isomers and tautomers. In such cases, the isomers are also usable. In cases where solvated products, hydrates and various crystal forms of the compounds exist, those solvated products, hydrates and various crystal forms are also usable. Some of the compounds used in the above-mentioned production processes have a substituent which can be protected such as amino group, hydroxyl group, mercapto group, carboxyl group and the like. When such a compound is used, it is also possible to protect these groups with conventional protecting group previously, and after the reaction, to eliminate these protecting groups by methods which are well known in themselves.

When the compound of this invention is used as a medical drug. adjuvants conventionally used for making a preparation such as excipient, carrier, diluent and the like may be incorporated appropriately. The preparations produced in the above-mentioned manner can be administered in the usual manner either orally or non-orally in the form of tablet, capsule, powder, syrup, granule, pill, suspension, emulsion, solution, powdery preparation, suppository, ointment, injection, etc. The method of administration, the dosage and the frequency of administration can be properly selected in accordance with age, body weight and symptoms of the patient. To adult patients, the compound of this invention is given orally or non-orally (for example, by injection, drip infusion, intrarectal administration, etc., at a dosage of 0.1 to 100 mg/kg/day in one portion or several portions.

Next, conformity of typical compounds of this invention to pharmacophore will be mentioned. In the tables presented below, the unit of distance is angstrom.

For example, in a cyclic peptide of Example 3 (5) represented by the following formula:

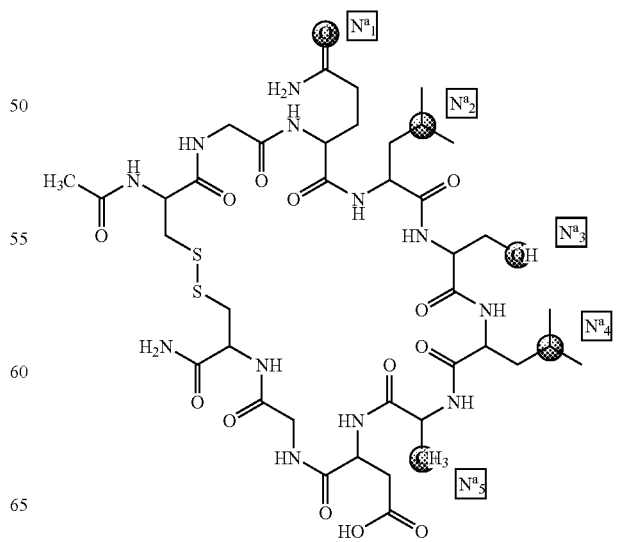

wherein the framed letters $N^a_1$, $N^a_2$, $N^a_3$, $N^a_4$ and $N^a_5$ represent the shaded atoms, respectively, to signify the atoms corresponding to $N_1$, $N_2$, $N_3$, $N_4$ and $N_5$ in formula 1, the $N^a_1$, $N^a_2$, $N^a_3$, $N^a_4$ and $N^a_5$ have the characters shown in the following Table 38, and there exists a local minimum structure in which the interatomic distances are as shown in Table 39.

TABLE 38

| Corresponding atom | Character |
|---|---|
| $N^a_1$ | Hydrogen-bond accepting atom in the hydrogen-bond accepting group |
| $N^a_2$ | Hydrophobic group |
| $N^a_3$ | Hydrogen-bond accepting atom in the hydrogen-bond accepting group |
| $N^a_4$ | Hydrophobic group |
| $N^a_5$ | Hydrophobic group |

TABLE 39

| Corresponding atoms | Distance |
|---|---|
| $N^a_1$-$N^a_2$ | 10.23 |
| $N^a_1$-$N^a_3$ | 11.89 |
| $N^a_1$-$N^a_4$ | 6.69 |
| $N^a_1$-$N^a_5$ | 12.21 |
| $N^a_2$-$N^a_3$ | 6.35 |
| $N^a_2$-$N^a_4$ | 9.73 |
| $N^a_2$-$N^a_5$ | 10.54 |
| $N^a_3$-$N^a_4$ | 7.75 |
| $N^a_3$-$N^a_5$ | 5.31 |
| $N^a_4$-$N^a_5$ | 5.85 |

Accordingly, this compound conforms to a pharmacophore at five atoms.

In the compound of Example 7 represented by the following formula:

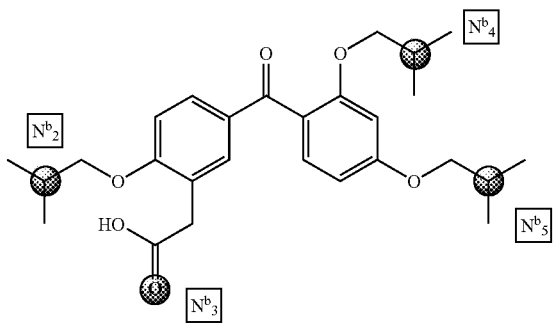

wherein the framed letters $N^b_2$, $N^b_3$, $N^b_4$ and $N^b_5$ represent the shaded atoms, respectively, to signify the atoms corresponding to $N_2$, $N_3$, $N_4$ and $N_5$ in formula 1, the $N^b_2$, $N^b_3$, $N^b_4$ and $N^b_5$ have the characters shown in the following Table 40, and there exists a local minimum structure in which the interatomic distances are as shown in Table 41.

TABLE 40

| Corresponding atom | Character |
|---|---|
| $N^b_2$ | Hydrophobic group |
| $N^b_3$ | Hydrogen-bond accepting atom in the hydrogen-bond accepting group |
| $N^b_4$ | Hydrophobic group |
| $N^b_5$ | Hydrophobic group |

TABLE 41

| Corresponding atom | Distance |
|---|---|
| $N^b_2$-$N^b_3$ | 6.55 |
| $N^b_2$-$N^b_4$ | 10.89 |
| $N^b_2$-$N^b_5$ | 13.10 |
| $N^b_3$-$N^b_4$ | 8.61 |
| $N^b_3$-$N^b_5$ | 7.64 |
| $N^b_4$-$N^b_5$ | 6.59 |

Accordingly, this compound conforms to a pharmacophore at four atoms.

In the compound of Example 4 represented by the following formula:

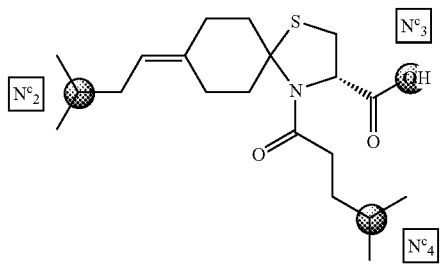

wherein the framed letters $N^c_2$, $N^c_3$ and $N^c_4$ represent the shaded atoms, respectively, to signify the atoms corresponding to $N_2$, $N_3$ and $N_4$ in formula 1, the $N^c_2$, $N^c_3$ and $N^c_4$ have the characters shown in the following Table 42, and there exists a locally stabilized structure in which the interatomic distances are as shown in Table 43.

TABLE 42

| Corresponding atom | Character |
|---|---|
| $N^c_2$ | Hydrophobic group |
| $N^c_3$ | Hydrogen-bond accepting atom in the hydrogen-bond accepting group |
| $N^c_4$ | Hydrophobic group |

TABLE 43

| Corresponding atoms | Distance |
|---|---|
| $N^c_2$-$N^c_3$ | 9.07 |
| $N^c_2$-$N^c_4$ | 10.08 |
| $N^c_3$-$N^c_4$ | 4.85 |

Accordingly, this compound conforms to a pharmacophore at three atoms.

In the cyclic peptide of Example 3 (1) represented by the following formula:

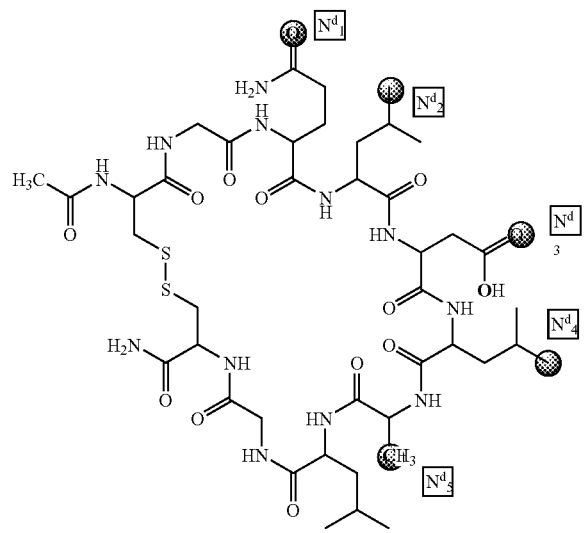

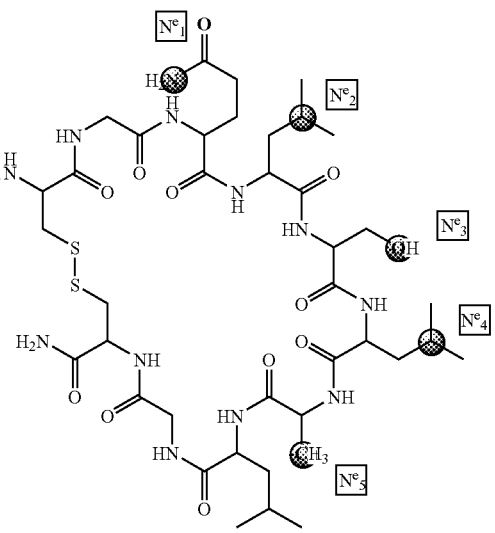

wherein the framed letters $N^d_1$, $N^d_2$, $N^d_3$, $N^d_4$ and $N^d_5$ represent the shaded atoms, respectively, to signify the atoms corresponding to $N_1$, $N_2$, $N_3$, $N_4$ and $N_5$ in formula 1, the $N^d_1$, $N^d_2$, $N^d_3$, $N^d_4$ and $N^d_5$ have the characters shown in the following Table 44, and there exists a local minimum structure in which the atomic distances are as shown in Table 45.

TABLE 44

| Corresponding atom | Character |
|---|---|
| $N^d_1$ | Hydrogen-bond accepting atom in the hydrogen-bond accepting group |
| $N^d_2$ | Hydrophobic group |
| $N^d_3$ | Hydrogen-bond accepting atom in the hydrogen-bond accepting group |
| $N^d_4$ | Hydrophobic group |
| $N^d_5$ | Hydrophobic group |

TABLE 45

| Corresponding atoms | Distance |
|---|---|
| $N^d_1$-$N^d_2$ | 10.23 |
| $N^d_1$-$N^d_3$ | 10.24 |
| $N^d_1$-$N^d_4$ | 3.63 |
| $N^d_1$-$N^d_5$ | 9.03 |
| $N^d_2$-$N^d_3$ | 5.97 |
| $N^d_2$-$N^d_4$ | 11.84 |
| $N^d_2$-$N^d_5$ | 12.23 |
| $N^d_3$-$N^d_4$ | 9.90 |
| $N^d_3$-$N^d_5$ | 7.86 |
| $N^d_4$-$N^d_5$ | 6.18 |

Accordingly, this compound conforms to a pharmacophore at five atoms.

In the cyclic peptide of Example 3 (2) represented by the following formula:

wherein the framed letters $N^e_1$, $N^e_2$, $N^e_3$, $N^e_4$ and $N^e_5$ represent the shaded atoms, respectively, to signify the atoms corresponding to $N_1$, $N_2$, $N_3$, $N_4$ and $N_5$ in formula 1, the $N^e_1$, $N^e_2$, $N^e_3$, $N^e_4$ and $N^e_5$ have the characters shown in the following Table 46, and there exists a local minimum structure in which the interatomic distances are as shown in Table 47.

TABLE 46

| Corresponding atom | Character |
|---|---|
| $N^e_1$ | The atom to which the donative hydrogen atom in the hydrogen-bond donating group is bonded |
| $N^e_2$ | Hydrophobic group |
| $N^e_3$ | Hydrogen-bond accepting atom in the hydrogen-bond accepting group |
| $N^e_4$ | Hydrophobic group |
| $N^e_5$ | Hydrophobic group |

TABLE 47

| Corresponding atoms | Distance |
|---|---|
| $N^e_1$-$N^e_2$ | 7.72 |
| $N^e_1$-$N^e_3$ | 12.14 |
| $N^e_1$-$N^e_4$ | 9.41 |
| $N^e_1$-$N^e_5$ | 15.29 |
| $N^e_2$-$N^e_3$ | 7.61 |
| $N^e_2$-$N^e_4$ | 9.29 |
| $N^e_2$-$N^e_5$ | 11.00 |
| $N^e_3$-$N^e_4$ | 6.18 |
| $N^e_3$-$N^e_5$ | 3.65 |
| $N^e_4$-$N^e_5$ | 7.54 |

Accordingly, this compound conforms to a pharmacophore at five atoms.

In the cyclic peptide of Example 3 (3) represented by the following formula:

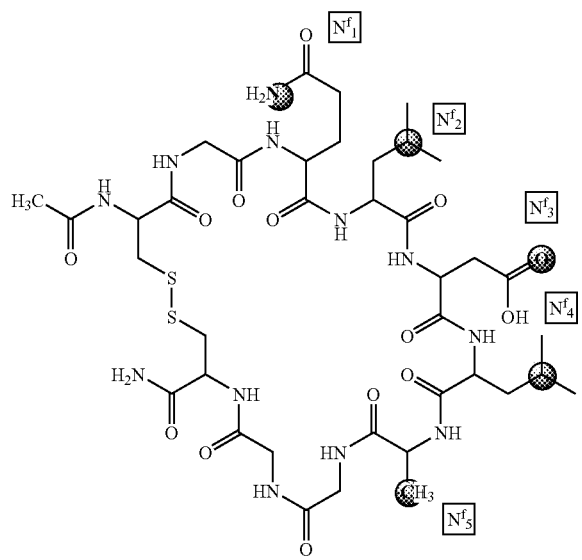

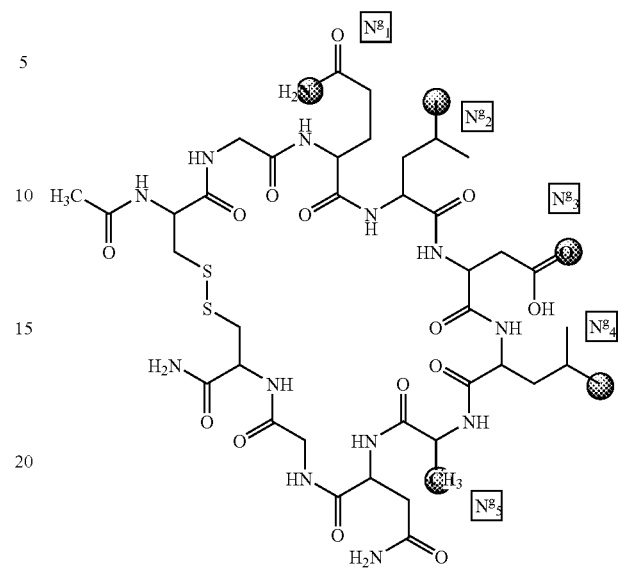

wherein the framed letters $N^f_1$, $N^f_2$, $N^f_3$, $N^f_4$ and $N^f_5$ represent the shaded atoms, respectively, to signify the atoms corresponding to $N_1$, $N_2$, $N_3$, $N_4$ and $N_5$ in formula 1, the $N^f_1$, $N^f_2$, $N^f_3$, $N^f_4$ and $N^f_5$ have the characters shown in the following Table 48, and there exists a local minimum structure in which the interatomic distances are as shown in Table 49.

TABLE 48

| Corresponding atom | Character |
|---|---|
| $N^f_1$ | The atom to which the donative hydrogen atom in the hydrogen-bond donating group is bonded |
| $N^f_2$ | Hydrophobic group |
| $N^f_3$ | Hydrogen-bond accepting atom in the hydrogen-bond accepting group |
| $N^f_4$ | Hydrophobic group |
| $N^f_5$ | Hydrophobic group |

TABLE 49

| Corresponding atoms | Distance |
|---|---|
| $N^f_1$-$N^f_2$ | 8.44 |
| $N^f_1$-$N^f_3$ | 13.51 |
| $N^f_1$-$N^f_4$ | 9.76 |
| $N^f_1$-$N^f_5$ | 14.87 |
| $N^f_2$-$N^f_3$ | 8.46 |
| $N^f_2$-$N^f_4$ | 9.77 |
| $N^f_2$-$N^f_5$ | 11.20 |
| $N^f_3$-$N^f_4$ | 6.66 |
| $N^f_3$-$N^f_5$ | 5.17 |
| $N^f_4$-$N^f_5$ | 7.13 |

Accordingly, this compound conforms to a pharmacophore at five atoms.

In the cyclic peptide of Example 3 (4) represented by the following formula:

wherein the framed letters $N^g_1$, $N^g_2$, $N^g_3$, $N^g_4$ and $N^g_5$ represent the shaded atoms, respectively, to signify the atoms corresponding to $N_1$, $N_2$, $N_3$, $N_4$ and $N_5$ in formula 1, the $N^g_1$, $N^g_2$, $N^g_3$, $N^g_4$ and $N^g_5$ have the characters shown in the following Table 50, and there exists a local minimum structure in which the interatomic distances are as shown in Table 51.

TABLE 50

| Corresponding atom | Character |
|---|---|
| $N^g_1$ | The atom to which the donative hydrogen atom in the hydrogen-bond donating group is bonded |
| $N^g_2$ | Hydrophobic group |
| $N^g_3$ | Hydrogen-bond accepting atom in the hydrogen-bond accepting group |
| $N_g^4$ | Hydrophobic group |
| $N_g^5$ | Hydrophobic group |

TABLE 51

| Corresponding atoms | Distance |
|---|---|
| $N^g_1$-$N^g_2$ | 11.24 |
| $N^g_1$-$N^g_3$ | 13.23 |
| $N^g_1$-$N^g_4$ | 12.01 |
| $N^g_1$-$N^g_5$ | 14.86 |
| $N^g_2$-$N^g_3$ | 4.35 |
| $N^g_2$-$N^g_4$ | 11.87 |
| $N^g_2$-$N^g_5$ | 10.66 |
| $N^g_3$-$N^g_4$ | 9.39 |
| $N^g_3$-$N^g_5$ | 7.09 |
| $N^g_4$-$N^g_5$ | 6.59 |

Accordingly, this compound conforms to a pharmacophore at five atoms.

In the cyclic peptide of Example 3 (6) represented by the following formula:

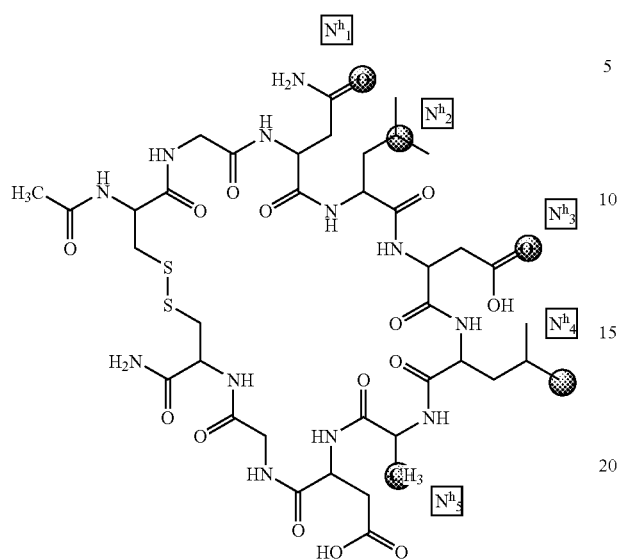

wherein the framed letters $N^h_1$, $N^h_2$, $N^h_3$, $N^h_4$ and $N^h_5$ represent the shaded atoms, respectively, to signify the atoms corresponding to $N_1$, $N_2$, $N_3$, $N_4$ and $N_5$ in formula 1, the $N^h_1$, $N^h_2$, $N^h_3$, $N^h_4$ and $N^h_5$ have the characters shown in the following Table 52, and there exists a local minimum structure in which the interatomic distances are as shown in Table 53.

TABLE 52

| Corresponding atom | Character |
| --- | --- |
| $N^h_1$ | Hydrogen-bond accepting atom in the hydrogen-bond accepting group |
| $N^h_2$ | Hydrophobic group |
| $N^h_3$ | Hydrogen-bond accepting atom in the hydrogen-bond accepting group |
| $N^h_4$ | Hydrophobic group |
| $N^h_5$ | Hydrophobic group |

TABLE 53

| Corresponding atoms | Distance |
| --- | --- |
| $N^h_1$-$N^h_2$ | 5.63 |
| $N^h_1$-$N^h_3$ | 9.79 |
| $N^h_1$-$N^h_4$ | 8.79 |
| $N^h_1$-$N^h_5$ | 13.51 |
| $N^h_2$-$N^h_3$ | 8.26 |
| $N^h_2$-$N^h_4$ | 9.19 |
| $N^h_2$-$N^h_5$ | 11.29 |
| $N^h_3$-$N^h_4$ | 6.95 |
| $N^h_3$-$N^h_5$ | 4.27 |
| $N^h_4$-$N^h_5$ | 8.07 |

Accordingly, this compound conforms to a pharmacophore at five atoms.

In the compound of Example 9 represented by the following formula:

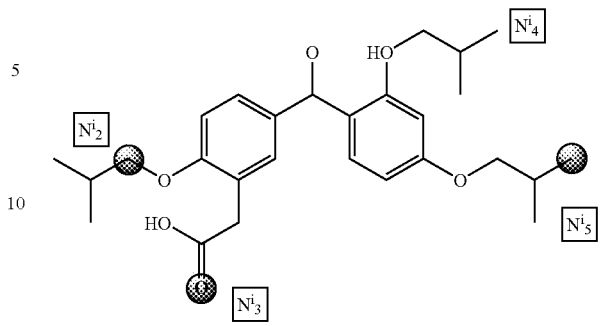

wherein the framed letters $N^i_2$, $N^i_3$, $N^i_4$ and $N^i_5$ represent the shaded atoms, respectively, to signify the atoms corresponding to $N_2$, $N_3$, $N_4$ and $N_5$ in formula 1, the $N^i_2$, $N^i_3$, $N^i_4$ and $N^i_5$ have the characters shown in the following Table 54, and there exists a local minimum structure in which the interatomic distances are as shown in Table 55.

TABLE 54

| Corresponding atom | Character |
| --- | --- |
| $N^i_2$ | Hydrophobic group |
| $N^i_3$ | Hydrogen-bond accepting atom in the hydrogen-bond accepting group |
| $N^i_4$ | Hydrophobic group |
| $N^i_5$ | Hydrophobic group |

TABLE 55

| Corresponding atoms | Distance |
| --- | --- |
| $N^i_2$-$N^i_3$ | 4.44 |
| $N^i_2$-$N^i_4$ | 6.97 |
| $N^i_2$-$N^i_5$ | 13.22 |
| $N^i_3$-$N^i_4$ | 5.19 |
| $N^i_3$-$N^i_5$ | 9.74 |
| $N^i_4$-$N^i_5$ | 7.06 |

Accordingly, this compound conforms to a pharmacophore at four atoms.

In the compound of Example 12 represented by the following formula:

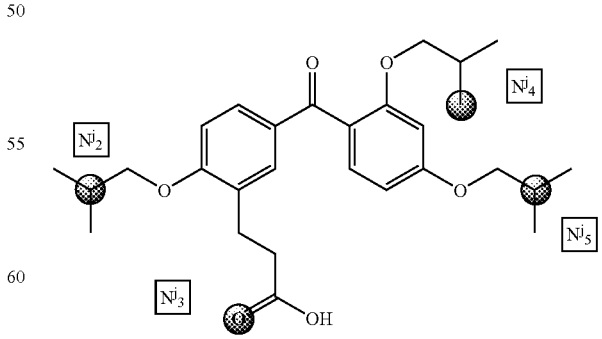

wherein the framed letters $N^j_2$, $N^j_3$, $N^j_4$ and $N^j_5$ represent the shaded atoms, respectively, to signify the atoms corresponding to $N_2$, $N_3$, $N_4$ and $N_5$ in formula 1, the $N^j_2$, $N^j_3$, $N^j_4$ and $N^j_5$ have the characters shown in the following Table 56, and there exists a local minimum structure in which the interatomic distances are as shown in Table 57.

TABLE 56

| Corresponding atom | Character |
|---|---|
| $N^j_2$ | Hydrophobic group |
| $N^j_3$ | Hydrogen-bond accepting atom in the hydrogen-bond accepting group |
| $N^j_4$ | Hydrophobic group |
| $N^j_5$ | Hydrophobic group |

TABLE 57

| Corresponding atoms | Distance |
|---|---|
| $N^j_2$-$N^j_3$ | 3.87 |
| $N^j_2$-$N^j_4$ | 8.33 |
| $N^j_2$-$N^j_5$ | 9.42 |
| $N^j_3$-$N^j_4$ | 8.12 |
| $N^j_3$-$N^j_5$ | 9.45 |
| $N^j_4$-$N^j_5$ | 4.80 |

Accordingly, this compound conforms to a pharmacophore at four atoms.

In the compound of Example 13 represented by the following formula:

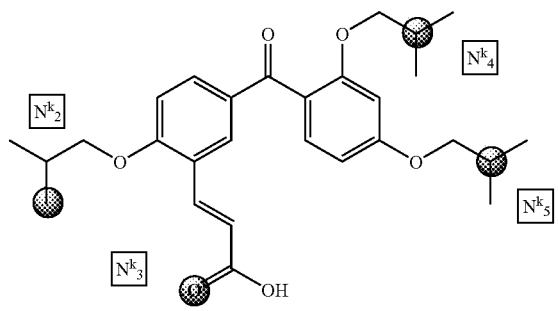

wherein the framed letters $N^k_2$, $N^k_3$, $N^k_4$ and $N^k_5$ represent the shaded atoms, respectively, to signify the atoms corresponding to $N_2$, $N_3$, $N_4$ and $N_5$ in formula 1, the $N^k_2$, $N^k_3$, $N^k_4$ and $N^k_5$ have the characters shown in the following Table 58, and there exists a local minimum structure in which the interatomic distances are as shown in Table 59.

TABLE 58

| Corresponding atom | Character |
|---|---|
| $N^k_2$ | Hydrophobic group |
| $N^k_3$ | Hydrogen-bond accepting atom in the hydrogen-bond accepting group |
| $N^k_4$ | Hydrophobic group |
| $N^k_5$ | Hydrophobic group |

TABLE 59

| Corresponding atoms | Distance |
|---|---|
| $N^k_2$-$N^k_3$ | 7.63 |
| $N^k_2$-$N^k_4$ | 13.26 |
| $N^k_2$-$N^k_5$ | 13.28 |
| $N^k_3$-$N^k_4$ | 10.39 |
| $N^k_3$-$N^k_5$ | 9.48 |
| $N^k_4$-$N^k_5$ | 7.68 |

Accordingly, this compound conforms to a pharmacophore at four atoms.

In the cyclic peptide of Example 3 (10) represented by the following formula:

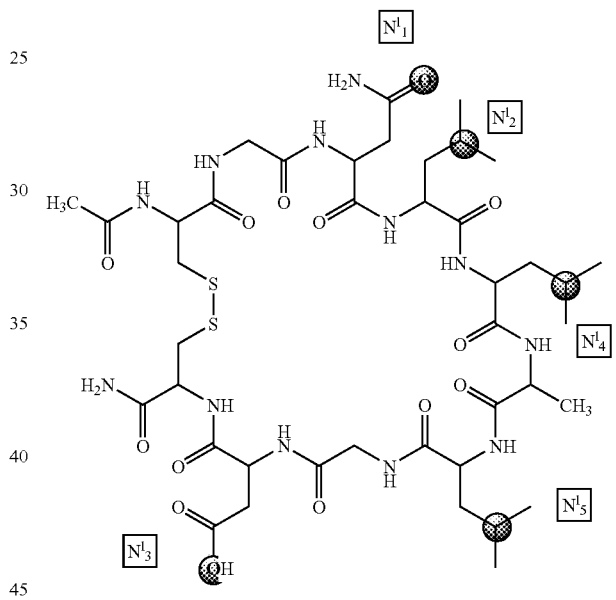

wherein the framed letters $N^l_1$, $N^l_2$, $N^l_3$, $N^l_4$ and $N^l_5$, represent the shaded atoms, respectively, to signify the atoms corresponding to $N_1$, $N_2$, $N_3$, $N_4$ and $N_5$ in formula 1, the $N^l_1$, $N^l_2$, $N^l_3$, $N^l_4$ and $N^l_5$ have the characters shown in the following Table 60, and there exists a local minimum structure in which the interatomic distances are as shown in Table 61.

TABLE 60

| Corresponding atom | Character |
|---|---|
| $N^l_1$ | Hydrogen-bond accepting atom in the hydrogen-bond accepting group |
| $N^l_2$ | Hydrophobic group |
| $N^l_3$ | Hydrogen-bond accepting atom in the hydrogen-bond accepting group |
| $N^l_4$ | Hydrophobic group |
| $N^l_5$ | Hydrophobic group |

TABLE 61

| Corresponding atoms | Distance |
| --- | --- |
| $N^l_1$-$N^l_2$ | 5.33 |
| $N^l_1$-$N^l_3$ | 12.02 |
| $N^l_1$-$N^l_4$ | 8.40 |
| $N^l_1$-$N^l_5$ | 12.16 |
| $N^l_2$-$N^l_3$ | 9.33 |
| $N^l_2$-$N^l_4$ | 8.42 |
| $N^l_2$-$N^l_5$ | 10.53 |
| $N^l_3$-$N^l_4$ | 8.88 |
| $N^l_3$-$N^l_5$ | 7.77 |
| $N^l_4$-$N^l_5$ | 4.36 |

Accordingly, this compound conforms to a pharmacophore at five atoms.

In the compound of Example 47 represented by the following formula:

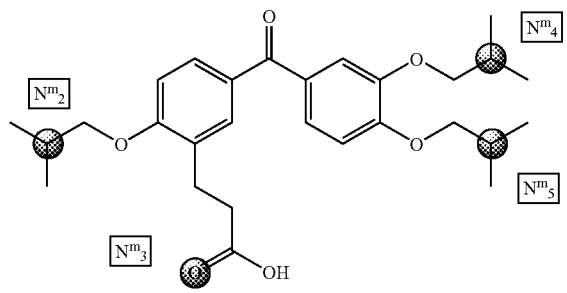

wherein the framed letters $N^m_2$, $N^m_3$, $N^m_4$ and $N^m_5$ represent the shaded atoms, respectively, to signify the atoms corresponding to $N_2$, $N_3$, $N_4$ and $N_5$ in formula 1, the $N^m_2$, $N^m_3$, $N^m_4$ and $N^m_5$ have the characters shown in the following Table 62, and there exists a local minimum structure in which the interatomic distances are as shown in Table 63.

TABLE 62

| Corresponding atoms | Character |
| --- | --- |
| $N^m_2$ | Hydrophobic group |
| $N^m_3$ | Hydrogen-bond accepting atom in the hydrogen-bond accepting group |
| $N^m_4$ | Hydrophobic group |
| $N^m_5$ | Hydrophobic group |

TABLE 63

| Corresponding atoms | Distance |
| --- | --- |
| $N^m_2$-$N^m_3$ | 6.51 |
| $N^m_2$-$N^m_4$ | 12.58 |
| $N^m_2$-$N^m_5$ | 12.01 |
| $N^m_3$-$N^m_4$ | 9.00 |
| $N^m_3$-$N^m_5$ | 5.85 |
| $N^m_4$-$N^m_5$ | 6.47 |

Accordingly, this compound conforms to a pharmacophore at four atoms.

In the compound of Example 43 represented by the following formula:

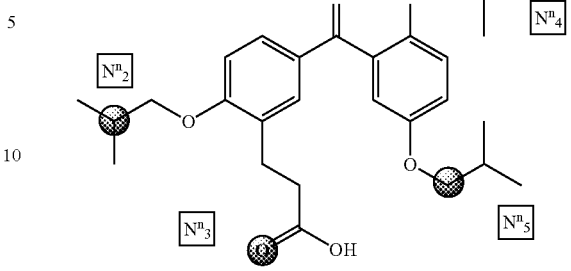

wherein the framed letters $N^n_2$, $N^n_3$, $N^n_4$ and $N^n_5$ represent the shaded atoms, respectively, to signify the atoms corresponding to $N_2$, $N_3$, $N_4$ and $N_5$ in formula 1, the $N^n_2$, $N^n_3$, $N^n_4$ and $N^n_5$ have the characters shown in the following Table 64, and there exists a local minimum structure in which the interatomic distances are as shown in Table 65.

TABLE 64

| Corresponding atom | Character |
| --- | --- |
| $N^n_2$ | Hydrophobic group |
| $N^n_3$ | Hydrogen-bond accepting atom in the hydrogen-bond accepting group |
| $N^n_4$ | Hydrophobic group |
| $N^n_5$ | Hydrophobic group |

TABLE 65

| Corresponding atoms | Distance |
| --- | --- |
| $N^n_2$-$N^n_3$ | 8.37 |
| $N^n_2$-$N^n_4$ | 8.72 |
| $N^n_2$-$N^n_5$ | 12.02 |
| $N^n_3$-$N^n_4$ | 6.80 |
| $N^n_3$-$N^n_5$ | 5.39 |
| $N^n_4$-$N^n_5$ | 7.43 |

Accordingly, this compound conforms to a pharmacophore at four atoms.

In the compound of Example 41 represented by the following formula:

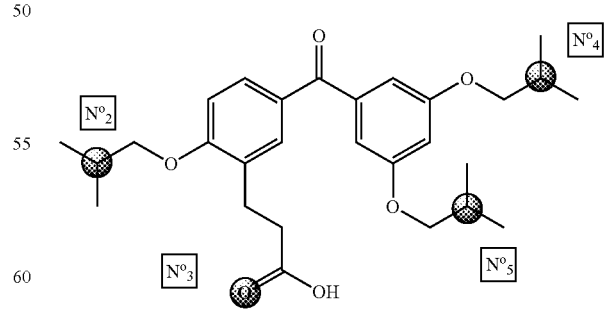

wherein the framed letters $N^o_2$, $N^o_3$, $N^o_4$ and $N^o_5$ represent the shaded atoms, respectively, to signify the atoms corresponding to $N_2$, $N_3$, $N_4$ and $N_5$ in formula 1, the $N^o_2$, $N^o_3$, $N^o_4$ and $N^o_5$ have the characters shown in the following Table 66, and there exists a local minimum structure in which the interatomic distances are as shown in Table 67.

TABLE 66

| Corresponding atom | Character |
| --- | --- |
| $N^o_2$ | Hydrophobic group |
| $N^o_3$ | Hydrogen-bond accepting atom in the hydrogen-bond accepting group |
| $N^o_4$ | Hydrophobic group |
| $N^o_5$ | Hydrophobic group |

TABLE 67

| Corresponding atoms | Distance |
| --- | --- |
| $N^o_2$-$N^o_3$ | 8.29 |
| $N^o_2$-$N^o_4$ | 8.47 |
| $N^o_2$-$N^o_5$ | 12.68 |
| $N^o_3$-$N^o_4$ | 5.66 |
| $N^o_3$-$N^o_5$ | 6.43 |
| $N^o_4$-$N^o_5$ | 8.08 |

Accordingly, this compound conforms to a pharmacophore at four atoms.

In the compound of Example 38 represented by the following formula:

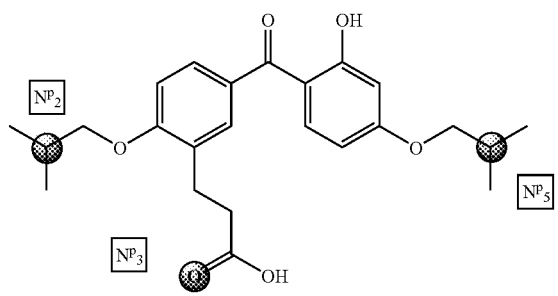

wherein the framed letters $N^p_2$, $N^p_3$ and $N^p_5$ represent the shaded atoms, respectively, to signify the atoms corresponding to $N_2$, $N_3$ and $N_5$ in formula 1, the $N^p_2$, $N^p_3$ and $N^p_5$ have the characters shown in the following Table 68, and there exists a local minimum structure in which the interatomic distances are as shown in Table 69.

TABLE 68

| Corresponding atom | Character |
| --- | --- |
| $N^p_2$ | Hydrophobic group |
| $N^p_3$ | Hydrogen-bond accepting atom in the hydrogen-bond accepting group |
| $N^p_5$ | Hydrophobic group |

TABLE 69

| Corresponding atoms | Distance |
| --- | --- |
| $N^p_2$-$N^p_3$ | 6.26 |
| $N^p_2$-$N^p_5$ | 12.96 |
| $N^p_3$-$N^p_5$ | 6.97 |

Accordingly, this compound conforms to a pharmacophore at three atoms.

In the compound of Example 88 represented by the following formula:

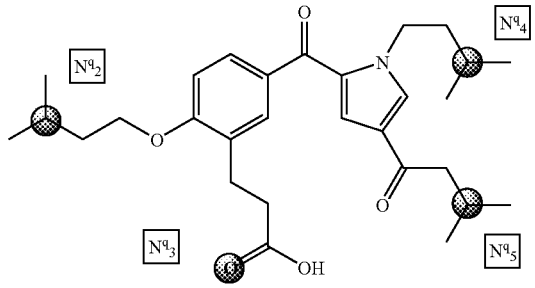

wherein the framed letters $N^q_2$, $N^q_3$, $N^q_4$ and $N^q_5$ represent the shaded atoms, respectively, to signify the atoms corresponding to $N_2$, $N_3$, $N_4$ and $N_5$ in formula 1, the $N^q_2$, $N^q_3$, $N^q_4$ and $N^q_5$ have the characters shown in the following Table 70, and there exists a local minimum structure in which the interatomic distances are as shown in Table 71.

TABLE 70

| Corresponding atom | Character |
| --- | --- |
| $N^q_2$ | Hydrophobic group |
| $N^q_3$ | Hydrogen-bond accepting atom in the hydrogen-bond accepting group |
| $N^q_4$ | Hydrophobic group |
| $N^q_5$ | Hydrophobic group |

TABLE 71

| Corresponding atoms | Distance |
| --- | --- |
| $N^q_2$-$N^q_3$ | 6.15 |
| $N^q_2$-$N^q_4$ | 10.68 |
| $N^q_2$-$N^q_5$ | 11.31 |
| $N^q_3$-$N^q_4$ | 7.84 |
| $N^q_3$-$N^q_5$ | 9.12 |
| $N^q_4$-$N^q_5$ | 8.15 |

Accordingly, this compound conforms to a pharmacophore at four atoms.

In the compound of Example 82 represented by the following formula:

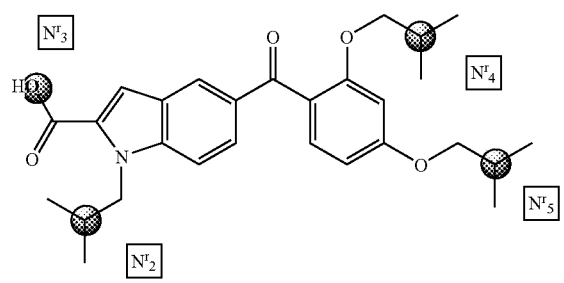

wherein the framed letters $N^r_2$, $N^r_3$, $N^r_4$ and $N^r_5$ represent the shaded atoms, respectively, to signify the atoms corresponding to $N_2$, $N_3$, $N_4$ and $N_5$ in formula 1, the $N^r_2$, $N^r_3$, $N^r_4$ and $N^r_5$ have the characters shown in the following Table 72, and there exists a local minimum structure in which the interatomic distances are as shown in Table 73.

TABLE 72

| Corresponding atom | Character |
| --- | --- |
| $N^r_2$ | Hydrophobic group |
| $N^r_3$ | Hydrogen bond accepting atom in the hydrogen-bond accepting group |
| $N^r_4$ | Hydrophobic group |
| $N^r_5$ | Hydrophobic group |

TABLE 73

| Corresponding atoms | Distance |
| --- | --- |
| $N^r_2$-$N^r_3$ | 5.41 |
| $N^r_2$-$N^r_4$ | 8.10 |
| $N^r_2$-$N^r_5$ | 12.32 |
| $N^r_3$-$N^r_4$ | 6.45 |
| $N^r_3$-$N^r_5$ | 9.56 |
| $N^r_4$-$N^r_5$ | 5.58 |

Accordingly, this compound conforms to a pharmacophore at four atoms.

In the compound of Example 90 represented by the following formula:

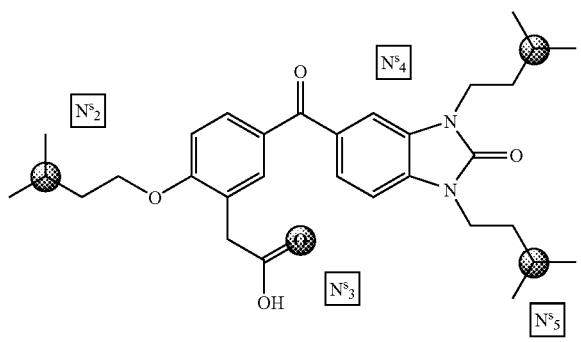

wherein the framed letters $N^s_2$, $N^s_3$, $N^s_4$ and $N^s_5$ represent the shaded atoms, respectively, to signify the atoms corresponding to $N_2$, $N_3$, $N_4$ and $N_5$ in formula 1, the $N^s_2$, $N^s_3$, $N^s_4$ and $N^s_5$ have the characters shown in the following Table 74, and there exists a local minimum structure in which the interatomic distances are as shown in Table 75.

TABLE 74

| Corresponding atom | Character |
| --- | --- |
| $N^s_2$ | Hydrophobic group |
| $N^s_3$ | Hydrogen bond accepting atom in the hydrogen-bond accepting group |
| $N^s_4$ | Hydrophobic group |
| $N^s_5$ | Hydrophobic group |

TABLE 75

| Corresponding atoms | Distance |
| --- | --- |
| $N^s_2$-$N^s_3$ | 5.11 |
| $N^s_2$-$N^s_4$ | 13.14 |
| $N^s_2$-$N^s_5$ | 10.85 |
| $N^s_3$-$N^s_4$ | 8.81 |
| $N^s_3$-$N^s_5$ | 5.95 |
| $N^s_4$-$N^s_5$ | 5.59 |

Accordingly, this compound conforms to a pharmacophore at four atoms.

In the compound of Example 25(8) represented by the following formula:

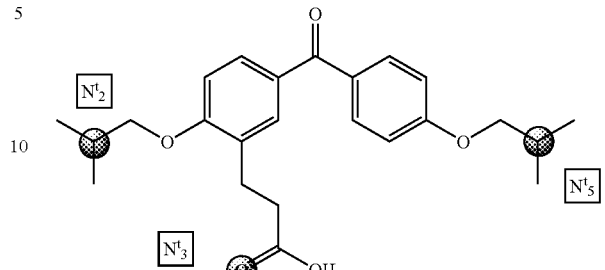

wherein the framed letters $N^t_2$, $N^t_3$ and $N^t_5$ represent the shaded atoms, respectively, to signify the atoms corresponding to $N_2$, $N_3$ and $N_5$ in formula 1, the $N^t_2$, $N^t_3$ and $N^t_5$ have the characters shown in the following Table 76, and there exists a local minimum structure in which the interatomic distances are as shown in Table 77.

TABLE 76

| Corresponding atom | Character |
| --- | --- |
| $N^t_2$ | Hydrophobic group |
| $N^t_3$ | Hydrogen bond accepting atom in the hydrogen-bond accepting group |
| $N^t_5$ | Hydrophobic group |

TABLE 77

| Corresponding atoms | Distance |
| --- | --- |
| $N^t_2$-$N^t_3$ | 5.83 |
| $N^t_2$-$N^t_5$ | 13.01 |
| $N^t_3$-$N^t_5$ | 7.79 |

Accordingly, this compound conforms to a pharmacophore at three atoms.

Next, pharmacological activities of typical compounds of this invention will be described.

[Testing Method]

TEST EXAMPLE 1

Activities on AP-1 Binding Reaction to Recognition Sequence (ELISA)

Nuclear extract protein containing transcription factor AP-1 prepared from HeLa cells was coated on 96-well ELISA plate (100 ng/well) in Hepes buffer (20 mM Hepes-potassium hydroxide (pH 7.9), 0,5 mM ethylenediaminetetraacetic acid, 50 mM potassium chloride, 10% glycerol). After washing, a blocking treatment was carried out with bovine serum albumin, and then used for a binding assay using nuclear extract protein.

On the other hand, Jun peptide and N-terminal biotinylated tetraglycine Fos peptide containing a DNA-binding site [Nature, Vol. 373, Pages 257-261, 1995] were synthesized and separately dissolved in tris buffer (20 mM tris-hydrochloride (pH 7.5), 50 mM potassium chloride, 1 mM ethylenediaminetetraacetic acid, 10 mM magnesium chloride, 1 mM dithiothreitol, 0.5M guanidine hydrochloride, 30% glycerol). Equimolar quantities of both the solutions were mixed together, and the mixture was used as an AP-1 complex (Fos/Jun peptide). The AP-1 complex was added to avidin-coating 96-well ELISA plate (10 pmol/well), washed, and then blocked with bovine serum albumin. The product was used for binding assay using AP-1 complex.

On the basis of the above-mentioned two coated AP-1, a digoxigenin-labeled double stranded oligonucleotide (22-mer) containing an AP-1 binding sequence (3'-TGAGTCA-5') which has been synthesized elsewhere was reacted in the presence and absence of a sample at room temperature for 30-60 minutes in a binding reaction solution [Hepes buffer or 25 mM tris-hydrochloric acid (pH 7.9), 0.5 mM ethylenediaminetetraacetic acid, 0.05% Nonidet P-40, 10% glycerol]. After of the reaction, unbound labeled oligonucleotide washed out with Hepes buffer solution containing 0.05 of Tween-20. Then, an anti-digoxigenin antibody labeled with peroxidase was added, and reacted with the labeled oligonucleotide bound to AP-1. After washing out the excessive antibody with Hepes buffer containing 0.05% of Tween-20, the residue was reacted for a predetermined period of time in a 100 mM citrate buffer (pH 5.0) containing hydrogen peroxide by using o-phenylenediamine as a substrate. After adding-sulfuric acid solution to each well, absorbance (492 nm) was measured. Taking the absorbance in the absence of sample as 100%, inhibition rate of sample was calculated from the absorbance in the presence of sample.

The results are shown in Table 78 and Table 79.

[Table 78]

TABLE 78

Results on ELISA using Fos/Jun peptide

| Example No. | Inhibition rate % | |
| --- | --- | --- |
| | 200 μM | 500 μM |
| 4 | 8 | 15 |
| 7 | 14 | 46 |
| 8 | 9 | 20 |
| 9 | 23 | 37 |
| 12 | 24 | 90 |
| 13 | 43 | 96 |
| 14 | 21 | 90 |
| 15 | 19 | 64 |
| 16 | 21 | 65 |
| 25 (5) | 39 | 98 |
| 25 (8) | 27 | 79 |
| 37 (7) | 4 | 22 |
| 38 | 18 | 91 |
| 41 | 27 | 78 |
| 43 | 28 | 72 |
| 47 | 35 | 92 |
| 53 | 30 | 79 |
| 57 | 13 | 62 |
| 58 | 22 | 88 |
| 68 (2) | 78 | 96 |
| 68 (8) | 24 | 94 |
| 73 | 18 | 74 |
| 82 | 28 | 97 |
| 88 | 29 | 72 |
| 90 | 26 | 96 |

The samples of Example No. 12, 15, 25(5) and 43 were converted to sodium salts and then measured according to the procedure of Example 17. In Example 6 8(8), measurement was carried out on the isomer having a lower polarity among the two isomers.

[Table 79]

TABLE 79

Results on ELISA using nucleus-extracted protein

| Example No. | Inhibition rate 100 μM |
| --- | --- |
| 2 | 81 |
| 3 (2) | 94 |
| 3 (3) | 43 |
| 3 (4) | 64 |
| 3 (5) | 43 |
| 3 (6) | 42 |
| 3 (7) | 74 |
| 3 (8) | 64 |
| 3 (9) | 48 |
| 3 (10) | 76 |
| 3 (11) | 48 |

In this test system, compounds exhibiting an inhibition of 10% or more at 500 μM are preferable when Fos/Jun is used; and compounds exhibiting an inhibition of 10% or more at 100 μM are preferable when nuclear extract protein is used.

TEST EXAMPLE 2

Type II Collagen-Induced Arthritis in Mice

The effect of the compound of Example 12 on the type II collagen-induced arthritis in mice was examined. As the animals, 8 weeks old male DBA/1J mice (Charles River Japan) were used. To 2 mg/mL solution of bovine type II collagen in 0.1 mol/L acetic acid (Kouken) was added an equivalent quantity of Freund complete adjuvant (Nacalai Tesque), and prepared an emulsion. 0.2 ml of the emulsion was subcutaneously injected into the tail root portion. On the 22nd day as counted from the day of first inoculation, the same treatment as above was repeated to induce arthritis. The compound was suspended in 0.5% methyl cellulose solution and administered orally at 100 mg/kg once every day from the 22nd day to the 36th day. To the control group (negative control group), a 0.5% methyl cellulose solution was administered similarly. Severity of the arthritis was evaluated in the following manner:

score 0: no change score 1: swelling on one or two toes or slight swelling in the foreleg root or hindleg root only;

score 2: swelling and rubor in more joints;

score 3: extensive swelling over whole foreleg or hindleg;

and total of the four legs was calculated. Taking the maximum score as 12, the arthritis score was calculated to evaluate the severity of arthritis. Regarding the destruction of joints and bones, X ray photographs of four paws were taken on the 37th day, and severity of destruction in the second to fifth articulationes interphalangeae, first to fifth articulationes metacarpophalangeae and metatarsophalangeae, and calcaneus was scored by 0 or 1 in accordance with presence or absence of destruction, and the severity of destruction in the carpus and tarsal was scored by 0 to 3. Total score for the four paws was taken as joint and bone destruction score, taking 50 points as maximum score.

The results on the 37th day from the first inoculation was as follows:

Control group: arthritis score 8, joint an bone destruction score 26;
Compound-administered group: arthritis score 3, joint and bone destruction score 10.
That is, the inhibition rate as compared with control group was 63% and 62%, respectively.

BEST MODE FOR CARRYING OUT THE INVENTION

Next, this invention is explained by referring to examples. The invention is by no means limited by these examples.
For expression of amino acid residue, the 3-letters expression system prescribed by IUPAC and IUB is used. Unless otherwise defined, an amino acid means L-form. The abbreviations have the following meanings:
Fmoc: 9-fluorenylmethoxycarbonyl
PyBOP: benzotriazole-1-yl-oxy-tris-pyrrolidino-phosphonium hexafluorophosphate
HOBt: N-hydroxybenzotriazole monohydrate
DMF: N,N-dimethylformamide
DIEA: N,N-diisopropylethylamine
DCM: dichloromethane
TFA: trifluoroacetic acid
DMSO: dimethyl sulfoxide
Cys(Trt): S-trityl-L-cysteine
Asp(tBu): β-tert-butyl L-aspartate
Ac: acetyl
Me: methyl
Et: ethyl
nPr: n-propyl
iPr: isopropyl
iBu: isobutyl
iAm: isoamyl
Ph: phenyl
Py: pyridyl
$(4\text{-}NO_2)PhCH_2$: p-nitrobenzyl
$CDCl_3$: heavy chloroform
$d_6$-DMSO: heavy dimethyl sulfoxide
($Cys^1$-$Cys^{10}$) means that a disulfide linkage is present between the first and 10th Cys residues.
($Cys^2$-$Cys^{11}$) means that a disulfide linkage is present between the second and 11th Cys residues.
HPLC purification was carried out under the following conditions:
Column: YMC PROTEIN-RP (250×20 mm I.D.)
Flow rate: 8.0 ml/min.
Detection wavelength: UV 230 nm
Mobile phase: $CH_3CN$ (10-30%) in 0.1% TFA-$H_2O$ (30 min.)
As the carrier for silica gel column chromatography, BW-127ZH (manufactured by Fuji Silicia Kagaku) was used.

EXAMPLE 1

DMF is added to 1.82 g of Rink amide MBHA resin (0.55 mmol/g) to swell the resin. Then, 15 ml of 20% piperidine/DMF solution is added and shaken for 20 minutes to remove the Fmoc group. After washing the resin thus obtained with DMF six times, 1.46 g of Fmoc-Cys(Trt)-OH, 0.38 g of HOBt, 1.30 g of PyBOP, 12 ml of DMF and 0.87 ml of DIEA are successively added and shaken for 60 minutes. After filtering off the liquid phase, the resin is washed with DMF six times. By the same procedure as above, amino acid derivatives are successively condensed from the C-terminal side by successively using Fmoc-Gly-OH, Fmoc-Asp(tBu)-OH, Fmoc-Ala-OH, Fmoc-Leu-OH, Fmoc-Asp(tBu)-OH, Fmoc-Leu-OH, Fmoc-Gln-OH, Fmoc-Gly-OH and Fmoc-Cys(Trt)-OH. After coupling with Fmoc amino acid, the Fmoc groups are removed with piperidine/DMF solution. In 15 ml OF DMF-DCM (1:1) mixture, 0.94 ml of acetic anhydride and 1.74 ml of DIEA are added and shaken for 30 minutes. After filtering off the liquid phase, the resin is washed with DMF four times and with DCM 3 times. Thus, 3.16 g of Ac-Cys(Trt)-Gly-Gln-Leu-Asp(tBu)-Leu-Ala-Asp (tBu)-Gly-Cys(Trt)-Rink amide MBHA resin is obtained.

EXAMPLE 2

1.42 g of the protected peptide resin obtained in Example 1 is added to 40 ml of 92.5:5:2.5 mixture of TFA-thioanisole-water, and shaken for 4 hours. The insoluble matter is filtered off, and the filtrate is concentrated under reduced pressure. 100 ml of diethyl ether is added to the residue, and the mixture is allowed to stand for 30 minutes at an ice-cooled temperature. After centrifuging the reaction mixture, 100 ml of 10% aqueous acetic acid is added to the residue. After filtering off the insoluble matter, the filtrate is freeze-dried to obtain a powder of straight chain peptide. About ¼ portion of the straight peptide powder thus obtained is taken and dissolved in 40 ml of 10% DMSO/TFA mixture, and the resulting solution is allowed to stand at ambient temperature for 15 hours. The reaction mixture is concentrated under reduced pressure, 50 ml of diethyl ether is added, and the mixture thus obtained is allowed to stand for 30 minutes at an ice-cooled temperature. After centrifuging the reaction mixture, 15 ml of 10% aqueous solution of acetic acid is added to the residue, and the insoluble matter is filtered off. The filtrate thus obtained is purified by HPLC and freeze-dried to obtain 6 mg of Ac-Cys¹-Gly-Gln-Leu-Asp-Leu-Ala-Asp-Gly-$Cys^{10}$-$NH_2$ ($Cys^1$-$Cys^{10}$)
ESI-MS: m/z 1033 for $[M+H]^+$ (calcd. 1032 for $C_{40}H_{64}N_{12}O_{16}S_2$)

EXAMPLE 3

The procedure of Example 2 is repeated to obtain the following compounds.
(3) 1 Ac-Cys¹-Gly-Gln-Leu-Asp-Leu-Ala-Leu-Gly-$Cys^{10}$-$NH_2$ ($Cys^1$-$Cys^{10}$)
ESI-MS: m/z 1031 for $[M+H]^+$ (calcd 1030 for $C_{42}H_{70}N_{12}O_{14}S_2$)
(3) 2 Ac-Cys¹-Gly-Gln-Leu-Ser-Leu-Ala-Leu-Gly-$Cys^{10}$-$NH_2$ ($Cys^1$-$Cys^{10}$)
ESI-MS: m/z 1003 for [M+H] (calcd 1002 for $C_{41}H_{70}N_{12}O_{13}S_2$)
3 (3) Ac-Cys¹-Gly-Gln-Leu-Asp-Leu-Ala-Gly-Gly-$Cys^{10}$-$NH_2$ ($Cys^1$-$Cys^{10}$)
ESI-MS: m/z 975 for $[M+H]^+$ (calcd 974 for $C_{38}H_{62}N_{12}O_{14}S_2$)
3(4) Ac-Cys¹-Gly-Gln-Leu-Asp-Leu-Ala-Asn-Gly-$Cys^{10}$-$NH_2$ ($Cys^1$-$Cys^{10}$)
ESI-MS: m/z 1032 for $[M+H]^+$ (calcd 1031 for $C_{40}H_{65}N_{13}O_{15}S_2$)
3 (5) Ac-Cys¹-Gly-Gln-Leu-Ser-Leu-Ala-Asp-Gly-$Cys^{10}$-$NH_2$ ($Cys^1$-$Cys^{10}$)
ESI-MS: m/z 1005 for $[M+H]^+$ (calcd 1004 for $C_{39}H_{64}N_{12}O_{15}S_2$)
3(6) Ac-Cys¹-Gly-Asn-Leu-Asp-Leu-Ala-Asp-Gly-$Cys^{10}$-$NH_2$ ($Cys^1$-$Cys^{10}$)

ESI-MS: m/z 1019 for [M+H]+ (calcd 1018 for $C_{39}H_{62}N_{12}O_{16}S_2$)

3 (7) Ac-Asn-Cys²-Gly-Asn-Leu-Leu-Ala-Leu-Gly-Ser-Cys¹¹-NH$_2$ (Cys²-Cys¹¹)

ESI-MS: m/z 1103 for [M+H]+ (calcd 1102 for $C_{44}H_{74}N_{14}O_{15}S_2$)

3(8) Ac-Cys¹-Gly-Asn-Leu-Leu-Ala-Leu-Gly-Ser-Cys¹⁰-NH$_2$ (Cys¹-Cys¹⁰)

ESI-MS: m/z 989 for [M+H]+ (calcd 988 for $C_{40}H_{68}N_{12}O_{13}S_2$)

3(9) Ac-Asn Cys²-Gly-Asn-Ala-Leu-Ala-Leu-Gly-Ser-Cys¹¹-NH$_2$ (Cys²-Cys¹¹)

ESI-MS: m/z 1061 for [M+H]+ (calcd 1060 for $C_{41}H_{69}N_{14}O_{15}S_2$)

3(10) Ac-Cys¹-Gly-Asn-Leu-Leu-Ala-Leu-Gly-Asp-Cys¹⁰-NH$_2$ (Cys¹-Cys¹⁰)

ESI-MS: m/z 1017 for [M+H]+ (calcd 1016 for $C_{41}H_{68}N_{12}O_{14}S_2$)

3(11) Ac-Cys¹-Gly-Asn-Leu-Leu-Ser-Leu-Gly-Asp-Cys¹⁰-NH$_2$ (Cys¹-Cys¹⁰)

ESI-MS: m/z 1033 for [M+H]+ (calcd 1032 for $C_{41}H_{68}N_{12}O_{15}S_2$)

EXAMPLE 4

In 8 ml of methylene chloride are dissolved 0.79 g of (3S)-8-(3-methylbutylidene)-1-thia-4-azaspiro[4.5]decane-3-carboxylic acid and 1.20 ml of triethylamine. Into the solution thus obtained are dropwise added a solution of isocaproyl chloride (prepared from 0.48 ml of isocaproic acid, 0.38 ml of oxalyl chloride and 5 ml of methylene chloride) in methylene chloride at 5-10° C., and stirred at ambient temperature for 2 hours. The whole was acidified to pH 2.0 with 2 mol/L HCl and extracted with CHCl$_3$. The combined organic extracts were washed with water and brine, dried on MgSO$_4$ and concentrated under reduced pressure. The residue was purified by chromatography, [eluent; chloroform:methanol=9:1] to obtain 1.10 g of (3S)-8-(3-methylbutylidene)-4-(4-methylpentanoyl)-1-thia-4-azaspiro[4.5]-decane-3-carboxylic acid as a colorless crystalline product.

NMR (CDCl$_3$) δ: 0.7-1.1 (12H, m), 1.2-3.4 (18H, m), 4.8-5.3 (2H, m), 6.9-7.4 (1H, bs)

EXAMPLE 5

In 6 ml of methylene chloride is dissolved 0.62 g of 4-isobutoxy-3-(2-methoxy-2-oxoethyl)benzoic acid. After adding 0.25 ml of oxalyl chloride at ambient temperature, the mixture thus obtained is stirred at ambient temperature for one hour. Then, 0.62 g of aluminum chloride and 0.77 g of 1,3-diisobutoxybenzene are successively added at 5-10° C., and the mixture is stirred at ambient temperature for one hour. The reaction mixture is added to a mixture of chloroform and water, and the organic layer is separated. The organic layer is successively washed with water and saturated aqueous solution of sodium chloride and dried over anhydrous magnesium sulfate, and the solvent is distilled off under reduced pressure. The residue thus obtained is purified by silica gel column chromatography [eluent; n-hexane:ethyl acetate=95:5] to obtain 0.63 g of methyl 2-[5-(2,4-diisobutoxybenzoyl)-2-isobutoxyphenyl]acetate as a colorless oily product.

NMR (CDCl$_3$) δ: 0.73 (6H, d, J=6.6 Hz), 1.02 (6H, d, J=6.6 Hz), 1.05 (6H, d, J=6.6 Hz), 1.5-2.4 (3H, m), 3.5-4.0 (11H, m), 6.4-6.7 (2H, m), 6.81 (1H, d, J=8.1 Hz), 7.35 (1H, d, J=8.5 Hz), 7.5-7.9 (2H, m)

EXAMPLE 6

The procedure of Example 5 is repeated to obtain isobutyl 5-(2,4-diisobutoxybenzoyl)-2-isobutoxybenzoate.

NMR (CDCl$_3$) δ: 0.69 (6H, d, J=6.6 Hz), 0.9-1.2 (18H, m), 1.2-2.4 (4H, m), 3.63 (2H, d, J=6.3 Hz), 3.77 (2H, d, J=6.6 Hz), 3.85 (2H, d, J=7.6 Hz), 4.06 (2H, d, J=6.6 Hz), 6.3-6.7 (2H, m), 6.95 (1H, d, J=8.8 Hz), 7.40 (1H, d, J=8.1 Hz), 7.94 (1H, dd, J=8.7, 2.4 Hz), 8.17 (1H, d, J=2.4 Hz)

EXAMPLE 7

In 6 ml of methanol is dissolved 0.57 g of methyl 2-[5-(2,4-diisobutoxybenzoyl)-2-isobutoxyphenyl]acetate. After adding 0.72 ml of 5 mol/L solution of sodium hydroxide, the mixture thus obtained is stirred at ambient temperature for one hour and thereafter at 50-60° C. for one hour. Chloroform and water are added to the reaction mixture, pH is adjusted to 2.0 with 2 mol/L hydrochloric acid, and the organic layer is separated. The organic layer is successively washed with water and saturated aqueous solution of sodium chloride and dried over anhydrous magnesium sulfate, and the solvent is distilled off under reduced pressure. Thus, 0.45 g of 2-[5-(2,4-diisobutoxybenzoyl)-2-isobutoxyphenyl]acetic acid is obtained as a colorless crystalline product.

NMR (CDCl$_3$) δ: 0.7-1.1 (18H, m), 1.5-2.3 (3H, m), 3.6-3.9 (8H, m), 6.4-7.8 (7H, m)

EXAMPLE 8

The procedure of Example 7 is repeated to obtain 5-(2,4-diisobutoxybenzoyl)-2-isobutoxybenzoic acid.

NMR (CDCl$_3$) δ: 0.65 (6H, d, J=6.8 Hz), 0.9-1.2 (12H, m), 1.2-2.4 (3H, m), 3.62 (2H, d, J=6.4 Hz), 3.78 (2H, d, J=6.6 Hz), 4.10 (2H, d, J=6.4 Hz), 6.4-6.6 (2H, m), 7.0-8.6 (1H, bs), 7.09 (1H, d, J=8.8 Hz), 7.44 (1H, d, J=8.5 Hz), 8.11 (1H, dd, J=8.8, 2.2 Hz), 8.47 (1H, d, J=2.2 Hz)

EXAMPLE 9

In 2 ml of methanol is dissolved 100 mg of 2-[5-(2,4-diisobutoxybenzoyl)-2-isobutoxyphenyl]acetic acid. After adding 18 mg of sodium borohydride at 5-10° C., the mixture thus obtained is stirred at 50-60° C. for one hour. Then, 40 mg of sodium borohydride and 40 mg of lithium chloride are further added at ambient temperature, and the mixture thus obtained is stirred at 50-60° C. for two hours. Chloroform and water are added to the reaction mixture, pH is adjusted to 2.0 with 2 mol/L hydrochloric acid, and the organic layer is separated. The organic layer is successively washed with water and saturated aqueous solution of sodium chloride and dried over anhydrous magnesium sulfate, and the solvent is distilled off under reduced pressure. Thus, 50 mg of 2-{5-[(2,4-diisobutoxyphenyl)(hydroxy)methyl]-2-isobutoxyphenyl}-acetic acid is obtained as a colorless oily product.

NMR (CDCl$_3$) δ: 0.7-1.1 (18H, m), 1.5-2.3 (3H, m), 3.4-3.9 (10H, m), 5.93 (1H, s), 5.7-7.5 (6H, m)

EXAMPLE 10

The procedure of Example 5 is repeated to obtain ethyl 3-[5-(2,4-diisobutoxybenzoyl)-2-isobutoxyphenyl]propionate.

NMR (CDCl$_3$) δ: 0.70 (6H, d, J=6.8 Hz), 1.0-1.1 (12H, m), 1.23 (3H, t, J=7.1 Hz), 1.5-2.3 (3H, m), 2.4-2.7 (2H, m), 2.8-3.1 (2H, m), 3.6-3.8 (6H, m), 4.12 (2H, q, J=6.8 Hz), 6.4-6.6 (2H, m), 6.78 (1H, d, J=9.3 Hz), 7.2-7.4 (1H, m), 7.5-7.7 (2H, m)

EXAMPLE 11

The procedure of Example 5 is repeated to obtain ethyl 3-[5-(2,4-diisobutoxybenzoyl)-2-isobutoxyphenyl]-2-propenoate.

NMR (CDCl$_3$) δ: 0.68 (6H, d, J=6.6 Hz), 1.01 (6H, d, J=6.3 Hz), 1.07 (6H, d, J=6.1 Hz), 1.33 (3H, t, J=7.1 Hz), 1.6-2.4 (3H, m), 3.6-3.9 (6H, m), 4.25 (2H, q, J=7.1 Hz), 6.3-8.1 (8H, m)

EXAMPLE 12

The procedure of Example 7 is repeated to obtain 3-[5-(2,4-diisobutoxybenzoyl)-2-isobutoxyphenyl]propionic acid.

NMR (CDCl$_3$) δ: 0.70 (6H, d, J=6.8 Hz), 1.0-1.1 (12H, m), 1.6-2.4 (3H, m), 2.5-2.8 (2H, m), 2.8-3.1 (2H, m), 3.62 (2H, d, J=6.4 Hz), 3.77 (2H, d, J=6.3 Hz), 3.80 (2H, d, J=6.1 Hz), 6.4-6.6 (2H, m), 6.79 (1H, d, J=9.0 Hz), 7.2-7.5 (1H, m), 7.6-7.8 (2H, m), 7.8-8.8 (1H, bs)

EXAMPLE 13

The procedure of Example 7 is repeated to obtain 3-[5-(2,4-diisobutoxybenzoyl)-2-isobutoxyphenyl]-2-propenoic acid.

NMR CDCl$_3$ δ: 0.68 (6H, d, J=6.6 Hz), 1.06 (6H, d, J=6.6 Hz), 1.08 (6H, d, J=6.8 Hz), 1.5-2.4 (3H, m), 3.63 (2H, d, J=6.3 Hz), 3.7-3.9 (4H, m), 6.4-8.2 (9H, m)

EXAMPLE 14

In 2 ml of tetrahydrofuran is dissolved 150 mg of 3-[5-(2,4-diisobutoxybenzoyl)-2-isobutoxyphenyl]-2-propenoic acid. After adding 14 mg of lithium aluminum hydride at 5-10° C., the mixture thus obtained is stirred for one hour. The reaction mixture is added to a mixture of chloroform and water, pH is adjusted to 3.0 with 2 mol/L hydrochloric acid, and the organic layer is separated. After successively washing the organic layer with water and saturated aqueous solution of sodium chloride and drying it over anhydrous magnesium sulfate, the solvent is distilled off under reduced pressure. The residue thus obtained is purified by silica gel column chromatography [eluent; n-hexane:ethyl acetate=4:1] to obtain 80 mg of 3-[5-[(2,4-diisobutoxyphenyl)(hydroxy)methyl]-2-isobutoxyphenyl]-2-propenoic acid as a colorless foaming product.

NMR (CDCl$_3$) δ: 0.9-1.1 (18, m), 1.8-2.4 (3H, m), 3.6-4.0 (7H, m), 5.94 (1H, bs), 6.3-7.7 (8H, m), 8.08 (1H, d, J=16.4 Hz)

EXAMPLE 15

The procedure of Example 14 is repeated to obtain 3-{5-[(2,4-diisobutoxyphenyl)(hydroxy)methyl]-2-isobutoxyphenyl}propionic acid.

NMR (CDCl$_3$) δ: 0.7-1.1 (18H, m), 1.7-2.3 (3H, m), 2.5-3.1 (4H, m), 3.4-3.9 (7H, m), 5.93 (1H, bs), 6.2-8.0 (7H, m)

EXAMPLE 16

In 2 ml of ethanol is dissolved 200 mg of 2-[5-(2,4-diisobutoxybenzoyl)-2-isobutoxyphenyl]acetic acid. After adding 40 mg of 5% palladium-carbon, the mixture thus obtained is stirred at ambient temperature for one hour in a stream of hydrogen gas. The reaction mixture is filtered with Celite, and the solvent is distilled off under reduced pressure from the filtrate. The residue thus obtained is purified by silica gel column chromatography [eluent; n-hexane:ethyl acetate=4:1] to obtain 140 mg of 2-[5-(2,4-diisobutoxybenzyl)-2-isobutoxyphenyl]acetic acid as a colorless oily product.

NMR (CDCl$_3$) δ: 0.9-1.1 (18H, m), 1.7-2.3 (3H, m), 3.4-3.9 (10H, m), 6.2-6.5 (2H, m), 6.6-7.3 (5H, m)

EXAMPLE 17

In 90 ml of ethanol is dissolved 9.0 g of 3-[5-(2,4-diisobutoxybenzoyl)-2-isobutoxyphenyl]-propionic acid. After adding 18.2 ml of 1 mol/L aqueous solution of sodium hydroxide, the mixture is stirred at ambient temperature for 10 minutes. The solvent is distilled off from the reaction mixture under reduced pressure, and the residue is purified by reverse phase silica gel column chromatography [eluent; acetonitrile:water=1:1] to obtain 7.6 g of sodium 3-[5-(2,4-diisobutoxybenzoyl)-2-isobutoxyphenyl]-propionate as a colorless foaming product.

NMR (CDCl$_3$) δ: 0.5-1.1 (18H, m), 1.5-2.5 (5H, m), 2.6-2.9 (2H, m), 3.4-3.9 (6H, m), 6.3-6.7 (3H, m), 7.1-7.5 (2H, m), 7.63 (1H, s)

EXAMPLE 18

The procedure of Example 17 is repeated to obtain sodium 3-{5-[(2,4-diisobutoxyphenyl)(hydroxy)-methyl]-2-isobutoxyphenyl}propionate.

EXAMPLE 19

In 4.8 ml of tetrahydrofuran are dissolved 0.16 g of (2R,4R)-4-isobutoxy-2-(4-methylpentyl)pyrrolidine and 0.78 ml of triethylamine, to which is dropwise added a solution of 3-(benzyloxycarbonylmethyl)-4-isobutoxybenzoyl chloride in tetrahydrofuran (prepared from 0.48 g of 3-(benzyloxycarbonylmethyl)-4-isobutoxybenzoic acid, 0.09 ml of oxalyl chloride and 4.8 ml of tetrahydrofuran) at 5-10° C. The mixture thus obtained is stirred at ambient temperature for 15 hours. Ethyl acetate and water are added to the reaction mixture, pH is adjusted to 3.0 with 6 mol/L hydrochloric acid, and the organic layer is separated. The organic layer thus obtained is washed with water and saturated aqueous solution of sodium chloride successively and dried over anhydrous magnesium sulfate, and the solvent is distilled off under reduced pressure. The residue thus obtained is purified by silica gel column chromatography [eluent; n-hexane:ethyl acetate=3:1] to obtain 0.18 g of benzyl 2-(2-isobutoxy-5-{[(2R,4R)-4-isobutoxy-2-(4-methylpentyl)pyrrolidinyl]carbonyl}phenyl)acetate as a yellow-colored oily product.

NMR (CDCl$_3$) δ: 0.85 (6H, d, J=6.1 Hz), 0.89 (6H, d, J=7.6 Hz), 1.08 (6H, d, J=7.2 Hz), 1.1-2.4 (11H, m), 2.9-3.2 (2H, m), 3.5-4.6 (7H, m), 5.12 (2H, bs), 6.82 (1H, d, J=8.3 Hz), 7.2-7.5 (8H, m)

EXAMPLE 20

The procedure of Example 7 is repeated to obtain 2-(2-isobutoxy-5-{[(2R,4R)-4-isobutoxy-2-(4-methylpentyl)pyrrolidinyl]carbonyl}phenyl)acetic acid.

NMR (CDCl$_3$) δ: 0.8-0.9 (12H, m), 1.02 (6H, d, J=6.6 Hz), 1.1-2.4 (11H, m), 2.9-3.2 (2H, m), 3.4-4.0 (7H, m), 4.1-4.5 (1H, m), 6.81 (1H, d, J=8.6 Hz), 7.2-7.6 (3H, m)

EXAMPLE 21

The procedure of Example 5 is repeated to obtain the compounds shown in Table 80.

TABLE 80

| No. | R$^1$ | R$^3$ | R$^4$ | A |
|---|---|---|---|---|
| 21(1) | O-iBu | H | O-iBu | CH$_2$COOMe |
| 21(2) | O-iBu | O-nPr | O-nPr | CH$_2$COOMe |
| 21(3) | O-iBu | O-iAm | O-iAm | CH$_2$COOMe |
| 21(4) | O-iAm | O-iBu | O-iBu | CH$_2$COOMe |
| 21(5) | O-iAm | O-iAm | O-iAm | CH$_2$COOMe |
| 21(6) | O-iBu | O-iAm | O-iAm | (CH$_2$)$_2$COOEt |
| 21(7) | O-iAm | O-iBu | O-iBu | (CH$_2$)$_2$COOEt |
| 21(8) | O-iBu | H | O-iBu | (CH$_2$)$_2$COOEt |
| 21(9) | O-iAm | O-iAm | O-iAm | (CH$_2$)$_2$COOEt |
| 21(10) | O-iBu | O-iBu | O-iBu | (CH$_2$)$_3$COOEt |
| 21(11) | O-iBu | O-iBu | O-iBu | CH$_2$CH=COOEt |
| 21(12) | O-iAm | O-iBu | O-iBu | CH$_2$CH=COOEt |
| 21(13) | O-iAc | O-iBu | O-iBu | (CH$_2$)$_2$COOEt |

21(1)
NMR (CDCl$_3$) δ: 1.05 (12H, d, J=6.6 Hz), 1.92-2.28 (2H, m), 3.69 (5H, s), 3.82 (4H, d, J=6.1 Hz), 6.84-7.00 (3H, m), 7.70-7.83 (4H, m)

21(2)
NMR (CDCl$_3$) δ: 0.74 (3H, t, J=7.1 Hz), 0.98-1.14 (9H, m), 1.42-2.25 (5H, m), 3.63 (2H, s), 3.66 (3H, s), 3.75-4.04 (6H, m), 6.48-6.56 (2H, m), 6.81 (1H, d, J=8.6 Hz), 7.35 (1H, d, J=8.8 Hz), 7.66-7.76 (2H, m)

21(3)
NMR (CDCl$_3$) δ: 0.76 (6H, d, J=5.9 Hz), 0.98 (6H, d, J=6.1 Hz), 1.02 (6H, d, J=6.6 Hz), 1.17-2.32 (7H, m), 3.63 (2H, s), 3.65 (3H, s), 3.79 (2H, d, J=6.1 Hz), 3.88-4.08 (2H, m), 4.04 (2H, t, J=6.6 Hz), 6.47-6.56 (2H, m), 6.80 (1H, d, J=8.8 Hz), 7.36 (1H, d, J=8.6 Hz), 7.64-7.73 (2H, m)

21(4)
NMR (CDCl$_3$) δ: 0.72 (6H, d, J=6.6 Hz), 0.95 (6H, d, J=6.1 Hz), 1.05 (6H, d, J=6.6 Hz), 1.59-2.05 (5H, m), 3.60-3.81 (6H, m), 3.65 (3H, s), 3.98-4.12 (2H, m), 6.47-6.57 (2H, m), 6.82 (1H, d, J=9.0 Hz), 7.36 (1H, d, J=8.3 Hz), 7.65-7.75 (2H, m)

21(5)
NMR (CDCl$_3$) δ: 0.76 (6H, d, J=5.9 Hz), 0.96 (6H, d, J=5.9 Hz), 0.99 (6H, d, J=5.9 Hz), 1.18-1.73 (9H, m), 3.61 (2H, s), 3.65 (3H, s), 3.81-4.04 (6H, m), 6.47-6.78 (2H, m), 6.83 (1H, d, J=8.5 Hz), 7.36 (1H, d, J=8.5 Hz), 7.64-7.73 (2H, m)

21(6)
NMR (CDCl$_3$) δ: 0.74 (6H, d, J=5.6 Hz), 0.95-1.34 (15H, m), 1.61-1.73 (3H, m), 2.04-2.30 (4H, m), 2.56-2.64 (2H, m), 2.86-3.05 (2H, m), 3.76-4.24 (8H, m), 6.47-6.56 (2H, m), 6.78 (1H, d, J=9.5 Hz), 7.36 (1H, d, J=8.3 Hz), 7.58-7.65 (2H, m)

21(7)
NMR (CDCl$_3$) δ: 0.70 (6H, d, J=6.6 Hz), 0.93-1.15 (12H, m), 1.23 (3H, t, J=7.1 Hz), 1.57-2.35 (5H, m), 2.48-2.67 (2H, m), 2.80-3.02 (2H, m), 3.61 (2H, d, J=6.5 Hz), 3.77 (2H, d, J=6.4 Hz), 3.99-4.23 (4H, m), 6.46-6.57 (2H, m), 6.81 (1H, d, J=8.1 Hz), 7.34 (1H, d, J=8.1 Hz), 7.59-7.68 (2H, m)

21(8)
NMR (CDCl$_3$) δ: 1.05 (6H, d, J=6.6 Hz), 1.07 (6H, d, J=6.6 Hz), 1.23 (3H, t, J=7.1 Hz), 1.90-2.30 (2H, m), 2.59-2.71 (2H, m), 2.91-3.12 (2H, m), 3.80 (2H, d, J=6.6 Hz), 3.82 (2H, d, J=6.1 Hz), 4.13 (2H, q, J=7.1 Hz), 6.81-6.99 (3H, m), 7.63-7.82 (4H, m)

21(9)
NMR (CDCl$_3$) δ: 0.74 (6H, d, J=6.1 Hz), 0.96 (6H, d, J=6.9 Hz), 0.98 (6H, d, J=6.1 Hz), 1.23 (3H, t, J=7.1 Hz), 1.56-2.04 (9H, m), 2.26-2.67 (2H, m), 2.85-3.02 (2H, m), 3.86-4.23 (8H, m), 6.44-6.56 (2H, m), 6.82 (1H, d, J=8.1 Hz), 7.38 (1H, d, J=8.1 Hz), 7.58-7.68 (2H, m)

21(10)
NMR (CDCl$_3$) δ: 0.72 (6H, d, J=6.6 Hz), 1.05 (12H, d, J=6.6 Hz), 1.23 (3H, t, J=7.0 Hz), 1.90-2.31 (7H, m), 2.68 (2H, t, J=7.3 Hz), 3.62 (2H, d, J=6.4 Hz), 3.78 (4H, d, J=6.6 Hz), 4.11 (2H, q, J=7.2 Hz), 6.47-6.59 (2H, m), 6.77 (1H, d, J=9.3 Hz), 7.35 (1H, d, J=7.8 Hz), 7.58-7.64 (2H, m)

21(11)
NMR (CDCl$_3$) δ: 0.70 (6H, d, J=6.4 Hz), 1.03 (6H, d, J=6.8 Hz), 1.04 (6H, d, J=6.6 Hz), 1.25 (3H, t, J=7.1 Hz), 1.68-2.23 (3H, m), 3.50 (2H, d, J=6.8 Hz), 3.62 (2H, d, J=6.4 Hz), 3.70 (2H, d, J=6.7 Hz), 3.79 (2H, d, J=6.4 Hz), 4.14 (2H, q, J=7.1 Hz), 5.74 (1H, d, J=16.1 Hz), 6.47-6.56 (2H, m), 6.80 (1H, d, J=8.3 Hz), 6.83-7.18 (1H, m), 7.36 (1H, d, J=8.3 Hz), 7.60-7.83 (2H, m)

21(12)
NMR (CDCl$_3$) δ: 0.70 (6H, d, J=6.6 Hz), 0.96 (6H, d, J=7.1 Hz), 1.05 (6H, d, J=6.8 Hz), 1.26 (3H, t, J=7.1 Hz), 1.64-2.25 (5H, m), 3.49 (2H, d, J=6.6 Hz), 3.62 (2H, d, J=6.4 Hz), 3.77 (2H, d, J=6.3 Hz), 3.98-4.27 (4H, m), 5.75 (1H, d, J=15.3 Hz), 6.47-6.56 (2H, m), 6.82 (1H, d, J=7.5 Hz), 7.06 (1H, d, J=15.3 Hz), 7.39 (1H, d, J=7.2 Hz), 7.60-7.72 (2H, m)

21(13)
NMR (CDCl$_3$) δ: 0.68 (6H, d, J=6.0 Hz), 1.05 (6H, d, J=6.6 Hz), 1.23 (3H, t, J=7.1 Hz), 1.50-2.28 (2H, m), 2.34 (3H, s), 2.44-2.94 (4H, m), 3.61 (2H, d, J=6.4 Hz), 3.78 (2H, d, J=6.4 Hz), 4.12 (2H, q, J=7.1 Hz), 6.32-6.57 (2H, m), 7.03-7.67 (4H, m)

EXAMPLE 22

In 18 ml of methylene chloride is dissolved 1.8 g of 2-isobutoxy-4-(isobutoxycarbonyl)-benzoic acid. After adding 0.7 ml of oxalyl chloride and subsequently 20 μl of N,N-dimethylformamide at ambient temperature, the mixture thus obtained is stirred at ambient temperature for one hour. Then, 1.6 g of aluminum chloride and subsequently 1.8 g of ethyl 3-(2-isobutoxyphenyl)propanoate are added at 5-10° C., and the resulting mixture is stirred at ambient temperature for one hour. The reaction mixture is added to a mixture of chloroform and water and the organic layer is separated. The organic layer thus obtained is washed with water and saturated aqueous solution of sodium chloride successively and dried over anhydrous magnesium sulfate, and the solvent is distilled off under reduced pressure. The residue thus obtained is purified by silica gel column chromatography (eluent; hexane:ethyl acetate=5:1) to obtain 2.1 g of isobutyl 4-[3-(3-ethoxy-3-oxopropyl)-4-isobutoxybenzoyl]-3-isobutoxybenzoate as a colorless oily product.

NMR (CDCl$_3$) δ: 0.74 (6H, d, J=6.6 Hz), 1.05 (12H, d, J=6.6 Hz), 1.23 (3H, t, J=7.1 Hz), 1.56-2.36 (3H, m), 2.45-2.66 (2H, m), 2.87-3.06 (2H, m), 3.74 (2H, d, J=6.1 Hz), 3.81 (2H, d, J=5.9 Hz), 4.11 (2H, q, J=7.1 Hz), 4.15 (2H, d, J=6.6 Hz), 6.80 (1H, d, J=9.3 Hz), 7.36 (1H, d, J=7.8 Hz), 7.57-7.76 (4H, m)

EXAMPLE 23

The procedure of Example 22 is repeated to obtain ethyl 3-[5-(2-fluoro-4-isobutoxybenzoyl)-2-isobutoxyphenyl]propanoate.

NMR (CDCl$_3$) δ: 1.05 (6H, d, J=6.6 Hz), 1.06 (6H, d, J=6.8 Hz), 1.23 (3H, t, J=7.1 Hz), 1.88-2.40 (2H, m), 2.48-2.70 (2H, m), 2.89-3.11 (2H, m), 3.78 (2H, d, J=6.4 Hz), 3.82 (2H, d, J=6.1 Hz), 4.12 (2H, q, J=7.1 Hz), 6.57-6.89 (3H, m), 7.50 (1H, t, J=8.5 Hz), 7.66-7.98 (2H, m)

EXAMPLE 24

The procedure of Example 22 is repeated to obtain ethyl 3-{5-[4-(acetyloxy)-2-isobutoxybenzoyl]-2-isobutoxyphenyl}propanoate.

NMR (CDCl$_3$) δ: 0.71 (6H, d, J=6.6 Hz), 1.05 (6H, d, J=6.8 Hz), 1.23 (3H, t, J=7.1 Hz), 1.59-2.35 (2H, m), 2.32 (3H, s), 2.48-2.67 (2H, m), 2.83-3.07 (2H, m), 3.63 (2H, d, J=6.4 Hz), 3.80 (2H, d, J=6.1 Hz), 4.12 (2H, q, J=6.8 Hz), 6.71-6.82 (3H, m), 7.35 (1H, d, J=7.6 Hz), 7.58-7.68 (2H, m)

EXAMPLE 25

The procedure of Example 7 is repeated to obtain the compounds shown in Table 81.

TABLE 81

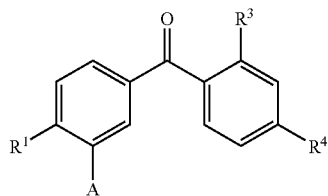

| No. | R$^1$ | R$^3$ | R$^4$ | A |
|---|---|---|---|---|
| 25(1) | O-iBu | H | O-iBu | CH$_2$COOH |
| 25(2) | O-iBu | O-nPr | O-nPr | CH$_2$COOH |
| 25(3) | O-iBu | O-iAm | O-iAm | CH$_2$COOH |
| 25(4) | O-iAm | O-iBu | O-iBu | CH$_2$COOH |
| 25(5) | O-iAm | O-iAm | O-iAm | CH$_2$COOH |
| 25(6) | O-iBu | O-iAm | O-iAm | (CH$_2$)$_2$COOH |
| 25(7) | O-iAm | O-iBu | O-iBu | (CH$_2$)$_2$COOH |
| 25(8) | O-iBu | H | O-iBu | (CH$_2$)$_2$COOH |
| 25(9) | O-iBu | F | O-iBu | (CH$_2$)$_2$COOH |
| 25(10) | O-iBu | O-iBu | OH | (CH$_2$)$_2$COOH |
| 25(11) | O-iBu | O-iBu | COOH | (CH$_2$)$_2$COOH |
| 25(12) | O-iBu | O-iBu | CONH-iPr | (CH$_2$)$_2$COOH |
| 25(13) | H | O-iBu | O-iBu | (CH$_2$)$_2$COOH |
| 25(14) | O-iAm | O-iAm | O-iAm | (CH$_2$)$_2$COOH |
| 25(15) | O-iBu | O-iBu | O-iBu | (CH$_2$)$_3$COOH |
| 25(16) | O-iBu | O-iBu | O-iBu | CH$_2$CH=CHCOOH |
| 25(17) | O-iAm | O-iBu | O-iBu | CH$_2$CH=CHCOOH |

25(1)
NMR (CDCl$_3$) δ: 1.04 (12H, d, J=6.6 Hz), 1.90-2.35 (2H, m), 3.70 (2H, s), 3.80 (2H, d, J=6.6 Hz), 3.82 (2H, d, J=6.3 Hz), 6.89-6.99 (3H, m), 7.69-7.82 (5H, m)

25(2)
NMR (CDCl$_3$) δ: 0.71 (3H, t, J=7.1 Hz), 0.98-1.14 (9H, m), 1.32-2.18 (5H, m), 3.65 (2H, s), 3.75-4.04 (6H, m), 6.48-6.57 (2H, m), 6.82 (1H, d, J=8.6 Hz), 7.35 (1H, d, J=8.7 Hz), 7.64-7.80 (3H, m)

25(3)
NMR (CDCl$_3$) δ: 0.73 (6H, d, J=5.9 Hz), 0.98 (6H, d, J=5.9 Hz), 1.02 (6H, d, J=6.6 Hz), 1.21-2.25 (7H, m), 3.65 (2H, s), 3.79 (2H, d, J=6.1 Hz), 3.86 (2H, t, J=6.1 Hz), 4.04 (2H, t, J=6.3 Hz), 6.47-6.58 (2H, m), 6.82 (1H, d, J=7.8 Hz), 7.37 (1H, d, J=8.3 Hz), 7.64-7.73 (3H, m)

25(4)
NMR (CDCl$_3$) δ: 0.70 (6H, d, J=6.6 Hz), 0.94 (6H, d, J=6.6 Hz), 1.04 (6H, d, J=6.6 Hz), 1.60-2.25 (5H, m), 3.57-3.80 (4H, m), 3.64 (2H, s), 4.06 (2H, t, J=6.1 Hz), 6.46-6.57 (2H, m), 6.84 (1H, d, J=8.3 Hz), 7.36 (1H, d, J=8.1 Hz), 7.63-7.76 (3H, m)

25(5)
NMR (CDCl$_3$) δ: 0.73 (6H, d, J=5.9 Hz), 0.94 (6H, d, J=5.8 Hz), 0.98 (6H, d, J=5.8 Hz), 1.26-1.43 (3H, m), 1.64-1.77 (6H, m), 3.64 (2H, s), 3.80-4.11 (6H, m), 6.47-6.58 (2H, m), 6.82 (1H, d, J=8.6 Hz), 7.36 (1H, d, J=8.3 Hz), 7.65-7.76 (3H, m)

25(6)
NMR (CDCl$_3$) δ: 0.73 (6H, d, J=5.9 Hz), 0.98 (6H, d, J=6.4 Hz), 1.06 (6H, d, J=6.8 Hz), 1.60-2.30 (7H, m), 2.53-3.08 (4H, m), 3.77-4.24 (6H, m), 6.47-6.59 (2H, m), 6.79 (1H, d, J=9.3 Hz), 7.37 (1H, d, J=8.3 Hz), 7.60-7.66 (3H, m)

25(7)
NMR (CDCl$_3$) δ: 0.69 (6H, d, J=6.6 Hz), 0.93-1.08 (12H, m), 1.59-2.25 (5H, m), 2.58-2.70 (2H, m), 2.85-3.03 (2H, m), 3.61 (2H, d, J=6.4 Hz), 3.77 (2H, d, J=6.5 Hz), 3.98 (2H, t, J=6.6 Hz), 6.46-6.58 (2H, m), 6.80 (1H, d, J=9.1 Hz), 7.35 (1H, d, J=8.1 Hz), 7.60-7.69 (3H, m)

25(8)
NMR (CDCl$_3$) δ: 1.04 (6H, d, J=6.6 Hz), 1.06 (6H, d, J=6.6 Hz), 1.88-2.39 (2H, m), 2.59-3.12 (4H, m), 3.80 (2H, d, J=6.4 Hz), 3.82 (2H, d, J=6.1 Hz), 6.82-7.00 (3H, m), 7.65-7.81 (4H, m), 9.60 (1H, brs)

25(9)

NMR (CDCl$_3$) δ: 1.04 (6H, d, J=6.6 Hz), 1.06 (6H, d, J=6.6 Hz), 1.85-2.41 (2H, m), 2.56-3.17 (4H, m), 3.77 (2H, d, J=6.3 Hz), 3.82 (2H, d, J=6.3 Hz), 6.57-6.90 (3H, m), 7.49 (1H, dd, J=8.6, 8.3 Hz), 7.67-7.76 (2H, m), 8.79 (1H, brs)

25(10)

NMR (CDCl$_3$) δ: 0.66 (6H, d, J=6.6 Hz), 1.04 (6H, d, J=6.6 Hz), 1.52-2.28 (2H, m), 2.55-3.04 (4H, m), 3.51 (2H, d, J=6.3 Hz), 3.79 (2H, d, J=6.1 Hz), 6.41-6.47 (2H, m), 6.80 (1H, d, J=8.3 Hz), 7.20-7.71 (5H, m)

25(11)

NMR (CDCl$_3$) δ: 0.74 (6H, d, J=6.6 Hz), 1.07 (6H, d, J=6.8 Hz), 1.66-2.31 (2H, m), 2.62-3.05 (4H, m), 3.75 (2H, d, J=7.1 Hz), 3.83 (2H, d, J=6.8 Hz), 6.87 (1H, d, J=8.5 Hz), 7.42 (1H, d, J=8.1 Hz), 7.60-7.84 (4H, m), 11.12 (2H, brs)

25(12)

NMR (CDCl$_3$) δ: 0.68 (6H, d, J=6.8 Hz), 1.05 (6H, d, J=6.8 Hz), 1.28 (6H, d, J=6.3 Hz), 1.54-2.34 (2H, m), 2.54-3.03 (4H, m), 3.70 (2H, d, J=6.4 Hz), 3.80 (2H, d, J=6.4 Hz), 4.04-4.50 (1H, m), 6.45 (1H, d, J=7.8 Hz), 6.80 (1H, d, J=9.3 Hz), 7.28-7.66 (5H, m), 9.87 (1H, brs)

25(13)

NMR (CDCl$_3$) δ: 0.65 (6H, d, J=6.4 Hz), 1.01 (6H, d, J=6.6 Hz), 1.55-2.20 (2H, m), 2.35-2.76 (4H, m), 3.78 (2H, d, J=6.3 Hz), 3.82 (2H, d, J=6.3 Hz), 6.55-6.62 (2H, m), 6.83 (1H, d, J=8.1 Hz), 7.17-7.45 (3H, m), 10.60 (1H, brs), 11.70 (1H, brs)

25(14)

NMR (CDCl$_3$) δ: 0.73 (6H, d, J=6.9 Hz), 0.98 (12H, d, J=6.1 Hz), 1.26-1.47 (3H, m), 1.66-1.95 (6H, m), 2.59-2.70 (2H, m), 2.86-3.04 (2H, m), 3.79-4.11 (6H, m), 6.47-6.59 (2H, m), 6.81 (1H, d, J=9.2 Hz), 7.36 (1H, d, J=8.3 Hz), 7.59-7.67 (3H, m)

25(15)

NMR (CDCl$_3$) δ: 0.70 (6H, d, J=6.6 Hz), 1.05 (12H, d, J=6.6 Hz), 1.68-2.18 (5H, m), 2.41 (2H, t, J=7.1 Hz), 2.70 (2H, t, J=7.6 Hz), 3.62 (2H, d, J=6.4 Hz), 3.77 (4H, d, J=6.4 Hz), 6.47-6.58 (2H, m), 6.78 (1H, d, J=9.3 Hz), 7.36 (1H, d, J=7.8 Hz), 7.59-7.65 (3H, m)

25(16)

NMR (CDCl$_3$) δ: 0.71 (6H, d, J=6.8 Hz), 1.05 (12H, d, J=6.6 Hz), 1.63-2.30 (3H, m), 3.30 (2H, d, J=7.7 Hz), 3.63 (2H, d, J=7.3 Hz), 3.75 (2H, d, J=2.8 Hz), 3.83 (2H, d, J=2.7 Hz), 6.42-6.56 (3H, m), 6.72-6.90 (3H, m), 7.36 (1H, d, J=8.5 Hz), 7.65 (1H, dd, J=8.7, 2.4 Hz), 7.89 (1H, d, J=2.0 Hz)

25(17)

NMR (CDCl$_3$) δ: 0.71 (6H, d, J=6.6 Hz), 0.98 (6H, d, J=6.4 Hz), 1.05 (6H, d, J=6.7 Hz), 1.69-2.25 (5H, m), 3.29 (2H, d, J=6.8 Hz), 3.63 (2H, d, J=6.3 Hz), 3.78 (2H, d, J=6.3 Hz), 4.07 (2H, t, J=6.3 Hz), 6.40-6.55 (3H, m), 6.70-6.89 (2H, m), 7.38 (1H, d, J=7.2 Hz), 7.65 (1H, dd, J=10.8, 2.2 Hz), 7.89 (1H, d, J=2.0 Hz), 8.23 (1H, brs)

EXAMPLE 26

In 2 ml of methylene chloride is dissolved 0.15 g of 4-[3-(2-carboxyethyl)-4-isobutoxybenzoyl]-3-isobutoxybenzoic acid, to which is added 0.12 g of 1,1'-carbonyldiimidazole. After stirring the mixture at ambient temperature for one hour, 15 μl of methanol is added, and the mixture thus obtained is stirred at the same temperature as above for one hour. Ethyl acetate and water are added to the reaction mixture, pH is adjusted to 2 with 2 mol/L hydrochloric acid, and the organic layer is separated. The organic layer is washed with water and saturated aqueous solution of sodium chloride successively and dried over anhydrous magnesium sulfate, and the solvent is distilled off under reduced pressure to obtain 0.05 g of 3-isobutoxy-4-[4-isobutoxy-3-(3-methoxy-3-oxopropyl)benzoyl]benzoic acid as a white solid product.

NMR (CDCl$_3$) δ: 0.75 (6H, d, J=6.6 Hz), 1.05 (6H, d, J=6.6 Hz), 1.70-2.28 (2H, m), 2.48-3.05 (4H, m), 3.66 (3H, s), 3.76 (2H, d, J=6.4 Hz), 3.81 (2H, d, J=6.4 Hz), 6.82 (1H, d, J=9.3 Hz), 7.31 (1H, d, J=8.6 Hz), 7.45-7.84 (5H, m)

EXAMPLE 27

In 2.5 ml of methylene chloride is dissolved 0.25 g of 3-isobutoxy-4-[4-isobutoxy-3-(3-methoxy-3-oxopropyl)benzoyl]benzoic acid. At ambient temperature, 60 μl of oxalyl chloride is added and then 20 μl of N,N-dimethylformamide is added, and the mixture thus obtained is stirred at ambient temperature for one hour. The reaction mixture is cooled with ice water, 0.12 ml of isopropylamine is dropwise added thereto, and the mixture thus obtained is stirred at ambient temperature for one hour. Ethyl acetate and water are added to the reaction mixture, pH is adjusted to 2 with 2 mol/L hydrochloric acid, and the organic layer is separated. The organic layer is washed with water and saturated aqueous solution of sodium chloride successively and dried over anhydrous magnesium sulfate, and the solvent is distilled off under reduced pressure to obtain 0.12 g of methyl 3-(2-isobutoxy-5-{2-isobutoxy-4-[(isopropylamino)carbonyl]benzoyl}-phenyl)propanoate as a white solid product.

NMR (CDCl$_3$) δ: 0.69 (6H, d, J=6.4 Hz), 1.05 (6H, d, J=6.6 Hz), 1.29 (6H, d, J=6.6 Hz), 1.64-2.35 (2H, m), 2.50-2.66 (2H, m), 2.87-3.04 (2H, m), 3.65 (3H, s), 3.73-3.83 (4H, m), 4.07-4.50 (1H, m), 6.54 (1H, brs), 6.80 (1H, d, J=9.3 Hz), 7.30-7.62 (5H, m)

EXAMPLE 28

To a solution of 17 g of 2-(2-isobutoxyphenyl)ethanal in 170 ml of acetonitrile, 29 g of sodium dihydrogenphosphate dissolved in 200 ml of water and subsequently 15 g of 30% aqueous hydrogen peroxide are added, and further 16 g of sodium chlorite dissolved in 80 ml of water is dropwise added, and the mixture thus obtained is stirred at ambient temperature for one hour. Ethyl acetate and water added to the reaction mixture, and the organic layer is separated. The organic layer is washed with water and saturated aqueous solution of sodium chloride successively and dried over anhydrous magnesium sulfate, and the solvent is distilled off under reduced pressure. The residue thus obtained is mixed with 22 g of potassium carbonate and 200 ml of N,N-dimethylformamide. While cooling the mixture with ice water, 19 g of iodomethane is added, and the mixture thus obtained is stirred at ambient temperature for 30 minutes. Ethyl acetate and water are added to the reaction mixture, and the organic layer is separated. The organic layer is washed with water and saturated aqueous solution of sodium chloride successively and dried over anhydrous magnesium sulfate, and the solvent is distilled off under reduced pressure. The residue thus obtained is purified by silica gel column chromatography (eluent; hexane:ethyl acetate=10:1) to obtain 10.4 g of methyl 2-(2-isobutoxyphenyl)acetate as a colorless oily product.

NMR (CDCl$_3$) δ: 1.02 (6H, d, J=6.8 Hz), 1.85-2.30 (1H, m), 3.64-3.76 (4H, m), 3.67 (3H, s), 6.79-7.02 (1H, m), 6.83 (1H, d, J=7.6 Hz), 7.15-7.25 (1H, m), 7.19 (1H, d, J=7.1 Hz)

EXAMPLE 29

The procedure of Example 16 is repeated to obtain 3-[5-(2,4-diisobutoxybenzyl)-2-isobutoxyphenyl]-propanoic acid.

NMR (CDCl$_3$) δ: 0.96-0.98 (18H, m), 1.82-2.25 (3H, m), 2.50-2.65 (2H, m), 2.71-3.00 (2H, m), 3.65-3.72 (6H, m), 3.82 (2H, s), 6.30-6.42 (2H, m), 6.69 (1H, d, J=9.0 Hz), 6.88-7.02 (3H, m), 9.88 (1H, brs)

EXAMPLE 30

The procedure of Example 16 is repeated to obtain 3-[5-(2-hydroxy-4-isobutoxybenzyl)-2-isobutoxyphenyl]propanoic acid.

NMR (CDCl$_3$) δ: 0.95-1.06 (12H, m), 1.89-2.24 (2H, m), 2.53-2.71 (2H, m), 2.83-3.04 (2H, m), 3.69 (2H, d, J=6.6 Hz), 3.69 (2H, d, J=6.3 Hz), 3.82 (2H, s), 6.36-7.02 (7H, m), 6.71 (1H, d, J=9.0 Hz)

EXAMPLE 31

The procedure of Example 16 is repeated to obtain 2-[5-(3,4-diisopentyloxybenzyl)-2-isopentyloxyphenyl]acetic acid.

NMR (CDCl$_3$) δ: 0.91-0.97 (18H, m), 1.62-1.92 (9H, m), 3.61 (2H, s), 3.83-4.04 (8H, m), 6.60-7.10 (7H, m)

EXAMPLE 32

In 15 ml of methylene chloride is dissolved 1.50 g of methyl 2-[5-(2,4-diisobutoxybenzoyl)-2-isobutoxyphenyl]acetate, to which is added 1.06 g of aluminum chloride at ambient temperature. The mixture is stirred at ambient temperature for 2 hours. The reaction mixture is added to a mixture of chloroform and ice water, and the organic layer is separated. The organic layer thus obtained is washed with water and saturated aqueous solution of sodium chloride successively and dried over anhydrous magnesium sulfate, and the solvent is distilled off under reduced pressure. The residue thus obtained is purified by silica gel column chromatography (eluent; hexane:ethyl acetate=5:1) to obtain 0.62 g of methyl 2-[5-(2-hydroxy-4-isobutoxybenzoyl)-2-isobutoxyphenyl]acetate as a yellow-colored solid product.

NMR (CDCl$_3$) δ: 1.04 (12H, d, J=6.6 Hz), 1.90-2.33 (2H, m), 3.70-3.86 (9H, m), 6.38-6.49 (2H, m), 6.91 (1H, d, J=8.8 Hz), 7.53-7.67 (3H, m), 12.64 (1H, s)

EXAMPLE 33

The procedure of Example 32 is repeated to obtain the compounds shown in Table 82.

TABLE 82

| No. | n | R$^1$ | R$^4$ | R$^{4'}$ | R$^2$ | R$^{37}$ |
|---|---|---|---|---|---|---|
| 33(1) | 0 | O-iBu | O-iAm | H | Me | H |
| 33(2) | 0 | O-iBu | O-nPr | H | Me | H |

TABLE 82-continued

| No. | n | R$^1$ | R$^4$ | R$^{4'}$ | R$^2$ | R$^{37}$ |
|---|---|---|---|---|---|---|
| 33(3) | 0 | O-iAm | O-iAm | H | Me | H |
| 33(4) | 1 | O-iBu | O-iBu | H | Me | H |
| 33(5) | 1 | O-iAm | O-iAm | H | Et | H |
| 33(6) | 1 | O-iAm | O-iBu | H | Et | H |
| 33(7) | 1 | O-iBu | O-iBu | H | Et | Me |
| 33(8) | 1 | O-iBu | H | O-iBu | Et | H |

33(1)
NMR (CDCl$_3$) δ: 0.97 (6H, d, J=5.9 Hz), 1.04 (6H, d, J=6.8 Hz), 1.59-2.34 (4H, m), 3.70 (5H, s), 3.82 (2H, d, J=6.4 Hz), 4.05 (2H, t, J=6.3 Hz), 6.37-6.51 (2H, m), 6.91 (1H, d, J=8.3 Hz), 7.52-7.65 (3H, m), 12.66 (1H, s)

33(2)
NMR (CDCl$_3$) δ: 0.96-1.12 (9H, m), 1.56-2.04 (3H, m), 3.70 (3H, s), 3.79-4.06 (6H, m), 6.35-6.51 (2H, m), 6.90 (1H, d, J=9.0 Hz), 7.52-7.67 (3H, m), 12.65 (1H, s)

33(3)
NMR (CDCl$_3$) δ: 0.97 (12H, d, J=6.1 Hz), 1.57-1.77 (6H, m), 3.67 (2H, s), 3.70 (3H, s), 4.05 (2H, t, J=6.6 Hz), 4.08 (2H, t, J=6.6 Hz), 6.35-6.51 (2H, m), 6.94 (1H, d, J=8.5 Hz), 7.52-7.65 (3H, m), 12.66 (1H, s)

33(4)
NMR (CDCl$_3$) δ: 1.03 (6H, d, J=6.6 Hz), 1.07 (6H, d, J=6.6 Hz), 1.90-2.40 (2H, m), 2.58-3.32 (4H, m), 3.67 (3H, s), 3.78 (2H, d, J=6.6 Hz), 3.82 (2H, d, J=6.1 Hz), 6.35-6.48 (2H, m), 6.88 (1H, d, J=9.0 Hz), 7.51-7.59 (3H, m), 12.69 (1H, s)

33(5)
NMR (CDCl$_3$) δ: 0.94-1.02 (12H, m), 1.23 (3H, t, J=7.1 Hz), 1.65-1.76 (6H, m), 2.53-2.69 (2H, m), 2.90-3.08 (2H, m), 4.01-4.28 (6H, m), 6.34-6.51 (2H, m), 6.90 (1H, d, J=9.3 Hz), 7.50-7.59 (3H, m), 12.70 (1H, s)

33(6)
NMR (CDCl$_3$) δ: 1.00 (6H, d, J=5.9 Hz), 1.04 (6H, d, J=6.6 Hz), 1.23 (3H, t, J=7.1 Hz), 1.72-2.34 (4H, m), 2.51-3.12 (4H, m), 3.79 (2H, d, J=6.6 Hz), 4.02-4.25 (4H, m), 6.38-6.51 (2H, m), 6.91 (1H, d, J=8.2 Hz), 7.52-7.60 (3H, m), 12.69 (1H, s)

33(7)
NMR (CDCl$_3$) δ: 1.00-1.26 (18H, m), 1.98-2.33 (2H, m), 2.63-3.17 (3H, m), 3.79 (2H, d, J=6.4 Hz), 3.88 (2H, d, J=6.3 Hz), 4.09 (2H, q, J=7.1 Hz), 6.34-6.48 (2H, m), 6.89 (1H, d, J=8.3 Hz), 7.49-7.59 (3H, m), 12.69 (1H, s)

33(8)
NMR (CDCl$_3$) δ: 0.95-1.12 (12H, m), 1.22 (3H, t, J=7.1 Hz), 1.83-2.32 (2H, m), 2.52-3.08 (4H, m), 3.62 (2H, d, J=6.4 Hz), 3.85 (2H, d, J=6.4 Hz), 4.13 (2H, q, J=6.8 Hz), 6.85-7.27 (4H, m), 7.59-7.66 (2H, m), 11.46 (1H, s)

EXAMPLE 34

In 3 ml of N,N-dimethylformamide are suspended 0.28 g of methyl 2-[5-(2-hydroxy-4-isobutoxybenzoyl)-2-isobutoxyphenyl]acetate, 0.32 g of potassium carbonate and 0.23 ml of isopentyl iodide. The suspension is stirred at 120° C. for 2 hours. The reaction mixture is added to a mixture of ethyl acetate and water, pH is adjusted to 2 with 6 mol/L hydrochloric acid, and the organic layer is separated. The organic layer thus obtained is washed with water and saturated aqueous solution of sodium chloride successively and dried over anhydrous magnesium sulfate, and the solvent is distilled off under reduced pressure. The residue thus obtained is purified by silica gel column chromatography (eluent; hexane:ethyl acetate=5:1) to obtain 0.17 g of methyl 2-[5-(4-isobutoxy-2-isopentyloxybenzoyl)-2-isobutoxyphenyl]-acetate as a colorless oily product.

NMR (CDCl$_3$) δ: 0.75 (6H, d, J=5.6 Hz), 1.02 (6H, d, J=6.6 Hz), 1.05 (6H, d, J=6.8 Hz), 1.26-1.55 (3H, m), 1.90-2.25 (2H, m), 3.62-3.94 (11H, m), 6.47-6.55 (2H, m), 6.80 (1H, d, J=8.3 Hz), 7.36 (1H, d, J=8.5 Hz), 7.63-7.72 (2H, m)

EXAMPLE 35

The procedure of Example 34 is repeated to obtain the compounds shown in Table 83.

TABLE 83

| No. | n | R$^1$ | R$^3$ | R$^4$ | R$^2$ |
|---|---|---|---|---|---|
| 35(1) | 1 | O-iBu | O-iBu | O-iAm | Me |
| 35(2) | 1 | O-iBu | O-nPr | O-iBu | Me |
| 35(3) | 1 | O-iBu | O-iBu | O-nPr | Me |
| 35(4) | 1 | O-iAm | O-iBu | O-iAm | Me |
| 35(5) | 2 | O-iBu | O—Me | O-iBu | Me |
| 35(6) | 2 | O-iBu | O—(CH$_2$)$_3$CO$_2$Et | O-iBu | Me |
| 35(7) | 2 | O-iBu | O—(CH$_2$)$_5$CONH$_2$ | O-iBu | Me |
| 35(8) | 2 | O-iBu | O—C(O)-iPr | O-iBu | H |

35(1)

NMR (CDCl$_3$) δ: 0.73 (6H, d, J=6.6 Hz), 0.99 (6H, d, J=6.1 Hz), 1.02 (6H, d, J=6.8 Hz), 1.51-2.31 (5H, m), 3.59-3.63 (4H, m), 3.65 (3H, s), 3.79 (2H, d, J=6.4 Hz), 4.04 (2H, t, J=6.4 Hz), 6.47-6.58 (2H, m), 6.82 (1H, d, J=8.3 Hz), 7.36 (1H, d, J=8.1 Hz), 7.66-7.77 (2H, m)

35(2)

NMR (CDCl$_3$) δ: 0.73 (3H, t, J=7.4 Hz), 1.01 (6H, d, J=6.6 Hz), 1.05 (6H, d, J=6.6 Hz), 1.42-1.64 (2H, m), 1.95-2.25 (2H, m), 3.62-3.90 (8H, m), 3.65 (3H, s), 6.47-6.58 (2H, m), 6.82 (1H, d, J=8.3 Hz), 7.34 (1H, d, J=8.8 Hz), 7.65-7.77 (2H, m)

35(3)

NMR (CDCl$_3$) δ: 0.73 (6H, d, J=6.8 Hz), 0.98-1.14 (9H, m), 1.65-2.25 (4H, m), 3.59-3.82 (6H, m), 3.65 (3H, s), 3.97 (2H, t, J=6.6 Hz), 6.47-6.58 (2H, m), 6.80 (1H, d, J=8.3 Hz), 7.35 (1H, d, J=7.8 Hz), 7.65-7.77 (2H, m)

35(4)

NMR (CDCl$_3$) δ: 0.72 (6H, d, J=6.6 Hz), 0.91 (6H, d, J=5.9 Hz), 0.95 (6H, d, J=5.9 Hz), 1.57-1.93 (7H, m), 3.59-3.65 (4H, m), 3.65 (3H, s), 4.04 (4H, t, J=6.3 Hz), 6.46-6.57 (2H, m), 6.83 (1H, d, J=8.0 Hz), 7.36 (1H, d, J=8.0 Hz), 7.65-7.75 (2H, m)

35(5)

NMR (CDCl$_3$) δ: 1.06 (12H, d, J=6.6 Hz), 1.91-2.36 (2H, m), 2.51-2.69 (2H, m), 2.88-3.08 (2H, m), 3.67 (3H, s), 3.73 (3H, s), 3.77-3.84 (4H, m), 6.48-6.56 (2H, m), 6.81 (1H, d, J=9.0 Hz), 7.31 (1H, dd, J=8.5, 1.0 Hz), 7.63-7.71 (2H, m)

35(6)

NMR (CDCl$_3$) δ: 1.05 (12H, d, J=6.6 Hz), 1.22 (3H, t, J=7.1 Hz), 1.72-2.30 (6H, m), 2.50-2.67 (2H, m), 2.87-3.07 (2H, m), 3.67 (3H, s), 3.74-4.20 (9H, m), 6.48-6.60 (2H, m), 6.80 (1H, d, J=9.3 Hz), 7.36 (1H, d, J=9.4 Hz), 7.59-7.65 (2H, m)

35(7)

NMR (CDCl$_3$) δ: 0.89-1.09 (14H, m), 1.40-1.80 (4H, m), 2.00-2.26 (4H, m), 2.51-2.69 (2H, m), 2.88-3.06 (2H, m), 3.66 (3H, s), 3.74-3.95 (6H, m), 5.48 (1H, brs), 5.90 (1H, brs), 6.47-6.55 (2H, m), 6.80 (1H, d, J=9.3 Hz), 7.32 (1H, d, J=8.3 Hz), 7.60-7.66 (2H, m)

35(8)

NMR (CDCl$_3$) δ: 1.03 (6H, d, J=6.6 Hz), 1.05 (6H, d, J=6.6 Hz), 1.13 (6H, d, J=5.9 Hz), 1.62-3.10 (7H, m), 3.77 (2H, d, J=6.3 Hz), 3.80 (2H, d, J=6.4 Hz), 6.66 (1H, d, J=2.2 Hz), 6.80 (1H, d, J=8.6 Hz), 6.82 (1H, d, J=9.5 Hz), 7.43 (1H, d, J=8.6 Hz), 7.52-7.71 (2H, m), 7.90 (1H, brs)

EXAMPLE 36

In 2 ml of methanol is dissolved 0.13 g of methyl 2-[5-(4-isobutoxy-2-isopentyloxybenzoyl)-2-isobutoxyphenyl]acetate, to which is added 0.2 ml of 5 mol/L solution of sodium hydroxide. The mixture thus obtained is stirred at ambient temperature for one hour and then at 50-60° C. for one hour. Chloroform and water are added to the reaction mixture, pH is adjusted to 2 with 6 mol/L hydrochloric acid, and the organic layer is separated. The organic layer is washed with water and saturated aqueous solution of sodium chloride successively and dried over anhydrous magnesium sulfate, and the solvent is distilled off under reduced pressure. The residue thus obtained is purified by silica gel column chromatography (eluent; hexane:ethyl acetate=2:1) to obtain 0.07 g of 2-[5-(4-isobutoxy-2-isopentyloxybenzoyl)-2-isobutoxyphenyl]acetic acid as a white-colored solid product.

NMR (CDCl$_3$) δ: 0.73 (6H, d, J=5.9 Hz), 1.01 (6H, d, J=6.6 Hz), 1.05 (6H, d, J=6.6 Hz), 1.20-1.50 (3H, m), 1.90-2.33 (2H, m), 3.64-3.93 (8H, m), 6.47-6.57 (2H, m), 6.81 (1H, d, J=8.3 Hz), 7.36 (1H, d, J=8.8 Hz), 7.64-7.75 (2H, m), 9.18 (1H, brs)

EXAMPLE 37

The procedure of Example 36 is repeated to obtain the compounds shown in Table 84.

TABLE 84

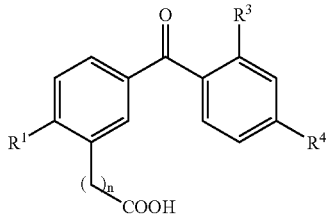

| No. | n | R¹ | R³ | R⁴ |
|---|---|---|---|---|
| 37(1) | 1 | O-iBu | O-iBu | O-iAm |
| 37(2) | 1 | O-iBu | O-nPr | O-iBu |
| 37(3) | 1 | O-iBu | O-iBu | O-nPr |
| 37(4) | 1 | O-iAm | O-iBu | O-iAm |
| 37(5) | 2 | O-iBu | O—Me | O-iBu |
| 37(6) | 2 | O-iBu | O—$(CH_2)_3CO_2H$ | O-iBu |
| 37(7) | 2 | O-iBu | O—$(CH_2)_5CONH_2$ | O-iBu |

37 (1)
NMR ($CDCl_3$) δ: 0.70 (6H, d, J=6.6 Hz), 0.98 (6H, d, J=5.9 Hz), 1.01 (6H, d, J=6.6 Hz), 1.65-2.32 (5H, m), 3.58-3.64 (4H, m), 3.79 (2H, d, J=6.3 Hz), 4.04 (2H, t, J=6.6 Hz), 6.46-6.55 (3H, m), 6.82 (1H, d, J=8.3 Hz), 7.36 (1H, d, J=8.1 Hz), 7.65-7.77 (2H, m)

37(2)
NMR ($CDCl_3$) δ: 0.71 (3H, t, J=7.3 Hz), 1.02 (6H, d, J=6.6 Hz), 1.05 (6H, d, J=6.6 Hz), 1.42-1.62 (2H, m), 1.97-2.25 (2H, m), 3.65 (2H, s), 3.73-3.89 (6H, m), 6.47-6.58 (2H, m), 6.83 (1H, d, J=8.3 Hz), 7.35 (1H, d, J=8.8 Hz), 7.63-7.79 (3H, m)

37(3)
NMR ($CDCl_3$) δ: 0.70 (6H, d, J=6.6 Hz), 0.97-1.14 (9H, m), 1.63-2.25 (4H, m), 3.58-3.82 (6H, m), 3.97 (2H, t, J=6.6 Hz), 6.46-6.58 (2H, m), 6.82 (1H, d, J=8.3 Hz), 7.35 (1H, d, J=8.5 Hz), 7.63-7.77 (3H, m)

37(4)
NMR ($CDCl_3$) δ: 0.82 (6H, d, J=6.8 Hz), 0.93 (6H, d, J=5.9 Hz), 0.98 (6H, d, J=5.9 Hz), 1.54-1.94 (7H, m), 3.57-3.64 (4H, m), 4.04 (2H, t, J=6.1 Hz), 4.06 (2H, t, J=6.1 Hz), 6.44-6.58 (2H, m), 6.85 (1H, d, J=8.3 Hz), 7.37 (1H, d, J=8.2 Hz), 7.66-7.78 (3H, m)

37(5)
NMR ($CDCl_3$) δ: 1.05 (12H, d, J=6.6 Hz), 1.84-2.34 (2H, m), 2.55-3.09 (4H, m), 3.72 (3H, s), 3.74-3.84 (4H, m), 6.46-6.58 (2H, m), 6.81 (1H, d, J=9.3 Hz), 7.30 (1H, d, J=9.0 Hz), 7.64-7.74 (2H, m), 8.06 (1H, brs)

37(6)
NMR ($CDCl_3$) δ: 1.01 (12H, d, J=6.6 Hz), 1.55-2.20 (6H, m), 2.37-2.54 (2H, m), 2.75-2.92 (2H, m), 3.80-3.97 (6H, m), 6.57-6.66 (2H, m), 6.98 (1H, d, J=9.0 Hz), 7.25 (1H, d, J=8.8 Hz), 7.44-7.51 (2H, m), 11.98 (2H, brs)

37(7)
NMR ($CDCl_3$) δ: 0.98-1.05 (12H, m), 1.20-1.50 (6H, m), 1.80-2.20 (4H, m), 2.40-2.60 (2H, m), 2.75-2.90 (2H, m), 3.40 (2H, brs), 3.81-3.88 (6H, m), 6.57-6.64 (2H, m), 6.94-7.31 (3H, m), 7.48-7.50 (2H, m)

EXAMPLE 38

In 155 ml of ethanol is dissolved 30.9 g of methyl 3-[5-(2-hydroxy-4-isobutoxybenzoyl)-2-isobutoxyphenyl] propanoate, to which is added 44 ml of 5 mol/L solution of sodium hydroxide. The mixture is stirred at ambient temperature for one hour. Water, followed by chloroform, is added to the reaction mixture, pH is adjusted to 2 with 6 mol/L hydrochloric acid, and the organic layer is separated. The organic layer is washed with water and saturated aqueous solution of sodium chloride successively and dried over anhydrous magnesium sulfate, and the solvent is distilled off under reduced pressure. Thus, 29.5 g of 3-[5-(2-hydroxy-4-isobutoxybenzoyl)-2-isobutoxyphenyl]-propanoic acid is obtained as a yellow-white colored solid product.

NMR ($CDCl_3$) δ: 1.02 (6H, d, J=6.6 Hz), 1.07 (6H, d, J=6.6 Hz), 1.89-2.39 (2H, m), 2.63-2.79 (2H, m), 2.93-3.10 (2H, m), 3.77 (2H, d, J=6.4 Hz), 3.82 (2H, d, J=6.1 Hz), 6.39-6.48 (2H, m), 6.89 (1H, d, J=9.0 Hz), 7.48-7.62 (3H, m), 9.76 (1H, brs), 12.67 (1H, s)

EXAMPLE 39

The procedure of Example 38 is repeated to obtain the compounds shown in Table 85.

TABLE 85

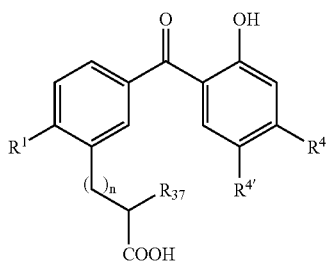

| No. | n | R¹ | R⁴ | R⁴' | R³⁷ |
|---|---|---|---|---|---|
| 39(1) | 1 | O-iAm | O-iAm | H | H |
| 39(2) | 1 | O-iAm | O-iBu | H | H |
| 39(3) | 1 | O-iBu | O-iBu | H | Me |
| 39(4) | 1 | O-iBu | H | O-iBu | H |
| 39(5) | 0 | O-iBu | O-iBu | H | H |
| 39(6) | 0 | O-iBu | O-iAm | H | H |

39(1)
NMR ($CDCl_3$) δ: 0.95 (12H, d, J=6.6 Hz), 1.52-2.00 (6H, m), 2.64-2.94 (4H, m), 3.89-4.09 (4H, m), 6.33-6.45 (2H, m), 6.80-6.90 (1H, m), 7.46-7.54 (4H, m), 12.50 (1H, brs)

39(2)
NMR ($CDCl_3$) δ: 0.99 (6H, d, J=5.6 Hz), 1.02 (6H, d, J=6.6 Hz), 1.56-2.26 (4H, m), 2.51-3.13 (4H, m), 3.78 (2H, d, J=6.6 Hz), 4.08 (2H, t, J=5.9 Hz), 6.36-6.48 (2H, m), 6.90 (1H, d, J=9.0 Hz), 7.49-7.58 (3H, m), 9.25 (1H, brs), 12.67 (1H, s)

39(3)
NMR ($CDCl_3$) δ: 0.98-1.23 (15H, m), 1.88-2.27 (2H, m), 2.63-3.16 (3H, m), 3.73-3.80 (4H, m), 6.32-6.39 (2H, m), 6.88 (1H, d, J=8.5 Hz), 7.46-7.60 (3H, m), 9.00 (1H, brs), 12.66 (1H, brs)

39(4)
NMR ($CDCl_3$) δ: 0.95-1.12 (12H, m), 1.82-2.40 (2H, m), 2.61-3.27 (4H, m), 3.63 (2H, d, J=6.3 Hz), 3.85 (2H, d, J=6.4 Hz), 6.86-7.27 (4H, m), 7.61-7.67 (2H, m), 9.38 (1H, brs), 11.45 (1H, brs)

39(5)

NMR (CDCl$_3$) δ: 1.01 (12H, d, J=6.8 Hz), 1.90-2.30 (2H, m), 3.70-3.84 (6H, m), 6.33-6.46 (2H, m), 6.90 (1H, d, J=8.3 Hz), 7.49-7.64 (3H, m), 10.22 (1H, brs), 12.60 (1H, brs)

39(6)

NMR (CDCl$_3$) δ: 0.94-1.07 (12H, m), 1.62-2.27 (4H, m), 3.72 (2H, s), 3.83 (2H, d, J=6.4 Hz), 4.05 (2H, t, J=6.2 Hz), 6.33-6.51 (2H, m), 6.92 (1H, d, J=8.1 Hz), 7.51-7.66 (4H, m), 12.64 (1H, s)

EXAMPLE 40

In 11 ml of methylene chloride is dissolved 1.11 g of 3,5-diisobutoxybenzoic acid. To the solution thus obtained, 0.44 ml of oxalyl chloride is added at ambient temperature, and then 20 μl of N,N-dimethylformamide is added and stirred at ambient temperature for 2 hours. Then, at −20° C., 1.67 g of aluminum chloride is added and thereafter 1.15 g of ethyl 3-(2-isobutoxyphenyl)propanoate is added, and the mixture thus obtained is stirred at 5-10° C. for 10 minutes. The reaction mixture is added to a mixture of chloroform and ice water, and the organic layer is separated. The organic layer is washed with water and saturated aqueous solution of sodium chloride successively and dried over anhydrous magnesium sulfate, and the solvent is distilled off under reduced pressure. The residue thus obtained is purified by silica gel column chromatography (eluent; hexane:ethyl acetate=5:1) to obtain 1.75 g of ethyl 3-[5-(3,5-diisobutoxybenzoyl)-2-isobutoxyphenyl]propanoate as a yellow-colored oily product.

NMR (CDCl$_3$) δ: 0.98-1.26 (18H, m), 1.23 (3H, t, J=7.1 Hz), 1.86-2.33 (3H, m), 2.51-2.74 (2H, m), 2.93-3.14 (2H, m), 3.70-3.86 (6H, m), 4.12 (2H, q, J=7.1 Hz), 6.63-6.91 (4H, m), 7.65-7.84 (2H, m)

EXAMPLE 41

In 9 ml of ethanol is dissolved 1.74 g of ethyl 3-[5-(3,5-diisobutoxybenzoyl)-2-isobutoxyphenyl]-propanoate. After adding 2 ml of 5 mol/L solution of sodium hydroxide, the mixture thus obtained is stirred at ambient temperature for one hour. Chloroform and water are added to the reaction mixture, pH is adjusted to 2 with 6 mol/L hydrochloric acid, and the organic layer is separated. The organic layer is successively washed with water and saturated aqueous solution of sodium chloride and dried over anhydrous magnesium sulfate, and the solvent is distilled off under reduced pressure. Thus, 1.53 g of 3-[5-(3,5-diisobutoxybenzoyl)-2-isobutoxyphenyl]propanoic acid is obtained as a white solid product.

NMR (CDCl$_3$) δ: 0.98-1.11 (18H, m), 1.86-2.38 (3H, m), 2.58-3.18 (4H, m), 3.70-3.87 (6H, m), 6.60-6.91 (4H, m), 7.68-7.88 (2H, m), 8.58 (1H, brs)

EXAMPLE 42

In 50 ml of methylene chloride is dissolved 5.00 g of 2,5-diisobutoxybenzoic acid. After adding 2.0 ml of oxalyl chloride and subsequently 20 μl of N,N-dimethylformamide at ambient temperature, the mixture thus obtained is stirred at ambient temperature for one hour. Then, 7.51 g of aluminum chloride and subsequently 5.17 g of ethyl 3-(2-isobutoxyphenyl)-propanoate are added at −30° C., the mixture thus obtained is stirred at −10° C. for 10 minutes. The reaction mixture is added to a mixture of chloroform and ice water and the organic layer is separated. The organic layer thus obtained is washed with water and saturated aqueous solution of sodium chloride successively and dried over anhydrous magnesium sulfate, and the solvent is distilled off under reduced pressure. The residue thus obtained is purified by silica gel column chromatography (eluent; hexane:ethyl acetate=5:1) to obtain 9.21 g of ethyl 3-[5-(2,5-diisobutoxybenzoyl)-2-isobutoxyphenyl]propanoate as a yellow-colored oily product.

NMR (CDCl$_3$) δ: 0.70 (6H, d, J=6.6 Hz), 1.00 (6H, d, J=6.6 Hz), 1.05 (6H, d, J=6.6 Hz), 1.23 (3H, t, J=7.1 Hz), 1.62-2.35 (3H, m), 2.46-2.66 (2H, m), 2.87-3.06 (2H, m), 3.59 (2H, d, J=6.4 Hz), 3.69 (2H, d, J=6.4 Hz), 3.80 (2H, d, J=6.4 Hz), 4.12 (2H, q, J=7.1 Hz), 6.74-7.06 (4H, m), 7.56-7.75 (2H, m)

EXAMPLE 43

In 26 ml of ethanol is dissolved 5.2 g of ethyl 3-[5-(2,5-diisobutoxybenzoyl)-2-isobutoxyphenyl]-propanoate. After adding 6 ml of 5 mol/L aqueous solution of sodium hydroxide, the mixture is stirred at ambient temperature for 30 minutes. Chloroform and water are added to the reaction mixture, pH is adjusted to 2 with 6 mol/L hydrochloric acid, and the organic layer is separated. The organic layer is washed with water and saturated aqueous solution of sodium chloride successively, and the solvent is distilled off from the reaction mixture under reduced pressure. Thus, 4.9 g of 3-[5-(2,5-diisobutoxybenzoyl)-2-isobutoxyphenyl]-propanoic acid is obtained as a yellow solid product.

NMR (CDCl$_3$) δ: 0.69 (6H, d, J=6.6 Hz), 1.00 (6H, d, J=6.6 Hz), 1.05 (6H, d, J=6.4 Hz), 1.60-2.29 (3H, m), 2.50-3.13 (4H, m), 3.58 (2H, d, J=6.4 Hz), 3.69 (2H, d, J=6.6 Hz), 3.80 (2H, d, J=6.4 Hz), 6.76-6.91 (4H, m), 7.61-7.69 (2H, m), 8.28 (1H, brs)

EXAMPLE 44

In 8 ml of methylene chloride is dissolved 0.80 g of 3,4-diisopentyloxybenzoic acid. Then, 20 μl of N,N-dimethylformamide is added, and the mixture thus obtained is stirred at ambient temperature for one hour. To the mixture thus obtained are successively added 1.10 g of aluminum chloride and 0.95 g of isopentyl 2-(2-isopentyloxyphenyl)acetate at 5-10° C., and the mixture thus obtained is stirred at 5-10° C. for 10 minutes. The reaction mixture is added to a mixture of chloroform and ice water, and the organic layer is separated. After washing the organic layer with water and saturated aqueous solution of sodium chloride successively and dried over anhydrous magnesium sulfate, the solvent is distilled off under reduced pressure. The residue thus obtained is purified by silica gel column chromatography [eluent; hexane:ethyl acetate=10:1] to obtain 1.20 g of isopentyl 2-[5-(3,4-diisopentyloxybenzoyl)-2-isopentyloxyphenyl]-acetate as a yellow oily product.

NMR (CDCl$_3$) δ: 0.86-1.00 (24H, m), 1.46-1.95 (12H, m), 3.64 (2H, s), 4.00-4.19 (8H, m), 6.84-6.93 (2H, m), 7.26-7.41 (2H, m), 7.69-7.78 (2H, m)

EXAMPLE 45

The procedure of Example 44 is repeated to obtain ethyl 3-[5-(3,4-diisobutoxybenzoyl)-2-isobutoxyphenyl]propanoate.

NMR (CDCl$_3$) δ: 1.01-1.14 (18H, m), 1.23 (3H, t, J=7.1 Hz), 1.90-2.36 (3H, m), 2.47-2.81 (2H, m), 2.86-3.14 (2H, m), 3.77-3.86 (6H, m), 4.12 (2H, q, J=7.1 Hz), 6.81-6.91 (2H, m), 7.26-7.38 (2H, m), 7.64-7.71 (2H, m)

EXAMPLE 46

In 12 ml of ethanol is dissolved 1.20 g of isopentyl 2-[5-(3,4-diisopentyloxybenzoyl)-2-isopentyloxyphenyl]acetate. After adding 0.6 ml of 5 mol/L aqueous solution of sodium hydroxide, the mixture is stirred at 50° C. for one hour. Chloroform and water are added to the reaction mixture, pH is adjusted to 2 with 6 mol/L hydrochloric acid, and the organic layer is separated. The organic layer is washed with water and saturated aqueous solution of sodium chloride successively, and the solvent is distilled off from the reaction mixture under reduced pressure. Thus, 0.88 g of 2-[5-(3,4-diisopentyloxybenzoyl)-2-isopentyloxyphenyl] acetic acid is obtained as a white solid product.

NMR (CDCl$_3$) δ: 0.96 (12H, d, J=5.6 Hz), 0.98 (6H, d, J=5.9 Hz), 1.59-1.78 (9H, m), 3.70 (2H, s), 4.00-4.16 (6H, m), 6.88 (1H, d, J=8.3 Hz), 6.92 (1H, d, J=8.8 Hz), 7.26-7.43 (2H, m), 7.71-7.82 (2H, m), 9.35 (1H, brs)

EXAMPLE 47

The procedure of Example 46 is repeated to obtain 3-[5-(3,4-diisobutoxybenzoyl)-2-isobutoxyphenyl]-propanoic acid.

NMR (CDCl$_3$) δ: 1.06 (18H, d, J=6.6 Hz), 1.92-2.50 (3H, m), 2.65-3.24 (4H, m), 3.82 (6H, d, J=6.6 Hz), 6.82-6.92 (2H, m), 7.26-7.40 (2H, m), 7.65-7.73 (2H, m), 8.54 (1H, brs)

EXAMPLE 48

In 10 ml of methylene chloride is dissolved 1.00 g of 3-(acetyloxy)-4-isobutoxybenzoic acid. After adding 0.41 ml of oxalyl chloride and 20 µl of N,N-dimethylformamide successively at ambient temperature, the mixture thus obtained is stirred at ambient temperature for one hour. Then, 1.06 g of aluminum chloride and 1.15 g of 1,3-diisobutoxybenzene are successively added at 5-10° C., and the mixture is stirred at the same temperature as above for one hour. The reaction mixture is added to a mixture of methylene chloride and ice water, and the organic layer is separated. The organic layer is successively washed with water and saturated aqueous solution of sodium chloride and dried over anhydrous magnesium sulfate, and the solvent is distilled off under reduced pressure. The residue thus obtained is purified by silica gel column chromatography [eluent; n-hexane:ethyl acetate=5:1] to obtain 1.24 g of 5-(2,4-diisobutoxybenzoyl)-2-isobutoxyphenyl acetate as a yellow oily product.

NMR (CDCl$_3$) δ: 0.73 (6H, d, J=6.8 Hz), 1.00 (6H, d, J=6.8 Hz), 1.05 (6H, d, J=6.6 Hz), 1.65-2.40 (3H, m), 2.28 (3H, s), 3.63 (2H, d, J=6.3 Hz), 3.77 (2H, d, J=6.4 Hz), 3.80 (2H, d, J=6.4 Hz), 6.46-6.57 (2H, m), 6.91 (1H, d, J=8.5 Hz), 7.35 (1H, d, J=8.6 Hz), 7.47 (1H, d, J=2.2 Hz), 7.67 (1H, dd, J=8.6, 2.2 Hz)

EXAMPLE 49

The procedure of Example 48 is repeated to obtain ethyl 2-[5-(2,4-diisobutoxybenzoyl)-2-isopentyloxyphenoxy]acetate.

NMR (CDCl$_3$) δ: 0.72 (6H, d, J=6.6 Hz), 0.97 (6H, d, J=6.4 Hz), 1.05 (6H, d, J=6.8 Hz), 1.28 (3H, t, J=7.1 Hz), 1.70-2.34 (5H, m), 3.62 (2H, d, J=6.4 Hz), 3.77 (2H, d, J=6.4 Hz), 4.10 (2H, t, J=6.6 Hz), 4.24 (2H, q, J=7.1 Hz), 4.66 (2H, s), 6.46-6.55 (2H, m), 6.85 (1H, d, J=9.0 Hz), 7.29-7.42 (3H, m)

EXAMPLE 50

The procedure of Example 48 is repeated to obtain ethyl 2-[5-(2,4-diisopentyloxybenzoyl)-2-isopentyloxyphenoxy] acetate.

NMR (CDCl$_3$) δ: 0.77 (6H, d, J=5.6 Hz), 0.98 (12H, d, J=5.9 Hz), 1.28 (3H, t, J=7.1 Hz), 1.64-2.04 (9H, m), 3.88-4.36 (8H, m), 4.66 (2H, s), 6.47-6.55 (2H, m), 6.85 (1H, d, J=9.0 Hz), 7.29-7.38 (3H, m)

EXAMPLE 51

In 10 ml of ethanol is dissolved 0.48 g of 5-(2,4-diisobutoxybenzoyl)-2-isobutoxyphenyl acetate, to which is added 3.2 ml of 1 mol/L solution of sodium hydroxide. The mixture thus obtained is stirred at ambient temperature for one hour. Water and chloroform are added to the reaction mixture, pH is adjusted to 2 with 6 mol/L hydrochloric acid, and the organic layer is separated. The organic layer is washed with water and saturated aqueous solution of sodium chloride successively and dried on anhydrous magnesium sulfate, and the solvent is distilled off under reduced pressure. Thus, 0.40 g of (2,4-diisobutoxyphenyl)(3-hydroxy-4-isobutoxyphenyl)methanone is obtained as a light yellow solid product.

NMR (CDCl$_3$) δ: 0.72 (6H, d, J=6.8 Hz), 1.04 (12H, d, J=6.6 Hz), 1.60-2.30 (3H, m), 3.63 (2H, d, J=6.4 Hz), 3.76 (2H, d, J=6.6 Hz), 3.86 (2H, d, J=6.6 Hz), 5.59 (1H, s), 6.46-6.56 (2H, m), 6.81 (1H, d, J=8.8 Hz), 7.26-7.39 (3H, m)

EXAMPLE 52

In 9 ml of N,N-dimethylformamide is dissolved 0.86 g of (2,4-diisobutoxyphenyl)(3-hydroxy-4-isobutoxyphenyl) methanone, to which is added 0.12 g of 60% sodium hydride. After elevating the temperature to 80° C., 0.52 ml of ethyl 2-bromoacetate is added, and the mixture thus obtained is stirred at 80-90° C. for 30 minutes. The reaction mixture is cooled to ambient temperature and added to a mixture of ethyl acetate and water, pH is adjusted to 2 with 6 mol/L hydrochloric acid, and the organic layer is separated. The organic layer thus obtained is washed with water and saturated aqueous solution of sodium chloride successively and dried over anhydrous magnesium sulfate, and the solvent is distilled off under reduced pressure. The residue thus obtained is purified by silica gel column chromatography (eluent; hexane:ethyl acetate=5:1) to obtain 1.00 g of ethyl 2-[5-(2,4-diisobutoxybenzoyl)-2-isobutoxyphenoxy] acetate as a light yellow oily product.

NMR (CDCl$_3$) δ: 0.72 (6H, d, J=6.6 Hz), 1.05 (12H, d, J=6.6 Hz), 1.23 (3H, t, J=7.1 Hz), 1.50-2.33 (3H, m), 3.62 (2H, d, J=6.1 Hz), 3.76 (2H, d, J=5.6 Hz), 3.83 (2H, d, J=6.4 Hz), 4.24 (2H, q, J=7.1 Hz), 4.66 (2H, s), 6.46-6.58 (2H, m), 6.84 (1H, d, J=9.0 Hz), 7.27-7.43 (3H, m)

EXAMPLE 53

In 10 ml of ethanol is dissolved 0.95 g of ethyl 2-[5-(2,4-diisobutoxybenzoyl)-2-isobutoxyphenoxy]acetate, to which is added 5.7 ml of 1 mol/L solution of sodium hydroxide. The mixture thus obtained is stirred at ambient temperature for one hour. Water and chloroform are added to the reaction mixture, pH is adjusted to 2 with 6 mol/L hydrochloric acid, and the organic layer is separated. The organic layer is washed with water and saturated aqueous solution of sodium chloride successively and dried on anhydrous magnesium sulfate, and the solvent is distilled off under reduced pressure. Thus, 0.83 g of 2-[5-(2,4-diisobutoxybenzoyl)-2-isobutoxyphenoxy]acetic acid is obtained as a white solid product.

NMR (CDCl$_3$) δ: 0.71 (6H, d, J=6.6 Hz), 1.05 (12H, d, J=6.6 Hz), 1.55-2.40 (3H, m), 3.62 (2H, d, J=6.1 Hz), 3.78 (2H, d, J=6.6 Hz), 3.85 (2H, d, J=6.8 Hz), 4.68 (2H, s), 6.45-6.58 (2H, m), 6.88 (1H, d, J=9.0 Hz), 7.32-7.52 (3H, m), 8.50 (1H, brs)

EXAMPLE 54

The procedure of Example 53 is repeated to obtain 2-[5-(2,4-diisobutoxybenzoyl)-2-isopentyloxyphenoxy]acetic acid.

NMR (CDCl$_3$) δ: 0.70 (6H, d, J=6.6 Hz), 0.98 (6H, d, J=6.1 Hz), 1.05 (6H, d, J=6.6 Hz), 1.52-2.34 (5H, m), 3.62 (2H, d, J=6.4 Hz), 3.77 (2H, d, J=6.6 Hz), 4.12 (2H, t, J=6.6 Hz), 4.67 (2H, s), 6.45-6.59 (3H, m), 6.89 (1H, d, J=9.0 Hz), 7.33-7.53 (3H, m)

EXAMPLE 55

The procedure of Example 53 is repeated to obtain 2-[5-(2,4-diisopentyloxybenzoyl)-2-isopentyloxyphenoxy]acetic acid.

NMR (CDCl$_3$) δ: 0.75 (6H, d, J=6.1 Hz), 0.98 (12H, d, J=6.1 Hz), 1.18-1.52 (3H, m), 1.60-2.04 (6H, m), 3.87 (2H, t, J=6.1 Hz), 4.04 (2H, t, J=6.6 Hz), 4.12 (2H, t, J=6.8 Hz), 4.66 (2H, s), 5.65 (1H, brs), 6.45-6.59 (2H, m), 6.89 (1H, d, J=9.0 Hz), 7.33-7.49 (3H, m)

EXAMPLE 56

In 40 ml of tetrahydrofuran is dissolved 4.00 g of 5-(2,4-diisobutoxybenzoyl)-2-isobutoxybenzoic acid, to which are added 0.95 ml of oxalyl chloride and 20 μl of N,N-dimethylformamide. The mixture thus obtained is stirred at ambient temperature for one hour. To the reaction mixture are added 3.03 g of glycine ethyl ester hydrochloride and 4.2 ml of triethylamine successively, and the mixture thus obtained is stirred for one hour under reflux with heating. The reaction mixture is cooled to ambient temperature, chloroform and water are added, and the organic layer is separated. The organic layer thus obtained is washed with water and saturated aqueous solution of sodium chloride successively and dried over anhydrous magnesium sulfate, and the solvent is distilled off under reduced pressure. The residue thus obtained is purified by silica gel column chromatography (eluent; hexane:ethyl acetate=2:1) to obtain 4.00 g of ethyl 2-{[5-(2,4-diisobutoxybenzoyl)-2-isobutoxybenzoyl]amino}acetate as a colorless oily product.

NMR (CDCl$_3$) δ: 0.66 (6H, d, J=6.6 Hz), 1.04 (6H, d, J=6.1 Hz), 1.10 (6H, d, J=5.1 Hz), 1.29 (3H, t, J=7.1 Hz), 1.92-2.55 (3H, m), 3.62 (2H, d, J=6.1 Hz), 3.76 (2H, d, J=6.6 Hz), 3.99 (2H, d, J=6.4 Hz), 4.12-4.36 (4H, m), 6.46-6.56 (2H, m), 7.01 (1H, d, J=8.8 Hz), 6.97-7.15 (1H, m), 7.92-8.07 (1H, m), 8.29-8.51 (2H, m)

EXAMPLE 57

In 7 ml of ethanol is dissolved 0.64 g of ethyl 2-{[5-(2,4-diisobutoxybenzoyl)-2-isobutoxybenzoyl]amino}acetate, to which is added 0.73 ml of 5 mol/L solution of sodium hydroxide. The mixture thus obtained is stirred at ambient temperature for one hour. Water and ethyl acetate are added to the reaction mixture, pH is adjusted to 2 with 6 mol/L hydrochloric acid, and the organic layer is separated. The organic layer thus obtained is washed with water and saturated aqueous solution of sodium chloride successively and dried over anhydrous magnesium sulfate, and the solvent is distilled off under reduced pressure. The residue thus obtained is purified by silica gel column chromatography (eluent; chloroform:ethanol=20:1) to obtain 0.25 g of 2-{[5-(2,4-diisobutoxybenzoyl)-2-isobutoxybenzoyl]amino}-acetic acid as a white solid product.

NMR (DMSO-d$_6$) δ: 0.61 (6H, d, J=6.6 Hz), 1.01 (12H, d, J=6.4 Hz), 1.42-2.40 (3H, m), 3.68 (2H, d, J=6.1 Hz), 3.84 (2H, d, J=6.4 Hz), 4.00-4.06 (4H, m), 6.59-6.66 (2H, m), 7.22-7.35 (2H, m), 7.80 (1H, d, J=7.8 Hz), 8.17 (1H, d, J=2.0 Hz), 8.34-8.48 (1H, m), 12.76 (1H, brs)

EXAMPLE 58

In 10 ml of tetrahydrofuran is dissolved 1.00 g of 3-[5-(2,4-diisobutoxybenzoyl)-2-isobutoxyphenyl]-propanoic acid, to which is added 0.52 g of 1,1'-carbonyldiimidazole at ambient temperature. The mixture thus obtained is heated under reflux for one hour with stirring. To the reaction mixture cooled to ambient temperature are added 0.22 g of methane-sulfonamide and 0.4 ml of 1,8-diazabicyclo[5.4.0]undec-7-ene, and the mixture thus obtained is stirred for 30 minutes at ambient temperature. The reaction mixture is added to a mixture of chloroform and water, pH is adjusted to 2 with 6 mol/L hydrochloric acid, and the organic layer is separated. The organic layer thus obtained is washed with water and saturated aqueous solution of sodium chloride successively and dried over anhydrous magnesium sulfate, and the solvent is distilled off under reduced pressure. The residue thus obtained is purified by silica gel column chromatography (eluent; hexane:ethyl acetate=2:1) to obtain 1.10 g of N-{3-[5-(2,4-diisobutoxybenzoyl)-2-isobutoxyphenyl]propanoyl}methanesulfonamide as a white-colored foaming product.

NMR (CDCl$_3$) δ: 0.68 (6H, d, J=6.6 Hz), 1.03 (12H, d, J=6.6 Hz), 1.54-2.35 (3H, m), 2.46-3.20 (4H, m), 3.23 (3H, s), 3.60 (2H, d, J=6.4 Hz), 3.73-3.80 (4H, m), 6.45-6.55 (2H, m), 6.78 (1H, d, J=8.5 Hz), 7.31 (1H, d, J=8.3 Hz), 7.53-7.64 (2H, m), 8.94 (1H, brs)

EXAMPLE 59

In 100 ml of tetrahydrofuran is dissolved 10.6 g of ethyl 3-[5-(2,4-diisobutoxybenzoyl)-2-isobutoxyphenyl]propanoate, to which is dropwise added at −60° C. a solution of lithium diisopropylamide in 30 ml tetrahydrofuran (prepared from 88 ml of 1.6 mol/L solution of n-butyllithium in n-hexane and 17 ml of isopropylamine). The mixture thus obtained is stirred at the same temperature as above for one hour. After dropping the reaction mixture thus obtained at −60° C. into a solution of 26 ml of methyl iodide in 30 ml of tetrahydrofuran, the temperature is elevated to ambient temperature over a period of one hour. The reaction mixture is added to a mixture of ethyl acetate and water, and the organic layer is separated. The organic layer is washed with water and saturated aqueous solution of sodium chloride successively and dried over anhydrous magnesium sulfate, and the solvent is distilled off under reduced pressure. The residue thus obtained is purified by silica gel column chromatography (eluent; hexane:ethyl acetate=5:1) to obtain 4.9 g of ethyl 3-[5-(2,4-diisobutoxybenzoyl)-2-isobutoxyphenyl]-2-methylpropanoate as a colorless oily product.

NMR (CDCl$_3$) δ: 0.71 (6H, d, J=6.8 Hz), 1.02-1.30 (18H, m), 1.57-2.30 (3H, m), 2.46-3.15 (3H, m), 3.62 (2H, d, J=6.4 Hz), 3.78 (4H, d, J=6.1 Hz), 3.97-4.25 (2H, m), 6.46-6.60 (3H, m), 7.34 (1H, d, J=8.3 Hz), 7.58-7.70 (2H, m)

EXAMPLE 60

In 3 ml of ethanol is dissolved 0.55 g of ethyl 3-[5-(2,4-diisobutoxybenzoyl)-2-isobutoxyphenyl]-2-methylpropanoate, to which is added 1.5 ml of 5 mol/L solution of sodium hydroxide. The mixture thus obtained is stirred at ambient temperature for two hours. Chloroform and water are added to the reaction mixture, pH is adjusted to 2 with 6 mol/L hydrochloric acid, and the organic layer is separated. The organic layer thus obtained is washed with water and saturated aqueous solution of sodium chloride successively and dried over anhydrous magnesium sulfate, and the solvent is distilled off under reduced pressure. The residue thus obtained is purified by silica gel column chromatography (eluent; n-hexane:ethyl acetate=2:1) to obtain 0.45 g of 3-[5-(2,4-diisobutoxybenzoyl)-2-isobutoxyphenyl]-2-methylpropanoic acid as a white solid product.

NMR (CDCl$_3$) δ: 0.70 (6H, d, J=6.6 Hz), 0.88-1.26 (15H, m), 1.61-2.33 (3H, m), 2.54-3.25 (3H, m), 3.61 (2H, d, J=6.3 Hz), 3.77 (4H, d, J=6.4 Hz), 6.46-6.58 (2H, m), 6.79 (1H, d, J=9.0 Hz), 7.24 (1H, brs), 7.35 (1H, d, J=8.1 Hz), 7.60-7.71 (2H, m)

EXAMPLE 61

In 20 ml of ethanol is dissolved 10.00 g of ethyl 3-[5-(2,4-diisobutoxybenzoyl)-2-isobutoxyphenyl]-propanoate, to which are added 5.59 g of hydroxylamine hydrochloride and 7 ml of pyridine. The mixture is heated under reflux for 4.5 hours with stirring. After cooling the mixture to ambient temperature, chloroform and water are added, and the organic layer is separated. The organic layer thus obtained is washed with water and saturated aqueous solution of sodium chloride successively and dried over anhydrous magnesium sulfate, and the solvent is distilled off under reduced pressure. The residue thus obtained is purified by silica gel column chromatography (eluent; n-hexane:ethyl acetate=5:1) to obtain 10.20 g of ethyl 3-{5-[(2,4-diisobutoxyphenyl)(hydroxyimino)-methyl]-2-isobutoxyphenyl}propanoate as a light brown oily product.

NMR (CDCl$_3$) δ: 0.72-1.30 (21H, m), 1.62-2.33 (3H, m), 2.42-3.00 (4H, m), 3.46-3.79 (6H, m), 4.10 (2H, q, J=7.3 Hz), 6.39-6.82 (3H, m), 7.04-7.31 (3H, m), 7.99 (1H, brs)

EXAMPLE 62

The procedure of Example 61 is repeated to obtain isopentyl 2-{5-[(3,4-diisopentyloxyphenyl)-(hydroxyimino)methyl]-2-isopentyloxyphenyl}acetate.

NMR (CDCl$_3$) δ: 0.86-0.98 (24H, m), 1.46-1.92 (12H, m), 3.56-3.61 (2H, m), 3.93-4.17 (8H, m), 6.75-6.95 (3H, m), 7.17-7.40 (3H, m), 8.20 (1H, brs)

EXAMPLE 63

The procedure of Example 61 is repeated to obtain 2-{5-[(3,4-diisopentyloxyphenyl)-(hydroxyimino)methyl]-2-isopentyloxyphenyl}acetic acid.

NMR (CDCl$_3$) δ: 0.91-0.97 (18H, m), 1.57-1.93 (9H, m), 3.68-3.71 (2H, m), 3.88-4.13 (6H, m), 5.20 (1H, brs), 6.73-7.60 (7H, m)

EXAMPLE 64

The procedure of Example 61 is repeated to obtain methyl 3-{5-[(2-hydroxy-4-isobutoxyphenyl)-(hydroxyimino)methyl]-2-isobutoxyphenyl}propanoate. Further, isomers are separated by silica gel column chromatography (eluent; hexane:ethyl acetate=5:1).

Less polar oxime:
NMR (CDCl$_3$) δ: 1.00 (6H, d, J=6.4 Hz), 1.07 (6H, d, J=6.4 Hz), 1.92-2.31 (2H, m), 2.56-2.73 (2H, m), 2.92-3.09 (2H, m), 3.65 (3H, s), 3.70 (2H, d, J=6.6 Hz), 3.80 (2H, d, J=6.1 Hz), 6.30 (1H, dd, J=8.8, 2.4 Hz), 6.51 (1H, d, J=2.4 Hz), 6.75 (1H, d, J=8.8 Hz), 6.90 (1H, d, J=8.8 Hz), 7.11-7.26 (2H, m), 7.44 (1H, s), 11.33 (1H, s)

More polar oxime:
NMR (CDCl$_3$) δ: 1.03 (6H, d, J=6.8 Hz), 1.05 (6H, d, J=6.6 Hz), 1.94-2.26 (2H, m), 2.44-2.62 (2H, m), 2.80-2.96 (2H, m), 3.64 (3H, s), 3.76 (4H, d, J=6.4 Hz), 6.45 (1H, dd, J=8.8, 2.4 Hz), 6.59 (1H, d, J=2.2 Hz), 6.75 (1H, d, J=9.0 Hz), 6.85 (1H, d, J=9.0 Hz), 7.18-7.26 (2H, m), 7.49 (2H, brs)

EXAMPLE 65

In 5 ml of N,N-dimethylformamide is dissolved 2.0 g of ethyl 3-{5-[(2,4-diisobutoxyphenyl)-(hydroxyimino)methyl]-2-isobutoxyphenyl}propanoate, to which is added 0.19 g of 60% sodium hydride. The mixture thus obtained is stirred at ambient temperature for 30 minutes. Then, 1.07 g of 2-bromoacetamide is added and the mixture thus obtained is stirred at ambient temperature for one hour and further at 80° C. for 15 minutes. The reaction mixture is added to a mixture of ethyl acetate and water, pH is adjusted to 2 with 6 mol/L hydrochloric acid, and the organic layer is separated. The organic layer thus obtained is washed with water and saturated aqueous solution of sodium chloride successively and dried over anhydrous magnesium sulfate, and the solvent is distilled off under reduced pressure. The residue thus obtained is purified by silica gel column chromatography (eluent; hexane:ethyl acetate=2:1) to obtain 1.09 g of ethyl 3-{5-[[(2-amino-2-oxoethoxy)imino](2,4-diisobutoxyphenyl)methyl]-2-isobutoxyphenyl}propanoate as a colorless oily product.

NMR (CDCl$_3$) δ: 0.79 (6H, d, J=6.8 Hz), 1.05 (12H, d, J=6.6 Hz), 1.23 (3H, t, J=7.1 Hz), 1.60-2.40 (3H, m), 2.44-2.67 (2H, m), 2.80-3.05 (2H, m), 3.47-3.80 (6H, m), 4.11 (2H, q, J=7.3 Hz), 4.61 (2H, s), 5.45-5.61 (1H, m), 6.42-7.02 (5H, m), 7.19-7.39 (2H, m)

EXAMPLE 66

The procedure of Example 65 is repeated to obtain the compounds shown in Table 86.

TABLE 86

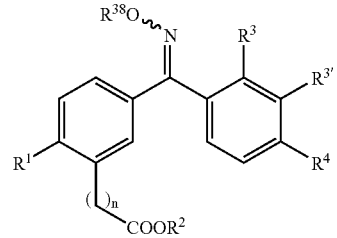

| No. | n | $R^1$ | $R^3$ | $R^{3'}$ | $R^4$ | $R^{38}$ | $R^2$ |
|---|---|---|---|---|---|---|---|
| 66(1) | 1 | O-iAm | H | O-iAm | O-iAm | CH$_2$CO$_2$Et | iAm |
| 66(2) | 1 | O-iAm | H | O-iAm | O-iAm | CH$_2$CONH$_2$ | iAm |
| 66(3) | 2 | O-iBu | OH | H | O-iBu | CH$_2$Ph | Me |
| 66(4) | 2 | O-iBu | OH | H | O-iBu | CH$_2$-3-Py | Me |
| 66(5) | 2 | O-iBu | OH | H | O-iBu | CH$_2$CONH$_2$ | Me |
| 66(6) | 1 | O-iAm | H | O-iAm | O-iAm | nPr | iAm |

66(1)

NMR (CDCl$_3$) δ: 0.86-0.98 (24H, m), 1.29 (3H, t, J=7.1 Hz), 1.42-1.93 (12H, m), 3.56-3.59 (2H, m), 3.86-4.36 (10H, m), 4.70 (2H, s), 6.70-7.53 (6H, m)

66(2)

NMR (CDCl$_3$) δ: 0.87-0.99 (24H, m), 1.42-1.93 (12H, m), 3.57-3.62 (2H, m), 3.97-4.18 (8H, m), 4.63-4.64 (2H, m), 5.56 (1H, brs), 6.15 (1H, brs), 6.71-6.94 (3H, m), 7.20-7.40 (3H, m)

66(3)

NMR (CDCl$_3$) δ: 0.99 (6H, d, J=6.6 Hz), 1.06 (6H, d, J=7.6 Hz), 1.90-2.31 (2H, m), 2.54-2.71 (2H, m), 2.90-3.06 (2H, m), 3.64 (3H, s), 3.68 (2H, d, J=7.3 Hz), 3.79 (2H, d, J=6.3 Hz), 5.10 (2H, s), 6.26 (1H, dd, J=8.8, 2.4 Hz), 6.47 (1H, d, J=2.5 Hz), 6.70 (1H, d, J=8.8 Hz), 6.87 (1H, d, J=8.8 Hz), 7.06-7.34 (7H, m), 11.11 (1H, s)

66(4)

NMR (CDCl$_3$) δ: 0.99 (6H, d, J=7.1 Hz), 1.07 (6H, d, J=6.8 Hz), 1.92-2.31 (2H, m), 2.71 (2H, t, J=6.8 Hz), 2.98 (2H, t, J=6.8 Hz), 3.64 (3H, s), 3.68 (2H, d, J=8.4 Hz), 3.79 (2H, d, J=6.1 Hz), 5.14 (2H, s), 6.28 (1H, dd, J=4.7, 2.4 Hz), 6.47 (1H, d, J=2.4 Hz), 6.70 (1H, d, J=8.8 Hz), 6.88 (1H, d, J=8.5 Hz), 7.04-7.36 (3H, m), 7.62-7.72 (1H, m), 8.50-8.54 (2H, m), 10.97 (1H, s)

66(5)

NMR (CDCl$_3$) δ: 1.00 (6H, d, J=6.6 Hz), 1.08 (6H, d, J=6.8 Hz), 1.95-2.33 (2H, m), 2.60-2.74 (2H, m), 2.91-3.07 (2H, m), 3.62 (3H, s), 3.72 (2H, d, J=6.6 Hz), 3.81 (2H, d, J=6.4 Hz), 4.58 (2H, s), 5.64 (1H, brs), 6.05 (1H, brs), 6.31 (1H, dd, J=8.7, 2.4 Hz), 6.52 (1H, d, J=2.4 Hz), 6.72 (1H, d, J=8.8 Hz), 6.91 (1H, d, J=8.8 Hz), 7.08-7.21 (2H, m), 10.63 (1H, s)

EXAMPLE 67

In 10 ml of ethanol is dissolved 1.08 g of ethyl 3-{5-[[(2-amino-2-oxoethoxy)imino](2,4-diisobutoxyphenyl)methyl]-2-isobutoxyphenyl}propanoate, to which is added 1.1 ml of 5 mol/L sodium hydroxide solution. The mixture is stirred at ambient temperature for 3 hours. Chloroform and water are added to the reaction mixture, pH is adjusted to 2 with 6 mol/L hydrochloric acid, and the organic layer is separated. The organic layer thus obtained is washed with water and saturated aqueous solution of sodium chloride successively and dried over anhydrous magnesium sulfate, and the solvent is distilled off under reduced pressure. The residue thus obtained is purified by silica gel column chromatography (eluent; chloroform:ethanol=10:1) to obtain 0.68 g of 3-{5-[[(2-amino-2-oxoethoxy)imino](2,4-diisobutoxyphenyl)methyl]-2-isobutoxyphenyl}propanoic acid as a white foaming product.

NMR (CDCl$_3$) δ: 0.63-1.09 (18H, m), 1.51-2.35 (3H, m), 2.47-3.09 (4H, m), 3.47-3.79 (6H, m), 4.59-4.65 (2H, m), 6.40-7.65 (9H, m)

EXAMPLE 68

The procedure of Example 67 is repeated to obtain the compounds shown in Table 87.

TABLE 87

| No. | n | R$^1$ | R$^3$ | R$^{3'}$ | R$^4$ | R$^{38}$ |
|---|---|---|---|---|---|---|
| 68(1) | 1 | O-iAm | H | O-iAm | O-iAm | nPr |
| 68(2) | 1 | O-iAm | H | O-iAm | O-iAm | CH$_2$CO$_2$H |
| 68(3) | 1 | O-iAm | H | O-iAm | O-iAm | CH$_2$CONH$_2$ |
| 68(4) | 2 | O-iBu | OH | H | O-iBu | CH$_2$Ph |
| 68(5) | 2 | O-iBu | OH | H | O-iBu | CH$_2$-3-Py |
| 68(6) | 2 | O-iBu | OH | H | O-iBu | CH$_2$CO$_2$H |
| 68(7) | 2 | O-iBu | OH | H | O-iBu | CH$_2$CONH$_2$ |
| 68(8) | 2 | O-iBu | OH | H | O-iBu | H |
| 68(9) | 2 | O-iBu | O-iBu | H | O-iBu | H |

68(1)

NMR (CDCl$_3$) δ: 0.92-0.98 (21H, m), 1.68-1.94 (11H, m), 3.63 (2H, s), 3.93-4.20 (8H, m), 6.78-7.48 (7H, m)

68(2)

NMR (CDCl$_3$) δ: 0.90-0.96 (18H, m), 1.57-1.92 (9H, m), 3.64 (2H, s), 3.89-4.18 (6H, m), 4.73 (2H, s), 6.75-7.41 (6H, m), 8.77 (2H, brs)

68(3)

NMR (CDCl$_3$) δ: 0.92-0.99 (18H, m), 1.61-1.72 (9H, m), 3.67 (2H, s), 3.90-4.12 (6H, m), 4.61-4.68 (2H, m), 6.20 (1H, brs), 6.59 (1H, brs), 6.74-7.60 (7H, m)

68(4)

NMR (CDCl$_3$) δ: 0.96 (6H, d, J=6.8 Hz), 1.06 (6H, d, J=6.8 Hz), 1.80-2.30 (2H, m), 2.60-2.75 (2H, m), 2.90-3.05 (2H, m), 3.67 (2H, d, J=6.4 Hz), 3.78 (2H, d, J=6.4 Hz), 5.09 (2H, s), 6.27 (1H, dd, J=9.0, 2.4 Hz), 6.47 (1H, d, J=2.5 Hz), 6.71 (1H, d, J=8.8 Hz), 6.87 (1H, d, J=9.0 Hz), 7.07-7.33 (8H, m), 11.00 (1H, brs)

68(5)

NMR (CDCl$_3$) δ: 0.98 (6H, d, J=6.6 Hz), 1.07 (6H, d, J=7.1 Hz), 1.83-2.40 (2H, m), 2.71 (2H, t, J=6.6 Hz), 3.03 (2H, t, J=6.6 Hz), 3.68 (2H, d, J=6.6 Hz), 3.80 (2H, d, J=6.4 Hz), 5.16 (2H, s), 6.26 (1H, dd, J=8.8, 2.4 Hz), 6.46 (1H, d, J=2.4 Hz), 6.71 (1H, d, J=8.8 Hz), 6.89 (1H, d, J=9.3 Hz), 7.07-7.40 (4H, m), 7.60-7.73 (1H, m), 8.40-8.48 (3H, m)

68(6)

NMR (CDCl$_3$) δ: 0.99 (6H, d, J=6.6 Hz), 1.06 (6H, d, J=6.1 Hz), 1.92-2.37 (2H, m), 2.64-2.78 (2H, m), 2.92-3.09 (2H, m), 3.70 (2H, d, J=6.6 Hz), 3.78 (2H, d, J=7.1 Hz), 4.65 (2H, s), 6.30 (1H, dd, J=8.8, 2.4 Hz), 6.50 (1H, d, J=2.2 Hz), 6.78 (1H, d, J=8.8 Hz), 6.87 (1H, d, J=8.8 Hz), 7.10 (1H, dd, J=8.8, 2.0 Hz), 7.38 (1H, d, J=1.5 Hz), 10.30 (3H, brs)

68(7)

NMR (CDCl$_3$) δ: 1.00 (6H, d, J=6.8 Hz), 1.07 (6H, d, J=6.8 Hz), 1.93-2.29 (2H, m), 2.67-3.00 (4H, m), 3.67-3.83 (4H, m), 4.54 (2H, s), 6.23-6.36 (3H, m), 6.50 (1H, d, J=2.2 Hz), 6.73 (1H, d, J=8.8 Hz), 6.88 (1H, d, J=9.0 Hz), 6.99-7.25 (3H, m), 10.60 (1H, brs)

68(8)

Isomers were separated by silica gel column chromatography (eluent; hexane:ethyl acetate=2:1), and NMR spectra were measured.

Less polar oxime

NMR (DMSO-d6) δ: 0.96 (6H, d, J=6.8 Hz), 1.03 (6H, d, J=6.6 Hz), 1.78-2.21 (2H, m), 2.49-2.85 (4H, m), 3.69-3.86 (4H, m), 6.29-6.46 (2H, m), 6.71 (1H, d, J=8.6 Hz), 6.94-7.08 (4H, m), 11.70 (2H, brs)

More polar oxime

NMR (DMSO-d6) δ: 1.00 (12H, d, J=6.6 Hz), 1.80-2.17 (2H, m), 2.47-2.80 (4H, m), 3.74 (4H, d, J=3.9 Hz), 6.41-6.47 (2H, m), 6.80-7.15 (3H, m), 7.39-7.40 (1H, m), 9.20 (1H, brs), 11.50 (2H, brs)

68(9)

NMR (CDCl$_3$) δ: 0.73 (6H, d, J=6.6 Hz), 1.00-1.07 (12H, m), 1.78-2.31 (3H, m), 2.69-3.00 (4H, m), 3.59-3.76 (6H, m), 6.40-6.80 (3H, m), 7.05-7.28 (2H, m), 7.49 (1H, s), 8.76 (2H, brs)

EXAMPLE 69

At 5° C., 5.56 g of nickel (II) chloride hexahydrate is added to a solution of 6.00 g of ethyl 3-{5-[(2,4-diisobutoxyphenyl)(hydroxyimino)methyl]-2-isobutoxyphenyl}propanoate in 60 ml of methanol. Then, 4.42 g of sodium borohydride is portionwise added over a period of one hour. Water is added to the reaction mixture, and then 6 mol/L hydrochloric acid is dropwise added and stirred at ambient temperature for 10 minutes. pH is adjusted to 9 with saturated aqueous solution of sodium bicarbonate, methylene chloride is added, and the organic layer is separated. The organic layer thus obtained is washed with water and saturated aqueous solution of sodium chloride successively and dried over anhydrous magnesium sulfate, and the solvent is distilled off under reduced pressure. Thus, 4.97 g of ethyl 3-{5-[amino(2,4-diisobutoxyphenyl)methyl]-2-isobutoxyphenyl}propanoate is obtained as a brown oily product.

NMR (CDCl$_3$) δ: 0.94-1.06 (18H, m), 1.22 (3H, t, J=7.1 Hz), 1.66-2.29 (5H, m), 2.44-2.69 (2H, m), 2.79-3.05 (2H, m), 3.68 (6H, d, J=6.4 Hz), 4.09 (2H, q, J=7.1 Hz), 5.36 (1H, s), 6.32-6.50 (2H, m), 6.73 (1H, d, J=9.0 Hz), 7.02-7.28 (3H, m)

EXAMPLE 70

To a solution of 1.10 g of ethyl 3-{5-[amino(2,4-diisobutoxyphenyl)methyl]-2-isobutoxyphenyl}propanoate in 11 ml of methylene chloride are dropwise added 0.4 ml of triethylamine and 0.2 ml of methanesulfonyl chloride successively at 5-10° C. The mixture thus obtained is stirred at the same temperature as above for 3 hours. Methylene chloride and water are added to the reaction mixture, and the organic layer is separated. The organic layer thus obtained is washed with water and saturated aqueous solution of sodium chloride successively and dried over anhydrous magnesium sulfate, and the solvent is distilled off under reduced pressure. Thus, 1.26 g of ethyl 3-(5-{2,4-diisobutoxyphenyl)[(methylsulfonyl)-amino]methyl}-2-isobutoxyphenyl)propanoate is obtained as a yellow-brown colored oily product.

NMR (CDCl$_3$) δ: 0.78-1.30 (21H, m), 1.72-2.31 (3H, m), 2.40-3.15 (4H, m), 2.65 (3H, s), 3.63-3.80 (6H, m), 4.09 (2H, q, J=7.1 Hz), 5.40 (1H, d, J=8.3 Hz), 5.69 (1H, d, J=8.3 Hz), 6.39-6.57 (2H, m), 6.71 (1H, d, J=8.3 Hz), 7.02-7.31 (3H, m)

EXAMPLE 71

The procedure of Example 70 is repeated to obtain ethyl 3-{5-[(acetylamino)(2,4-diisobutoxyphenyl)methyl]-2-isobutoxyphenyl}propanoate.

NMR (CDCl$_3$) δ: 0.84-1.06 (18H, m), 1.22 (3H, t, J=7.1 Hz), 1.71-2.22 (3H, m), 2.03 (3H, s), 2.22-2.71 (2H, m), 2.78-3.08 (2H, m), 3.61-3.74 (6H, m), 4.09 (2H, q, J=7.1 Hz), 6.18-6.72 (5H, m), 6.93-7.15 (3H, m)

EXAMPLE 72

The procedure of Example 70 is repeated to obtain ethyl 3-{5-[[(aminocarbonyl)amino](2,4-diisobutoxyphenyl)methyl]-2-isobutoxyphenyl}propanoate.

NMR (CDCl$_3$) δ: 0.85-1.06 (18H, m), 1.21 (3H, t, J=7.1 Hz), 1.83-2.29 (3H, m), 2.40-2.60 (2H, m), 2.79-3.08 (2H, m), 3.61-3.72 (6H, m), 4.08 (2H, q, J=7.1 Hz), 4.47 (2H, brs), 5.41 (1H, d, J=6.8 Hz), 5.93 (1H, d, J=6.8 Hz), 6.37-6.45 (2H, m), 6.60-6.73 (1H, m), 7.00-7.15 (3H, m)

EXAMPLE 73

In 7 ml of ethanol is dissolved 1.26 g of ethyl 3-(5-{(2,4-diisobutoxyphenyl)[(methylsulfonyl)-amino]methyl}-2-isobutoxyphenyl)propanoate, to which is added 1.3 ml of 5 mol/L solution of sodium hydroxide. The mixture is stirred at ambient temperature for one hour. Water and chloroform are added to the reaction mixture, pH is adjusted to 2 with 6 mol/L hydrochloric acid, and the organic layer is separated. The organic layer is washed with water and saturated aqueous solution of sodium chloride successively and dried over anhydrous magnesium sulfate, and the solvent is distilled off under reduced pressure. The residue thus obtained is purified by silica gel column chromatography (eluent; hexane:ethyl acetate=1:1) to obtain 0.92 g of 3-(5-{(2,4-diisobutoxyphenyl)[(methylsulfonyl)amino]methyl}-2-isobutoxyphenyl)propanoic acid as a light yellow oily product.

NMR (CDCl$_3$) δ: 0.80-1.06 (18H, m), 1.80-2.30 (3H, m), 2.44-3.07 (4H, m), 2.66 (3H, s), 3.58-3.81 (6H, m), 5.73 (2H, brs), 6.39-6.58 (2H, m), 6.71 (1H, d, J=9.3 Hz), 7.02-7.25 (3H, m), 8.78 (1H, brs)

EXAMPLE 74

The procedure of Example 73 is repeated to obtain 3-{5-[(acetylamino)(2,4-diisobutoxyphenyl)methyl]-2-isobutoxyphenyl}propanoic acid.

NMR (CDCl$_3$) δ: 0.83-1.04 (18H, m), 1.89-2.25 (6H, m), 2.55-3.00 (4H, m), 3.57-3.80 (6H, m), 6.20-7.19 (8H, m), 9.04 (1H, brs)

EXAMPLE 75

The procedure of Example 73 is repeated to obtain 3-{5-[[(aminocarbonyl)amino](2,4-diisobutoxyphenyl)methyl]-2-isobutoxyphenyl}propanoic acid.

NMR (CDCl$_3$) δ: 0.87-1.04 (18H, m), 1.84-2.28 (3H, m), 2.48-3.07 (4H, m), 3.04-3.70 (6H, m), 5.20 (2H, brs), 5.90-6.03 (2H, m), 6.39-7.18 (7H, m)

EXAMPLE 76

In 5 ml of N,N-dimethylformamide is suspended 0.85 g of 60% sodium hydride, to which is dropwise added 4.2 ml of ethyl diethylphosphonoacetate at ambient temperature over a period of 10 minutes. After stirring the mixture thus obtained for 30 minutes, 1.00 g of 3-[5-(2,4-diisobutoxybenzoyl)-2-isobutoxyphenyl]propanoic acid is added and stirred at 110° C. for 5 hours. The reaction mixture is cooled to ambient temperature and added to a mixture of ethyl acetate and water, and the organic layer is separated. The organic layer thus obtained is washed with water and saturated aqueous solution of sodium chloride successively and dried over anhydrous magnesium sulfate, and the solvent is distilled off under reduced pressure. The residue is purified by silica gel column chromatography (eluent; hexane:ethyl acetate=4:1) to obtain 0.36 g of 3-{5-[1-(2,4-diisobutoxyphenyl)-3-ethoxy-3-oxo-1-propenyl]-2-isobutoxyphenyl}propanoic acid as a light yellow oily product.

NMR (CDCl$_3$) δ: 0.70-1.30 (21H, m), 1.56-2.33 (3H, m), 2.47-3.05 (4H, m), 3.52-3.76 (6H, m), 3.91-4.21 (2H, m), 6.17-7.18 (7H, m), 8.44 (1H, brs)

EXAMPLE 77

The procedure of Example 76 is repeated to obtain 2-{5-[1-(3,4-diisopentyloxyphenyl)-3-ethoxy-3-oxo-1-propenyl]-2-isobutoxyphenyl}acetic acid.

NMR (CDCl$_3$) δ: 0.92-0.98 (18H, m), 1.13 (3H, t, J=7.1 Hz), 1.56-1.94 (9H, m), 3.64 (2H, s), 3.89-4.09 (8H, m), 6.21 (1H, s), 6.78-7.08 (7H, m)

EXAMPLE 78

In a mixture of 7 ml of ethanol and 3 ml of tetrahydrofuran is dissolved 0.79 g of 3-{5-[1-(2,4-diisobutoxyphenyl)-3-ethoxy-3-oxo-1-propenyl]-2-isobutoxyphenyl}propanoic acid. After adding 8 ml of 5 mol/L sodium hydroxide solution, the mixture thus obtained is stirred at ambient temperature for 2.5 hours and then at 60° C. for 1.5 hours. Chloroform and water are added to the reaction mixture, pH is adjusted to 2 with 6 mol/L hydrochloric acid, and the organic layer is separated. The organic layer thus obtained is washed with water and saturated aqueous solution of sodium chloride successively and dried over anhydrous magnesium sulfate, and the solvent is distilled off under reduced pressure. The residue is purified by silica gel column chromatography (eluent; hexane:ethyl acetate=2:1) to obtain 0.58 g of 3-[3-(2-carboxyethyl)-4-isobutoxyphenyl]-3-(2,4-diisobutoxyphenyl)-2-propenoic acid as a light yellow foaming product.

NMR (CDCl$_3$) δ: 0.70-1.06 (18H, m), 1.60-2.33 (3H, m), 2.40-3.07 (4H, m), 3.56 (2H, d, J=6.1 Hz), 3.72 (4H, d, J=6.1 Hz), 6.16-7.12 (7H, m), 9.36 (2H, brs)

EXAMPLE 79

In 6 ml of ethanol is dissolved 0.60 g of 3-{5-[1-(2,4-diisobutoxyphenyl)-3-ethoxy-3-oxo-1-propenyl]-2-isobutoxyphenyl}propanoic acid. After adding 0.12 g of 5% palladium-carbon, the mixture is stirred at ambient temperature for one hour in a stream of hydrogen. The reaction mixture is filtered with Celite, and the solvent is distilled off from the filtrate under a reduced pressure to obtain a crude product. The crude product is dissolved in 4 ml of ethanol, 0.7 ml of 5 mol/L sodium hydroxide is added, and the mixture thus obtained is stirred at ambient temperature for one hour. Chloroform and water are added to the reaction mixture, pH is adjusted to 2 with 6 mol/L hydrochloric acid, and the organic layer is separated. The organic layer is washed with water and saturated aqueous solution of sodium chloride successively and dried over anhydrous magnesium sulfate, and the solvent is distilled off under reduced pressure. Thus, 0.53 g of 3-[3-(2-carboxyethyl)-4-isobutoxyphenyl]-3-(2,4-diisobutoxyphenyl)propanoic acid is obtained as a white foaming product.

NMR (CDCl$_3$) δ: 0.99 (18H, d, J=6.6 Hz), 1.80-2.30 (3H, m), 2.44-3.09 (6H, m), 3.66 (6H, d, J=6.4 Hz), 4.64-4.91 (1H, m), 6.33-6.40 (2H, m), 6.67 (1H, d, J=9.0 Hz), 6.91-7.06 (3H, m), 9.90 (2H, brs)

EXAMPLE 80

In 3 ml of methylene chloride is dissolved 0.12 g of 2-(ethoxycarbonyl)-1-isobutyl-1H-indole-5-carboxylic acid, to which are successively added 50 µl of oxalyl chloride and 20 µl of N,N-dimethylformamide at ambient temperature. The mixture is stirred at ambient temperature for one hour. Then, at 5-10° C., 0.12 g of aluminum chloride and 0.13 g of 1,3-diisobutoxybenzene are successively added and stirred at the same temperature as above for 30 minutes. The reaction mixture is added to a mixture of chloroform and ice water, and the organic layer is separated. The organic layer thus obtained is washed with water and saturated aqueous solution of sodium chloride successively and dried over anhydrous magnesium sulfate, and the solvent is distilled off under reduced pressure. The residue thus obtained is purified by silica gel column chromatography (eluent; hexane:ethyl acetate=1:1) to obtain 0.18 g of ethyl 5-(2,4-diisobutoxybenzoyl)-1-isobutyl-1H-indole-2-carboxylate as a colorless oily product.

NMR (CDCl$_3$) δ: 0.57 (6H, d, J=6.6 Hz), 0.84-1.10 (12H, m), 1.40 (3H, t, J=7.1 Hz), 1.85-2.44 (3H, m), 3.57-3.82 (4H, m), 4.33-4.45 (4H, m), 6.44-6.58 (2H, m), 7.05-8.07 (5H, m)

EXAMPLE 81

The procedure of Example 80 is repeated to obtain ethyl 3-bromo-5-(2,4-diisobutoxybenzoyl)-1-isobutyl-1H-indole-2-carboxylate.

NMR (CDCl$_3$) δ: 0.56 (6H, d, J=6.6 Hz), 0.65-1.58 (16H, m), 1.91-2.36 (2H, m), 3.62 (2H, d, J=6.1 Hz), 3.80 (2H, d, J=6.4 Hz), 4.23-4.58 (4H, m), 6.30-6.63 (2H, m), 7.31-7.52 (2H, m), 7.90 (1H, dd, J=8.9, 2.2 Hz), 8.10 (1H, s)

EXAMPLE 82

In 2 ml of ethanol is dissolved 0.18 g of ethyl 5-(2,4-diisobutoxybenzoyl)-1-isobutyl-1H-indole-2-carboxylate. After adding 0.3 ml of 5 mol/L sodium hydroxide, the mixture thus obtained is stirred at ambient temperature for one hour. Water and chloroform are added to the reaction mixture, pH is adjusted to 2 with 6 mol/L hydrochloric acid, and the organic layer is separated. The organic layer is washed with water and saturated aqueous solution of sodium chloride successively and dried over anhydrous magnesium sulfate, and the solvent is distilled off under reduced pressure. The residue thus obtained is purified by silica gel column chromatography (eluent; hexane:ethyl acetate=1:1). Thus, 0.15 g of 5-(2,4-diisobutoxybenzoyl)-1-isobutyl-1H-indole-2-carboxylic acid is obtained as a white solid product.

NMR (CDCl$_3$) δ: 0.57 (6H, d, J=6.8 Hz), 0.90 (6H, d, J=6.6 Hz), 1.06 (6H, d, J=6.6 Hz), 1.46-2.40 (3H, m), 3.61 (2H, d, J=6.3 Hz), 3.80 (2H, d, J=6.4 Hz), 4.43 (2H, d, J=7.3 Hz), 6.50-6.63 (2H, m), 7.35-7.52 (4H, m), 7.90 (1H, dd, J=7.8, 1.5 Hz), 8.10 (1H, s)

EXAMPLE 83

The procedure of Example 82 is repeated to obtain 3-bromo-5-(2,4-diisobutoxybenzoyl)-1-isobutyl-1H-indole-2-carboxylic acid.

NMR (CDCl$_3$) δ: 0.56 (6H, d, J=6.6 Hz), 0.88 (6H, d, J=6.6 Hz), 1.06 (6H, d, J=6.6 Hz), 1.40-1.80 (1H, m), 1.86-2.34 (2H, m), 3.63 (2H, d, J=6.1 Hz), 3.80 (2H, d, J=6.3 Hz), 4.43 (2H, d, J=7.1 Hz), 4.93 (1H, brs), 6.51-6.61 (2H, m), 7.35-7.54 (2H, m), 7.89-8.08 (2H, m)

EXAMPLE 84

To a solution of 8.0 g of 3-(3-ethoxy-3-oxopropyl)-4-isobutoxybenzoic acid in 80 ml of tetrahydrofuran are dropwise added 3.6 ml of oxalyl chloride and 60 μl of N,N-dimethylformamide successively, and the mixture thus obtained is stirred at ambient temperature for one hour. Then, to the reaction mixture obtained herein is dropwise added, at −70° C., a pyrrole reagent prepared from 8.5 ml of pyrrole and 82 ml of 1 mol/L solution of methylmagnesium bromide in tetrahydrofuran. After dropping, the temperature is elevated to ambient temperature over a period of one hour, and the mixture is stirred at ambient temperature for one hour. The reaction mixture is cooled with ice water, a saturated aqueous solution of ammonium chloride is dropwise added, the mixture thus obtained is stirred at ambient temperature for 15 minutes, ethyl acetate is added, and the organic layer is separated. The organic layer thus obtained is washed with water and saturated aqueous solution of sodium chloride successively and dried over anhydrous magnesium sulfate, and the solvent is distilled off under reduced pressure. The residue thus obtained is purified by silica gel column chromatography (eluent; hexane:ethyl acetate=5:1) to obtain 5.0 g of ethyl 3-[2-isobutoxy-5-(1H-pyrrol-2-ylcarbonyl)phenyl]-propanoate as a brown-colored solid product.

NMR (CDCl$_3$) δ: 1.07 (6H, d, J=6.8 Hz), 1.23 (3H, t, J=7.3 Hz), 1.95-2.32 (1H, m), 2.62-2.71 (2H, m), 2.93-3.13 (2H, m), 3.82 (2H, d, J=6.4 Hz), 4.13 (2H, q, J=7.1 Hz), 6.25-6.36 (1H, m), 6.83-6.93 (2H, m), 7.05-7.15 (1H, m), 7.79-7.87 (2H, m), 9.80 (1H, brs)

EXAMPLE 85

In 10 ml of methylene chloride is dissolved 1.1 ml of 3-methylbutanoyl chloride, to which is dropwise added at 0° C. a solution of 1.00 g of ethyl 3-[2-isobutoxy-5-(1H-pyrrol-2-ylcarbonyl)phenyl]-propanoate in 10 ml of methylene chloride. The mixture thus obtained is stirred at 0° C. for 30 minutes and then at ambient temperature for 30 minutes. The reaction mixture is added to a mixture of methylene chloride and water, and the organic layer is separated. The organic layer is washed with water and saturated aqueous solution of sodium chloride successively and dried over anhydrous magnesium sulfate, and the solvent is distilled off under reduced pressure. The residue is purified by silica gel column chromatography (eluent; hexane:ethyl acetate=5:1) to obtain 0.94 g of 2-(3-ethoxy-3-oxopropyl)-4-{[4-(3-methylbutanoyl)-1H-pyrrol-2-yl]carbonyl}phenyl 3-methylbutanoate as a light brown-colored solid product.

NMR (CDCl$_3$) δ: 0.99 (6H, d, J=6.4 Hz), 1.10 (H, d, J=6.4 Hz), 1.23 (3H, t, J=7.1 Hz), 2.06-3.06 (10H, m), 4.15 (2H, q, J=7.1 Hz), 7.16-7.29 (2H, m), 7.71-7.89 (3H, m), 10.50 (1H, brs)

EXAMPLE 86

To a solution of 0.9 g of 2-(3-ethoxy-3-oxopropyl)-4-{[4-(3-methylbutanoyl)-1H-pyrrol-2-yl]carbonyl}phenyl 3-methylbutanoate in 18 ml N,N-dimethylformamide are added 0.12 g of 60% sodium hydride and 0.4 ml of isopentyl iodide successively, and the mixture thus obtained is stirred at 50-60° C. for one hour. The reaction mixture is added to a mixture of ethyl acetate and water, pH is adjusted to 2 with 6 mol/L hydrochloric acid, and the organic layer is separated. The organic layer is washed with water and saturated aqueous solution of sodium chloride and dried over anhydrous magnesium sulfate, and the solvent is distilled off under reduced pressure. Thus, 0.7 g of 2-(3-ethoxy-3-oxopropyl)-4-{[1-isopentyl-4-(3-methylbutanoyl)-1H-pyrrol-2-yl]carbonyl}phenyl 3-methylbutanoate is obtained as a white solid product.

NMR (CDCl$_3$) δ: 0.97 (12H, d, J=6.4 Hz), 1.09 (6H, d, J=6.3 Hz), 1.23 (3H, t, J=7.1 Hz), 1.46-1.87 (3H, m), 2.09-3.06 (10H, m), 4.13 (2H, q, J=7.1 Hz), 4.32-4.50 (2H, m), 7.10-7.21 (2H, m), 7.54-7.76 (3H, m)

EXAMPLE 87

A solution of 0.68 g of 2-(3-ethoxy-3-oxopropyl)-4-{[1-isopentyl-4-(3-methylbutanoyl)-1H-pyrrol-2-yl] carbonyl}phenyl 3-methylbutanoate in 4 ml of tetrahydrofuran is dropwise added to a mixture of 14 ml of ethanol and 13 ml of 1 mol/L sodium hydroxide solution at 40-50° C., and the mixture thus obtained is stirred at the same temperature as above for one hour. Water and chloroform are added to the reaction mixture, pH is adjusted to 2 with 6 mol/L hydrochloric acid, and the organic layer is separated. The organic layer is washed with water and saturated aqueous solution of sodium chloride successively and dried over anhydrous magnesium sulfate, and the solvent is distilled off under reduced pressure. The residue thus obtained is dissolved in 14 ml of N,N-dimethylformamide, 0.89 g of potassium carbonate and 0.9 ml of isopentyl iodide are added, and the mixture thus obtained is stirred at 100° C. for 15 minutes. The reaction mixture cooled to ambient temperature is added to a mixture of ethyl acetate and water, pH is adjusted to 2 with 6 mol/L hydrochloric acid, and the organic layer is separated. The organic layer is washed with water and saturated aqueous solution of sodium chloride and dried over anhydrous magnesium sulfate, and the solvent is distilled off under reduced pressure. The residue is purified by silica gel column chromatography (eluent; hexane:ethyl acetate=5:1) to obtain 0.69 g of isopentyl 3-[5-{[1-isopentyl-4-(3-methylbutanoyl)-1H-pyrrol-2-yl]carbonyl}-2-(isopentyloxy)phenyl]propanoate.

NMR (CDCl$_3$) δ: 0.86-1.02 (24H, m), 1.45-2.40 (10H, m), 2.56-2.70 (4H, m) 2.90-3.08 (2H, m), 4.06 (2H, d, J=6.4 Hz), 4.13 (2H, d, J=6.6 Hz), 4.38 (2H, t, J=7.2 Hz), 6.89 (1H, d, J=9.3 Hz), 7.07 (1H, d, J=1.5 Hz), 7.52 (1H, d, J=1.5 Hz), 7.69-7.79 (2H, m)

EXAMPLE 88

To a solution of 0.67 g of isopentyl 3-[5-{[1-isopentyl-4-(3-methylbutanoyl)-1H-pyrrol-2-yl]carbonyl}-2-(isopentyloxy)phenyl]propanoate in 14 ml of ethanol is added 3.6 ml of 1 mol/L sodium hydroxide solution. The mixture thus obtained is stirred at 50° C. for one hour. Water and chloroform are added to the reaction mixture, pH is adjusted to 2 with 6 mol/L hydrochloric acid, and the organic layer is separated. The organic layer is washed with water and saturated aqueous solution of sodium chloride and dried over anhydrous magnesium sulfate, and the solvent is distilled off under reduced pressure. Thus, 0.56 g of 3-[5-{[1-isopentyl-4-(3-methylbutanoyl)-1H-pyrrol-2-yl]carbonyl}-2-(isopentyloxy)phenyl]propanoic acid is obtained as a white solid product.

NMR (CDCl$_3$) δ: 0.97 (18H, d, J=6.1 Hz), 1.52-2.41 (7H, m), 2.58-2.73 (4H, m), 2.94-3.10 (2H, m), 4.09 (2H, t, J=5.6

Hz), 4.38 (2H, t, J=6.3 Hz), 6.04 (1H, brs), 6.91 (1H, d, J=8.8 Hz), 7.11 (1H, d, J=1.7 Hz), 7.47 (1H, d, J=1.7 Hz), 7.69-7.77 (2H, m)

EXAMPLE 89

To a solution of 0.17 g of 1,3-diisopentyl-2-oxo-2,3-dihydro-1H-benzimidazole-5-carboxylic acid in 9 ml of methylene chloride are added 60 μl of oxalyl chloride and 20 μl of N,N-dimethylformamide successively. The mixture thus obtained is stirred at ambient temperature for 2 hours. Then, 0.42 g of aluminum chloride and 0.38 g of isopentyl 2-(2-isopentyloxyphenyl)acetate are successively added at ambient temperature, and the mixture thus obtained is stirred at the same temperature as above for 30 minutes. The reaction mixture is added to a mixture of methylene chloride and ice water, and the organic layer is separated. The organic layer thus obtained is washed with water and saturated aqueous solution of sodium chloride successively and dried over anhydrous magnesium sulfate, and the solvent is distilled off under reduced pressure. The residue is purified by silica gel column chromatography (eluent; hexane:ethyl acetate=5:1) to obtain 0.29 g of isopentyl 2-[5-[(1,3-diisopentyl-2-oxo-2,3-dihydro-1H-benzimidazol-5-yl)carbonyl]-2-(isopentyloxy)phenyl]acetate as a light yellow oily product.

NMR (CDCl$_3$) δ: 0.87-1.01 (24H, m), 1.31-1.92 (12H, m), 3.65 (2H, s), 3.84-4.20 (8H, m), 6.89-7.05 (2H, m), 7.52-7.81 (4H, m)

EXAMPLE 90

In a mixture of 3 ml of ethanol and 3 ml of tetrahydrofuran is dissolved 0.28 g of isopentyl 2-[5-[(1,3-diisopentyl-2-oxo-2,3-dihydro-1H-benzimidazol-5-yl)carbonyl]-2-(isopentyloxy)phenyl]acetate. After adding 1.4 ml of 1 mol/L sodium hydroxide solution, the mixture is stirred at ambient temperature for 3 hours. Water and chloroform are added to the reaction mixture, pH is adjusted to 2 with 2 mol/L hydrochloric acid, and the organic layer is separated. The organic layer thus obtained is washed with water and saturated aqueous solution of sodium chloride successively and dried over anhydrous magnesium sulfate, and the solvent is distilled off under reduced pressure. Thus, 0.21 g of 2-[5-[(1,3-diisopentyl-2-oxo-2,3-dihydro-1H-benzimidazol-5-yl)carbonyl]-2-(isopentyloxy)phenyl]-acetic acid is obtained as a white foaming product.

NMR (CDCl$_3$) δ: 0.96 (18H, d, J=5.6 Hz), 1.38-2.02 (9H, m), 3.71 (2H, s), 3.85-4.16 (6H, m), 6.88-7.81 (7H, m)

EXAMPLE 91

At ambient temperature, 9.9 ml of iodomethane is dropwise added to a suspension of 50.0 g of 3-[5-(2,4-diisobutoxybenzoyl)-2-isobutoxyphenyl]propanoic acid and 22.0 g of potassium carbonate in 150 ml of N,N-dimethylformamide. The mixture thus obtained is stirred at the same temperature as above for 30 minutes. The reaction mixture is added to a mixture of ethyl acetate and water, pH is adjusted to 2 with 6 mol/L hydrochloric acid, and the organic layer is separated. The organic layer is washed with water and saturated aqueous solution of sodium chloride and dried over anhydrous magnesium sulfate, and then the solvent is distilled off under reduced pressure. The residue thus obtained is purified by silica gel column chromatography (eluent; hexane:ethyl acetate=5:1) to obtain 51.0 g of methyl 3-[5-(2,4-diisobutoxybenzoyl)-2-isobutoxyphenyl]propanoate as a light brown-colored solid product.

NMR (CDCl$_3$) δ: 0.70 (6H, d, J=6.6 Hz), 1.05 (12H, d, J=6.8 Hz), 1.58-2.40 (3H, m), 2.49-3.05 (4H, m), 3.59-3.82 (6H, m), 3.66 (3H, s), 6.47-6.59 (2H, m), 6.79 (1H, d, J=9.3 Hz), 7.35 (1H, d, J=8.1 Hz), 7.60-7.68 (2H, m)

EXAMPLE 92

It is also possible to synthesize the compound 33(6) of Example 33 by the following method.

In 9 ml of methylene chloride is dissolved 0.90 g of 3-(3-ethoxy-3-oxopropyl)-4-isopentyloxybenzoic acid. At ambient temperature, 0.31 ml of oxalyl chloride and 20 μl of N,N-dimethylformamide are successively added and the mixture thus obtained is stirred at ambient temperature for one hour. Then, at 5-10° C., 0.78 g of aluminum chloride and 0.78 g of 1,3-diisobutoxybenzene are successively added. The mixture thus obtained is stirred first at the same temperature as above for 30 minutes and then at ambient temperature for 30 minutes. Further, 0.39 g of aluminum chloride is added at ambient temperature and stirred at the same temperature as above for 30 minutes. The reaction mixture is added to a mixture of chloroform and ice water and the organic layer is separated. The organic layer thus obtained is washed with water and saturated aqueous solution of sodium chloride successively and dried over anhydrous magnesium sulfate, and then the solvent is distilled off under reduced pressure. The residue thus obtained is purified by silica gel column chromatography (eluent; hexane:ethyl acetate=10:1) to obtain 0.67 g of ethyl 3-[5-(2-hydroxy-4-isobutoxybenzoyl)-2-isopentyloxyphenyl]propanoate as a light yellow oily product.

EXAMPLE 93

In 10 ml of methylene chloride is dissolved 1.00 g of 3-(3-ethoxy-3-oxopropyl)-4-isobutoxybenzoic acid. After adding 0.36 ml of oxalyl chloride and 20 μl of N,N-dimethylformamide successively at ambient temperature, the mixture thus obtained is stirred at ambient temperature for one hour. Then, 0.95 g of aluminum chloride and 1.02 g of 1,3-diisopentyloxybenzene are successively added at 5-10° C., and stirred at the same temperature as above for 30 minutes and then at ambient temperature for 30 minutes. Then, 0.45 g of aluminum chloride is added at ambient temperature and stirred at the same temperature as above for 30 minutes. The reaction mixture is added to a mixture of methylene chloride and water, and the organic layer is separated. The organic layer thus obtained is washed with water and saturated aqueous solution of sodium chloride successively and dried over anhydrous magnesium sulfate, and the solvent is distilled off under reduced pressure. The residue thus obtained is purified by silica gel column chromatography (eluent; hexane:ethyl acetate=10:1) to obtain 0.63 g of ethyl 3-[5-(2-hydroxy-4-isopentyloxybenzoyl)-2-isobutoxyphenyl]propanoate as a light yellow oily product. A 0.60 g portion of the oily product obtained above is dissolved in 12 ml of ethanol, 1.3 ml of 5 mol/L sodium hydroxide solution is added, and the mixture thus obtained is stirred at ambient temperature for 2 hours. Chloroform and water are added to the reaction mixture, pH is adjusted to 2 with 6 mol/L hydrochloric acid, and the organic layer is separated. The organic layer thus obtained is washed with water and saturated aqueous solution of sodium chloride successively and dried over anhydrous magnesium sulfate, and then the solvent is distilled off under reduced pressure.

Thus, 0.48 g of [5-(2-hydroxy-4-isopentyloxybenzoyl)-2-isobutoxyphenyl]-propanoic acid is obtained as a light yellow solid product.

NMR (CDCl$_3$) δ: 0.96 (6H, d, J=6.1 Hz), 1.07 (6H, d, J=6.6 Hz), 1.59-2.32 (4H, m), 2.66-3.11 (4H, m), 3.82 (2H, d, J=6.1 Hz), 4.04 (2H, t, J=6.1 Hz), 6.33-6.62 (2H, m), 6.89 (1H, d, J=9.0 Hz), 7.48-7.57 (3H, m), 8.70 (1H, brs), 12.67 (1H, s)

REFERENTIAL EXAMPLE 1

In 100 ml of tetrahydrofuran is suspended 39.8 g of isopentyltriphenylphosphonium iodide. At −25° C. to −20° C., 52 ml of a 1.6 mol/L solution of n-butyllithium in n-hexane is dropwise added to the suspension. After stirring the mixture thus obtained at −25° C. to −15° C. for one hour, the temperature is elevated to ambient temperature over a period of one hour. A solution of 10.0 g of 1,4-dioxaspiro[4.5]-decan-8-one in 50 ml of tetrahydrofuran is added to the reaction mixture and stirred at ambient temperature for one hour. The reaction mixture is added to a mixture of ethyl acetate and water, and the organic layer is separated. The organic layer thus obtained is washed with water and saturated aqueous solution of sodium chloride successively and dried over anhydrous magnesium sulfate, and then the solvent is distilled off under reduced pressure. The residue thus obtained is purified by silica gel column chromatography (eluent; n-hexane:ethyl acetate=95:5) to obtain 10.5 g of 8-(3-methylbutylidene)-1,4-dioxaspiro[4.5]decane as a colorless oily product.

NMR (CDCl$_3$) δ: 0.87 (6H, d, J=6.3 Hz), 1.1-2.4 (11H, m), 3.96 (2H, s), 3.97 (2H, s), 5.16 (1H, t, J=7.4 Hz)

REFERENTIAL EXAMPLE 2

In 50 ml of tetrahydrofuran is dissolved 10.0 g of 8-(3-methylbutylidene)-1,4-dioxaspiro[4.5]decane. After adding 50 ml of 6 mol/L hydrochloric acid, the mixture thus obtained is stirred at ambient temperature for one hour. Chloroform and water are added to the reaction mixture and the organic layer is separated. The organic layer thus obtained is washed with water and saturated aqueous solution of sodium chloride successively and dried over anhydrous magnesium sulfate, and then the solvent is distilled off under reduced pressure. The residue thus obtained is purified by silica gel column chromatography (eluent; n-hexane:ethyl acetate=98:2) to obtain 6.6 g of 4-(3-methylbutylidene)-1-cyclohexanone as a colorless oily product.

NMR (CDCl$_3$) δ: 0.91 (6H, d, J=6.4 Hz), 1.2-2.8 (11H, m), 5.37 (1H, t, J=7.3 Hz)

REFERENTIAL EXAMPLE 3

In a mixture of 3.5 ml of ethanol and 1.5 ml of water are dissolved 1.0 g of 4-(3-methylbutylidene)-1-cyclohexanone, 1.1 g of D-cysteine hydrochloride monohydrate and 0.52 g of sodium acetate. The resulting solution is stirred at ambient temperature for 2 hours. Water is added to the reaction mixture and the deposited crystal is collected by filtration. Thus, 0.81 g of (3S)-8-(3-methylbutylidene)-1-thia-4-azaspiro[4.5]decane-3-carboxylic acid is obtained as a colorless crystalline product.

NMR (CDCl$_3$) δ: 0.87 (6H, d, J=6.1 Hz), 1.2-2.8 (11H, m), 3.1-3.6 (2H, m), 4.34 (1H, t, J=7.8 Hz), 5.19 (1H, t, J=7.1 Hz), 6.9-7.5 (2H, bs)

REFERENTIAL EXAMPLE 4

In 100 ml of N,N-dimethylformamide are dissolved 10.0 g of methyl salicylate, 18.1 g of potassium carbonate and 11.3 ml of isobutyl iodide. The solution is heated under reflux for 1.5 hours with stirring. The reaction mixture is added to a mixture of ethyl acetate and water, pH is adjusted to 2.0 with 6 mol/L hydrochloric acid, and the organic layer is separated. The organic layer thus obtained is washed with water and saturated aqueous solution of sodium chloride successively and dried over anhydrous magnesium sulfate, and then the solvent is distilled off under reduced pressure. The residue thus obtained is purified by silica gel column chromatography (eluent; n-hexane:ethyl acetate=95:5) to obtain 4.2 g of methyl 2-isobutoxybenzoate as a light yellow oily product.

NMR (CDCl$_3$) δ: 1.06 (6H, d, J=6.6 Hz), 1.8-2.4 (1H, m), 3.79 (2H, d, J=6.4 Hz), 3.98 (3H, s), 6.8-7.1 (2H, m), 7.3-7.6 (1H, m), 7.7-7.9 (1H, m)

REFERENTIAL EXAMPLE 5

In 20 ml of methanol is dissolved 4.1 g of methyl 2-isobutoxybenzoate. After adding 6 ml of 5 mol/L solution of sodium hydroxide, the mixture thus obtained is stirred at ambient temperature for 2 hours. Ethyl acetate and water are added to the reaction mixture, pH is adjusted to 2 with 2 mol/L hydrochloric acid, and the organic layer is separated. The organic layer thus obtained is washed with water and saturated aqueous solution of sodium chloride successively and dried over anhydrous magnesium sulfate, and then the solvent is distilled off under reduced pressure. Thus, 3.9 g of 2-isobutoxybenzoic acid is obtained as a colorless crystalline product.

REFERENTIAL EXAMPLE 6

In 40 ml of methylene chloride are dissolved 3.8 g of 2-isobutoxybenzoic acid and 2.8 ml of thionyl chloride. The solution is heated under reflux for one hour with stirring. The reaction mixture obtained herein is dropwise added at 5-10° C. to a solution of diazomethane in ethyl ether prepared from 53.0 g of N-methylnitrosourea, 83.0 g of potassium hydroxide, 120 ml of water and 150 ml of ethyl ether, and the mixture thus obtained is stirred at ambient temperature for 2 hours. Ethyl ether, acetic acid and water are added to the reaction mixture, and the organic layer is separated. The organic layer thus obtained is washed with water and saturated aqueous solution of sodium chloride successively and dried over anhydrous magnesium sulfate, and then the solvent is distilled off under reduced pressure. The residue thus obtained is dissolved in 30 ml of methanol, and the resulting solution is added to a mixture of 2.3 g of silver benzoate and 23 ml of triethylamine at 25-30° C., and stirred for 1.5 hours. Ethyl acetate and water are added to the reaction mixture, pH is adjusted to 2.0 with concentrated hydrochloric acid, and the organic layer is separated. The organic layer thus obtained is washed with water and saturated aqueous solution of sodium chloride successively and dried over anhydrous magnesium sulfate, and then the solvent is distilled off under reduced pressure. The residue is purified by silica gel column chromatography (eluent; n-hexane:ethyl acetate=9:1) to obtain 3.8 g of methyl 2-(2-isobutoxyphenyl)acetate as a colorless oily product.

NMR (CDCl$_3$) δ: 1.02 (6H, d, J=6.8 Hz), 1.8-2.4 (1H, m), 3.5-3.9 (7H, m), 6.7-7.1 (2H, m), 7.1-7.4 (2H, m)

REFERENTIAL EXAMPLE 7

In 10 ml of methylene chloride is dissolved 1.00 g of methyl 2-(2-isobutoxyphenyl)acetate. After successively adding 0.99 ml of titanium tetrachloride and 0.45 ml of α,α-dichloromethyl methyl ether at 5-10° C., the mixture thus obtained is stirred at ambient temperature for 30 minutes. The reaction mixture is added to a mixture of methylene chloride and water, and the organic layer is separated. The organic layer thus obtained is washed with water and saturated aqueous solution of sodium chloride successively and dried over anhydrous magnesium sulfate, and then the solvent is distilled off under reduced pressure. The residue is purified by silica gel column chromatography (eluent; n-hexane:ethyl acetate=95:5) to obtain 0.80 g of methyl 2-(5-formyl-2-isobutoxyphenyl)acetate as a colorless oily product.

NMR (CDCl$_3$) δ: 1.03 (6H, d, J=6.8 Hz), 1.8-2.4 (1H, m), 3.69 (5H, s), 3.83 (2H, d, J=6.4 Hz), 6.95 (1H, d, J=8.3 Hz), 7.6-7.9 (2H, m), 9.86 (1H, s)

REFERENTIAL EXAMPLE 8

In 8 ml of acetonitrile is dissolved 0.80 g of methyl 2-(5-formyl-2-isobutoxyphenyl)acetate. After successively adding 2.03 g of sodium dihydrogen-phosphate dissolved in 25 ml of water, 0.69 ml of 30% aqueous hydrogen peroxide and 0.73 g of sodium chlorite dissolved in 15 ml of water at a temperature of 5-10° C., the mixture thus obtained is stirred at 5-10° C. for 3.5 hours. Chloroform and water are added to the reaction mixture, pH is adjusted to 2.0 with 6 mol/L hydrochloric acid, and the organic layer is separated. The organic layer thus obtained is washed with water and saturated aqueous solution of sodium chloride successively and dried over anhydrous magnesium sulfate, and then the solvent is distilled off under reduced pressure. Thus, 0.62 g of 3-(methoxycarbonylmethyl)-4-isobutoxybenzoic acid is obtained as a colorless crystalline product.

NMR (CDCl$_3$) δ: 1.03 (6H, d, J=6.6 Hz), 1.8-2.4 (1H, m), 3.69 (5H, s), 3.81 (2H, d, J=6.4 Hz), 6.89 (1H, d, J=8.3 Hz), 7.8-8.2 (2H, m), 8.8-9.6 (1H, bs)

REFERENTIAL EXAMPLE 9

In a mixture of 10 ml of pyridine and 10 ml of water is dissolved 0.50 g of isobutyl 2-isobutoxy-5-methylbenzoate. After adding 0.45 g of potassium permanganate at 60-70° C., the mixture thus obtained is heated under reflux for 2 hours with stirring. The reaction mixture is filtered with Celite, ethyl acetate is added to the filtrate, pH is adjusted to 2.0 with 6 mol/L hydrochloric acid, and the organic layer is separated. The organic layer thus obtained is washed with water and saturated aqueous solution of sodium chloride successively and dried over anhydrous magnesium sulfate, and then the solvent is distilled off under reduced pressure. Thus, 0.35 g of 3-(isobutoxycarbonyl)-4-isobutoxybenzoic acid is obtained as a colorless crystalline product.

NMR (CDCl$_3$) δ: 1.02 (6H, d, J=6.4 Hz), 1.07 (6H, d, J=6.4 Hz), 1.9-2.4 (2H, m), 3.88 (2H, d, J=6.4 Hz), 4.12 (2H, d, J=6.8 Hz), 7.00 (1H, d, J=9.0 Hz), 8.19 (1H, dd, J=8.7, 2.2 Hz), 8.54 (1H, d, J=2.2 Hz), 7.0-9.0 (1H, bs)

REFERENTIAL EXAMPLE 10

In 700 ml of N,N-dimethylformamide are dissolved 70.0 g of salicylaldehyde and 158.5 g of potassium carbonate. After dropwise adding 67.9 ml of 3-chloro-2-methyl-1-propene at 70° C. over a period of 30 minutes, the mixture thus obtained is stirred at 70° C. for 30 minutes. The reaction mixture is added to a mixture of ethyl acetate and water, pH is adjusted to 3.0 with 6 mol/L hydrochloric acid, and the organic layer is separated. The organic layer thus obtained is successively washed with water and saturated aqueous solution of sodium chloride and dried over anhydrous magnesium sulfate, and then the solvent is distilled off under reduced pressure. The residue thus obtained is dissolved in 350 ml of ethanol, 7.0 g of 5% palladium-carbon is added, and the mixture is stirred at 35° C. for 4 hours in a stream of hydrogen. The reaction mixture is filtered with Celite, the solvent is distilled off from the filtrate under reduced pressure. The residue thus obtained is purified by silica gel column chromatography (eluent; n-hexane:toluene=2:1) to obtain 92.4 g of 2-isobutoxybenzaldehyde as a light yellow oily product.

NMR (CDCl$_3$) δ: 1.07 (6H, d, J=6.6 Hz), 2.0-2.2 (1H, m), 3.85 (2H, d, J=6.4 Hz), 6.9-7.1 (2H, m), 7.4-7.7 (1H, m), 7.83 (1H, dd, J=8.1, 2.0 Hz), 10.55 (1H, s)

EXAMPLE 11

In 30 ml of tetrahydrofuran is suspended 0.92 g of 60% sodium hydride. After dropping 5.0 ml of ethyl diethylphosphonoacetate thereinto at ambient temperature over a period of 5 minutes, the mixture thus obtained is stirred at 40° C. for 30 minutes. Then, a solution of 3.40 g of 2-isobutoxybenzaldehyde in 20 ml of tetrahydrofuran is dropwise added at ambient temperature over a period of 20 minutes, and the mixture thus obtained is stirred for one hour. The reaction mixture is added to a mixture of ethyl acetate and water, and the organic layer is separated. The organic layer thus obtained is washed with water and saturated aqueous solution of sodium chloride and dried over anhydrous magnesium sulfate, and then the solvent is distilled off under reduced pressure. The residue thus obtained is purified by silica gel column chromatography (eluent; n-hexane:ethyl acetate=9:1) to obtain 4.30 g of ethyl 3-(2-isobutoxyphenyl)-2-propenoate as a light yellow oily product.

NMR (CDCl$_3$) δ: 1.06 (6H, d, J=6.6 Hz), 1.32 (3H, t, J=7.1 Hz), 1.8-2.4 (1H, m), 3.78 (2H, d, J=6.4 Hz), 4.25 (2H, q, J=7.1 Hz), 6.53 (1H, d, J=16.4 Hz), 6.8-7.6 (4H, m), 8.10 (1H, d, J=16.1 Hz)

REFERENTIAL EXAMPLE 12

In 15 ml of ethanol is dissolved 1.50 g of ethyl 3-(2-isobutoxyphenyl)-2-propenoate, to which is added 0.30 g of 5% palladium-carbon. The mixture is stirred at ambient temperature for one hour in a stream of hydrogen. The reaction mixture is filtered with Celite, and the solvent is distilled off from the filtrate under reduced pressure. The residue thus obtained is purified by silica gel column chromatography to obtain 0.76 g of ethyl 3-(2-isobutoxyphenyl)propionate as a colorless oily product.

NMR (CDCl$_3$) δ: 1.04 (6H, d, J=6.6 Hz), 1.22 (3H, t, J=7.1 Hz), 1.9-2.3 (1H, m), 2.5-2.7 (2H, m), 2.9-3.1 (2H, m), 3.73 (2H, d, J=6.4 Hz), 4.12 (2H, q, J=6.8 Hz), 6.7-7.3 (4H, m)

REFERENTIAL EXAMPLE 13

The procedure of referential Example 7 is repeated to obtain ethyl 3-(5-formyl-2-isobutoxyphenyl)propionate.

NMR (CDCl$_3$) δ: 1.07 (6H, d, J=6.6 Hz), 1.23 (3H, t, J=7.1 Hz), 2.0-2.4 (1H, m), 2.5-2.8 (2H, m), 2.9-3.1 (2H, m), 3.84 (2H, d, J=6.4 Hz), 4.13 (2H, q, J=7.1 Hz), 6.93 (1H, d, J=9.0 Hz), 7.7-7.9 (2H, m), 9.85 (1H, s)

REFERENTIAL EXAMPLE 14

The procedure of Referential Example 7 is repeated to obtain ethyl 3-(5-formyl-2-isobutoxyphenyl)-2-propenoate.

NMR (CDCl$_3$) δ: 1.09 (6H, d, J=6.6 Hz), 1.34 (3H, t, J=7.1 Hz), 2.0-2.5 (1H, m), 3.90 (2H, d, J=6.3 Hz), 4.28 (2H, q, J=7.1 Hz), 6.61 (1H, d, J=16.1 Hz), 7.02 (1H, d, J=8.6 Hz), 7.8-8.3 (3H, m), 9.90 (1H, s)

REFERENTIAL EXAMPLE 15

The procedure of Referential Example 8 is repeated to obtain 3-(2-ethoxycarbonylethyl)-4-isobutoxybenzoic acid.

NMR (CDCl$_3$) δ: 1.07 (6H, d, J=6.6 Hz), 1.25 (3H, t, J=7.3 Hz), 2.0-2.4 (1H, m), 2.5-2.8 (2H, m), 2.9-3.1 (2H, m), 3.82 (2H, d, J=6.1 Hz), 4.14 (2H, q, J=7.1 Hz), 6.85 (1H, d, J=8.0 Hz), 7.9-8.1 (2H, m), 9.0-9.8 (1H, bs)

EXAMPLE 16

The procedure of Referential Example 8 is repeated to obtain 3-(2-ethoxycarbonylethenyl)-4-isobutoxybenzoic acid.

NMR (CDCl$_3$) δ: 1.09 (6H, d, J=6.8 Hz), 1.35 (3H, t, J=6.8 Hz), 1.9-2.4 (1H, m), 3.89 (2H, d, J=6.4 Hz), 4.28 (2H, q, J=6.8 Hz), 6.62 (1H, d, J=16.1 Hz), 6.95 (1H, d, 9.0 Hz), 7.9-8.3 (3H, m), 8.6-9.8 (1H, bs)

REFERENTIAL EXAMPLE 17

In 59 ml of methylene chloride are dissolved 11.8 g of 1-benzyl 2-ethyl (2S,4R)-4-hydroxy-1,2-pyrrolidinedicarboxylate, 11 ml of 3,4-dihydropyrane and 2.0 g of pyridinium p-toluenesulfonate. The solution is heated under reflux for one hour. The reaction mixture is added to 50 ml of saturated aqueous solution of sodium bicarbonate, and the organic layer is separated. The organic layer is washed with water and saturated aqueous solution of sodium chloride successively and dried over anhydrous magnesium sulfate, and then the solvent is distilled off under reduced pressure. The residue thus obtained is purified by silica gel column chromatography (eluent; n-hexane:ethyl acetate=2:1) to obtain 12.9 g of 1-benzyl 2-ethyl (2S,4R)-4-(tetrahydro-2H-pyran-2-yloxy)-1,2-pyrrolidinedicarboxylate as a colorless oily product.

NMR (CDCl$_3$) δ: 1.0-2.6 (11H, m), 3.3-4.7 (9H, m), 4.9-5.3 (2H, m), 7.1-7.5 (5H, m)

REFERENTIAL EXAMPLE 18

In 127 ml of ethanol is dissolved 12.7 g of 1-benzyl 2-ethyl (2S,4R)-4-(tetrahydro-2H-pyran-2-yloxy)-1,2-pyrrolidinedicarboxylate. After adding 37.0 ml of 1 mol/L sodium hydroxide solution at 5-10° C., the mixture thus obtained is stirred at ambient temperature for 1.5 hours. The solvent is distilled off from the reaction mixture under reduce pressure, the residue thus obtained is dissolved in 90 ml of N,N-dimethylformamide, 10.9 ml of diphenylphosphoryl azide, 14.1 ml of triethylamine and 3.94 g of N,O-dimethylhydroxylamine hydrochloride are successively added at 5-10° C., and the mixture thus obtained is stirred at ambient temperature for one hour. Ethyl acetate and water are added to the reaction mixture, pH is adjusted to 6.5 with 6 mol/L hydrochloric acid, and the organic layer is separated. The organic layer is washed with water and saturated aqueous solution of sodium chloride successively and dried over anhydrous sodium sulfate, and then the solvent is distilled off under reduced pressure. The residue thus obtained is purified by silica gel column chromatography (eluent; n-hexane:ethyl acetate=4:1) to obtain 3.75 g of benzyl (2S,4R)-2-{[methoxy(methyl)amino]carbonyl}-4-(tetrahydro-2H-pyran-2-yloxy)-1-pyrrolidinecarboxylate as a light yellow oily product.

NMR (CDCl$_3$) δ: 1.2-2.6 (8H, m), 3.0-4.0 (10H, m), 4.3-5.3 (5H, m), 7.2-7.5 (5H, m)

REFERENTIAL EXAMPLE 19

In 33 ml of tetrahydrofuran is dissolved 3.3 g of benzyl (2S,4R)-2-{[methoxy(methyl)amino]carbonyl}-4-(tetrahydro-2H-pyran-2-yloxy)-1-pyrrolidine-carboxylate. After adding 0.64 g of lithium aluminum hydride at −70° C., the mixture thus obtained is stirred at −70° C. for one hour. After dropwise adding 33 ml of ethyl acetate to the reaction mixture over a period of 30 minutes and then 66 ml of tetrahydrofuran containing 20% of water over a period of 30 minutes, the mixture thus obtained is stirred at ambient temperature for 30 minutes. The mixture is filtered with Celite, and the organic layer is separated from the filtrate. The organic layer is washed with water and saturated aqueous solution of sodium chloride successively and dried over anhydrous magnesium sulfate, and then the solvent is distilled off under reduced pressure. The residue thus obtained is purified by silica gel column chromatography (eluent; n-hexane:ethyl acetate=1:1) to obtain 1.25 g of benzyl (2S,4R)-2-formyl-4-(tetrahydro-2H-pyran-2-yloxy)-1-pyrrolidinecarboxylate as a light yellow oily product.

NMR (CDCl$_3$) δ: 1.2-2.5 (8H, m), 3.3-4.0 (4H, m), 4.1-4.8 (3H, m), 5.17 (2H, bs), 7.1-7.5 (5H, m), 9.4-9.7 (1H, m)

REFERENTIAL EXAMPLE 20

In 11 ml of tetrahydrofuran is suspended 3.34 g of isopentyltriphenylphosphonium iodide, to which is dropwise added 4.3 ml of a 1.53 mol/L solution of n-butyllithium in n-hexane at −25° C. to −20° C. After stirring the mixture at −25° C. to −15° C. for one hour, the temperature is elevated to ambient temperature in one hour. To the reaction mixture is dropwise added 1.10 g of benzyl (2S,4R)-2-formyl-4-(tetrahydro-2H-pyran-2-yloxy)-1-pyrrolidinecarboxylate dissolved in 11 ml of tetrahydrofuran over a period of 20 minutes. The mixture thus obtained is stirred at ambient temperature for 5 hours. The reaction mixture is added to a mixture of ethyl acetate and water, and the organic layer is separated. The organic layer thus obtained is washed with water and saturated aqueous solution of sodium chloride successively and dried over anhydrous magnesium sulfate, and then the solvent is distilled off under reduced pressure. The residue thus obtained is purified by silica gel column chromatography (eluent; n-hexane:ethyl acetate=4:1) to obtain 0.62 g of benzyl (2S,4R)-2-(4-methyl-1-pentenyl)-4-(tetrahydro-2H-pyran-2-yloxy)-1-pyrrolidinecarboxylate as a light yellow oily product.

NMR (CDCl$_3$) δ: 0.85 (6H, d, J=6.1 Hz), 1.3-2.5 (11H, m), 3.3-4.0 (4H, m), 4.2-4.9 (3H, m), 5.10 (2H, bs), 5.2-5.6 (2H, m), 7.32 (5H, bs)

REFERENTIAL EXAMPLE 21

In 12 ml of tetrahydrofuran is dissolved 0.60 g of benzyl (2S,4R)-2-(4-methyl-1-pentenyl)-4-(tetrahydro-2H-pyran-2-yloxy)-1-pyrrolidinecarboxylate, to which is added 12 ml of 6 mol/L hydrochloric acid. The mixture thus obtained is stirred at ambient temperature for 2 hours. A mixture of chloroform and water is added to the reaction mixture, and the organic layer is separated. The organic layer thus obtained is washed with water and saturated aqueous solution of sodium chloride successively and dried over anhydrous magnesium sulfate, and then the solvent is distilled off under reduced pressure. The residue thus obtained is purified by silica gel column chromatography (eluent; n-hexane: ethyl acetate=2:1) to obtain 0.43 g of benzyl (2S,4R)-4-hydroxy-2-(4-methyl-1-pentenyl)-1-pyrrolidinecarboxylate as a light yellow oily product.

NMR (CDCl$_3$) δ: 0.85 (6H, d, J=5.9 Hz), 1.2-2.4 (5H, m), 3.4-3.9 (2H, m), 4.3-4.6 (1H, m), 4.6-5.0 (2H, m), 5.10 (2H, bs), 5.2-5.7 (2H, m), 7.2-7.5 (5H, m)

REFERENTIAL EXAMPLE 22

After adding 0.04 g of tetrabutylammonium bromide to 8 ml of 50% aqueous solution of sodium hydroxide, the mixture is heated to 120° C. Thereto is dropwise added a solution of 0.40 g of benzyl (2S,4R)-4-hydroxy-2-(4-methyl-1-pentenyl)-1-pyrrolidinecarboxylate and 0.65 ml of 3-chloro-2-methyl-1-propene in 0.8 ml of toluene over a period of 5 minutes. The mixture thus obtained is heated under reflux for 30 minutes with stirring. The reaction mixture is cooled to ambient temperature, toluene and water are added, and the organic layer is separated. The organic layer thus obtained is washed with water and saturated aqueous solution of sodium chloride successively and dried over anhydrous magnesium sulfate, and then the solvent is distilled off under reduced pressure. The residue thus obtained is purified by silica gel column chromatography (eluent; n-hexane:ethyl acetate=10:1) to obtain 0.31 g of benzyl (2S,4R)-2-(4-methyl-1-pentenyl)-4-[(2-methyl-2-propenyl)oxy]-1-pyrrolidinecarboxylate as a colorless oily product.

NMR (CDCl$_3$) δ: 0.84 (6H, d, J=5.9 Hz), 1.2-2.5 (8H, m), 3.3-4.1 (5H, m), 4.6-5.6 (7H, m), 7.32 (5H, bs)

REFERENTIAL EXAMPLE 23

In 5.8 ml of ethanol is dissolved 0.29 g of benzyl (2S,4R)-2-(4-methyl-1-pentenyl)-4-[(2-methyl-2-propenyl)oxy]-1-pyrrolidinecarboxylate. After adding 0.06 g of 5% palladium-carbon, the mixture is stirred at ambient temperature for 1.5 hours in a stream of hydrogen. The reaction mixture is filtered with Celite, and the solvent is distilled off from the filtrate under reduced pressure. Thus, 0.18 g of (2R,4R)-4-isobutoxy-2-(4-methylpentyl)-pyrrolidine is obtained as a yellow oily product.

NMR (CDCl$_3$) δ: 0.86 (6H, d, J=6.1 Hz), 0.89 (6H, d, J=6.6 Hz), 1.0-2.2 (11H, m), 2.7-3.4 (5H, m), 3.8-4.1 (1H, m)

EXAMPLE 24

The procedure of Referential Example 4 is repeated to obtain the compounds shown in Table 88.

TABLE 88

| No. | R$^a$ | R$^b$ | R$^c$ | R$^d$ | R$^e$ |
|-----|-------|-------|-------|-------|-------|
| 24(1) | nPr | CHO | H | H | H |
| 24(2) | iAm | CHO | H | H | H |

TABLE 88-continued

| No. | R$^a$ | R$^b$ | R$^c$ | R$^d$ | R$^e$ |
|-----|-------|-------|-------|-------|-------|
| 24(3) | iBu | COOMe | H | H | OCH$_2$Ph |
| 24(4) | iBu | COO-iBu | H | Me | H |
| 24(5) | iBu | Me | H | H | COO-iBu |
| 24(6) | CH$_2$Ph | H | OH | COOMe | H |
| 24(7) | (4-NO$_2$)PhCH$_2$ | (CH$_2$)$_2$COOEt | H | H | H |
| 24(8) | iBu | (CH$_2$)$_2$COO-iBu | H | H | H |
| 24(9) | iAm | CH$_2$COO-iAm | H | H | H |

24 (1)
NMR (CDCl$_3$) δ: 1.07 (3H, t, J=7.3 Hz), 1.65-2.07 (2H, m), 4.04 (2H, t, J=6.3 Hz), 7.00 (2H, t, J=7.3 Hz), 7.43-7.63 (1H, m), 7.83 (1H, dd, J=8.1, 2.2 Hz), 10.53 (1H, d, J=0.7 Hz)

24(2)
NMR (CDCl$_3$) δ: 0.98 (6H, d, J=5.9 Hz), 1.64-2.03 (3H, m), 4.11 (2H, t, J=6.4 Hz), 6.92-7.08 (2H, m), 7.43-7.63 (1H, m), 7.83 (1H, dd, J=7.7, 2.0 Hz), 10.52 (1H, s)

24(3)
NMR (CDCl$_3$) δ: 1.06 (6H, d, J=6.6 Hz), 2.07-2.36 (1H, m), 3.75 (2H, d, J=6.4 Hz), 3.85 (3H, s), 5.09 (2H, s), 6.48-6.61 (2H, m), 7.31-7.47 (5H, m), 7.84 (1H, d, J=9.3 Hz)

24(4)
NMR (CDCl$_3$) δ: 1.00 (6H, d, J=6.8 Hz), 1.03 (6H, d, J=6.6 Hz), 2.00-2.19 (2H, m), 2.28 (3H, s), 3.75 (2H, d, J=6.4 Hz), 4.08 (2H, d, J=6.6 Hz), 6.82 (1H, d, J=8.5 Hz), 7.20 (1H, dd, J=8.5, 2.4 Hz), 7.57 (1H, d, J=2.4 Hz)

24(5)
NMR (CDCl$_3$) δ: 1.02 (6H, d, J=6.6 Hz), 1.06 (6H, d, J=6.6 Hz), 1.88-2.41 (2H, m), 2.28 (3H, s), 3.79 (2H, d, J=6.4 Hz), 4.09 (2H, d, J=6.6 Hz), 7.17 (1H, d, J=8.1 Hz), 7.47-7.59 (2H, m)

24(6)
NMR (CDCl$_3$) δ: 3.91 (3H, s), 5.07 (2H, s), 6.44-6.58 (2H, m), 7.25-7.40 (5H, s), 7.74 (1H, d, J=9.5 Hz), 10.96 (1H, s)

24(7)
NMR (CDCl$_3$) δ: 1.23 (3H, t, J=7.1 Hz), 2.53-2.71 (2H, m), 2.94-3.12 (2H, m), 4.12 (2H, q, J=7.1 Hz), 5.20 (2H, s), 6.79-7.09 (2H, m), 7.11-7.25 (2H, m), 7.61 (2H, d, J=8.6 Hz), 8.26 (2H, d, J=8.6 Hz)

24(8)
NMR (CDCl$_3$) δ: 0.90 (6H, d, J=6.6 Hz), 1.05 (6H, d, J=6.6 Hz), 1.67-2.26 (2H, m), 2.51-3.04 (4H, m), 3.73 (2H, d, J=6.4 Hz), 3.85 (2H, d, J=6.6 Hz), 6.74-6.91 (2H, m), 7.09-7.25 (2H, m)

24(9)
NMR (CDCl$_3$) δ: 0.89 (6H, d, J=5.6 Hz), 0.95 (6H, d, J=5.6 Hz), 1.40-1.94 (6H, m), 3.60 (2H, s), 3.98 (2H, t, J=6.1 Hz), 4.11 (2H, t, J=5.9 Hz), 6.80-6.95 (2H, m), 7.14-7.35 (2H, m)

REFERENTIAL EXAMPLE 25

Isobutyl 2-fluoro-4-isobutoxybenzoate is treated in the same manner as in Referential Example 5 to obtain 2-fluoro-4-isobutoxybenzoic acid.

NMR (CDCl$_3$) δ: 1.03 (6H, d, J=6.6 Hz), 1.90-2.41 (1H, m), 3.77 (2H, d, J=6.6 Hz), 6.56-6.80 (2H, m), 7.97 (1H, dd, J=9.0, 8.6 Hz), 9.10 (1H, brs)

REFERENTIAL EXAMPLE 26

The procedure of Referential Example 6 is repeated to obtain methyl 2-(2-propoxyphenyl)acetate.

NMR (CDCl$_3$) δ: 1.02 (3H, t, J=7.2 Hz), 1.58-1.96 (2H, m), 3.63 (2H, s), 3.68 (3H, s), 3.92 (2H, t, J=6.4 Hz), 6.88 (2H, t, J=6.4 Hz), 7.14-7.33 (2H, m)

REFERENTIAL EXAMPLE 27

The procedure of Referential Example 6 is repeated to obtain methyl 2-(2-isopentyloxyphenyl)-acetate.

NMR (CDCl$_3$) δ: 0.95 (6H, d, J=7.1 Hz), 1.56-1.90 (3H, m), 3.63 (2H, s), 3.68 (3H, s), 3.99 (2H, t, J=6.3 Hz), 6.84 (2H, t, J=7.3 Hz), 7.15-7.32 (2H, m)

REFERENTIAL EXAMPLE 28

The procedure of Referential Example 7 is repeated to obtain the compounds shown in Table 89.

TABLE 89

| No. | R$^1$ | W' |
|---|---|---|
| 28(1) | O-nPr | CH$_2$COOMe |
| 28(2) | O-iAm | CH$_2$COOMe |
| 28(3) | O-iAm | (CH$_2$)$_2$COOEt |
| 28(4) | (4-NO$_2$)PhCH$_2$—O— | (CH$_2$)$_2$COOEt |
| 28(5) | O-iBu | (CH$_2$)$_3$COOEt |
| 28(6) | O-iBu | CH$_2$CH=CHCOOEt |
| 28(7) | O-iAm | CH$_2$CH=CHCOOEt |

28(1)
NMR (CDCl$_3$) δ: 1.04 (3H, t, J=7.3 Hz), 1.63-1.94 (2H, m) 3.68 (2H, s), 3.70 (3H, s), 4.03 (2H, t, J=6.3 Hz), 6.96 (1H, d, J=8.1 Hz), 7.74-7.86 (2H, m), 9.87 (1H, s)

28(2)
NMR (CDCl$_3$) δ: 0.97 (6H, d, J=6.1 Hz), 1.65-1.84 (3H, m), 3.67 (2H, s), 3.69 (3H, s), 4.10 (2H, t, J=6.2 Hz), 6.98 (1H, d, J=8.0 Hz), 7.74-7.86 (2H, m), 9.87 (1H, s)

28(3)
NMR (CDCl$_3$) δ: 0.99 (6H, d, J=6.1 Hz), 1.23 (3H, t, J=7.1 Hz), 1.59-2.04 (3H, m), 2.51-2.70 (2H, m), 2.89-3.06 (2H, m), 4.01-4.25 (4H, m), 6.94 (1H, d, J=9.3 Hz), 7.69-7.80 (2H, m), 9.85 (1H, s)

28(4)
NMR (CDCl$_3$) δ: 1.23 (3H, t, J=7, 1 Hz), 2.58-2.76 (2H, m), 3.00-3.18 (2H, m), 4.12 (2H, q, J=7.1 Hz), 5.32 (2H, s), 6.99 (1H, d, J=9.0 Hz), 7.59-7.78 (4H, m), 8.27 (2H, d, J=8.8 Hz), 9.88 (1H, s)

28(5)
NMR (CDCl$_3$) δ: 1.07 (6H, d, J=6.8 Hz), 1.25 (3H, t, J=7.1 Hz), 1.85-2.16 (3H, m), 2.35 (2H, t, J=6.8 Hz), 2.73 (2H, t, J=6.8 Hz), 3.83 (2H, d, J=6.4 Hz), 4.12 (2H, q, J=7.1 Hz), 6.92 (1H, d, J=9.0 Hz), 7.67-7.77 (2H, m), 9.86 (1H, s)

28(6)
NMR (CDCl$_3$) δ: 1.05 (6H, d, J=6.3 Hz), 1.27 (3H, t, J=7.1 Hz), 2.07-2.28 (1H, m), 3.58 (2H, d, J=6.6 Hz), 3.84 (2H, d, J=6.4 Hz), 4.19 (2H, q, J=7.1 Hz), 5.80 (1H, d, J=15.6 Hz), 6.91-7.19 (2H, m), 7.68-7.82 (2H, m), 9.86 (1H, s)

28(7)
NMR (CDCl$_3$) δ: 0.97 (6H, d, J=5.9 Hz), 1.27 (3H, t, J=7.2 Hz), 1.65-1.96 (3H, m), 3.55 (2H, d, J=6.8 Hz), 4.03-4.29 (4H, m), 5.79 (1H, dt, J=15.6, 1.5 Hz), 6.92-7.30 (2H, m), 7.67-7.80 (2H, m), 9.86 (1H, d, J=1.0 Hz)

REFERENTIAL EXAMPLE 29

The procedure of Referential Example 8 is repeated to obtain the compounds shown in Table 90.

TABLE 90

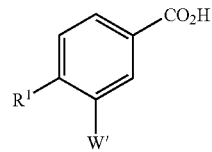

| No. | R$^1$ | W' |
|---|---|---|
| 29(1) | O-nPr | CH$_2$COOMe |
| 29(2) | O-iAm | CH$_2$COOMe |
| 29(3) | O-iAm | (CH$_2$)$_2$COOEt |
| 29(4) | (4-NO$_2$)PhCH$_2$—O— | (CH$_2$)$_2$COOEt |
| 29(5) | O-iBu | (CH$_2$)$_3$COOEt |
| 29(6) | O-iBu | CH$_2$CH=CHCOOEt |
| 29(7) | O-iAm | CH$_2$CH=CHCOOEt |

29 (1)
NMR (CDCl$_3$) δ: 1.04 (3H, t, J=7.4 Hz), 1.65-2.03 (2H, m), 3.67 (2H, s), 3.70 (3H, s), 4.01 (2H, t, J=6.4 Hz), 7.00 (1H, d, J=8.4 Hz), 7.93-8.10 (2H, m), 8.60 (1H, brs)

29(2)
NMR (CDCl$_3$) δ: 0.96 (6H, d, J=5.9 Hz), 1.56-1.99 (3H, m), 3.66 (2H, s), 3.69 (3H, s), 4.17 (2H, t, J=6.3 Hz), 6.90 (1H, d, J=8.4 Hz), 7.93-8.11 (2H, m), 11.63 (1H, brs)

29(3)
NMR (CDCl$_3$) δ: 0.98 (6H, d, J=6.0 Hz), 1.25 (3H, t, J=7.1 Hz), 1.60-2.05 (3H, m), 2.51-2.69 (2H, m), 2.89-3.05 (2H, m), 4.01-4.26 (4H, m), 5.70 (1H, brs), 6.88 (1H, d, J=8.3 Hz), 7.92-8.03 (2H, m)

29(4)
NMR (CDCl$_3$) δ: 1.22 (3H, t, J=7.1 Hz), 2.56-2.71 (2H, m), 2.96-3.04 (2H, m), 4.10 (2H, q, J=7.1 Hz), 5.32 (2H, s), 6.94 (1H, d, J=9.0 Hz), 7.64-7.92 (5H, m), 8.27 (2H, d, J=8.1 Hz)

29(5)
NMR (CDCl$_3$) δ: 1.06 (6H, d, J=6.6 Hz), 1.25 (3H, t, J=7.1 Hz), 1.95-2.10 (3H, m), 2.34 (2H, t, J=6.6 Hz), 2.72 (2H, t, J=7.1 Hz), 3.80 (2H, d, J=6.4 Hz), 4.12 (2H, q, J=7.1 Hz), 6.85 (1H, d, J=8.3 Hz), 7.90-8.00 (2H, m), 12.00 (1H, brs)

29(6)

NMR (CDCl₃) δ: 1.05 (6H, d, J=6.6 Hz), 1.27 (3H, t, J=7.1 Hz), 2.00-2.25 (1H, m), 3.56 (2H, d, J=6.6 Hz), 3.82 (2H, d, J=6.3 Hz), 4.17 (2H, q, J=7.1 Hz), 5.79 (1H, d, J=15.6 Hz), 6.83-7.20 (2H, m), 7.87-8.07 (2H, m), 11.30 (1H, brs)

29(7)

NMR (CDCl₃) δ: 0.97 (6H, d, J=5.9 Hz), 1.27 (3H, t, J=7.1 Hz), 1.63-2.00 (3H, m), 3.53 (2H, d, J=6.6 Hz), 3.88-4.30 (4H, m), 5.79 (1H, d, J=15.6 Hz), 6.85-7.18 (2H, m), 7.86-8.07 (2H, m), 9.45 (1H, brs)

REFERENTIAL EXAMPLE 30

The procedure of Referential Example 9 is repeated to obtain 2-isobutoxy-4-(isobutoxycarbonyl)-benzoic acid.

NMR (CDCl₃) δ: 1.04 (6H, d, J=7.3 Hz), 1.12 (6H, d, J=6.8 Hz), 1.89-2.49 (2H, m), 4.10 (2H, d, J=6.4 Hz), 4.15 (2H, d, J=6.3 Hz), 7.71-7.81 (3H, m), 8.26 (1H, d, J=7.6 Hz)

REFERENTIAL EXAMPLE 31

In 200 ml of tetrahydrofuran are suspended 144 g of (methoxymethyl)triphenylphosphonium chloride and 43 g of diisopropylamine, to which is dropwise added 253 ml of a 1.6 mol/L solution of n-butyllithium in hexane at −50° C. over a period of one hour. The mixture thus obtained is stirred at ambient temperature for one hour. Then, a solution of 25 g of 2-isobutoxy-benzaldehyde in 100 ml of tetrahydrofuran is dropwise added to the reaction mixture obtained above at −50° C. over a period of one hour, and the mixture thus obtained is stirred at ambient temperature for one hour. The reaction mixture is added to a mixture of ethyl acetate and water, and the organic layer is separated. The organic layer is washed with water and saturated aqueous solution of sodium chloride successively and dried over anhydrous magnesium sulfate, and then the solvent is distilled off under reduced pressure. The residue obtained above is mixed with 260 ml of 5% aqueous solution of sulfuric acid and 100 ml of dioxane, heated under reflux for 2 hours, cooled to ambient temperature and diluted with 500 ml of water. Ethyl acetate is added to the reaction mixture and the organic layer is separated. The organic layer is washed with water and saturated aqueous solution of sodium chloride successively and dried over anhydrous magnesium sulfate, and then the solvent is distilled off under reduced pressure. The residue thus obtained is purified by silica gel column chromatography (eluent; hexane:ethyl acetate=95:5) to obtain 17.5 g of 2-(2-isobutoxyphenyl)ethanal as a colorless oily product.

NMR (CDCl₃) δ: 1.02 (6H, d, J=6.8 Hz), 1.88-2.32 (1H, m), 3.65 (2H, d, J=2.0 Hz), 3.74 (2H, d, J=6.3 Hz), 6.83-6.99 (2H, m), 7.12-7.28 (2H, m), 9.70 (1H, t, J=2.0 Hz)

REFERENTIAL EXAMPLE 32

The procedure of Referential Example 31 is repeated to obtain 2-(2-isopentyloxyphenyl)ethanal.

NMR (CDCl₃) δ: 0.95 (6H, d, J=6.9 Hz), 1.56-1.95 (3H, m), 3.63 (2H, d, J=2.2 Hz), 4.02 (2H, t, J=6.6 Hz), 6.83-7.01 (2H, m), 7.10-7.34 (2H, m), 9.68 (1H, t, J=2.2 Hz)

REFERENTIAL EXAMPLE 33

The procedure of Referential Example 11 is repeated to obtain ethyl 3-(2-isopentyloxyphenyl)-2-propenoate.

NMR (CDCl₃) δ: 0.98 (6H, d, J=6.1 Hz), 1.33 (3H, t, J=6.9 Hz), 1.70-1.98 (3H, m), 3.99-4.37 (4H, m), 6.52 (1H, d, J=16.4 Hz), 6.93 (2H, t, J=6.4 Hz), 7.23-7.54 (2H, m), 8.00 (1H, t, J=8.5 Hz)

REFERENTIAL EXAMPLE 34

The procedure of Referential Example 11 is repeated to obtain ethyl 4-(2-isobutoxyphenyl)-2-butenoate.

NMR (CDCl₃) δ: 1.03 (6H, d, J=6.8 Hz), 1.26 (3H, t, J=7.1 Hz), 1.89-2.32 (1H, m), 3.53 (2H, dd, J=5.9, 1.0 Hz), 3.73 (2H, d, J=6.1 Hz), 4.16 (2H, q, J=7.1 Hz), 5.78 (1H, dt, J=15.4, 1.3 Hz), 6.79-6.94 (2H, m), 7.09 (1H, dd, J=6.4, 2.0 Hz), 7.21-7.29 (2H, m)

REFERENTIAL EXAMPLE 35

The procedure of Referential Example 11 is repeated to obtain ethyl 4-(2-isopentyloxyphenyl)-2-butenoate.

NMR (CDCl₃) δ: 0.95 (6H, d, J=6.9 Hz), 1.26 (3H, t, J=7.1 Hz), 1.60-1.90 (3H, m), 3.05 (2H, dd, J=6.6, 1.2 Hz), 3.98 (2H, t, J=5.6 Hz), 4.17 (2H, q, J=7.1 Hz), 5.78 (1H, dt, J=15.6, 1.5 Hz), 6.78-6.94 (2H, m), 7.02-7.34 (3H, m)

REFERENTIAL EXAMPLE 36

The procedure of Referential Example 12 is repeated to obtain ethyl 3-(2-isopentyloxyphenyl)-propanoate.

NMR (CDCl₃) δ: 0.97 (6H, d, J=5.9 Hz), 1.23 (3H, t, J=7.1 Hz), 1.60-2.03 (3H, m), 2.49-2.68 (2H, m), 2.85-3.05 (2H, m), 3.92-4.24 (4H, m), 6.76-6.91 (2H, m), 7.09-7.24 (2H, m)

REFERENTIAL EXAMPLE 37

The procedure of Referential Example 12 is repeated to obtain ethyl 4-(2-isobutoxyphenyl)-butanoate.

NMR (CDCl₃) δ: 1.05 (6H, d, J=6.6 Hz), 1.24 (3H, t, J=7.1 Hz), 1.83-2.18 (3H, m), 2.33 (2H, t, J=6.6 Hz), 2.68 (2H, t, J=7.1 Hz), 3.72 (2H, d, J=6.1 Hz), 4.11 (2H, q, J=7.1 Hz), 6.84 (2H, t, J=5.9 Hz), 7.08-7.23 (2H, m)

REFERENTIAL EXAMPLE 38

In 170 ml of ethanol is dissolved 16.7 g of 3-(3-ethoxy-3-oxopropyl)-4-[4-nitrobenzyloxy]benzoic acid, to which is added 1.7 g of 5% palladium-carbon. The mixture thus obtained is stirred at ambient temperature for 5 hours in a stream of hydrogen. The reaction mixture is filtered with Celite and the solvent is distilled off from the filtrate to obtain 7.5 g of 3-(3-ethoxy-3-oxopropyl)-4-hydroxybenzoic acid as a light brown solid product.

NMR (CDCl₃) δ: 1.16 (3H, t, J=7.1 Hz), 2.52-2.84 (4H, m), 4.05 (2H, q, J=7.1 Hz), 6.94 (1H, d, J=9.1 Hz), 7.65-7.73 (4H, m)

REFERENTIAL EXAMPLE 39

In 75 ml of N,N-dimethylformamide are suspended 7.5 g of 3-(3-ethoxy-3-oxopropyl)-4-hydroxybenzoic acid, 17.5 g of potassium carbonate and 7.4 ml of acetic anhydride. The mixture thus obtained is stirred at ambient temperature for 2 hours. The reaction mixture is added to a mixture of ethyl acetate and water, pH is adjusted to 2 with 6 mol/L hydrochloric acid, and the organic layer is separated. The organic layer is washed with water and saturated aqueous solution of sodium chloride successively and dried over anhydrous magnesium sulfate, and then the solvent is distilled off under reduced pressure. The residue is purified by silica gel column chromatography (eluent; hexane:ethyl acetate=5:1) to obtain 1.8 g of 4-(acetyloxy)-3-(3-ethoxy-3-oxopropyl) benzoic acid as a light brown-colored solid product.

NMR (CDCl$_3$) δ: 1.25 (3H, t, J=7.1 Hz), 2.37 (3H, s), 2.51-2.70 (2H, m), 2.86-3.01 (2H, m), 4.15 (2H, q, J=7.1 Hz), 7.17 (1H, d, J=9.3 Hz), 7.95-8.05 (3H, m)

REFERENTIAL EXAMPLE 40

In a mixture of 15 ml of ethyl acetate and 15 ml of ethanol is dissolved 5.00 g of methyl 4-(benzyloxy)-2-isobutoxybenzoate, to which is added 1.0 g of 5% palladium-carbon. The mixture thus obtained is stirred at ambient temperature for 3 hours in a stream of hydrogen. The reaction mixture is filtered with Celite, and the solvent is distilled off therefrom under reduced pressure. Then, 19 ml of 5 mol/L solution of sodium hydroxide is added to a solution of the residue obtained above in 35 ml of ethanol, and the mixture thus obtained is stirred at 50° C. for one hour. The reaction mixture is added to a mixture of chloroform and water, pH is adjusted to 2 with 6 mol/L hydrochloric acid, and the organic layer is separated. To a solution of the residue thus obtained in 20 ml of tetrahydrofuran are successively added 2.0 ml of triethylamine and 0.8 ml of acetyl chloride, and the mixture thus obtained is stirred at ambient temperature for 10 minutes. The reaction mixture is added to a mixture of ethyl acetate and water, pH is adjusted to 2 with 6 mol/L hydrochloric acid, and the organic layer is separated. The organic layer is washed with water and saturated aqueous solution of sodium chloride successively and dried over anhydrous magnesium sulfate, and then the solvent is distilled off under reduced pressure. Thus, 1.37 g of 4-acetyloxy-2-isobutoxybenzoic acid is obtained as a light yellow oily product.

NMR (CDCl$_3$) δ: 1.05 (6H, d, J=6.6 Hz), 1.92-2.40 (1H, m), 2.31 (3H, s), 3.78 (2H, d, J=6.4 Hz), 6.68-6.83 (3H, m), 7.89 (1H, d, J=9.0 Hz)

REFERENTIAL EXAMPLE 41

In 50 ml of N,N-dimethylformamide are suspended 5.0 g of 3,5-dihydroxybenzoic acid, 29.8 g of potassium carbonate and 11 ml of isobutyl iodide. The mixture thus obtained is stirred at 110° C. for 7 hours. The reaction mixture is added to a mixture of ethyl acetate and water, pH is adjusted to 2 with 6 mol/L hydrochloric acid, and the organic layer is separated. The organic layer is washed with water and saturated aqueous solution of sodium chloride successively and dried over anhydrous magnesium sulfate, and then the solvent is distilled off under reduced pressure. The residue thus obtained is purified by silica gel column chromatography (eluent; hexane:ethyl acetate=10:1) to obtain 2.6 g of isobutyl 3,5-diisobutoxybenzoate as a light yellow oily product.

NMR (CDCl$_3$) δ: 1.02 (18H, d, J=6.6 Hz), 1.85-2.30 (3H, m), 3.74 (4H, d, J=6.6 Hz), 4.09 (2H, d, J=6.6 Hz), 6.62-6.67 (1H, m), 7.16 (2H, d, J=2.2 Hz)

REFERENTIAL EXAMPLE 42

In 13 ml of methanol is dissolved 2.5 g of isobutyl 3,5-diisobutoxybenzoate, to which is then added 2.3 ml of 5 mol/L sodium hydroxide solution. The mixture thus obtained is stirred at 50° C. for 3 hours. Chloroform and water are added to the reaction mixture, pH is adjusted to 2 with 6 mol/L hydrochloric acid, and the organic layer is separated. The organic layer is washed with water and saturated aqueous solution of sodium chloride successively and dried over anhydrous magnesium sulfate, and then the solvent is distilled off under reduced pressure. Thus, 1.8 g of 3,5-diisobutoxybenzoic acid is obtained as a white solid product.

NMR (CDCl$_3$) δ: 1.03 (12H, d, J=6.6 Hz), 1.87-2.33 (2H, m), 3.76 (4H, d, J=6.4 Hz), 6.65-7.24 (4H, m)

REFERENTIAL EXAMPLE 43

In 200 ml of N,N-dimethylformamide are suspended 10 g of 2,5-dihydroxybenzoic acid, 148 g of potassium carbonate and 106 ml of isobutyl bromide. The mixture is stirred at 110° C. for 6 hours. The reaction mixture is added to a mixture of ethyl acetate and water, pH is adjusted to 2 with 6 mol/L hydrochloric acid, and the organic layer is separated. The organic layer is washed with water and saturated aqueous solution of sodium chloride successively and dried over anhydrous magnesium sulfate, and then the solvent is distilled off under reduced pressure. The residue thus obtained is purified by silica gel column chromatography (eluent; hexane:ethyl acetate=10:1) to obtain 18 g of isobutyl 2,5-diisobutoxybenzoate as a light yellow oily product.

NMR (CDCl$_3$) δ: 0.97-1.06 (18H, m), 1.60-2.40 (3H, m), 3.69 (2H, d, J=6.3 Hz), 3.73 (2H, d, J=6.6 Hz), 4.09 (2H, d, J=6.6 Hz), 6.80-7.05 (2H, m), 7.31 (1H, d, J=2.7 Hz)

REFERENTIAL EXAMPLE 44

In 88 ml of ethanol is dissolved 17.48 g of isobutyl 2,5-diisobutoxybenzoate. After adding 33 ml of 5 mol/L sodium hydroxide solution, the mixture is stirred at ambient temperature for 30 minutes. Chloroform and water are added to the reaction mixture, pH is adjusted to 2 with 6 mol/L hydrochloric acid, and the organic layer is separated. The organic layer is washed with water and saturated aqueous solution of sodium chloride successively and dried over anhydrous magnesium sulfate, and then the solvent is distilled off under reduced pressure. Thus, 12.16 g of 2,5-diisobutoxybenzoic acid is obtained as a white solid product.

NMR (CDCl$_3$) δ: 1.01 (6H, d, J=6.4 Hz), 1.08 (6H, d, J=6.4 Hz), 1.80-2.48 (2H, m), 3.73 (2H, d, J=6.5 Hz), 3.98 (2H, d, J=6.4 Hz), 6.91-7.18 (2H, m), 7.66 (1H, d, J=3.0 Hz), 10.74 (1H, brs)

REFERENTIAL EXAMPLE 45

In 50 ml of N,N-dimethylformamide are suspended 5.0 g of 3,4-dihydroxybenzaldehyde, 15.5 g of potassium carbonate and 14 ml of isopentyl iodide. The mixture is stirred at 60° C. for 2 hours. The reaction mixture is added to a mixture of ethyl acetate and water, pH is adjusted to 2 with 6 mol/L hydrochloric acid, and the organic layer is separated. The organic layer is washed with water and saturated aqueous solution of sodium chloride successively and dried over anhydrous magnesium sulfate, and then the solvent is distilled off under reduced pressure. The residue thus obtained is purified by silica gel column chromatography (eluent; hexane:ethyl acetate=10:1) to obtain 9.4 g of 3,4-diisopentyloxybenzaldehyde as a light yellow oily product.

NMR (CDCl$_3$) δ: 0.98 (12H, d, J=6.1 Hz), 1.63-1.81 (6H, m), 4.01-4.18 (4H, m), 6.95 (1H, d, J=8.8 Hz), 7.36-7.46 (2H, m), 9.83 (1H, s)

REFERENTIAL EXAMPLE 46

The procedure of Referential Example 45 is repeated to obtain isobutyl 3,4-diisobutoxybenzoate.

NMR (CDCl$_3$) δ: 0.88-1.09 (18H, m), 1.93-2.31 (3H, m), 3.80 (4H, d, J=6.3 Hz), 4.08 (2H, d, J=6.6 Hz), 6.85 (1H, d, J=8.3 Hz), 7.54 (1H, d, J=2.0 Hz), 7.64 (1H, dd, J=8.3, 2.0 Hz)

REFERENTIAL EXAMPLE 47

In 30 ml of acetonitrile is dissolved 3.0 g of 3,4-diisopentyloxybenzaldehyde, to which are successively added at ambient temperature a solution of 4.5 g of sodium dihydrogenphosphate in 15 ml of water and 1.8 ml of 30% aqueous hydrogen peroxide. Then, a solution of 2.0 g of sodium chlorite in 30 ml of water is dropwise added thereto at 5-10° C., and the mixture thus obtained is stirred at ambient temperature for 3.5 hours. Chloroform and water are added to the reaction mixture, pH is adjusted to 2 with 6 mol/L hydrochloric acid, and the organic layer is separated. The organic layer thus obtained is washed with water and saturated aqueous solution of sodium chloride successively and dried over anhydrous magnesium sulfate, and then the solvent is distilled off under reduced pressure. Thus, 3.0 g of 3,4-diisopentyloxybenzoic acid is obtained as a white solid product.

NMR (CDCl$_3$) δ: 0.98 (12H, d, J=5.4 Hz), 1.60-1.90 (6H, m), 4.02-4.09 (4H, m), 6.90 (1H, d, J=8.8 Hz), 7.60-7.80 (3H, m)

REFERENTIAL EXAMPLE 48

In 50 ml of N,N-dimethylformamide are suspended 5.0 g of 3,4-dihydroxybenzaldehyde, 10.0 g of potassium carbonate and 8.3 ml of isobutyl iodide. The suspension is stirred at 80° C. for 2 hours. The reaction mixture is added to a mixture of ethyl acetate and water, pH is adjusted to 2 with 6 mol/L hydrochloric acid, and the organic layer is separated. The organic layer thus obtained is washed with water and saturated aqueous solution of sodium chloride successively and dried over anhydrous magnesium sulfate, and then the solvent is distilled off under reduced pressure. The residue thus obtained is purified by silica gel column chromatography (eluent; hexane:ethyl acetate=5:1) to obtain 3.3 g of 3-hydroxy-4-isobutoxybenzaldehyde as a light yellow solid product.

NMR (CDCl$_3$) δ: 1.06 (6H, d, J=6.6 Hz), 1.96-2.41 (1H, m), 3.91 (2H, d, J=6.6 Hz), 5.80 (1H, s), 6.94 (1H, d, J=8.8 Hz), 7.36-7.46 (2H, m), 9.84 (1H, s)

REFERENTIAL EXAMPLE 49

The Procedure of Referential Example 48 is repeated to obtain 3-hydroxy-4-isopentyloxy-benzaldehyde.

NMR (CDCl$_3$) δ: 0.99 (6H, d, J=5.9 Hz), 1.62-1.91 (3H, m), 4.17 (2H, t, J=6.6 Hz), 5.85 (1H, s), 6.96 (1H, d, J=8.8 Hz), 7.36-7.45 (2H, m), 9.84 (1H, s)

REFERENTIAL EXAMPLE 50

In 31 ml of N,N-dimethylformamide are suspended 3.1 g of 3-hydroxy-4-isobutoxybenzaldehyde, 0.7 g of 60% sodium hydride and 3 ml of acetic anhydride. The suspension is stirred for 2 hours at 100° C. The reaction mixture is added to a mixture of ethyl acetate and water, pH is adjusted to 2 with 6 mol/L hydrochloric acid, and the organic layer is separated. The organic layer thus obtained is washed with water and saturated aqueous solution of sodium chloride successively and dried over anhydrous magnesium sulfate, and then the solvent is distilled off under reduced pressure. Thus, 4.2 g of 5-formyl-2-isobutoxyphenyl acetate is obtained as a yellow oily product.

NMR (CDCl$_3$) δ: 1.02 (6H, d, J=6.6 Hz), 1.98-2.40 (1H, m), 2.32 (3H, s), 3.84 (2H, d, J=6.4 Hz), 7.04 (1H, d, J=8.3 Hz), 7.58 (1H, d, J=2.0 Hz), 7.74 (1H, dd, J=8.3, 2.0 Hz), 9.86 (1H, s)

REFERENTIAL EXAMPLE 51

The procedure of Referential Example 50 is repeated to obtain ethyl 2-(5-formyl-2-isobutoxyphenoxy)acetate.

NMR (CDCl$_3$) δ: 0.96 (6H, d, J=6.1 Hz), 1.27 (3H, t, J=7.1 Hz), 1.70-1.83 (3H, m), 4.11 (2H, t, J=6.8 Hz), 4.24 (2H, q, J=7.1 Hz), 4.69 (2H, s), 6.97 (1H, d, J=8.3 Hz), 7.33 (1H, d, J=1.7 Hz), 7.47 (1H, dd, J=8.2, 1.7 Hz), 9.79 (1H, s)

REFERENTIAL EXAMPLE 52

In 38 ml of acetonitrile is dissolved 4.1 g of 5-formyl-2-isobutoxyphenyl acetate. To the solution thus obtained, 6.8 g of sodium dihydrogenphosphate dissolved in 20 ml of water and 3.6 ml of 30% aqueous hydrogen peroxide are successively added at ambient temperature, and then 3.6 g of sodium chlorite dissolved in 18 ml of water is dropwise added at 5-10° C. The mixture thus obtained is stirred at ambient temperature for 2 hours. Chloroform and water are added to the reaction mixture, the organic layer is separated, the organic layer thus obtained is washed successively with 5% aqueous solution of sodium thiosulfate and saturated aqueous solution of sodium chloride, dried over anhydrous magnesium sulfate, and then the solvent is distilled off under reduced pressure. Thus, 4.0 g of 3-(acetyloxy)-4-isobutoxybenzoic acid is obtained as a light yellow solid product.

NMR (CDCl$_3$) δ: 1.02 (6H, d, J=6.6 Hz), 1.90-2.30 (1H, m), 2.32 (3H, s), 3.82 (2H, d, J=6.3 Hz), 6.97 (1H, d, J=8.5 Hz), 7.79 (1H, d, J=2.2 Hz), 7.99 (1H, dd, J=8.7, 2.2 Hz), 11.85 (1H, brs)

REFERENTIAL EXAMPLE 53

The procedure of Referential Example 52 is repeated to obtain 3-(2-ethoxy-2-oxoethoxy)-4-isopentyloxybenzoic acid.

NMR (CDCl$_3$) δ: 0.98 (6H, d, J=5.9 Hz), 1.31 (3H, t, J=7.3 Hz), 1.64-1.85 (3H, m), 4.13 (2H, t, J=6.8 Hz), 4.28 (2H, q, J=7.3 Hz), 4.71 (2H, s), 6.94 (1H, d, J=8.6 Hz), 7.58 (1H, d, J=2.0 Hz), 7.80 (1H, dd, J=8.4, 2.0 Hz), 8.53 (1H, brs)

REFERENTIAL EXAMPLE 54

In 30 ml of N,N-dimethylformamide are suspended 2.81 g of ethyl 5-methyl-1H-indole-2-carboxylate, 17.0 g of potassium carbonate and 11.3 ml of isobutyl iodide. The suspension is stirred at 120° C. for one hour. The reaction mixture is added to a mixture of ethyl acetate and water, and the organic layer is separated. The organic layer thus obtained is washed with water and saturated aqueous solution of sodium chloride successively and dried over anhydrous magnesium sulfate, and then the solvent is distilled off under reduced pressure. The residue thus obtained is purified by silica gel column chromatography (eluent: toluene) to obtain 1.75 g of ethyl 1-isobutyl-5-methyl-1H-indole-2-carboxylate as a light yellow oily product.

NMR (CDCl$_3$) δ: 0.87 (6H, d, J=6.6 Hz), 1.39 (3H, t, J=7.1 Hz), 1.90-2.50 (1H, m), 2.43 (3H, s), 4.35 (2H, q, J=7.1 Hz), 4.36 (2H, d, J=7.6 Hz), 7.06-7.42 (4H, m)

REFERENTIAL EXAMPLE 55

In 10 ml of benzene are suspended 1.00 g of ethyl 1-isobutyl-5-methyl-1H-indole-2-carboxylate, 0.76 g of N-bromosuccinimide and 0.07 g of 2,2'-azobisisobutyronitrile. The suspension is heated under reflux for two hours.

The reaction mixture is concentrated under reduced pressure, and the residue thus obtained is dissolved in 10 ml of N,N-dimethylformamide. After adding 0.57 g of potassium acetate, the mixture is stirred at 40° C. for 30 minutes. The reaction mixture is added to a mixture of ethyl acetate and water, and the organic layer is separated. The organic layer thus obtained is washed with water and saturated aqueous solution of sodium chloride successively and dried over anhydrous magnesium sulfate, and then the solvent is distilled off under reduced pressure. The residue thus obtained is purified by silica gel column chromatography (eluent; hexane:ethyl acetate=6:1) to obtain 0.68 g of ethyl 3-bromo-5-formyl-1-isobutyl-1H-indole-2-carboxylate as a yellow oily product.

NMR (CDCl$_3$) δ: 0.88 (6H, d, J=6.6 Hz), 1.48 (3H, t, J=7.1 Hz), 1.89-2.44 (1H, m), 4.37-4.51 (4H, m), 7.47 (1H, d, J=8.8 Hz), 7.92 (1H, dd, J=8.9, 1.5 Hz), 8.20 (1H, d, J=0.7 Hz), 10.08 (1H, s)

REFERENTIAL EXAMPLE 56

In 7 ml of acetonitrile is dissolved 0.65 g of ethyl 3-bromo-5-formyl-1-isobutyl-1H-indole-2-carboxylate. To the solution are successively added at ambient temperature 1.56 g of sodium dihydrogen-phosphate dihydrate dissolved in 22 ml of water and 0.64 ml of 30% aqueous hydrogen peroxide. Then, 0.68 g of sodium chlorite dissolved in 20 ml of water is dropwise added thereto at 5-10° C. The mixture thus obtained is stirred at 60° C. for one hour. Ethyl acetate and water are added to the reaction mixture, and the organic layer is separated. The organic layer thus obtained is washed with water and saturated aqueous solution of sodium chloride successively and dried over anhydrous magnesium sulfate, and then the solvent is distilled off under reduced pressure. Thus, 0.37 g of 3-bromo-2-(ethoxycarbonyl)-1-isobutyl-1H-indole-5-carboxylic acid is obtained as a yellow solid product.

NMR (CDCl$_3$) δ: 0.88 (6H, d, J=6.6 Hz), 1.48 (3H, t, J=7.1 Hz), 1.87-2.33 (1H, m), 4.35-4.58 (4H, m), 5.62 (1H, brs), 7.43 (1H, d, J=9.0 Hz), 8.10 (1H, dd, J=8.8, 1.5 Hz), 8.54 (1H, d, J=1.0 Hz)

REFERENTIAL EXAMPLE 57

In 6 ml of N,N-dimethylformamide are suspended 0.30 g of 3-bromo-2-(ethoxycarbonyl)-1-isobutyl-1H-indole-5-carboxylic acid, 0.10 g of tetrakis(triphenylphosphine)palladium(0), 0.24 ml of formic acid and 1.36 ml of triethylamine. The suspension is stirred at 80° C. for 5 hours. The reaction mixture is added to a mixture of ethyl acetate and water, and the organic layer is separated. The organic layer thus obtained is washed with water and saturated aqueous solution of sodium chloride successively and dried over anhydrous magnesium sulfate, and then the solvent is distilled off under reduced pressure. The residue thus obtained is purified by silica gel column chromatography (eluent; hexane:ethyl acetate=3:1) to obtain 0.12 g of 2-(ethoxycarbonyl)-1-isobutyl-1H-indole-5-carboxylic acid as a yellow solid product.

NMR (CDCl$_3$) δ: 0.90 (6H, d, J=6.6 Hz), 1.43 (3H, t, J=7.1 Hz), 2.00-2.47 (1H, m), 4.27-4.51 (4H, m), 7.39-7.48 (3H, m), 8.06 (1H, dd, J=8.9, 1.5 Hz), 8.54 (1H, d, J=1.2 Hz)

REFERENTIAL EXAMPLE 58

In 10 ml of dioxane is added 1.00 g of 2-amino-3,5-dibromo-4-(methoxycarbonyl)benzoic acid, to which are successively added 0.6 ml of triethylamine and 0.9 ml of diphenyl phosphoryl azide. The mixture thus obtained is heated under reflux for 1.5 hours. Ethyl acetate and water are added to the reaction mixture, pH is adjusted to 6 with 6 mol/L hydrochloric acid, and the organic layer is separated. The organic layer thus obtained is washed with water and saturated aqueous solution of sodium chloride successively and dried over anhydrous magnesium sulfate, and then the solvent is distilled off under reduced pressure. Thus, 0.96 g of methyl 4,6-dibromo-2-oxo-2,3-dihydro-1H-benzimidazole-5-carboxylate is obtained as a light brown-colored solid product.

NMR (DMSO-d6) δ: 3.94 (3H, s), 7.13-7.18 (1H, m), 11.00 (2H, brs)

REFERENTIAL EXAMPLE 59

In 10 ml of N,N-dimethylformamide are suspended 0.95 g of methyl 4,6-dibromo-2-oxo-2,3-dihydro-1H-benzimidazole-5-carboxylate, 0.24 g of 60% sodium hydride and 0.7 ml of isopentyl bromide. The suspension is stirred at 50-60° C. for 3 hours. The reaction mixture is added to a mixture of ethyl acetate and water, pH is adjusted to 2 with 2 mol/L hydrochloric acid, and the organic layer is separated. The organic layer thus obtained is washed with water and saturated aqueous solution of sodium chloride successively and dried over anhydrous magnesium sulfate, and then the solvent is distilled off under reduced pressure. Thus, 0.71 g of methyl 4,6-dibromo-1,3-diisopentyl-2-oxo-2,3-dihydro-1H-benzimidazole-5-carboxylate is obtained as a light brown-colored solid product.

NMR (CDCl$_3$) δ: 0.98 (12H, d, J=5.6 Hz), 1.43-1.77 (6H, m), 3.77-3.93 (2H, m), 3.98 (3H, s), 4.15-4.32 (2H, m), 7.08 (1H, s)

REFERENTIAL EXAMPLE 60

In 7 ml of N,N-dimethylformamide are suspended 0.70 g of methyl 4,6-dibromo-1,3-diisopentyl-2-oxo-2,3-dihydro-1H-benzimidazole-5-carboxylate, 0.16 g of tetrakis(triphenylphosphine)palladium(0), 0.44 ml of formic acid and 2.4 ml of triethylamine. The suspension is stirred at 100° C. for 3 hours. The reaction mixture is added to a mixture of ethyl acetate and water, pH is adjusted to 4 with 2 mol/L hydrochloric acid, and the organic layer is separated. The organic layer thus obtained is washed with water and saturated aqueous solution of sodium chloride successively and dried over anhydrous magnesium sulfate, and then the solvent is distilled off under reduced pressure. The residue thus obtained is purified by silica gel column chromatography (eluent; hexane:ethyl acetate=5:1) to obtain 0.37 g of methyl 1,3-diisopentyl-2-oxo-2,3-dihydro-1H-benzimidazole-5-carboxylate as a colorless oily product.

NMR (CDCl$_3$) δ: 0.98 (12H, d, J=5.4 Hz), 1.48-1.88 (6H, m), 3.84-3.93 (4H, m), 3.93 (3H, s), 6.98 (1H, d, J=8.3 Hz), 7.67 (1H, s), 7.84 (1H, dd, J=8.2, 1.2 Hz)

REFERENTIAL EXAMPLE 61

In 7 ml of methanol is dissolved 0.34 g of methyl 1,3-diisopentyl-2-oxo-2,3-dihydro-1H-benzimidazole-5-carboxylate. After adding 1.5 ml of 1 mol/L solution of sodium hydroxide, the mixture is stirred at 50° C. for one hour. Water and chloroform are successively added to the reaction mixture, pH is adjusted to 2 with 6 mol/L hydrochloric acid, and the organic layer is separated. The organic layer thus obtained is washed with water and saturated aqueous solution of sodium chloride successively and dried over anhydrous magnesium sulfate, and then the solvent is distilled off under reduced pressure. Thus, 0.29 g of 1,3-diisopentyl-2-oxo-2,3-dihydro-1H-benzimidazole-5-carboxylic acid is obtained as a white solid product.

NMR (CDCl$_3$) δ: 1.00 (12H, d, J=5.1 Hz), 1.54-1.79 (6H, m), 3.87-4.03 (4H, m), 7.03 (1H, d, J=8.1 Hz), 7.73 (1H, s), 7.94 (1H, d, J=8.3 Hz), 8.20 (1H, brs)

INDUSTRIAL UTILIZABILITY

This invention relates to a compound having an inhibitory action on the activity of transcription factor AP-1 or a salt thereof, an agent for preventing and treating diseases into which an excessive expression of AP-1 participates which contains said compound or said salt, and an AP-1 inhibiting agent. The compounds and agents of this invention are useful as therapeutic and preventive drugs causing lessened side reactions.

The invention claimed is:
1. A benzene derivative represented by the following formula:

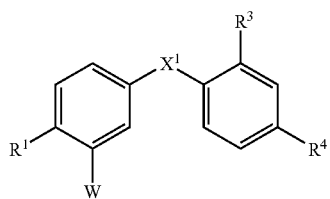

wherein
R$^1$ represents a halogen atom, a cyano group, a nitro group, an unprotected or protected hydroxyl group, an unprotected or protected amino group, a mercapto group or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group;

R$^3$ represents a halogen atom, a cyano group, a nitro group, an unprotected or protected carboxyl group, an unprotected or protected hydroxyl group, an unprotected or protected amino group, a mercapto group, a carbamoyl, group or an unsubstituted or substituted alkyl, alkenyl, cycloalkyl, aryl, aralkyl, alkoxy, aryloxy, acyl, alkoxycarbonyl, aryloxycarbonyl, alkylthio, alkylsulfinyl, alkylsulfonyl, alkylamino, acylamino, alkylsulfonylamino, arylsulfonylamino or heterocyclic group;

R$^4$ represents a cyano group, a nitro group, an unprotected or protected carboxyl group, an unprotected or protected hydroxyl group, an unprotected or protected amino group, a mercapto group or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group;

X$^1$ represents —C(O)—, —CH(OH)—, —CH$_2$— or a group of the following formula:

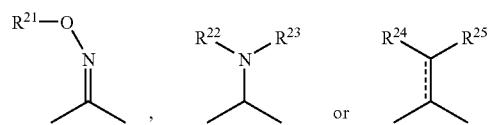

wherein R$^{21}$ represents an unsubstituted or substituted alkyl, alkenyl, cycloalkyl, aryl, aralkyl, acyl or heterocycle-lower alkyl group;

R$^{22}$ and R$^{23}$ may be the same or different represent a hydrogen atom or an unsubstituted or substituted alkyl, alkenyl, cycloalkyl, aryl, aralkyl, acyl, carbamoyl, alkylsulfinyl, alkylsulfonyl, arylsulfonyl or heterocyclic group; and $R^{24}$ and $R^{25}$ may be the same or different represent a hydrogen atom, a halogen atom, a cyano group, a nitro group, an unprotected or protected carboxyl group, an unprotected or protected hydroxyl group, an unprotected or protected amino group, a mercapto group or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; the double line of which one line is a broken line denotes a single bond or a double bond; and W represents —Z—COR$^{26}$, —Z—COOR$^2$, —O—CH$_2$COOR$^2$ or —O—CH$_2$CH$_2$COOR$^2$, wherein Z represents —(CH$_2$)$_n$— in which n represents 0, 1, 2 or 3 with the proviso that when W is —Z—COOR$^2$, n is 2 or 3, —CH$_2$CH(CH$_3$)—, —CH═CH— or —CH$_2$CH═CH—; R$^2$ represents a hydrogen atom or a protecting group for carboxyl group; and R$^{26}$ represents —NHR$^{27}$ or —NHSO$_2$R$^{28}$ in which R$^{27}$ and R$^{28}$ independently represent an unsubstituted or substituted alkyl, alkenyl, cycloalkyl, aryl or aralkyl group;

or a salt thereof.

2. A benzene derivative or a salt thereof according to claim 1, wherein W is —Z'—COOR$^{2'}$, —Z'—CONH—SO$_2$R$^{28'}$, —CONH—CH$_2$COOR$^{2'}$ or —CONH—CH$_2$CH$_2$COOR$^{2'}$ wherein Z' represents —(CH$_2$)$_{n'}$— in which n' is 0, 1 or 2, with the proviso that when W is —Z—COOR$^2$, n is 2 or 3, or —CH═CH—; R$^{28'}$ represents an unsubstituted or substituted alkyl group; and R$^{2'}$ represents a hydrogen atom or a protecting group for carboxyl group; and X$^1$ is —C(O)—, —CH(OH)— or —CH$_2$—.

3. A benzene derivative or a salt thereof according to claim 2, wherein R$^1$ is an unprotected or protected hydroxyl group or an unsubstituted or substituted alkoxy group; R$^3$ is an unprotected or protected hydroxyl group or an unsubstituted or substituted alkoxy group; and R$^4$ is an unprotected or protected hydroxyl group or an unsubstituted or substituted alkoxy group.

4. A benzene derivative represented by the following formula:

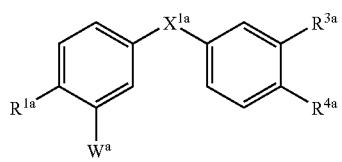

wherein R$^{1a}$ represents a halogen atom, a cyano group, a nitro group, an unprotected or protected hydroxyl group, a mercapto group or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; R$^{3a}$ and R$^{4a}$, which may be the same or different, each represent a halogen atom, a cyano group, a nitro group, an unprotected or protected carboxyl group, an unprotected or protected hydroxyl group, an unprotected or protected amino group, a mercapto group or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; X$^{1a}$ represents —C(O)—, —CH(OH)—, —CH$_2$— or a group of the following formula:

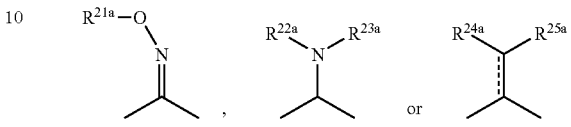

wherein R$^{21a}$ represents an unsubstituted or substituted alkyl, alkenyl, cycloalkyl, aryl, aralkyl, acyl or heterocycle-lower alkyl group; R$^{22a}$ and R$^{23a}$ may be the same or different represent a hydrogen atom or an unsubstituted or substituted alkyl, alkenyl, cycloalkyl, aryl, aralkyl, acyl, carbamoyl, alkylsulfinyl, alkylsulfonyl, arylsulfonyl or heterocyclic group; R$^{24a}$ and R$^{25a}$ may be the same or different represent a hydrogen atom, a halogen atom, a cyano group, a nitro group, an unprotected or protected carboxyl group, an unprotected or protected hydroxyl group, an unprotected or protected amino group, a mercapto group or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; and the double line of which one line is a broken line represents a single bond or a double bond; and W$^a$ represents —Z$^a$—COR$^{26a}$, —Z$^a$—COOR$^{2a}$, —O—CH$_2$COOR$^{2a}$ or —O—CH$_2$CH$_2$COOR$^{2a}$ wherein Z$^a$ represents —(CH$_2$)$_{n^a}$—, n$^a$ is 0, 1, 2 or 3 with the proviso that when W$^a$ is —Z$^a$—COOR$^{2a}$, n$^a$ can not be 1, —CH$_2$CH(CH$_3$)—, —CH═CH— or —CH$_2$CH═CH—; R$^{2a}$ represents a hydrogen atom or a protecting group for carboxyl group; and R$^{26a}$ represents —NHR$^{27a}$ or —NHSO$_2$R$^{28a}$ in which R$^{27a}$ and R$^{28a}$ independently represent an unsubstituted or substituted alkyl, alkenyl, cycloalkyl, aryl or aralkyl group;

or a salt thereof.

5. A benzene derivative or a salt thereof according to claim 4, wherein R$^{1a}$ is an unprotected or protected hydroxyl group or an unsubstituted or substituted alkoxy group; R$^{3a}$ and R$^{4a}$ may be the same or different and represent an unprotected or protected hydroxyl group or an unsubstituted or substituted alkoxy group; X$^{1a}$ is —C(O)—, —CH(OH)—, —CH$_2$— or a group of the following formula:

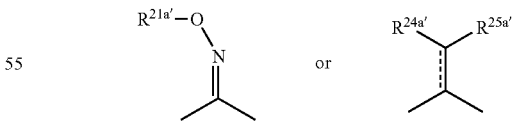

wherein R$^{21a'}$ represents an unsubstituted or substituted alkyl, aralkyl or heterocycle-lower alkyl group; R$^{24a'}$ and R$^{25a'}$ may be the same or different represent a hydrogen atom, an unprotected or protected carboxyl group or an unsubstituted or substituted alkyl, alkoxycarbonyl, aryloxycarbonyl or carbamoyl group; and W$^a$ represents —Z$^{a'}$—COR$^{26a'}$, Z$^{a'}$—COOR$^{2a'}$, —O—CH$_2$COOR$^{2a'}$, —O—CH$_2$CH$_2$COOR$^{2a'}$, —CONH—CH$_2$COOR$^{2a'}$, or —CONH—CH$_2$CH$_2$COOR$^{2a'}$ wherein Z$^{a'}$ represents —(CH$_2$)$_{n^{a'}}$— in which n$^{a'}$ is 0, 1, 2 or 3 with the proviso that when W$^a$ is —Z$^{a'}$—COOR$^{2a'}$, n$^{a'}$ is 2 or 3, —CH$_2$CH (CH$_3$)—, —CH=CH— or —CH$_2$CH=CH—; R$^{2a'}$ represents a hydrogen atom or a protecting group for carboxyl group; and R$^{26a'}$ represents —NHSO$_2$R$^{28a'}$ in which R$^{28a'}$ is an unsubstituted or substituted alkyl group.

6. A benzene derivative represented by the following formula:

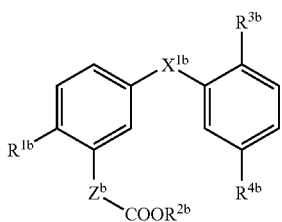

wherein R$^{1b}$ represents a halogen atom, a cyano group, a nitro group, an unprotected or protected hydroxyl group, an unprotected or protected amino group, a mercapto group or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; R$^{2b}$ represents a hydrogen atom or a protecting group for carboxyl group; R$^{3b}$ and R$^{4b}$ may be the same or different represent a cyano group, a nitro group, an unprotected or protected carboxyl group, an unprotected or protected hydroxyl group, an unprotected or protected amino group, a mercapto group or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; X$^{1b}$ represents —C(O)—, —CH(OH)— or —CH$_2$—; and Z$^b$ represents —(CH$_2$)$_{n^b}$—, wherein n$^b$ represents 2 or 3 or —CH=CH—;

or a salt thereof.

7. A benzene derivative or a salt thereof according to claim 6, wherein R$^{1b}$ is an unsubstituted or substituted alkoxy group; R$^{3b}$ and R$^{4b}$ may be the same or different represent an unprotected or protected hydroxyl group or an unsubstituted or substituted alkoxy group; X$^{1b}$ is —C(O)—; and Z$^b$ is —(CH$_2$)$_2$— or —(CH$_2$)$_3$—.

8. A benzene derivative represented by the following formula:

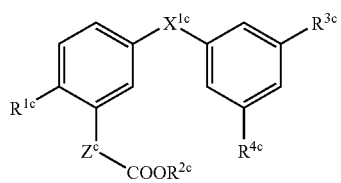

wherein R$^{1c}$ represents a halogen atom, a cyano group, a nitro group, an unprotected or protected hydroxyl group, an unprotected or protected amino group, a mercapto group or an unsubstituted or substituted alkyl, alkenyl, cycloalkyl, aryl, aralkyl, alkoxy, aryloxy, acyl, alkoxycarbonyl, aryloxy-carbonyl, carbamoyl, alkylthio, alkylsulfinyl, alkylsulfonyl, alkylamino, acylamino, alkylsulfonylamino, arylsulfonylamino or heterocyclic group; R$^{2c}$ represents a hydrogen atom or a protecting group for carboxyl group; R$^{3c}$ and R$^{4c}$ may be the same or different represent a halogen atom, a cyano group, a nitro group, an unprotected or protected carboxyl group, an unprotected or protected hydroxyl group, an unprotected or protected amino group, a mercapto group or an unsubstituted or substituted alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; X$^{1c}$ represents —C(O)—, —CH(OH)— or —CH$_2$—; and Z$^c$ represents —(CH$_2$)$_{n^c}$—, wherein n$^c$ represents 2 or 3 or —CH=CH—;

or a salt thereof.

9. A benzene derivative or a salt thereof according to claim 8, wherein R$^{1c}$ is an unsubstituted or substituted alkoxy group; R$^{2c}$ is a hydrogen atom or a protecting group for carboxyl group; R$^{3c}$ and R$^{4c}$ may be the same or different represent an unsubstituted or substituted alkoxy group; X$^{1c}$ represents —C(O)—; and Z$^c$ represents —(CH$_2$)$_2$— or —(CH$_2$)$_3$—.

10. A benzene derivative represented by the following formula:

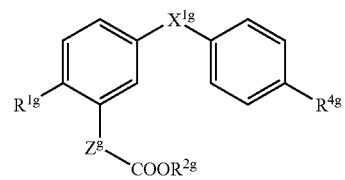

wherein R$^{1g}$ and R$^{4g}$ may be the same or different represent an unprotected or protected hydroxyl group or an unsubstituted or substituted alkoxy group; X$^{1g}$ is —C(O)—, —CH(OH)— or —CH$_2$—; Z$^g$ is —(CH$_2$)$_{n^g}$—, wherein n$^g$ represents 2 or 3; and R$^{29}$ is a hydrogen atom or a protecting group for carboxyl group;

or a salt thereof.

11. A compound or a salt thereof according to claim 1, wherein said compound is a compound that has an activity of antagonistically inhibiting the combination between AP-1 and a recognition sequence thereof.

12. A method for inhibiting AP-1 which comprises contacting a compound or a salt thereof according to claim 1 with an AP-1 binding site.

13. The compound or a salt thereof according to claim 1, which antagonistically inhibits the combination between AP-1 and a recognition sequence thereof.

14. A method for inhibiting AP-1 which comprises administering an effective amount of the compound or a salt thereof according to claim 1 to a subject in need thereof.

15. An agent for treating an autoimmune disease, which comprises a compound or a salt thereof according to claim 1.

16. A composition comprising the compound or a salt thereof according to claim 1 in an amount sufficient to inhibit AP-1 activity.

17. A benzene derivative according to claim 1, having the following formula:

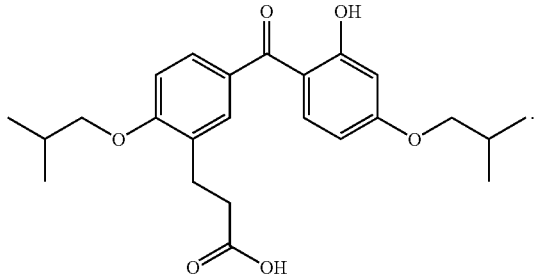

18. A benzene derivative according to claim 6, having the formula:

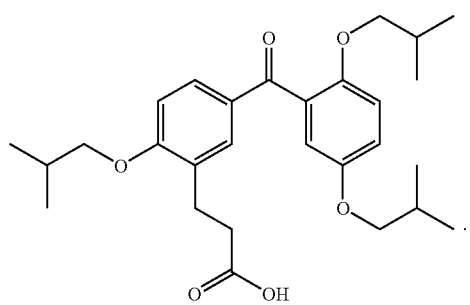

19. The benzene derivative according to claim 8, having the formula:

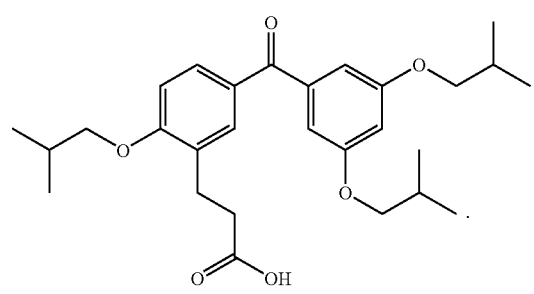

20. The benzene derivative according to claim 10, having the formula:

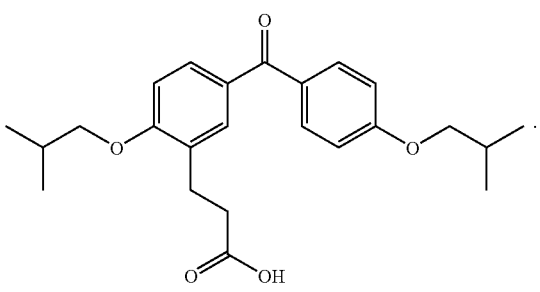

21. A benzene derivative represented by the following formula:

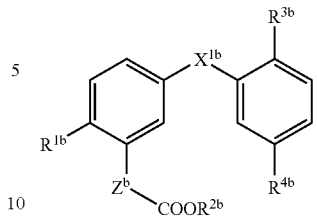

wherein $R^{1b}$ represents a halogen atom, a cyano group, a nitro group, a protected hydroxyl group, an unprotected or protected amino group, a mercapto group or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; $R^{2b}$ represents a hydrogen atom or a protecting group for carboxyl group; $R^{3b}$ and $R^{4b}$ may be the same or different represent a cyano group, a nitro group, an unprotected or protected carboxyl group, an unprotected or protected hydroxyl group, an unprotected or protected amino group, a mercapto group or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; $X^{1b}$ represents —C(O)—, —CH(OH)— or —CH$_2$—; and $Z^b$ represents —(CH$_2$)$_n{}^b$— ($n^b$ represents 2 or 3 or —CH=CH—;

or a salt thereof.

22. A benzene derivative represented by the following formula:

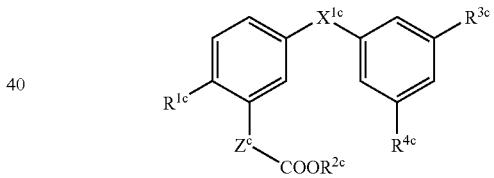

wherein $R^{1c}$ represents a halogen atom, a cyano group, a nitro group, a protected hydroxyl group, an unprotected or protected amino group, a mercapto group or an unsubstituted or substituted alkyl, alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; $R^{2c}$ represents a hydrogen atom or a protecting group for carboxyl group; $R^{3c}$ and $R^{4c}$ may be the same or different represent a halogen atom, a cyano group, a nitro group, an unprotected or protected carboxyl group, an unprotected or protected hydroxyl group, an unprotected or protected amino group, a mercapto group or an unsubstituted or substituted alkenyl, cycloalkyl, aryl, aralkyl, alkoxy, aryloxy, acyl, alkoxycarbonyl, aryloxycarbonyl, carbamoyl, alkylthio, alkylsulfinyl, alkylsulfonyl, alkylamino, acylamino, alkylsulfonylamino, arylsulfonylamino or heterocyclic group; $X^{1c}$ represents —C(O)—, —CH(OH)— or —CH$_2$—; and $Z^c$ represents —(CH$_2$)$_n{}^c$— ($n^c$ represents 2 or 3) or —CH=CH—;

or a salt thereof.

23. A benzene derivative represented by the following formula:

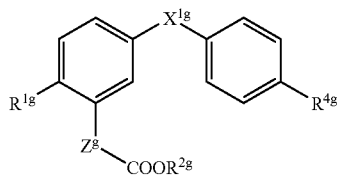
wherein $R^{1g}$ is a protected hydroxyl group and $R^{4g}$ an unprotected or protected hydroxyl group or an unsubstituted or substituted alkoxy group; $X^{1g}$ is —C(O)—, —CH(OH)— or —CH$_2$—; $Z^g$ is —(CH$_2$)$_{n^f}$— ($n^g$ represents 2 or 3); and $R^{2g}$ is a hydrogen atom or a protecting group for carboxyl group;
or a salt thereof.
* * * * *